United States Patent
Saxon et al.

(10) Patent No.: US 7,879,334 B1
(45) Date of Patent: Feb. 1, 2011

(54) FUSION MOLECULES AND TREATMENT OF IGE-MEDIATED ALLERGIC DISEASES

(75) Inventors: Andrew Saxon, Santa Monica, CA (US); Ke Zhang, Los Angeles, CA (US); Daocheng Zhu, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 11/799,442

(22) Filed: Apr. 30, 2007

Related U.S. Application Data

(63) Continuation of application No. 09/847,208, filed on May 1, 2001, now Pat. No. 7,265,208.

(51) Int. Cl.
*C07K 16/46* (2006.01)
*A61K 39/00* (2006.01)
*A61K 39/35* (2006.01)
*A61K 39/36* (2006.01)

(52) U.S. Cl. .............. 424/185.1; 424/134.1; 424/192.1; 424/275.1; 530/350

(58) Field of Classification Search ........................ None
See application file for complete search history.

(56) References Cited

U.S. PATENT DOCUMENTS

| | | | |
|---|---|---|---|
| 4,902,495 A | 2/1990 | Kaliner et al. | |
| 5,017,693 A | 5/1991 | Hylarides et al. | |
| 5,116,964 A | 5/1992 | Capon et al. | |
| 5,141,648 A | 8/1992 | Hylarides et al. | |
| 5,329,028 A | 7/1994 | Ashkenazi et al. | |
| 5,336,603 A | 8/1994 | Capon et al. | 435/69.7 |
| 5,358,710 A | 10/1994 | Sehon et al. | |
| 5,420,247 A | 5/1995 | Gearing et al. | |
| 5,512,283 A | 4/1996 | Byers et al. | |
| 5,558,869 A | 9/1996 | Burks, Jr. et al. | |
| 5,560,915 A | 10/1996 | Patterson et al. | |
| 5,563,250 A | 10/1996 | Hylarides et al. | |
| 5,565,335 A | 10/1996 | Capon et al. | |
| 5,637,454 A | 6/1997 | Harley | |
| 5,645,820 A | 7/1997 | Hafler et al. | |
| 5,672,683 A | 9/1997 | Friden et al. | |
| 5,698,679 A * | 12/1997 | Nemazee | 530/387.3 |
| 5,736,507 A | 4/1998 | Boots et al. | |
| 5,811,265 A | 9/1998 | Quertermous et al. | |
| 5,817,308 A * | 10/1998 | Scott et al. | 424/93.21 |
| 5,827,516 A | 10/1998 | Urban et al. | |
| 5,843,449 A | 12/1998 | Boots et al. | |
| 5,858,980 A | 1/1999 | Weiner | 514/13 |
| 5,869,093 A | 2/1999 | Weiner et al. | |
| 5,880,103 A | 3/1999 | Urban et al. | |
| 5,925,351 A | 7/1999 | Browning et al. | 424/143.1 |
| 5,945,294 A | 8/1999 | Frank et al. | |
| 5,965,605 A | 10/1999 | Cheng et al. | |
| 5,973,121 A | 10/1999 | Burks et al. | |
| 5,977,307 A | 11/1999 | Friden et al. | |
| 6,043,345 A | 3/2000 | Saxon et al. | |
| 6,093,699 A | 7/2000 | Sehon et al. | |
| 6,103,697 A | 8/2000 | Bergstrand et al. | |
| 6,214,974 B1 | 4/2001 | Rosenblum et al. | |
| 6,228,373 B1 | 5/2001 | Bergstrand et al. | |
| 6,228,374 B1 | 5/2001 | Bergstrand et al. | |
| 6,287,792 B1 | 9/2001 | Pardridge et al. | |
| 6,372,250 B1 | 4/2002 | Pardridge et al. | |
| 7,101,581 B2 * | 9/2006 | Ehrman | 426/392 |
| 7,265,208 B2 * | 9/2007 | Saxon et al. | 530/387.1 |
| 7,488,804 B2 * | 2/2009 | Saxon et al. | 530/387.3 |
| 7,534,440 B2 * | 5/2009 | Saxon | 424/192.1 |
| 2001/0053770 A1 | 12/2001 | Thomas et al. | |
| 2003/0049237 A1 | 3/2003 | Bannon et al. | |
| 2003/0077282 A1 | 4/2003 | Bigler et al. | |
| 2004/0198961 A1 | 10/2004 | An et al. | |
| 2005/0250934 A1 | 11/2005 | Wang et al. | |
| 2006/0171942 A1 * | 8/2006 | Saxon et al. | 424/133.1 |
| 2009/0136493 A1 * | 5/2009 | Saxon et al. | 424/133.1 |
| 2009/0317389 A1 * | 12/2009 | Saxon | 424/134.1 |

FOREIGN PATENT DOCUMENTS

WO      WO 88/09344      * 12/1988

(Continued)

OTHER PUBLICATIONS

Fasler et al., J. Allergy and Clinical Immunology 101(4 pt 1): 521-30, Apr. 1998.*
Burks et al, Eur. J Biochem 245: 334-339; 1997.*
Stanley et al, Archives of Biochemistry and Biophysics 342(2): 244-253; 1997.*
Daeron et al, J Clin Invest 95(2): 577-85, Feb. 1995.*
Rafnar et al, J Biol Chem 266(2): 1229-1236, 1991.*
Terada et al, Clinical Immunology 120(1): 45-56, 2006.*
Tangley et al, A therapy for cat allergies, Thanks to mice, the New York time, pp. 1-2, Apr. 5, 2005.*
Saxon et al, J Allergy Clin Immunol 121: 320-325, 2008.*
Zhang et al, Immunol Allergy Clin North Am 27(1): 93-103, Feb. 2007.*
Zhu et al, Nat Med 11(4): 446-449, Epub Mar. 27, 2005.*
Krauss et al., Eur. J. Immunol., 25(1): pp. 192-199 (1995).
Basu et al., The Journal of Biological Chemistry, 268(18): pp. 13118-13127 (1993).
New Riverside University Dictionary, Boston, MA, pp. 933 (1994).
Ngo et al., The Protein Folding Problem and Tertiary Structure Prediction, Merz et al., (ed.), Birkhauser, Boston, MA, pp. 433 and 492-495 (1994).

(Continued)

*Primary Examiner*—Phuong Huynh
(74) *Attorney, Agent, or Firm*—James A. Fox; Ginger R. Dreger; Arnold & Porter LLP

(57) ABSTRACT

The invention concerns bifunctional fusion molecules for the treatment of IgE-mediated allergic conditions and FcεRI-mediated autoimmune conditions. The invention provides a new therapeutic approach for the treatment of both acute and late-phase allergic responses due to ingestion, inhalation, cutaneous and parenteral exposure to allergens, responses including asthma, allergic rhinitis, atopic dermatitis, severe food allergies, chronic urticaria and angioedema, as well as anaphylactic reactions due to exposures such as bee stings or penicillin allergy. In addition, the invention provides for a novel, safer and more efficacious form of allergy vaccination.

24 Claims, 11 Drawing Sheets

FOREIGN PATENT DOCUMENTS

| WO | WO 95/14779 | | 6/1995 |
|---|---|---|---|
| WO | WO 95/26365 | | 10/1995 |
| WO | WO 96/26961 | * | 2/1996 |
| WO | WO 96/12740 | | 5/1996 |
| WO | WO 96/16086 | | 5/1996 |
| WO | WO 96/22024 | | 7/1996 |
| WO | WO 96/26961 | | 9/1996 |
| WO | WO 96/40789 | | 12/1996 |
| WO | WO 99/02709 | | 1/1999 |
| WO | WO 99/02710 | | 1/1999 |
| WO | WO 99/02711 | | 1/1999 |
| WO | WO 99/57241 | | 11/1999 |
| WO | WO 99/67293 | | 12/1999 |
| WO | WO 00/05254 | | 2/2000 |
| WO | WO 02/102320 A2 | | 12/2002 |
| WO | WO 02/102320 A3 | | 12/2002 |

OTHER PUBLICATIONS

Skolnick et al., Trends in Biotech., 18(1): pp. 34-39 (2000).
Tao et al., The Journal of Immunology, 143(8): pp. 2595-2601 (1989).
Zhu et al., Nature Medicine, 1219: pp. 1-4 (2005).
Allen, L., et al., "Modifications to an Fcγ-Fcε Fusion Protein Alter Its Effectiveness in the Inhibition of FcεRI-Mediated Functions," J. Allergy Clin. Immunol., 120: 462-468, 2007.
Terada, T., et al., "A Chimeric Human-Cat Fcγ-Fel d1 Fusion Protein Inhibits Systemic, Pulmonary, and Cutaneous Allergic Reactivity to Intratracheal Challenge in Mice Sensitized to Fel D1, the Major Cat Allergen," Clinical Immunology, 4C: 1-12, 2006.
Zhang, Ke, et al., "Chimeric Human Fcγ-Allergen Fusion Proteins in the Prevention of Allergy," Immunol. Allergy Clin. N. Am., 27: 93-103, 2007.
Zhu, D. et al., "A Chimeric Human-Cat Fusion Protein Blocks Cat-Induced Allergy," Nature Medicine, pp. 1-4, 2005.
"alphaβ-Crystallin in Multiple Sclerosis", J. Immunol, vol. 129-135, pp. 1-5, Jul. 20, 2001 (http://www.albany.net/~tjc/crystalline.html).
"Autoantigen Sequences", pp. 1-3, Jul. 11, 2001 (http://129.206.51.31/mb/ana_base.html).
"Autoimmune Disease: Rapid Progress in our Understanding of Immune Function Promises More Effective Treatments for Autoimmune Disorders", Nature Biotechnology, vol. 18, pp. IT7-IT9, Supplement 2000.
"Histones and Subclasses", Jul. 30, 2001, PurifiedAntigens for Autoimmune Testing, (http://www.immunovision.com/pg0019.htm).
Abdelilah, S.G., et al., "Molecular Characterization of the Low-Affinity IgE Receptor Fc EpsilonRII/CD23 Expressed by Human Eosinophils", Int Immunol, Apr. 1998; 10(4):395-404.
Abramson, M.J., et al., "Allergen immunotherapy for asthma", The Cochrane Library, Jan. 1998; 1:1-32.
Adamczewski, M., and Kinet, J.P., "The High-Affinity Receptor for Immunoglobulin E" Chemical Immun., 59:173190(1994).
Akdis, C., et al., Epitope-Specific T Cell Tolerance to Phospholipase $A_2$ in Bee Venom Immunotherapy and Recovery by IL-2 and IL-15 In Vitro, The American Society for Clinical Investigations, Inc., vol. 98(7), pp. 1676-1683,1996.
Alvarez-Fernandez, Marcia, et al., "Inhibition of Mammalian Legumain by Some Cystatins is Due to a Novel Second Reactive Site", The Journal of Biological Chemistry, vol. 274, No. 27, Issue of Jul. 2, pp. 19195-19203, 1999.
American Autoimmune Related Diseases Association, Questions and Answers, pp. 1-4, Jul. 26, 2001 (http://www.aarda.org/questions_and_answers.html).
Ansari, AA, et al., "Epitope Mapping of the Branched Chain Alpha-Ketoacid Dehydrogenase Dihydrolipoyl Transacylase (BCKD-E2) Protein that Reacts with Sera from Patients with Idiopathic Dilated Cardiomyopathy", (abstract), J Immunol, 153(10):4754-65, Nov. 15, 1994.
Antoniou, A. N., et al., "Control of Antigen Presentation by a Single Protease Cleavage Site", Immunity, vol. 12, pp. 391-398, Apr. 2000.

Arm et al., "Molecular Cloning of gp49, a Cell-surface Antigen That is Preferentially Expressed by Mouse Mast Cell Progenitors and is a New Member of the Immunoglobulin Superfamily" J. Biol. Chem. 266:15966-73 (1991).
Arm, J.P., et al., "Molecular Identification of a Novel Family of Human Ig Superfamily Members That Possess Immunoreceptor Tyrosine-Based Inhibition Motifs and Homology to the Mouse gp49B1 Inhibitory Receptor[1, 2]", J. Immunol., vol. 159, pp. 2342-2349, 1997.
AroTec Diagnostics Limited—Jo-1 Antigen, pp. 1-2, Jul. 11, 2001 (http://webnz.com/arotec/masa5005.htm).
AroTec Diagnostics Limited—La (SSB) Antigen, pp. 1-3, Jul. 12, 2001 (http://webnz.com/arotec/masa5010.htm).
AroTec Diagnostics Limited—Myeloperoxidase (pANCA) Antigen, pp. 1-3, Jul. 12, 2001. (http://webnz.com/arotec/masa5009.htm).
AroTec Diagnostics Limited—Parietal Cell Antigen (H/K-ATPase), pp. 1-3, Jul. 12, 2001 (http://webnz.com/arotec/masa5004.htm).
AroTec Diagnostics Limited—Proteinase 3 (cANCA) Antigen, pp. 1-3, Jul. 12, 2001 (http://webnz.com/arotec/masa5008.htm).
AroTec Diagnostics Limited—RNP/Sm Antigen, pp. 1-3, Jul. 12, 2001 (http://webnz.com/arotec/masa5006.htm).
AroTec Diagnostics Limited—Ro (SSA) Antigen, pp. 1-3, Jul. 11, 2001 (http://webnz.com/arotec/masa5011.htm).
AroTec Diagnostics Limited—Scl-70 Antigen, pp. 1-3, Jul. 12, 2001 (http://webnz.com/arotec/masa5001.htm).
AroTec Diagnostics Limited—Sm Antigen, pp. 1-3, Jul. 12, 2001 (http://webnz.com/arotec/masa5007.htm).
AroTec Diagnostics Limited—β2-Glycoprotein 1 (human), pp. 1-3, Jul. 12, 2001 (http://webnz.com/arotec/masa5002.htm).
Ashman, Robert F., et al., "Fc Receptor Off Signal in the B Cell Involves Apoptosis", The Journal of Immunology, vol. 157, pp. 5-11, 1996.
Atwood, T. K., et al., "The Babel of Bioinformatics", Science, vol. 290, No. 5491, pp. 471-473, Oct. 2000.
Auto Immune, Inc., "Overview of Oral tolerance Therapy" Research and Development—OT Technology, Jul. 30, 2001, (http://www.autoimmuneinc.com/R_D/tech.html).
Bajramovic, JJ, et al., "Presentation of αB-Crystallin to T Cells in Active Multiple Sclerosis Lesions: An Early Event Following Inflammatory Demyelination", The American Association of Immunologists, vol. 164, pp. 4359-4366, 2000.
Barker RN, et al., "Red Blood Cell Glycophorins as B and T-cell Antigens in Canine Autoimmune Haemolytic Anaemia", (abstract) Vet Immunol Immunopathol, 47(3-4):225-38, Aug. 1995.
Barnes, Peter, "Anti-IgE Antibody Therapy for Asthma" The New England Journal of Medicine 341:2006-2008 (1999).
Beasley et al., "prevalence and Etiology of asthma" J. Allergy Clin. Immunol. 105:466-472 (2000).
Bellmann, K., et al., "Potential risk of oral insulin with adjuvant for the prevention of Type I diabetes: a protocol effective in NOD mice may exacerbate disease in BB rats", Diabetologia, vol. 41, pp. 844-847, 1998.
Bielekova, B., et al., "Encephalitogenic potential of the myelin basic protein peptide (amino acids 83-99) in multiple sclerosis: results of a phase II clinical trial with an altered peptide ligand", Nat Med., vol. 6, No. 10, pp. 1167-1175, Oct. 2000.
Bigazzi, PE, MD, Lecture on "Autoimmune Disease", The University of Connecticut, pp. 1-6, Jul. 30, 2001, (http://155.37.1.60/Lectures/PB/Autoimmune.html).
Blanas, E. et al., "Induction of Autoimmune Diabetes by Oral Administration of Autoantigen", Science, vol. 274, pp. 1707-1709, Dec. 6, 1996.
Blondel, A. and Bedouelle, "Engineering the quaternary structure of an exported protein with a leucine zipper" Protein Engineering 4:457-461 (1991).
Bonfa, E., et al., "Frequency and Epitope Recognition of Anti-Ribosome P Antibodies from Humans with Systemic Lupus Erythematosus and MRL/lpr Mice are Similar", (abstract), J Immunol; 140(1):3434-3437, May 15, 1998.
Borel, et al., "A Novel Technique to Link either Proteins or Peptides to Gammaglobulin to Construct Tolerogens" J. of Immun. Methods, vol. 126, pp. 159-168 (1990).

Borel, et al., "Oligonucleotide Linked to Human Gammaglobulin Specifically Diminishes Anti-DNA Antibody Formation in Cultured Lymphoid Cells from Patients with Systemic Lupus Erythematosus" J. Clin. Invest., vol. 82, pp. 1901-1907 (1988).

Bowie, James U., et al., "Deciphering the Message in Protein Sequences: Tolerance to Amino Acid Substitutions", Science, vol. 247, pp. 1306-1310, Mar. 16, 1990.

Boyce and Austen, "No Audible Wheezing: Nuggets and Conundrums from Mouse Asthma Models," JEM, 201:(12) 1869-1873 (2005).

Brazis, P., et al., "Stem cell factor enhances IgE-mediated histamine and TNF-al release from dispersed canine cutaneous mast cells", Vet Immunol Immunopathol, Jun. 30, 2000; 75(1-2):97-108.

Breiteneder, H, PhD, et al., "Complementary DNA cloning and expression in *Escherichia coli* of Aln g I, the major allergen in pollen of alder (Alnus glutinosa)", J Allergy Clin. Immunol., vol. 90, No. 6, pp. 909-917, 1992.

Bridges, S. L., Jr., MD, PhD, et al., "T-cell Receptor Peptide Vaccination in the Treatment of Rheumatoid Arthritis", Emerging Therapies for Rheumatoid Arthritis, vol. 24, No. 3, pp. 641-651, 1998.

Bridges, SL, Jr., et al., "T-Cell Receptor Peptide Vaccination in the Treatment of Rheumatoid Arthritis", Emerging Therapies for Rheumatoid Arthritis, vol. 24, pp. 641-650, 1998.

Burks, et al. "Mapping and mutational analysis of the IgE-binding epitopes on Ara h 1, a legume vicilin and a major allergen in peanut hypersensitivity" Eur. J. Biochem. 245:334-339 (1997).

Cambier, J.C., "Inhibitory receptors abound?" Proc. Natl. Acad. Sci. USA 94:5992-5995 (1997).

Cambier, JC, "Commentary: Inhibitory receptors abound?", Proc. Natl. Acad. Sci. USA, vol. 94, pp. 5993-5995, 1997.

Campbell, K.A., "Co-crosslinking Fc epsilon RII/CD23 and B cell surface immunoglobulin modulates B cell activation", Eur J. Immunol Aug. 1992; 22(8):2107-12.

Casares et al. "Engineering an characterization of a murine MGC class II-immunoglobulin chimera expressing an immunodominant CD4 T viral epitope" Protein Engineering 10(11):1295-1301 (1997).

Casares et al., "Antigen-specific Signaling by a Soluble, Dimeric Peptide/Major Histocompatibility Complex Class II/Fc Chimera Leading to T helper Cell Type 2 Differentiation" J. Ex. Med. 190:543-553 (Nov. 1999).

Cascio P, et al., "26Sproteasomes and Immunoproteaseomes Produce Mainly N-Extended Cersions of an Antigenic Peptide", EMBO J, 20(10):2357-2366, May 15, 2001, (abstract).

Castells, M., "Mast Cells: Molecular and Cell Biology", The Journal of Asthma, Allergy and Immunology, vol. 1N1:1-17, 1999.

Chaillous, L, et al., "Combined analysis of islet cell antibodies which cross-react with mouse pancreas, antibodies to the $M_r$ 64,000 islet protein, and antibodies to glutamate decarboxylase in subjects at risk for IDDM", Diabetologia, vol. 37, pp. 491-499,1994.

Chaillous, L. et al., "Oral insulin administration and residual β-cell function in recent-onset type 1 diabetes: a multicentre randomized controlled trial", The Lancet, vol. 356, pp. 545-549, 2000.

Chan and Sinclair, "Regulation of the Immune Response" Immunology 21:967-981 (1971).

Chapman, Martin D., et al., "Recombinant Allergens for Diagnosis and Therapy of Allergic Disease", J Allergy Clin Immunol, pp. 409-418, 2000.

Coffman and Hessel, "Nonhuman Primate Models of Asthma," JEM, 201:(12) 1875-1879 (2005).

Costa et al., "The IgE-binding epitopes of rPar j2, a major allergen of Parietaria judaica polen, are heterogeneously recognized among allergic subjects" Allergy 55:246-50 (2000).

Couzin, J., et al., "Diabetes' Brave New World", Science, vol. 300, pp. 1862-1865, Jun. 2003.

Critchfield, JM, et al., "T Cell Deletion in High Antigen Dose Therapy of Autoimmune Encephalomyelitis", Science Feb. 25; 263(5150):1139-43, 1994 (abstract).

Cunningham, Brian C., et al., "High-Resolution Epitope Mappin of hGH-Receptor Interactions by Alanine-Scanning Mutagenesis", Science, vol. 244, pp. 1081-1085, Jun. 2, 1989.

Daëron et al. "The Same Tyrosine-Based Inhibition Motif, in the Intra-cytoplasmic Domain of FC(RIIB, Regulates Negatively BCR-, TCR-, and FcR-Dependent Cell Activation" Immunity 3:635-646 (Nov. 1995).

Daëron et al.., "Regulation of High-affinity IgE Receptor-mediated Mast Cell Activation by Murine Low-affinity IgG, Receptors". J. Clin. Invest 95:577-585 (Feb. 1995).

Daëron, et al., Clin. Invest., vol. 95:(2), pp. 577-585 (1995).

Daëron, Marc, "Fc Receptor Biology," Annu. Rev. Immunol. 15-203-2334 (1997).

Davidson, A., et al, "Autoimmune Diseases", N. Engl. J. Med., vol. 345, No. 5, pp. 340-350, Aug. 2, 2001.

De Lara, J.M. Tunon, "Immunoglobulines E et cellules de l'inflamation" Rev. Mal. Resp. 13:27-36 (1996).

De Palma, R, et al., "Use of Altered Peptide Ligands to Modulate Immune Responses as a Possible Immunotherapy for Allergies", Allergy: 55: Suppl 61: 56-59, 2000.

Decker, Patrice, et al., "Inhibition of Caspase-3-Mediated Poly (ADP-Ribose) Polymerase (PARP) Apoptotic Cleavage by Human PARP Autoantibodies and Effect on Cells Undergoing Apoptosis", The Journal of Biological Chemistry, © 2000 by The American Society for Biochemistry and Molecular Biology, Inc., vol. 275, No. 12, pp. 9043-9046, Mar. 24, 2000.

Delespesse, G., et al., "The Low-Affinity Receptor for IgE," Immunol. Rev., vol. 125, pp. 77-97, Feb. 1992.

Dieterich, W., et al., Identification of Tissue Transglutaminase as the Autoantigen of Celiac Disease, Nat Med; 3(7):797-801, Jul. 1997 (abstract).

Ditzel, Henrik J., "Human Antibodies in Cancer and Autoimmune Disease", Immunologic Research; 21(2-3):185-193, 2000.

Dombrowicz, D., et al., "Anaphylaxis Mediated Through a Humanized High Affinity IgE Receptor", The Journal of Immunology, vol. 157, pp. 1645-1651, 1996.

Earnshaw WC, et al., "Identification of a Family of Human Centromere Proteins Using Autoimmune Sera From Patients With Scleroderma", (abstract) Chromosoma, 91(3-4):313-321, 1985.

Elias et al., Post translational Addition of an Argine Moiety to Acidic NH2 Termini of Proteins is Required for Their Recognition by Ubiquitin-Protein Ligase, J. Biol. Chem., vol. 265, No. 26, pp. 15511-15517, Sep. 1990.

Elkon, KB, et al., "Lupus Autoantibodies Target Ribosomal P Proteins", (abstract) J Exp Med, 162(2): 459-471, Aug. 1, 1985.

Ellison and Hood., "Linkage and sequence homology of two human immunoglobulin ( heavy chain constant region genes" Proc. Nat. Acad. Sci. USA 79:1984-1988 (1982).

Ellison et al., "The nucleotide sequence of a human immunoglobulin c(1 gene" Nucl. Acids Res. 10(13):4071-4079 (1982).

Fabien N., et al., "Autoantibodies Directed Against the Ribosomal P Proteins are not Only Directed Against A Common Epitope of the P0, P1 and P2 Proteins", (abstract) J Autoimmune, 13(1): 103-110, Aug. 1999.

Faria AM, et al., "Oral Tolerance: Mechanisms and Therapeutic Applications", (abstract), Adv Immunol, 73:153-264, 1999.

Fiebiger E., et al., "Cytokines Regulate Proteolysis in Major Histocompatibility complex Class II-Dependent Antigen Presentationby Dendritic Cells" J. Exp. Med., 193(8):881-892, Apr. 16, 2001, (abstract).

Fiebiger et al., "Anti-FcεRIα Autoantibodies in Autoimmune-mediated Disorders Identification of a StructureFunction Relationship" J. Clin. Invest. 101:243-251 (Jan. 1998).

Fiebiger et al., "Serum IgG Autoantibodies Directed against the α Chain of a Fce RI: A Selective Marker and Pathogenic Factor for a Distinct Subset of Chronic Urticaria Patients" The Journal of Clinical Investigation 96:2006-2612 (Dec. 1995).

Frampton, G., et al., "Identification of Candidate Endothelial Cell Autoantigens in Systemic Lupus Erythematosus Using a Molecular Cloning Strategy: A Role for Ribosomal P Protein P0 as an Endothelial Cell Autoantigen", Rheumatology (Oxford), (abstract) 39(10):1114-1120, Oct. 2000.

Fridman, W., "Fc Receptors and Immunoglobulin binding factors" FASEB J., 5(12):2684-90 (1991).

Gerber, Jeffrey and Mosser, David, "Reversing Lipopolysaccharide Toxicitu by Ligating the Macrophage Fc( Receptors" The Journal of Immunology 6861-6868 (2001).

Germain, R.N., "The T Cell Receptor for Antigen: Signaling and Ligand Discrimination", The Journal of Biological Chemistry, vol. 276, No. 38, pp. 35223-35226, Jul. 2, 2001.

Giovannoni, G, et al., "Multiple Sclerosis and its Treatment", (abstract) J R Coll Physicians Lond, 33(4):315-22, Jul.-Aug. 1999.

Gold, D. P., et al., "T-Cell Receptor Peptides as Immunotherapy for Autoimmune Disease", Critical Reviews™ In Immunology, vol. 17, pp. 507-510, 1997.

Gold, Daniel P., et al., "T-Cell Receptor Peptides as Immunotherapy for Autoimmune Disease", Critical Reviews™ In Immunology, (abstract) 17:507-510, 1997.

Gold, DP, "Results of a Phase I Clinical Trial of a T-Cell Receptor Vaccine in Patients with Multiple Sclerosis. II. Comparative Analysis of TCR Utilization in CSF T-Cell Populations Before and After Vaccination with a TCRV Beta 6 CDR2 Peptide", (abstract) J Neuroimmunol, 76(1-2):29-38, Jul. 1997.

Gold, HA, et al., "The RNA Processing Enzyme RNase MRP is Identical to the Th RNP and Related to RNase P", (abstract) Science, 245(4924):1377-80, Sep. 22, 1989.

Gollnick et al., "Isolation, Characterization, and Expression of Cdna Clones Encoding the Mouse Fc Receptor for IgE (FcεRII)" The Journal of Immunology 144:1974-1982 (1974).

Goodkin, D. E., et al., "A phase I trial of solubilized DR2:MBP$^{84-102}$ (AG284) in multiple sclerosis", Neurology, vol. 54, pp. 1414-1420, 2000.

Gottlieb, A.B., et al., Anti-CD4 Monoclonal Antibody Treatment of Moderate to Severe Psoriasis Vulgaris: Results of a Pilot, Multicenter, Multiple-Dose, Placebo-Controlled Study, (abstract) J Am Acad Dermatol, 43(4):595-604, Oct. 2000.

Gunnarsson, Andreas, et al., "Molecular Properties of the Goodpasture Epitope", The Journal of Biological Chemistry, vol. 275, No. 40, pp. 30844-30848, Oct. 6, 2000.

Guo, C.B., et al., "Identification of IgE-bearing cells in the late-phase response to antigen in the lungs as basophils", Am J Respir Cell Mol Biol., Apr. 1994; 10(4):384-90.

Harrison, L.C. and Hafler, D.A., "Antigen-Specific Therapy for Autoimmune Disease," Current Opinion in Immunology, vol. 12, pp. 704-711, 2000.

Haselden, B. M., et al., "Immunoglobulin E-Independent Major Histocompatibility Complex-Restricted T Cell Peptide Epitope-induced Late Asthmatic Reactions", J. Exp. Med., vol. 189, No. 12, pp. 1885-1894, Jun. 21, 1999.

Haselden, B.M., et al., "Peptide-Mediated Immune Responses in Specific Immunotherapy", Int Arch Allergy Immunol, 122(4):229-37, 2000.

Hayami et al., "Molecular Cloning og a Novel Murine Cell-surface Glycoportein Homologous to Killer Cell Inhibitory Receptors" J. Biol. Chem. 272:7320-7 (1997).

Hellman, Lars, "Characterization of four novel ε chain of mRNA and a comparative analysis of ghenes for immunoglobulin E in rodents and man". Eur. J. Immunol. 23:159-167 (1993).

Hellmark, T., et al., "Characterization of Anti-GBM Antibodies Involved in Goodpasture's Syndrome", (abstract) Kidney Int, 46(3):823-9, Sep. 1994.

Helm, B. A., et al., "Identification of the High Affinity Receptor Binding Region in Human Immunoglobulin E", The Journal of Biological Chemistry, vol. 271, No. 13, Issue of Mar. 29, pp. 7494-7500, 1996.

Henz, B.M., et al., [Urticaria. New developments and perspectives]., Hautarzt May 2000;51(5):302-8.

Hide et al., "Autoantibodies against the high-affinity IgE receptor as a cause of histamine release inchronic urticaria" N. Engl. J. Med. 328:1599-1604 (1993).

Hirano, T., et al., "Human Tissue Distribution of TA02, which is Homologous with a New Type of Aspartic Proteinase, Napsin A", (abstract) Jpn J Cancer Res, 91(10):1015-21, Oct. 2000.

Hughes, G.R., The Antiphospholipid Syndrome: Ten Years On, (abstract) Lancet, 342(8867):341-344, Aug. 7, 1993.

Hulett, Mark D., et al., "Fine Structure Analysis of Interaction of FcεRI with IgE", Journal of Biological Chemistry, vol. 274, No. 19:13345-13352, 1999.

Immunovision (Brochure), "PCNA Antigen", Purified Antigens for Autoimmune Testing, Jul. 30, 2001, (http://www.immunovision.com/pg0061.htm).

Immunovision (Brochure), "La/SS-B", Purified Antigens for Autoimmune Testing, (http://www.immunovision.com/pg0014.htm), Jul. 30, 2001.

Immunovision (Brochure), "Mitochondrial Antigen", Purified Antigens for Autoimmune Testing, (http://www.immunovision.com/pg0020.htm), Jul. 30, 2001.

Immunovision (Brochure), "Ribosomal P Antigen", Purified Antigens for Autoimmune Testing, Jul. 30, 2001, (http://www.immunovision.com/pg0021.htm).

Immunovision (Brochure), "Ro/SS-A Antigen", Jul. 30, 2001, (http://www.immunovision.com/pg0013.htm).

Immunovision (Brochure), "Scl-70 Antigen", Purified Antigens for Autoimmune Testing (http://www.immunovision.com/pg0017.htm), Jul. 30, 2001.

Immunovision (Brochure), "Smith (sm) Antigen", Purified Antigens for Autoimmune Testing (http://www.immunovision.com/pg0015.htm), Jul. 30, 2001.

Ji, Tae H., et al., "Bifunctional Reagents", Methods of Enzymology, vol. 91, pp. 581-609, 1983.

Kabat, Sequences of Proteins of Immunological Ointerst Voll III Fifth Ed. (1991).

Kaplan, A.P., "Urticaria and Angioedema," Inflammation: Basic Principles and Clinical Correlates, (Gallin and Snyderman eds.), $3^{rd}$ Edition, Lippincott & Wilkins, Philadelphia, 1999, pp. 915-928.

Kaplan, Allen P., "Urticaria and Angioedema" Inflammation: Basic Principles and Clinical Correlates Gallin and Snyderman Eds., Chapter 35:667-678 Raven press, NY (1998).

Kappos, L., et al., "Induction of a non-encephalitogenic type 2 T helper-cell autoimmune response in multiple sclerosis after administration of an altered peptide ligand in a placebo-controlled, randomized phase II trial", Nature Medicine, vol. 6, No. 10, pp. 1176-1182, Oct. 2000.

Karlsson, F.A., et al., "Major Parietal Cell Antigen in Autoimmune Gastritis with Pernicious Anemia is the acid-producing H+, K+adenosine Triphosphatase of the Stomach", (Abstract) J Clin Invest, 81(2):475-9, Feb. 1988.

Katz, Howard R., "gp49BE and its Related Family of Counterregulatory Receptors of the Immunoglobulin Superfamily", Int. Arch. Allergy Immunol. 118:177-179 (1999).

Kawabori, S., et al., "Existence of c-kit receptor-positive, tryptase-negative, IgE-neg cells in human allergic nasal mucosa: a candidate for mast cell progenitor", Int. Arch Allergy Immunol. Jan. 1997;112(1):36-43.

Kepley, C.L., et al., "Purification of human basophils by density and size alone", J. Immunol. Meth., 175:1-9, 1994.

Kepley, C.L., et al., "The identification and characterization of umbilical cord-blood derived basophils", J. Leukocyte Biol., 64:474-483, 1998.

Kepley, C.L., et al., "The identification and partial characterization of a unique marker for human basophils", J. Immunol., 154, 6548-6555, 1995.

Kepley, et al., "FcεRI-Fc-γRII Coaggregation inhibits IL-16 production from human langerhans-like dendritic cells", Clinical Immunology, 108: 89-94 (2003).

Kikutani et al. "Molecular Structure of Human Lymphocyte Receptor for Immunoglobulin E" Cell 47:657-665 (Dec. 1996).

Kikutani, H., et al., "Molecular structure of human lymphocyte receptor for immunoglobulin E", Cell Dec. 5, 1986;47(5):657-65.

Kinet, J-P, "The High-Affinity IGE Receptor (FcεRI): From Physiology to Pathology", Annu. Rev. Immunol., vol. 17, pp. 931-972, 1999.

Kisseley, A. F., "Proteasome Active Sites Allosterically Regulat Each Other, Suggesting a Cylical Bite-Chew Mechanism for Protein Breakdown", Molecular Cell, vol. 4, pp. 395-402, Sep. 1999.

Kondo et al. "Cloning of cDNAs for New Subtypes of Murine Low-Affinity Tc Receptor for IgE (FcεRII/CG23)" Int. Arch. Immunol. 105:38-48 (1994).

Kozlowski, Maya, et al., "SHP-1 Binds and Negatively Modulates the c-Kit Receptor by Interaction with Tyrosine 569 in the c-Kit Juxtamembrane Domain", Molecular and Cellular Biology, pp. 2089-2099, vol. 18, No. 4, Apr. 1998.

Krawinkel an Rabbitts, "Comparison of the hinge-coding segments in human immunoglobulin gamma heavy chjain genes and the linkage of the gamma 2 and gamma 4 subclass genes" The EMBO 1(4):403-307 (1982).

Krogsgaard, M., et al., "Visualization of Myelin Basic Protein (MBP) T Cell Epitopes in Multiple Sclerosis Lesions Using a Monoclonal Antibody Specific for the Human Histocompatibility Leukocyte Antigen (HLA)-DR2-MBP 85-99 complex", (abstract), J Exp Med, Apr. 17;191(8):1395-412, 2000.

Kronus, "Addison's Disease", Enzyme Steroid 21-Hydroxylase (21-OH) Antibody, (http:www.kronus.com/products/addisons.html), Jul. 30, 2001.

Kronus, "Celiac Disease", Tissue Transglutaminase (tTg) Autoantibody, (http:www.kronus.com/products/celiac.html), Jul. 30, 2001.

Kronus, "Diabetes", (http:www.kronus.com/products/diabetes.html), Jul. 30, 2001.

Kronus, "Neuromuscular", Myasthenia Gravis, (http:www.kronus.com/products/neuromuscular.html), Jul. 30, 2001.

Kronus, "Thyroid Autoimmune", (http:www.kronus.com/products/thyroid-auto.html), Jul. 30, 2001.

Landschulz, W. H., et al., "The Leucine Zipper: A Hypothetical Structure Common to a New Class of DNA Binding Proteins" Science 240:1759-1764 (1988).

Larche, Mark, "Specific Immunotherapy", British Medical Bulletin, 56 (No. 4): 1019-1036, 2000.

Legge et al., "Presentation of a T Cell Receptor Antagonist Peptide by Immunoglobulins Ablates Activation of T Cells by a Synthetic Peptide or Proteins Requiring Endicytic Processing" J. Ex. Med. 185(6):1043-1053 (Mar. 1997).

Legge et al., "Coupling of Peripheral Tolerance to Endogenous Interleukin 10 Promotes Effective Modulation of Nyelin-activated T Cells an Ameliorates Experimental Allergic Encephalomyelitis" J. Ex. Med. 191(12):2039-2051 (Jun. 2000).

Liénard, Hélène, et al., "Signal Regulatory Proteins Negatively Regulate Immunoreceptor-dependent Cell Activation", The Journal of Biological Chemistry, vol. 274, No. 45, Issue of Nov. 5, pp. 32493-32499, 1999.

Lin, Shih-Yao, et al., "Giving Inhibitory Receptors a Boost", Science, vol. 291, Issue of Jan. 19, pp. 445-446, 2001.

Luckey, C. J., et al., "Differences in the Expression of Human Class I MHC Alleles and Their Associated Peptides in the Presence of Proteasome Inhibitors", The Journal of Immunology, vol. 167, pp. 1212-1221, 2001.

Ludin et al.,"Cloning and expression of the cDNA coding for a human lymphocyte Ige receptor" EMBO J. 6:109-114 (1987).

Lu-Kuo et al., "gp49B1 Inhibitors IgE-initiated Mast Cell Activation through Both Immunoreceptor Tyrosine-based inhibitory Motifs, Recruitment of src Homology 2 Domain-containing Phosphatase-1, and Suppression of Early and Late Calcium Mobilization" J. Biol. Chem. 274:5791-96 (1999).

Lyczak, J. B., et al., "Expression of Novel Secreted Isoforms of Human Immunoglobulin E Proteins", The Journal of Biological Chemistry, vol. 271, No. 7, Issue of Feb. 16, pp. 3428-3436, 1996.

Machiels, J.J., et al. "Complexes of grass pollen allergens and specific antibodies reduce allergic symptoms andinhibit the seasonal increase of IgE antibody", Clin. Exp. Allergy, Nov. 20(6); 653-60, 1990.

Machiels, J.J., et al. "Significant Reduction of Nonspecific Bronchial Reactivity in Patents with Dermatophagoides pteronyssinus-sensitive Allergic Asthma under Therapy with Allergen-Antibody Complexes", Am. Rev. Respir. Dis., vol. 147, pp. 1407-1412, 1993.

Machiels, J.J., et al., "Allergen-antibody complexese can efficiently prevent seasonal rhinitis and asthma in grass pollen hypersensitive patients", Allergy, 1991, 46, 335-348.

Machiels, J.J., et al., "Allergic Brochial Asthma Due to Dermatophagoides pteronyssinus Hypersensitivty Can Be Efficiently Treated by Inoculation of Allergen-Antibody Complexes", J. Clin. Invest., vol. 85; Apr. 1990, 1024-1035.

Malbec and Fridman, "Negative Regulation of Hematopoietic Cell Activation and Proliferation bt Fc(RIIB" Curr. Top. Microbiol. Immunol. 244:13-27 (1999).

Malbec, Odile, et al., "The SH2 Domain-containing Inositol 5-Phosphatase SHIP1 Mediates Cell Cycle Arrest by FcγRIIB", JBC Papers in Press., pp. 1-29, May 18, 2001.

Manoury B., et al., "An Asparaginyl Endopeptidase Processes a Microbial Antigen for Class II MHC Presentation", Nature, 396(6712):625-627, Dec. 17, 1998, (abstract).

Marks, M. S. et al., "Protein Targeting by Tyrosine- and Di-leucine-based Signals: Evidence for Dostinct Saturable Components", The Journal of Cell Biology, vol. 135, No. 2, pp. 341-354, Oct. 1996.

Max et al., "Duplication and Deletion in the Human Immuniglobulin ϵ Genes" Cell 29:691-699 (Jun. 1992).

McDevitt, H., "Specific Antigen Vaccination to Treat Autoimmune Disease," PNAS, vol. 101:(2), pp. 14627-14630 (Oct. 5, 2004).

McKnight, Steven Lanier, "Molecular Zippers in Gene Regulation", Scientific American, pp. 54-64, Apr. 1991.

McNeil, H. Patrick, et al., "Anti-Phospholipid Antibodies are Directed Against a Complex Antigen that Includes a Lipid-Binding Inhibitor of Coagulation: $β_2$-Glycoprotein I (apolipoprotein H)", Proc. Natl. Acad. Sci. USA, vol. 87, pp. 4120-4124, Medical Sciences, Jun. 1990.

Merck Corp., "Disorders With Type III Hypersensitivity Reactions", The Merck Manual, Sec. 12, Ch. 148, Hypersensitivity Disorders, Jul. 12, 2001.

Metcalfe et al., "Mast Cells" Physiological Reviews 77:1033-1079 (Oct. 1997).

Metcalfe, D.D., et al., "Mast cell ontogeny and apoptosis", Exp. Dermato1.1995: 4:227-230.

Mikayama, T., et al., "Molecular cloning and functional expression of cDNA encoding gycoslaytion-inhibiting factor", Proc. Natl. Acad. Science, vol. 90, pp. 10056-10060, Nov. 1993.

Milgro, H., et al., "Treatment of Allergic Asthma with Monoclonal Anti-IgE Antibody", The New England Journal of Medicine, vol. 341, No. 26, 1966-1973, 1999.

Mimori, T., et al., "Characterization of the DNA-binding protein antigen Ku recognized by autoantibodies from Patients with Rheumatic Disorders", (abstract) J. Biol. Chem., 261(5):2274-8, Feb. 15, 1986.

Minerd, J., "Experimental Therapy Stops Allergic Reactions in Mice", NIAID News, 1-2 (May 2002).

Misaki, Y., et al., "The 56K Autoantigen is Identical to Human Annexin XI", (Abstract) J. Biol. Chem., 269(6):4240-6, Feb. 11, 1994.

Mocci, S., et al., "The role of autoantigens in autoimmune disease", Current Opinion in Immunology, vol. 12, pp. 725-730, 2000.

Moreland, L. W., et al., "T Cell Receptor Peptide Vaccination in Rheumatoid Arthritis—A Placebo-Controlled Trial Using a Combination of $V_β3$, $V_β14$, and $V_β17$ Peptides", Arthritis & Rheumatism, vol. 41, No. 11, pp. 1919-1929, Nov. 1998.

Moreland, L. W., et al., "Vβ17 T Cell Receptor Peptide Vaccination in Rheumatoid Arthritis: Results of Phase I Dose Escalation Study", The Journal of Rheumatology, vol. 23, No. 8, pp. 1353-1362, 1966.

Mu, F.T., et al., "EEA1, an Early Endosome-Associated Protein. EEA1 is a Conserved Alpha-Helical Peripheral Membrane Protein Flanked by Cysteine "Fingers" and Contains a Calmodulin-Binding IQ Motif", J. Biol. Chem., 270(22):13503-11, Jun. 2, 1995.

Muno D., et al., "Generation of both MHC Class I- and Class II-Restricted Antigenic Peptides from Exogenously Added Ovalbumin in Murin Phagosomes", FEBS Lett, 478(1-2)178-182, Jul. 28, 2000, (abstract).

Mustelin et al., "Lymphocyte Activation: The coming of the protein tyrosine phosphatases" Front. Biosci. 3:d 10601096(1998).

Nakagawa, T., et al., "Immunotherapy of allergic diseases", Int. Arch. Allergy Immunol 1993;102(2):117-20.

Nakajima, Atsuo, et al., "Antigen-Specific T Cell-Mediated Gene Therapy in Collagen-Induced Arthritis", The Journal of Clinical Investigation, vol. 107, No. 10, pp. 1293-1301 May 2001.

Naquet, P., et al., "T Cell Autoreactivity to Insulin in Diabetic and Related Non-Diabetic Individuals", The Journal of Immunology, vol. 140, No. 8, pp. 2569-2578, Apr. 15, 1988.

National Institute of Allergy and Infectious Diseases, Understanding Autoimmune Disease—What are some Examples of Autoimmune Diseases: Rheumatoid Arthritis. (http://www.niaid.nih.gov/publications/autoimmune/examples.htm), Jul. 11, 200.

Nepom, G. T., "Glutamic acid decarboxylase and other autoantigens in IDDM", Current Opinion in Immunology, vol. 7, pp. 825-830, 1995.

Nepom, G. T., et al., "Identification and modulation of a naturally processed T cell epitope from the diabetes-associated autoantigen human glutamic acid decarboxylase 65 (hGAD65)", PNAS, vol. 98, No. 4, pp. 1763-1768, Feb. 13, 2001.

Newkirk, Marianna M., et al., "Autoimmune Response to U1 Small Nuclear Ribonucleoprotein (U1 snRNP) Associated with Cytomegalovirus Infection", Arthritis Res, 3: 253-258, Jul. 30, 2001.

Noel Rose, et al., The Autoimmune Diseases: Table of Contents, Third Edition, Academic Press 1998.

Norman, Philip S., "Therapeutic Potential of Peptides in Allergic Disease", Annals of Allergy, vol. 71, pp. 330-333, Sep. 1993.

Okano, Y., et al., "Autoantibody to Th Ribonucleoprotein (Nucleolar 7-2 RNA Protein Particle) in Patients with Systemic Sclerosis", Arthritis Rheum, 33(12):1822-8, Dec. 1990, (abstract).

Oliver, J.M., et al., "Immunologically mediated signaling in basophils and mast cells: finding therapeutic targets for allergic diseases in the human FcεR1 signaling pathway", Immunopharmacology 48, 269-281, 2000.

Ono, S.J., "Molecular Genetics of Allergic Diseases", Annu Rev Immunol, 18:347-66, 2000, (abstract).

Osborne, M., et al., "The Inositol 5'-Phosphatase Ship Binds to Immunoreceptor Signaling Motifs and Responds to High Affinity IgE Receptor Aggregation", The Journal of Biological Chemistry, vol. 271, No. 46, Issue of Nov. 15, pp. 29271-29278, 1998.

O'Shea, E. K. et al., "Evidence That the Leucine Zipper is a Colied Coil" Science 243:38-542 (1989).

Ota, K., et al., "T-cell recognition of an immunodominant myelin basic protein epitope in multiple sclerosis", Nature, vol. 346, pp. 183-187, Jul. 12, 1990.

Ott and Cambier, "Activating and inhibitory signaling in mast cells: New opportunities for therapeutic intervention?" J. Allergy Clin. Immunol. 106(3):429-440 (2000).

Pamer, E., et al., "Mechanisms of MHC Class I—Restricted Antigen Processing", Annu. Rev. Immunol., vol. 16, pp. 323-358, 1998.

Peat and Li, "Reversing the trend: Reducing the prevalence of asthma" J. Allergy Clin. Immunol. 103:1-10 (1999).

Peng et al., "A New Isoform of Human Membrane-Bound IgE" Journal of Immunology. 148:129-136 (Jan. 1992).

Phillips and Parker, "Cross-Linked of B Lymphocyte Fc( Receptors and Membrane Immunoglobulin Inhibits AntiImmununoglobulin-Induced Blastogenesis" The Journal of Immunology 13292) 627-632 (1984).

Pisetsky, D.S., "The Role of Bacterial DNA in Autoantibody Induction", (abstract) Curr Top Microbiol Immunol, 247:143-155, 2000.

Pivnyuk, V. I., et al., "Human Low-Affinity IgE Receptor: cDNA from Cell Line 1B and its Expression in Peripheral Blood Cells",translated from Molekulyarnaya Biologiya, vol. 28, No. 1, pp. 840-845, Jul.-Aug. 1994.

Pivnyuk, V.I. et al., "Human Low-Affinity IgE Receptor: cDNA from Cell Line 1B and its Expression in Peripheral Blood Cells," Molecular Biology, vol. 28:(4), Part 2, pp. 549-552 (1994).

Pozzilli, P., et al., "No effect of oral insulin on residual beta-cell function in recent-onset Type I diabetes (the IMDIAB VII)", Diabetologia, vol. 43, pp. 1000-1004, 2000.

Presta et al., "The Binding Site on Human Immunoglobulin E for its High Affinity Receptor" J. Biol. Chem. 269:26368-73 (1994).

Rabjohn et al., "Molecular cloning and epitope analysis of the peanut allergen Ara h3" J. Clin. Invest. 103:535-542 1(1999).

Resources for Health Professionals: Anaphylaxis, pp. 1-10, Sep. 18, 2001 (http://www.worldallergy.org/professional/allergy_update/anap.../anaphylaxissynopsis.shtm).

Rickert, M., et al., "Fusion Proteins for Combined Analysis of Autoantibodies to the 65-kda Isoform of Glutamic Acid Decarboxylase and Islet Antigen-2 in Insulin-Dependent Diabetes Mellitus", Clin Chem, 47(5):926-34, May 2001, (abstract).

Rider, Lisa G., et al., "Laboratory Evaluation of the Inflammatory Myopathies", Clinical and Diagnostic Laboratory Immunology, vol. 2, No. 1, p. 1-9, Jan. 1995.

Riese, Richard J., et al., "Cathepsin S Activity Regulates Antigen Presentation and Immunity", J. Clin. Invest., vol. 101, No. 11, 2351-2363, Jun. 1998.

Rock, K. L., et al., "Degradation of Cell Proteins and the Generation of MHC Class I-Presented Peptides", Annu. Rev. Immunol., vol. 17, pp. 739-779, 1999.

Rock, Kenneth L., et al., "Degradation of Cell Proteins and the Generation of MHC Class I-Presented Peptides", Annu. Rev. Immunol., 17:739-79, 1999, (abstract).

Rose, N. R., "The Autoimmune Diseases: A Discussion of the Causes and Treatment of Autoimmune Diseases", American Autoimmune Related Diseases Associate, Jul. 26, 2001.

Ruckert et al. "IL-15-IgG2b fusion protein accelarates and enhances a Th2 but not a Th1 immune response in vivo, while IL-15-IgG2b fusion protein inhibits both" Eur. J. Inummol. 28:3312-3320 (1998).

Saxon et al., "Inhibition of Human IgE Production Via FcεR-II Stimulation Results From a Decrease in the mRNA for Secreted But not Membrane ε H Chains" The Journal of Immunology 147:4000-4006 (Dec. 1991).

Schmidt-Dorr, et al., "Construction, Purification, and Characterization of a Hybrid Portein Comprising the DNA Binding domain of a LexA Repressor and the Jun Leucine Zipper: A Circular Dichroism and Mutagenesis Study", Biochemistry 30:9657-9664 (1991).

Schuppan, D, et al., "Identification of the Autoantigen of Celiac Disease", Ann N Y Acad Sci., 859:121-6, Nov. 17, 1998, (abstract).

Schwartz, L., et al., "Development of markers for human basophils and mast cells", J. Allergy and Clin. Immunol., vol. 94, No. 6, pp. 1231-1240, 1994.

Sela, M., "Specific Vaccines Against Autoimmune Diseases", C R Acad Sci III; 322(11):933-8, Nov. 1999, (abstract).

Sharma, S. D., et al., "Antigen-specific therapy of experimental allergic encephalomyelitis by soluble class II major histocompatibility complex—peptide complexes", Proc. Natl. Acad. Sci. USA, vol. 88, pp. 11465-11469, Dec. 1991.

Shields, et al., "High Resolution Mapping of the Binding Site on Human IgG1 for FcγR1, FcγRII, FcγRIII, and FcRn and Design of IgG1 Variants with Improved Binding to the FcγR", The Journal of Biological Chemistry, 276:(9) 6591-6604 (2001).

Shingo Yabuuchi, et al., "Anti-Cd23 Monoclonal Antibody (IgE Inhibition Involves the Fc Portion of the Molecules", Abstract 597, J. Allergy Clin. Immunol., vol. 107, No. 2, Feb. 2001.

Sinclair, N.R. StC., "Why so Many Coinibitory Receptors?", Scand. J. Immunol., vol. 50, pp. 1-13, 1999.

Sinclair, NR, "Why so Many Coinhibitory Receptors?" Scand. J. Immunol. 50:10-13 (1999).

Sliedregt, L., et al., "Design and Synthesis of a Multivalent Homing Device for Targeting to Murine CD22", Bioorganic & Medicinal Chemistry, vol. 9, pp. 85-97, 2001.

Spack, E. G., et al., "Induction of Tolerance in Experimental Autoimmune Myasthenia Gravis with Solubilized MHC Class II: Acetylcholine Receptor Peptide Complexes", Journal of Autoimmunity, vol. 8, pp. 787-807, 1995.

Stanley et al., "Identification and Mutational Analysis of the hrummodominant IgE Binding Epitopes of the Major Peanut Allergen Ara h 2" Arch Biochem. Biophis. 342:244-53 (1997).

Steinman, L. et al., "Antigen Specific Immunotherapy of Multiple Sclerosis", Journal of Clinical Immunology, vol. 21, No. 2, pp. 93-98, 2001.

Steinman, L., "Multiple Sclerosis: a Coordinated Immunological Attack Against Myelin in the Central Nervous System", Cell, 85(3):299-302, May 3, 1996, (abstract).

Steinman, L., et al., "Prospects for Specific Immunotherapy in Myasthenia Gravis" FASEB J.; 4(10):2726-31, Jul. 1990, (abstract).

Stenmark, Harald, et al., "Endosomal Localization of the Autoantigen EEA1 is Mediated by a Zinc-Binding FYVE Finger", The Journal of Biological Chemistry, vol. 271, No. 39, pp. 24048-24054, Sep. 27 1996.

Stevenson, et al., J. Immunol., vol. 158:5, pp. 2242-2250, Mar. 1997.

Stoltze L, et al., "Two New Proteases in the MHC Class I Processing Pathway", Nat. Immunol., 1(5):413-418, Nov. 2000, (abstract).

Strver, L. et al, Biochemistry, Third Edition, W. H. Freeman Company, New York, New York, pp. 31-33, 1998.

Suter, U., et al., "Expression of human lymphocyte IgE receptor (Fc epsilon RII/CD23). Indetification of the Fc epsilon Riia promoter and functional analysis in B lymphocytes", J. Immunol. Nov. 1; 143(9):3087-92, 1989.

Sutterwala, et al., "Reversal of Proinflammatory Responses by Ligating die Macrophage Fc( Rceptor Type I" J. Exp. Med. 188:217-222 (Jul. 1998).

Sutterwala, et al., "Selective Suppression of Interleukin-12 induction after Macrophage Receptor Ligation" J. Exp. Med. 185:1977-1985 (Jun. 1997).

Takahasi et al., "Structure of Human Immunoglobulin Gamma Genes Implications for Evolution of a Gene Family" Cell 29:671-679 (1982).

Tan EM, "Antinuclear Antibodies: Diagnostic Markers for Autoimmune Diseases and Probes for Cell Biology", (abstract), Adv Immunol 1989, 44:93-151.

Targoff IN, Autoantibodies to Aminoacyl-Transfer RNA Synthetases for Isoleucine and Glycine. Two Additional Synthetases are Antigenic in Myositis; J Immunol, 144(5):1737-1743, Mar. 1, 1990, (abstract).

TePas, E. C., et al, "Immunotherapy of asthma and allergic diseases", Current Opinion in Pediatrics, vol. 12, pp. 574-578, 2000.

Tisch, R. et al., "Antigen-Specific Mediated Suppression of β Cell Autoimmunity by Plasmid DNA Vaccination," The Journal of Immunology, vol. 166, pp. 2122-2132 (2001).

Tunon, J. M. et al., "Immunoglobines E et cellules de l'inflammation", Rev. Mal. Resp., vol. 13, pp. 27-36, 1996.

U.S. Department of Health and Human Services, "Sequences of Proteins of Immunological Interest", vol. II and vol. III, Fifth Edition, Table of Contents, pp. iii-xi, 1991.

Van Rossenberg, S.M., et al, "A Structure-Function Study of Ligand Recognition by CD22β", Journal of Biological Chemistry, vol. 276, No. 16, Issue of Apr. 20, pp. 12967-12973, 2001.

Van Venrooij, W.J., Venroij Research Team, Research Topics, General Introduction, "Autoantigens", (abstract), Department of Biochemistry, University of Nijmegen, Jul. 11, 2001.

Varshavsky, A., "The N-End Rule", vol. 69, pp. 725-735, May 29, 1992.

Villadangos, J. A.., "Proteases involved in MHC class II antigen presentation", Immunological Reviews, vol. 172, pp. 109-120, 1999.

Villadangos, Jose A., "Proteolysis in MHC Class II Antigen Presentation: Who's in Charge?", Immunity, vol. 12, pp. 233-239, Mar. 2000.

Wagtmann et al., "GP49:An Ig-like Recptor with Inhibitory Properties on Mast Cells and Natural Killer Cells" Current Top. Micobiol. Immunol. 244:107-113 (1999).

Wallace, et al., Methods Enzymol., vol. 152, pp. 432-441, 1987.

Wallner, Barbara P., Short Analytical Review, Peptide Therapy for Treatment of Allergic Diseases, Clinical Immunology and Immunopathology, vol. 80, No. 2, Aug., pp. 105-109, 1996.

Wan, T., et al., "The Crystal Structure of IgE Fc Reveals an Asymmetrically Bent Conformation", Nature Immunology, vol. 3, No. 7, pp. 681-686, Jul. 2002.

Wang, M., et al., "Early IL-4 production driving Th2 differentiation in a human vivo allergic model is mast cell derived", lin. Immunol. Jan.;90(1):47-54, 1999.

Wardrop, III, R.M., et al, Oral Tolerance in the Treatment of Inflammatory Autoimmune Disease, Inflamm. res., 48, pp. 106-119, 1990.

Warren, K. G., "Increased Synthetic Peptide Specificity of Tissue-CSF Bound Anti-MBP in Multiple Sclerosis", Journal of Neuroimmunology, vol. 43, pp. 87-96, (1993).

Warren, K. G., "Synthetic Peptide Specificity of Anti-Myelin Basic Protein from Multiple Sclerosis Cerebrospinal Fluid", Journal of Neuroimmunology, vol. 39, pp. 81-90, (1992).

Warren, K.G., et al, "Fine Specificity of the Antibody Response to Myelin Basic Protein in the Central Nervous System in Multiple Sclerosis: The Minimal B-Cell Epitope and a Model of its Features", Proc. Natl. Acad. Sci. USA, vol. 92, pp. 11061-11065, (Nov. 1995).

Warren, K.G., et al, "Tolerance Induction to Myelin Basic Protein by Intravenous Synthetic Peptides Containing Epitope $P_{85}$VVHFFKNIVTP$_{96}$ in Chronic Progressive Multiple Sclerosis", Journal of Neurological Sciences, vol. 152, pp. 31-38, (1997).

Warren, KG, et al., "Administration of Myelin Basic Protein Synthetic Peptides to Multiple Sclerosis Patients", (abstract), J. Neurol. Sci., vol. 133, No. 1-2, pp. 85-94, Nov. 1995.

Watson et al.,"Molecular cloning and sequencing of the low-affinity IgE receptor (CD23) for horse and cattle" Vet. Inummol. Immunopathol. 73:323-9 (2000).

Watts, C., "Antigen processing in the endocytic compartment", Current Opinion in Immunology, vol. 13, pp. 26-31, 2001.

Watts, C., "Capture and Processing of Exogenous Antigens for Presentation on MHC Molecules", Annu. Rev. Immunol., vol. 15, pp. 821-850, 1997.

Weiner, H. L., "Double-Blind Pilot Trial of Oral Tolerization with Myelin Antigens in Multiple Sclerosis", Science, vol. 259, pp. 1321-1324, (Feb. 26, 1993).

Wetmur et al., "Kinetics of Renaturation of DNA" J. Mol. Biol. 31:349-70 (1966).

Wetmur, James G., "DNA Probes: Applications of the Principles of Nucleic Acid Hybridization" Critical Reviews in Biochemistry and Molecular Biology 26(34):227-59 (1991).

Wines et al., "The IgG Fc Contains Distinct Fc Receptor (FcR) Binding Sites: The Leukocyte Receptors Fc(RI and Fc(RIIa Bind to a Region in the Fc Distinct from That Recognized by Neonatal FcR and Protein A" J. Immunol. 164(10):5313-5318 (2000).

Wucherpfennig, K. W., et al, "Recognition of the Immunodominant Myelin Basic Protein Peptide by Autoantibodies and HLA-DR2-restricted T Cell Clones from Multiple Sclerosis Patients", J. Clin. Invest., vol. 100, No. 5, pp. 1114-1122, Sep. 1997.

Yabuuchi, S., et al., "Anti-CD23 Monoclonal Antibody Inhibits Germline Œ Transcription in B Cells," International Immunopharmacology 2, pp. 453-461, 2002.

Yamamoto, A.M., et al., "Anti-Titin Antibodies in Myasthenia Gravis: Tight Association with Thymoma of Nonthymoma Patients", Archives of Neurology, vol. 58, No. 6, Jun. 2001.

Yamashita, T., et al., "Expression cloning of complementary DNA encoding three distinct isoforms of guinea pig Fc receptor for IgG1 and IgG2", J. Immunol. Aug. 15;151(4) pp. 2014-2023, 1993.

Yamashita, Y., et al., "Inhibitory and Stimulatory Functions of Paired Ig-Like Receptor (PIR) Family in RBL-2H3 Cells[1]", The Journal of Immunology, 1998, 161: 4042-4047.

Yarden et al., "Human proto-oncogene c-kit: a new cell surface receptor tyrosine kinase for an unidentified ligand", EMBO J. 6:3341-51 (1987).

Yewdell, JW., et al., "Not Such a Dismal Science: The Economics of Protein Sythesis, Folding, Degradation and Antigen Processing", Trends Cell Biol, 11(7):294-297, Jul. 2001, (abstract).

Yodoi, J., et al, "Low affinity IgE receptors: regulation and functional roles in cell activation", Ige, Mast Cells and the Allergic Response, Wiley Chichester (Ciba Foundation Symposium 147) pp. 133-153, 1989.

Yoon, J-W., et al, "Control of Autoimmune Diabetes in NOD Mice by GAD Expression or Suppression in β Cells", Science, vol. 284, pp. 1183-1187, May 14, 1999.

Zhang et al., "Twi Unusual Forms of Human Immunoglobulin E Encoded by Alternative RNA splicing of ε Heavy Cjain Membrane Exons", the Journal of Experimental Med. 175:233-243 (Jul. 1992).

Zhu, D., et al., "A novel human immunoglobulin Fcγ-Fcε bifunctional fusion protein inhibits FcεRI-mediated degranulation", Nature Medicine, 8:(5) 518-521 (May 2002).

Zhu, D., et al., "A Novel Human Ig Fcγ-Fcε Chimeric Fusion Protein Inhibits FcεRI-Mediated Degranulation", (abstract), May 4-7, 2001.

Zhu, D., et al., "A Novel Ig Fcγ-Fcε Chimeric Fusion Protein Inhibits FcεRI Mediated Degranulation", Abstract 273, Clinical Immunology, vol. 99, No. 1, p. 193, Apr. 19, 2001.

* cited by examiner

FIGURE 1

```
gagcccaaat cttgtgacaa aactcacaca tgcccaccgt gcccagcacc tgaactcctg  60
gggggaccgt cagtcttcct cttccccca aaacccaagg acaccctcat gatctcccgg 120
acccctgagg tcacatgcgt ggtggtggac gtgagccacg aagaccctga ggtcaagttc 180
aactggtacg tggacggcgt ggaggtgcat aatgttaaga caaagccgcg ggaggagcag 240
tacaacagca cgtaccgtgt ggtcagcgtc ctcaccgtcc tgcaccagaa ctggatgaat 300
ggaaaggagt acaagtgcaa ggtctccaac aaagccctcc cagcccccat cgagaaaacc 360
atctccaaag ccaaagtgca gccccgagaa ccacaggtgt acaccctgcc cccatcccgg 420
gatgagctga ccaagaacca ggtcagcctg acctgcctgg tcaaaggctt ctatcccagc 480
gacatcgccg tggagtggga gagcaatggg cagccggaga acaactacaa gaccacgcct 540
cccgtgctgg actccgtcgg ctccttcttc ctctacagca agctcaccgt ggacaagagc 600
aggtggcagc aggggaacgt cttctcatgc tccgtgatgc atgaggctct gcacaaccac 660
taccagcaga ggagcctctc cctgtctccg ggtaaa                            696
```

FIGURE 2

```
Ala Ser Thr Lys Gly Pro Ser Val Phe Pro Leu Ala Pro Ser Ser Lys
Ser Thr Ser Gly Gly Thr Ala Ala Leu Gly Cys Leu Val Lys Asp Tyr
Phe Pro Glu Pro Val Thr Val Ser Trp Asn Ser Gly Ala Leu Thr Ser
Gly Val His Thr Phe Pro Ala Val Leu Gln Ser Ser Gly Leu Tyr Ser
Leu Ser Ser Val Val Thr Val Pro Ser Ser Ser Leu Gly Thr Gln Thr
Tyr Ile Cys Asn Val Asn His Lys Pro Ser Asn Thr Lys Val Asp Lys
Lys Val Glu Pro Lys Ser Cys Asp Lys Thr His Thr Cys Pro Pro Cys
Pro Ala Pro Glu Leu Leu Gly Gly Pro Ser Val Phe Leu Phe Pro Pro
Lys Pro Lys Asp Thr Leu Met Ile Ser Arg Thr Pro Glu Val Thr Cys
Val Val Val Asp Val Ser His Glu Asp Pro Glu Val Lys Phe Asn Trp
Tyr Val Asp Gly Val Glu Val His Asn Val Lys Thr Lys Pro Arg Glu
Glu Gln Tyr Asn Ser Thr Tyr Arg Val Val Ser Val Leu Thr Val Leu
His Gln Asn Trp Met Asn Gly Lys Glu Tyr Lys Cys Lys Val Ser Asn
Lys Ala Leu Pro Ala Pro Ile Glu Lys Thr Ile Ser Lys Ala Lys Val
Gln Pro Arg Glu Pro Gln Val Tyr Thr Leu Pro Pro Ser Arg Asp Glu
Leu Thr Lys Asn Gln Val Ser Leu Thr Cys Leu Val Lys Gly Phe Tyr
Pro Ser Asp Ile Ala Val Glu Trp Glu Ser Asn Gly Gln Pro Glu Asn
Asn Tyr Lys Thr Thr Pro Pro Val Leu Asp Ser Val Gly Ser Phe Phe
Leu Tyr Ser Lys Leu Thr Val Asp Lys Ser Arg Trp Gln Gln Gly Asn
Val Phe Ser Cys Ser Val Met His Glu Ala Leu His Asn His Tyr Gln
Gln Arg Ser Leu Ser Leu Ser Pro Gly Lys
```

FIGURE 3

```
Glu Pro Lys Ser Cys Asp Lys Thr His Thr Cys Pro Pro Cys Pro Ala
Pro Glu Leu Leu Gly Gly Pro Ser Val Phe Leu Phe Pro Pro Lys Pro
Lys Asp Thr Leu Met Ile Ser Arg Thr Pro Glu Val Thr Cys Val Val
Val Asp Val Ser His Glu Asp Pro Glu Val Lys Phe Asn Trp Tyr Val
Asp Gly Val Glu Val His Asn Val Lys Thr Lys Pro Arg Glu Glu Gln
Tyr Asn Ser Thr Tyr Arg Val Val Ser Val Leu Thr Val Leu His Gln
Asn Trp Met Asn Gly Lys Glu Tyr Lys Cys Lys Val Ser Asn Lys Ala
Leu Pro Ala Pro Ile Glu Lys Thr Ile Ser Lys Ala Lys Val Gln Pro
Arg Glu Pro Gln Val Tyr Thr Leu Pro Pro Ser Arg Asp Glu Leu Thr
Lys Asn Gln Val Ser Leu Thr Cys Leu Val Lys Gly Phe Tyr Pro Ser
Asp Ile Ala Val Glu Trp Glu Ser Asn Gly Gln Pro Glu Asn Asn Tyr
Lys Thr Thr Pro Pro Val Leu Asp Ser Val Gly Ser Phe Phe Leu Tyr
Ser Lys Leu Thr Val Asp Lys Ser Arg Trp Gln Gln Gly Asn Val Phe
Ser Cys Ser Val Met His Glu Ala Leu His Asn His Tyr Gln Gln Arg
Ser Leu Ser Leu Ser Pro Gly Lys
```

FIGURE 4

```
tccacacaga gcccatccgt cttcccttg  acccgctgct gcaaaaacat tccctccaat   60
gccacctccg tgactctggg ctgcctggcc acgggctact tcccggagcc ggtgatggtg  120
acctgggaca caggctccct caacgggaca actatgacct taccagccac caccctcacg  180
ctctctggtc actatgccac catcagcttg ctgaccgtct cgggtgcgtg ggccaagcag  240
atgttcacct gccgtgtggc acacactcca tcgtccacag actgggtcga caacaaaacc  300
ttcagcgtct gctccaggga cttcaccccg cccaccgtga agatcttaca gtcgtcctgc  360
gacggcggcg ggcacttccc cccgaccatc cagctcctgt gcctcgtctc tgggtacacc  420
ccagggacta tcaacatcac ctggctggag gacgggcagg tcatggacgt ggacttgtcc  480
accgcctcta ccacgcagga gggtgagctg gcctccacac aaagcgagct caccctcagc  540
cagaagcact ggctgtcaga ccgcacctac acctgccagg tcacctatca aggtcacacc  600
tttgaggaca gcaccaagaa gtgtgcagat tccaacccga gagggtgag  cgcctaccta  660
agccggccca gcccgttcga cctgttcatc cgcaagtcgc ccacgatcac ctgtctggtg  720
gtggacctgg cacccagcaa ggggaccgtg aacctgacct ggtcccgggc cagtgggaag  780
cctgtgaacc actccaccag aaaggaggag aagcagcgca atggcacgtt aaccgtcacg  840
tccaccctgc cggtgggcac ccgagactgg atcgaggggg agacctacca gtgcagggtg  900
acccaccccc acctgcccag ggccctcatg cggtccacga ccaagaccag cggcccgcgt  960
gctgccccgg aagtctatgc gtttgcgacg ccggagtggc cggggagccg ggacaagcgc 1020
accctcgcct gcctgatcca gaacttcatg cctgaggaca tctcggtgca gtggctgcac 1080
aacgaggtgc agctcccgga cgccggcac  agcacgacgc agccccgcaa gaccaagggc 1140
tccggcttct tcgtcttcag ccgcctggag gtgaccaggg ccgaatggga gcagaaagat 1200
gagttcatct gccgtgcagt ccatgaggca gcgagcccct cacagaccgt ccagcgagcg 1260
gtgtctgtaa atcccggtaa atgacgtact cctgcctccc tcctcccag  ggctccatcc 1320
agctgtgcag tggggaggac tggccagacc ttctgtccac tgttgcaatg accccaggaa 1380
gctaccccca ataaactgtg cctgctcaga gccccagtac accattctt  gggagcgggc 1440
agggc                                                             1445
```

FIGURE 5

```
Ser Thr Gln Ser Pro Ser Val Phe Pro Leu Thr Arg Cys Cys Lys Asn
Ile Pro Ser Asn Ala Thr Ser Val Thr Leu Gly Cys Leu Ala Thr Gly
Tyr Phe Pro Glu Pro Val Met Val Thr Trp Asp Thr Gly Ser Leu Asn
Gly Thr Thr Met Thr Leu Pro Ala Thr Thr Leu Thr Leu Ser Gly His
Tyr Ala Thr Ile Ser Leu Leu Thr Val Ser Gly Ala Trp Ala Lys Gln
Met Phe Thr Cys Arg Val Ala His Thr Pro Ser Ser Thr Asp Trp Val
Asp Asn Lys Thr Phe Ser Val Cys Ser Arg Asp Phe Thr Pro Pro Thr
Val Lys Ile Leu Gln Ser Ser Cys Asp Gly Gly Gly His Phe Pro Pro
Thr Ile Gln Leu Leu Cys Leu Val Ser Gly Tyr Thr Pro Gly Thr Ile
Asn Ile Thr Trp Leu Glu Asp Gly Gln Val Met Asp Val Asp Leu Ser
Thr Ala Ser Thr Thr Gln Glu Gly Glu Leu Ala Ser Thr Gln Ser Glu
Leu Thr Leu Ser Gln Lys His Trp Leu Ser Asp Arg Thr Tyr Thr Cys
Gln Val Thr Tyr Gln Gly His Thr Phe Glu Asp Ser Thr Lys Lys Cys
Ala Asp Ser Asn Pro Arg Gly Val Ser Ala Tyr Leu Ser Arg Pro Ser
Pro Phe Asp Leu Phe Ile Arg Lys Ser Pro Thr Ile Thr Cys Leu Val
Val Asp Leu Ala Pro Ser Lys Gly Thr Val Asn Leu Thr Trp Ser Arg
Ala Ser Gly Lys Pro Val Asn His Ser Thr Arg Lys Glu Glu Lys Gln
Arg Asn Gly Thr Leu Thr Val Thr Ser Thr Leu Pro Val Gly Thr Arg
Asp Trp Ile Glu Gly Glu Thr Tyr Gln Cys Arg Val Thr His Pro His
Leu Pro Arg Ala Leu Met Arg Ser Thr Thr Lys Thr Ser Gly Pro Arg
Ala Ala Pro Glu Val Tyr Ala Phe Ala Thr Pro Glu Trp Pro Gly Ser
Arg Asp Lys Arg Thr Leu Ala Cys Leu Ile Gln Asn Phe Met Pro Glu
Asp Ile Ser Val Gln Trp Leu His Asn Glu Val Gln Leu Pro Asp Ala
Arg His Ser Thr Thr Gln Pro Arg Lys Thr Lys Gly Ser Gly Phe Phe
Val Phe Ser Arg Leu Glu Val Thr Arg Ala Glu Trp Glu Gln Lys Asp
Glu Phe Ile Cys Arg Ala Val His Glu Ala Ala Ser Pro Ser Gln Thr
Val Gln Arg Ala Val Ser Val Asn Pro Gly Lys
```

FIGURE 6

```
Phe Thr Pro Pro Thr Val Lys Ile Leu Gln Ser Ser Cys Asp Gly Gly
Gly His Phe Pro Pro Thr Ile Gln Leu Leu Cys Leu Val Ser Gly Tyr
Thr Pro Gly Thr Ile Asn Ile Thr Trp Leu Glu Asp Gly Gln Val Met
Asp Val Asp Leu Ser Thr Ala Ser Thr Thr Gln Glu Gly Glu Leu Ala
Ser Thr Gln Ser Glu Leu Thr Leu Ser Gln Lys His Trp Leu Ser Asp
Arg Thr Tyr Thr Cys Gln Val Thr Tyr Gln Gly His Thr Phe Glu Asp
Ser Thr Lys Lys Cys Ala Asp Ser Asn Pro Arg Gly Val Ser Ala Tyr
Leu Ser Arg Pro Ser Pro Phe Asp Leu Phe Ile Arg Lys Ser Pro Thr
Ile Thr Cys Leu Val Val Asp Leu Ala Pro Ser Lys Gly Thr Val Asn
Leu Thr Trp Ser Arg Ala Ser Gly Lys Pro Val Asn His Ser Thr Arg
Lys Glu Glu Lys Gln Arg Asn Gly Thr Leu Thr Val Thr Ser Thr Leu
Pro Val Gly Thr Arg Asp Trp Ile Glu Gly Glu Thr Tyr Gln Cys Arg
Val Thr His Pro His Leu Pro Arg Ala Leu Met Arg Ser Thr Thr Lys
Thr Ser Gly Pro Arg Ala Ala Pro Glu Val Tyr Ala Phe Ala Thr Pro
Glu Trp Pro Gly Ser Arg Asp Lys Arg Thr Leu Ala Cys Leu Ile Gln
Asn Phe Met Pro Glu Asp Ile Ser Val Gln Trp Leu His Asn Glu Val
Gln Leu Pro Asp Ala Arg His Ser Thr Thr Gln Pro Arg Lys Thr Lys
Gly Ser Gly Phe Phe Val Phe Ser Arg Leu Glu Val Thr Arg Ala Glu
Trp Glu Gln Lys Asp Glu Phe Ile Cys Arg Ala Val His Glu Ala Ala
Ser Pro Ser Gln Thr Val Gln Arg Ala Val Ser Val Asn Pro Gly Lys
```

FIGURE 7

```
Glu Pro Lys Ser Cys Asp Lys Thr His Thr Cys Pro Pro Cys Pro Ala
Pro Glu Leu Leu Gly Gly Pro Ser Val Phe Leu Phe Pro Pro Lys Pro
Lys Asp Thr Leu Met Ile Ser Arg Thr Pro Glu Val Thr Cys Val Val
Val Asp Val Ser His Glu Asp Pro Glu Val Lys Phe Asn Trp Tyr Val
Asp Gly Val Glu Val His Asn Val Lys Thr Lys Pro Arg Glu Glu Gln
Tyr Asn Ser Thr Tyr Arg Val Val Ser Val Leu Thr Val Leu His Gln
Asn Trp Met Asn Gly Lys Glu Tyr Lys Cys Lys Val Ser Asn Lys Ala
Leu Pro Ala Pro Ile Glu Lys Thr Ile Ser Lys Ala Lys Val Gln Pro
Arg Glu Pro Gln Val Tyr Thr Leu Pro Pro Ser Arg Asp Glu Leu Thr
Lys Asn Gln Val Ser Leu Thr Cys Leu Val Lys Gly Phe Tyr Pro Ser
Asp Ile Ala Val Glu Trp Glu Ser Asn Gly Gln Pro Glu Asn Asn Tyr
Lys Thr Thr Pro Pro Val Leu Asp Ser Val Gly Ser Phe Phe Leu Tyr
Ser Lys Leu Thr Val Asp Lys Ser Arg Trp Gln Gln Gly Asn Val Phe
Ser Cys Ser Val Met His Glu Ala Leu His Asn His Tyr Gln Gln Arg
Ser Leu Ser Leu Ser Pro Gly Lys Val Glu Gly Gly Gly Gly Ser Gly
Gly Gly Gly Ser Gly Gly Gly Gly Ser Phe Thr Pro Pro Thr Val Lys
Ile Leu Gln Ser Ser Cys Asp Gly Gly Gly His Phe Pro Pro Thr Ile
Gln Leu Leu Cys Leu Val Ser Gly Tyr Thr Pro Gly Thr Ile Asn Ile
Thr Trp Leu Glu Asp Gly Gln Val Met Asp Val Asp Leu Ser Thr Ala
Ser Thr Thr Gln Glu Gly Glu Leu Ala Ser Thr Gln Ser Glu Leu Thr
Leu Ser Gln Lys His Trp Leu Ser Asp Arg Thr Tyr Thr Cys Gln Val
Thr Tyr Gln Gly His Thr Phe Glu Asp Ser Thr Lys Lys Cys Ala Asp
Ser Asn Pro Arg Gly Val Ser Ala Tyr Leu Ser Arg Pro Ser Pro Phe
Asp Leu Phe Ile Arg Lys Ser Pro Thr Ile Thr Cys Leu Val Val Asp
Leu Ala Pro Ser Lys Gly Thr Val Asn Leu Thr Trp Ser Arg Ala Ser
Gly Lys Pro Val Asn His Ser Thr Arg Lys Glu Glu Lys Gln Arg Asn
Gly Thr Leu Thr Val Thr Ser Thr Leu Pro Val Gly Thr Arg Asp Trp
Ile Glu Gly Glu Thr Tyr Gln Cys Arg Val Thr His Pro His Leu Pro
Arg Ala Leu Met Arg Ser Thr Thr Lys Thr Ser Gly Pro Arg Ala Ala
Pro Glu Val Tyr Ala Phe Ala Thr Pro Glu Trp Pro Gly Ser Arg Asp
Lys Arg Thr Leu Ala Cys Leu Ile Gln Asn Phe Met Pro Glu Asp Ile
Ser Val Gln Trp Leu His Asn Glu Val Gln Leu Pro Asp Ala Arg His
Ser Thr Thr Gln Pro Arg Lys Thr Lys Gly Ser Gly Phe Phe Val Phe
Ser Arg Leu Glu Val Thr Arg Ala Glu Trp Glu Gln Lys Asp Glu Phe
Ile Cys Arg Ala Val His Glu Ala Ala Ser Pro Ser Gln Thr Val Gln
Arg Ala Val Ser Val Asn Pro Gly Lys
```

A: 250 ng human IgE-anti NP            B: saline
C: 250 nm human IgE-anti NP + 250ng GE2    D: 250 ng human IgE-anti NP + 250ng PS IgE

FIGURE 10
GE2 binding to HMC-1 cells that express FcγRIIb but not FcεRIa
A. Cell gating
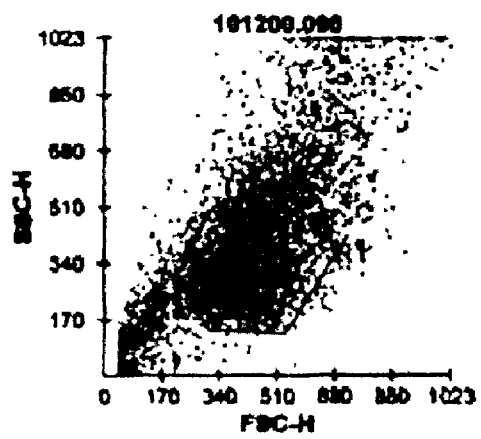
B. Control staining with goat anti-human IgG
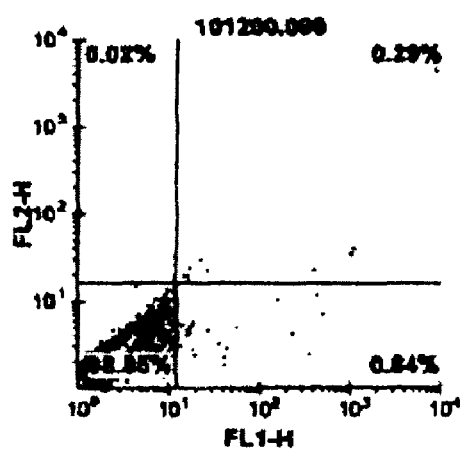
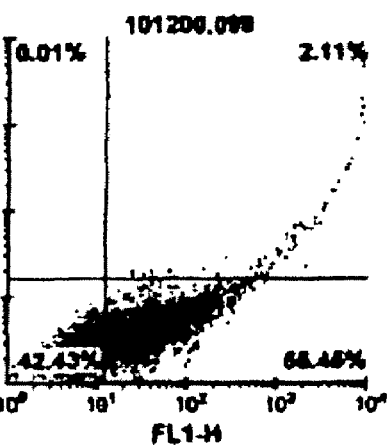
C. Human IgG followed by staining with goat anti-human IgG
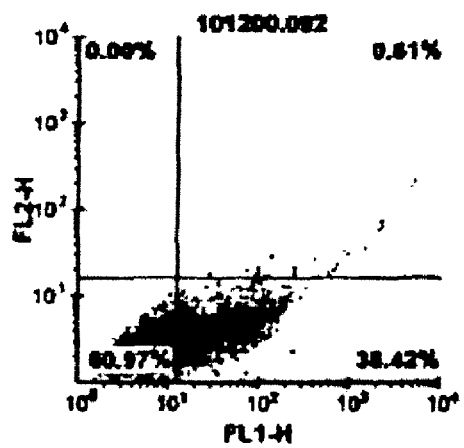
D. GE2 protein followed by staining with goat anti-human IgG

FIGURE 11
GE2 binding to 3D10 cells that express FcεRIa but not FcγRIIb
A. Cell gating on 3D10 cells which express FcεRIa but not FcγR
B. Staining with goat anti-human IgE alone
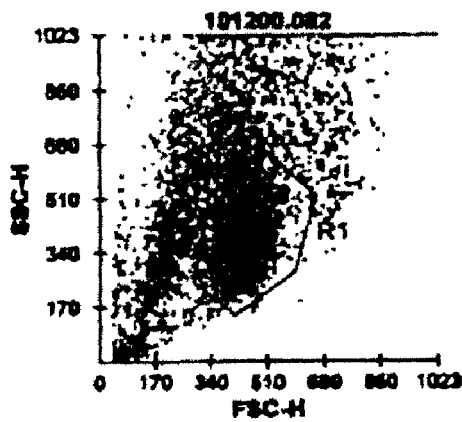
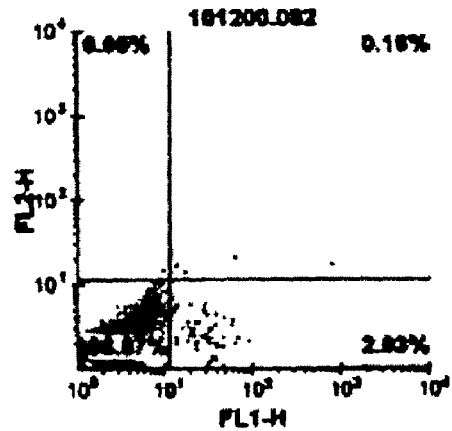
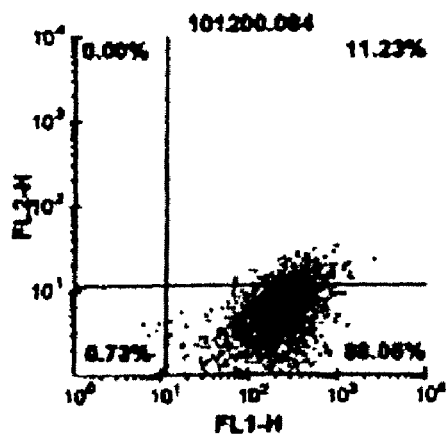
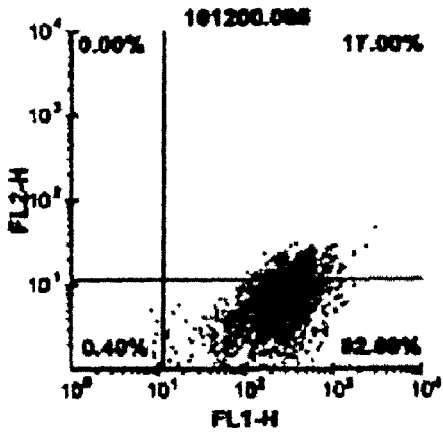
C. Human IgE myeloma followed by staining with goat anti-human IgE
D. GE2 followed by staining with goat anti-human IgE

SEQUENCE LISTING

<160> NUMBER OF SEQ ID NOS: 177

<210> SEQ ID NO 1
<211> LENGTH: 696
<212> TYPE: DNA
<213> ORGANISM: Homo sapiens

<400> SEQUENCE: 1

```
gagcccaaat cttgtgacaa aactcacaca tgcccaccgt gcccagcacc tgaactcctg      60
gggggaccgt cagtcttcct cttccccca aaacccaagg acaccctcat gatctcccgg     120 accctgagg tcacatgcgt ggtggtggac gtgagccacg aagaccctga ggtcaagttc     180
aactggtacg tggacggcgt ggaggtgcat aatgttaaga caaagccgcg ggaggagcag     240
tacaacagca cgtaccgtgt ggtcagcgtc ctcaccgtcc tgcaccagaa ctggatgaat     300
ggaaaggagt acaagtgcaa ggtctccaac aaagccctcc cagcccccat cgagaaaacc     360
atctccaaag ccaaagtgca gccccgagaa ccacaggtgt acaccctgcc cccatcccgg     420
gatgagctga ccaagaacca ggtcagcctg acctgcctgg tcaaaggctt ctatcccagc     480
gacatcgccg tggagtggga gagcaatggg cagccggaga acaactacaa gaccacgcct     540
cccgtgctgg actccgtcgg ctccttcttc ctctacagca agctcaccgt ggacaagagc     600
aggtggcagc aggggaacgt cttctcatgc tccgtgatgc atgaggctct gcacaaccac     660
taccagcaga ggagcctctc cctgtctccg ggtaaa                               696
```

<210> SEQ ID NO 2
<211> LENGTH: 330
<212> TYPE: PRT
<213> ORGANISM: Homo sapiens

<400> SEQUENCE: 2

```
Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60
```

```
Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Val Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asn Trp Met Asn Gly Lys Glu Tyr Lys Cys Lys Val Ser Asn
        195                 200                 205

Lys Ala Leu Pro Ala Pro Ile Glu Lys Thr Ile Ser Lys Ala Lys Val
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Val Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Gln
305                 310                 315                 320

Gln Arg Ser Leu Ser Leu Ser Pro Gly Lys
                325                 330

<210> SEQ ID NO 3
<211> LENGTH: 232
<212> TYPE: PRT
<213> ORGANISM: Homo sapiens

<400> SEQUENCE: 3

Glu Pro Lys Ser Cys Asp Lys Thr His Thr Cys Pro Pro Cys Pro Ala
 1               5                  10                  15

Pro Glu Leu Leu Gly Gly Pro Ser Val Phe Leu Phe Pro Pro Lys Pro
                 20                  25                  30

Lys Asp Thr Leu Met Ile Ser Arg Thr Pro Glu Val Thr Cys Val Val
             35                  40                  45

Val Asp Val Ser His Glu Asp Pro Glu Val Lys Phe Asn Trp Tyr Val
         50                  55                  60

Asp Gly Val Glu Val His Asn Val Lys Thr Lys Pro Arg Glu Glu Gln
 65                  70                  75                  80

Tyr Asn Ser Thr Tyr Arg Val Val Ser Val Leu Thr Val Leu His Gln
                 85                  90                  95

Asn Trp Met Asn Gly Lys Glu Tyr Lys Cys Lys Val Ser Asn Lys Ala
```

```
                    100                 105                 110
Leu Pro Ala Pro Ile Glu Lys Thr Ile Ser Lys Ala Lys Val Gln Pro
        115                 120                 125
Arg Glu Pro Gln Val Tyr Thr Leu Pro Pro Ser Arg Asp Glu Leu Thr
    130                 135                 140
Lys Asn Gln Val Ser Leu Thr Cys Leu Val Lys Gly Phe Tyr Pro Ser
145                 150                 155                 160
Asp Ile Ala Val Glu Trp Glu Ser Asn Gly Gln Pro Glu Asn Asn Tyr
                165                 170                 175
Lys Thr Thr Pro Pro Val Leu Asp Ser Val Gly Ser Phe Phe Leu Tyr
            180                 185                 190
Ser Lys Leu Thr Val Asp Lys Ser Arg Trp Gln Gln Gly Asn Val Phe
        195                 200                 205
Ser Cys Ser Val Met His Glu Ala Leu His Asn His Tyr Gln Gln Arg
    210                 215                 220
Ser Leu Ser Leu Ser Pro Gly Lys
225                 230

<210> SEQ ID NO 4
<211> LENGTH: 1445
<212> TYPE: DNA
<213> ORGANISM: Homo sapiens

<400> SEQUENCE: 4
tccacacaga gcccatccgt cttcccttg  acccgctgct gcaaaaacat tccctccaat      60
gccacctccg tgactctggg ctgcctggcc acgggctact cccggagcc  ggtgatggtg     120
acctgggaca caggctccct caacgggaca actatgacct accagccac  caccctcacg     180
ctctctggtc actatgccac catcagcttg ctgaccgtct cgggtgcgtg ggccaagcag     240
atgttcacct gcgtgtggc  acacactcca tcgtccacag actgggtcga caacaaaacc     300
ttcagcgtct gctccaggga cttcaccccg ccaccgtga  agatcttaca gtcgtcctgc     360
gacggcggcg gcacttccc  cccgaccatc cagctcctgt gcctcgtctc tgggtacacc     420
ccagggacta tcaacatcac ctggctggag acgggcagg  tcatggacgt ggacttgtcc     480
accgcctcta ccacgcagga gggtgagctg gcctccacac aaagcgagct caccctcagc     540
cagaagcact ggctgtcaga ccgcacctac acctgccagg tcacctatca aggtcacacc     600
tttgaggaca gcaccaagaa gtgtgcagat ccaacccga  gagggtgag  cgcctaccta     660
agccggccca gccgttcga  cctgttcatc cgcaagtcgc ccacgatcac ctgtctggtg     720
gtggacctgg cacccagcaa ggggaccgtg aacctgacct ggtcccgggc cagtgggaag     780
cctgtgaacc actccaccag aaaggaggag aagcagcgca atggcacgtt aaccgtcacg     840
tccaccctgc cggtgggcac ccgagactgg atcgagggg  agacctacca gtgcagggtg     900
acccacccc  acctgcccag ggccctcatg cggtccacga ccaagaccag cggcccgcgt     960
gctgccccgg aagtctatgc gtttgcgacg ccggagtggc cggggagccg ggacaagcgc    1020
accctcgcct gcctgatcca gaacttcatg cctgaggaca tctcggtgca gtggctgcac    1080
aacgaggtgc agctcccgga cgccggcac  agcacgacgc agccccgcaa gaccaagggc    1140
tccggcttct tcgtcttcag ccgctggag  gtgaccaggg ccgaatggga gcagaaagat    1200
gagttcatct gccgtgcagt ccatgaggca gcgagcccct cacagaccgt ccagcgagcg    1260
gtgtctgtaa atcccggtaa atgacgtact cctgcctccc tccctcccag ggctccatcc    1320
agctgtgcag tggggaggac tggccagacc ttctgtccac tgttgcaatg acccccaggaa   1380
```

```
gctaccccca ataaactgtg cctgctcaga gccccagtac acccattctt gggagcgggc    1440
agggc                                                                1445
```

<210> SEQ ID NO 5
<211> LENGTH: 427
<212> TYPE: PRT
<213> ORGANISM: Homo sapiens

<400> SEQUENCE: 5

```
Ser Thr Gln Ser Pro Ser Val Phe Pro Leu Thr Arg Cys Cys Lys Asn
 1               5                  10                  15

Ile Pro Ser Asn Ala Thr Ser Val Thr Leu Gly Cys Leu Ala Thr Gly
                20                  25                  30

Tyr Phe Pro Glu Pro Val Met Val Thr Trp Asp Thr Gly Ser Leu Asn
            35                  40                  45

Gly Thr Thr Met Thr Leu Pro Ala Thr Thr Leu Thr Leu Ser Gly His
        50                  55                  60

Tyr Ala Thr Ile Ser Leu Leu Thr Val Ser Gly Ala Trp Ala Lys Gln
 65                  70                  75                  80

Met Phe Thr Cys Arg Val Ala His Thr Pro Ser Ser Thr Asp Trp Val
                 85                  90                  95

Asp Asn Lys Thr Phe Ser Val Cys Ser Arg Asp Phe Thr Pro Pro Thr
            100                 105                 110

Val Lys Ile Leu Gln Ser Ser Cys Asp Gly Gly Gly His Phe Pro Pro
        115                 120                 125

Thr Ile Gln Leu Leu Cys Leu Val Ser Gly Tyr Thr Pro Gly Thr Ile
130                 135                 140

Asn Ile Thr Trp Leu Glu Asp Gly Gln Val Met Asp Val Asp Leu Ser
145                 150                 155                 160

Thr Ala Ser Thr Thr Gln Glu Gly Glu Leu Ala Ser Thr Gln Ser Glu
                165                 170                 175

Leu Thr Leu Ser Gln Lys His Trp Leu Ser Asp Arg Thr Tyr Thr Cys
            180                 185                 190

Gln Val Thr Tyr Gln Gly His Thr Phe Glu Asp Ser Thr Lys Lys Cys
        195                 200                 205

Ala Asp Ser Asn Pro Arg Gly Val Ser Ala Tyr Leu Ser Arg Pro Ser
    210                 215                 220

Pro Phe Asp Leu Phe Ile Arg Lys Ser Pro Thr Ile Thr Cys Leu Val
225                 230                 235                 240

Val Asp Leu Ala Pro Ser Lys Gly Thr Val Asn Leu Thr Trp Ser Arg
                245                 250                 255

Ala Ser Gly Lys Pro Val Asn His Ser Thr Arg Lys Glu Glu Lys Gln
            260                 265                 270

Arg Asn Gly Thr Leu Thr Val Thr Ser Thr Leu Pro Val Gly Thr Arg
        275                 280                 285

Asp Trp Ile Glu Gly Glu Thr Tyr Gln Cys Arg Val Thr His Pro His
    290                 295                 300

Leu Pro Arg Ala Leu Met Arg Ser Thr Thr Lys Thr Ser Gly Pro Arg
305                 310                 315                 320

Ala Ala Pro Glu Val Tyr Ala Phe Ala Thr Pro Glu Trp Pro Gly Ser
                325                 330                 335

Arg Asp Lys Arg Thr Leu Ala Cys Leu Ile Gln Asn Phe Met Pro Glu
            340                 345                 350
```

-continued

Asp Ile Ser Val Gln Trp Leu His Asn Glu Val Gln Leu Pro Asp Ala
        355                 360                 365

Arg His Ser Thr Thr Gln Pro Arg Lys Thr Lys Gly Ser Gly Phe Phe
    370                 375                 380

Val Phe Ser Arg Leu Glu Val Thr Arg Ala Glu Trp Glu Gln Lys Asp
385                 390                 395                 400

Glu Phe Ile Cys Arg Ala Val His Glu Ala Ala Ser Pro Ser Gln Thr
                405                 410                 415

Val Gln Arg Ala Val Ser Val Asn Pro Gly Lys
            420                 425

<210> SEQ ID NO 6
<211> LENGTH: 320
<212> TYPE: PRT
<213> ORGANISM: Homo sapiens

<400> SEQUENCE: 6

Phe Thr Pro Pro Thr Val Lys Ile Leu Gln Ser Ser Cys Asp Gly Gly
  1               5                  10                  15

Gly His Phe Pro Pro Thr Ile Gln Leu Leu Cys Leu Val Ser Gly Tyr
                20                  25                  30

Thr Pro Gly Thr Ile Asn Ile Thr Trp Leu Glu Asp Gly Gln Val Met
            35                  40                  45

Asp Val Asp Leu Ser Thr Ala Ser Thr Thr Gln Glu Gly Glu Leu Ala
 50                  55                  60

Ser Thr Gln Ser Glu Leu Thr Leu Ser Gln Lys His Trp Leu Ser Asp
 65                  70                  75                  80

Arg Thr Tyr Thr Cys Gln Val Thr Tyr Gln Gly His Thr Phe Glu Asp
                85                  90                  95

Ser Thr Lys Lys Cys Ala Asp Ser Asn Pro Arg Gly Val Ser Ala Tyr
                100                 105                 110

Leu Ser Arg Pro Ser Pro Phe Asp Leu Phe Ile Arg Lys Ser Pro Thr
            115                 120                 125

Ile Thr Cys Leu Val Val Asp Leu Ala Pro Ser Lys Gly Thr Val Asn
130                 135                 140

Leu Thr Trp Ser Arg Ala Ser Gly Lys Pro Val Asn His Ser Thr Arg
145                 150                 155                 160

Lys Glu Glu Lys Gln Arg Asn Gly Thr Leu Thr Val Thr Ser Thr Leu
                165                 170                 175

Pro Val Gly Thr Arg Asp Trp Ile Glu Gly Glu Thr Tyr Gln Cys Arg
            180                 185                 190

Val Thr His Pro His Leu Pro Arg Ala Leu Met Arg Ser Thr Thr Lys
            195                 200                 205

Thr Ser Gly Pro Arg Ala Ala Pro Glu Val Tyr Ala Phe Ala Thr Pro
    210                 215                 220

Glu Trp Pro Gly Ser Arg Asp Lys Arg Thr Leu Ala Cys Leu Ile Gln
225                 230                 235                 240

Asn Phe Met Pro Glu Asp Ile Ser Val Gln Trp Leu His Asn Glu Val
                245                 250                 255

Gln Leu Pro Asp Ala Arg His Ser Thr Thr Gln Pro Arg Lys Thr Lys
            260                 265                 270

Gly Ser Gly Phe Phe Val Phe Ser Arg Leu Glu Val Thr Arg Ala Glu
        275                 280                 285

Trp Glu Gln Lys Asp Glu Phe Ile Cys Arg Ala Val His Glu Ala Ala
    290                 295                 300

```
Ser Pro Ser Gln Thr Val Gln Arg Ala Val Ser Val Asn Pro Gly Lys
305                 310                 315                 320
```

<210> SEQ ID NO 7
<211> LENGTH: 569
<212> TYPE: PRT
<213> ORGANISM: Unknown
<220> FEATURE:
<223> OTHER INFORMATION: Fusion between hinge-CH2-CH3 (IgG1) to
      CH2-CH3-CH4 (IgE)

<400> SEQUENCE: 7

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Val Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asn Trp Met Asn Gly Lys Glu Tyr Lys Cys Lys Val Ser Asn Lys Ala
            100                 105                 110

Leu Pro Ala Pro Ile Glu Lys Thr Ile Ser Lys Ala Lys Val Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Val Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Gln Gln Arg
210                 215                 220

Ser Leu Ser Leu Ser Pro Gly Lys Val Glu Gly Gly Gly Ser Gly
225                 230                 235                 240

Gly Gly Gly Ser Gly Gly Gly Ser Phe Thr Pro Pro Thr Val Lys
                245                 250                 255

Ile Leu Gln Ser Ser Cys Asp Gly Gly Gly His Phe Pro Pro Thr Ile
            260                 265                 270

Gln Leu Leu Cys Leu Val Ser Gly Tyr Thr Pro Gly Thr Ile Asn Ile
        275                 280                 285

Thr Trp Leu Glu Asp Gly Gln Val Met Asp Val Asp Leu Ser Thr Ala
290                 295                 300

Ser Thr Thr Gln Glu Gly Glu Leu Ala Ser Thr Gln Ser Glu Leu Thr
305                 310                 315                 320

Leu Ser Gln Lys His Trp Leu Ser Asp Arg Thr Tyr Thr Cys Gln Val
                325                 330                 335

Thr Tyr Gln Gly His Thr Phe Glu Asp Ser Thr Lys Lys Cys Ala Asp
```

```
                        340                 345                 350
Ser Asn Pro Arg Gly Val Ser Ala Tyr Leu Ser Arg Pro Ser Pro Phe
            355                 360                 365

Asp Leu Phe Ile Arg Lys Ser Pro Thr Ile Thr Cys Leu Val Val Asp
    370                 375                 380

Leu Ala Pro Ser Lys Gly Thr Val Asn Leu Thr Trp Ser Arg Ala Ser
385                 390                 395                 400

Gly Lys Pro Val Asn His Ser Thr Arg Lys Glu Lys Gln Arg Asn
            405                 410                 415

Gly Thr Leu Thr Val Thr Ser Leu Pro Val Gly Thr Arg Asp Trp
        420                 425                 430

Ile Glu Gly Glu Thr Tyr Gln Cys Arg Val Thr His Pro His Leu Pro
            435                 440                 445

Arg Ala Leu Met Arg Ser Thr Thr Lys Thr Ser Gly Pro Arg Ala Ala
    450                 455                 460

Pro Glu Val Tyr Ala Phe Ala Thr Pro Glu Trp Pro Gly Ser Arg Asp
465                 470                 475                 480

Lys Arg Thr Leu Ala Cys Leu Ile Gln Asn Phe Met Pro Glu Asp Ile
            485                 490                 495

Ser Val Gln Trp Leu His Asn Glu Val Gln Leu Pro Asp Ala Arg His
            500                 505                 510

Ser Thr Thr Gln Pro Arg Lys Thr Lys Gly Ser Gly Phe Phe Val Phe
        515                 520                 525

Ser Arg Leu Glu Val Thr Arg Ala Glu Trp Glu Gln Lys Asp Glu Phe
        530                 535                 540

Ile Cys Arg Ala Val His Glu Ala Ala Ser Pro Ser Gln Thr Val Gln
545                 550                 555                 560

Arg Ala Val Ser Val Asn Pro Gly Lys
            565

<210> SEQ ID NO 8
<211> LENGTH: 159
<212> TYPE: PRT
<213> ORGANISM: Alnus glutinosa (Alder)
<220> FEATURE:

<400> SEQUENCE: 8

Gly Val Phe Asn Tyr Glu Ala Glu Thr Pro Ser Val Ile Pro Ala Ala
1               5                   10                  15

Arg Leu Phe Lys Ala Phe Ile Leu Asp Gly Asp Lys Leu Leu Pro Lys
            20                  25                  30

Val Ala Pro Glu Ala Val Ser Ser Val Glu Asn Ile Glu Gly Asn Gly
        35                  40                  45

Gly Pro Gly Thr Ile Lys Lys Ile Thr Phe Pro Glu Gly Ser Pro Phe
    50                  55                  60

Lys Tyr Val Lys Glu Arg Val Asp Glu Val Asp Arg Val Asn Phe Lys
65                  70                  75                  80

Tyr Ser Phe Ser Val Ile Glu Gly Gly Ala Val Gly Asp Ala Leu Glu
            85                  90                  95

Lys Val Cys Asn Glu Ile Lys Ile Val Ala Ala Pro Asp Gly Gly Ser
            100                 105                 110

Ile Leu Lys Ile Ser Asn Lys Phe His Thr Lys Gly Asp His Glu Ile
        115                 120                 125

Asn Ala Glu Gln Ile Lys Ile Glu Lys Glu Lys Ala Val Gly Leu Leu
    130                 135                 140
```

-continued

```
Lys Ala Val Glu Ser Tyr Leu Leu Ala His Ser Asp Ala Tyr Asn
145                 150                 155

<210> SEQ ID NO 9
<211> LENGTH: 113
<212> TYPE: PRT
<213> ORGANISM: Alternaria alternata

<400> SEQUENCE: 9

Met Lys His Leu Ala Ala Tyr Leu Leu Leu Gly Leu Gly Gly Asn Thr
1               5                   10                  15

Ser Pro Ser Ala Ala Asp Val Lys Ala Val Leu Glu Ser Val Gly Ile
                20                  25                  30

Glu Ala Asp Ser Asp Arg Leu Asp Lys Leu Ile Ser Glu Leu Glu Gly
            35                  40                  45

Lys Asp Ile Asn Glu Leu Ile Ala Ser Gly Ser Glu Lys Leu Ala Ser
    50                  55                  60

Val Pro Ser Gly Gly Ala Gly Gly Ala Ala Ser Gly Gly Ala Ala
65                  70                  75                  80

Ala Ala Gly Gly Ser Ala Gln Ala Glu Ala Ala Pro Glu Ala Ala Lys
                85                  90                  95

Glu Glu Glu Lys Glu Glu Ser Asp Glu Asp Met Gly Phe Gly Leu Phe
            100                 105                 110

Asp

<210> SEQ ID NO 10
<211> LENGTH: 204
<212> TYPE: PRT
<213> ORGANISM: Alternaria alternata

<400> SEQUENCE: 10

Met Ala Pro Lys Ile Ala Ile Val Tyr Tyr Ser Met Tyr Gly His Ile
1               5                   10                  15

Lys Lys Met Ala Asp Ala Glu Leu Lys Gly Ile Gln Glu Ala Gly Gly
                20                  25                  30

Asp Ala Lys Leu Phe Gln Val Ala Glu Thr Leu Pro Gln Glu Val Leu
            35                  40                  45

Asp Lys Met Tyr Ala Pro Pro Lys Asp Ser Ser Val Pro Val Leu Glu
    50                  55                  60

Asp Pro Ala Val Leu Glu Glu Phe Asp Gly Ile Leu Phe Gly Ile Pro
65                  70                  75                  80

Thr Arg Tyr Gly Asn Phe Pro Ala Gln Phe Lys Thr Phe Trp Asp Lys
                85                  90                  95

Thr Gly Lys Gln Trp Gln Gly Ala Phe Trp Gly Lys Tyr Ala Gly
            100                 105                 110

Val Phe Val Ser Thr Gly Thr Leu Gly Gly Gly Gln Glu Thr Thr Ala
    115                 120                 125

Ile Thr Ser Met Ser Thr Leu Val Asp His Gly Phe Ile Tyr Val Pro
130                 135                 140

Leu Gly Tyr Lys Thr Ala Phe Ser Met Leu Ala Asn Leu Asp Glu Val
145                 150                 155                 160

His Gly Gly Ser Pro Trp Gly Ala Gly Thr Phe Ser Ala Gly Asp Gly
                165                 170                 175

Ser Arg Gln Pro Ser Glu Leu Glu Leu Asn Ile Ala Gln Ala Gln Gly
            180                 185                 190
```

Lys Ala Phe Tyr Glu Ala Val Ala Lys Ala His Gln
        195                 200

<210> SEQ ID NO 11
<211> LENGTH: 495
<212> TYPE: PRT
<213> ORGANISM: Alternaria alternata

<400> SEQUENCE: 11

Met Thr Ser Val Lys Leu Ser Thr Pro Gln Thr Gly Glu Phe Glu Gln
 1               5                  10                  15

Pro Thr Gly Leu Phe Ile Asn Asn Glu Phe Val Lys Ala Val Asp Gly
            20                  25                  30

Lys Thr Phe Asp Val Ile Asn Pro Ser Thr Glu Glu Val Ile Cys Ser
        35                  40                  45

Val Gln Glu Ala Thr Glu Lys Asp Val Asp Ile Ala Val Ala Ala Ala
    50                  55                  60

Arg Lys Ala Phe Asn Gly Pro Trp Ala Lys Glu Thr Pro Glu Asn Arg
65                  70                  75                  80

Gly Lys Leu Leu Asn Lys Leu Ala Asp Leu Phe Glu Lys Asn Ala Asp
                85                  90                  95

Leu Ile Ala Ala Val Glu Ala Leu Asp Asn Gly Lys Ala Phe Ser Met
            100                 105                 110

Ala Lys Asn Val Asp Val Pro Ala Ala Ala Gly Cys Leu Arg Tyr Tyr
        115                 120                 125

Gly Gly Trp Ala Asp Lys Ile Glu Gly Lys Val Asp Thr Ala Pro
    130                 135                 140

Asp Ser Phe Asn Tyr Ile Arg Lys Ser Leu Leu Val Phe Ala Val Arg
145                 150                 155                 160

Ser Ser Met Glu Leu Pro Ile Leu Met Trp Ser Trp Lys Ile Gly Pro
                165                 170                 175

Ala Ile Ala Thr Gly Asn Thr Val Val Leu Lys Thr Ala Glu Gln Thr
            180                 185                 190

Pro Leu Ser Ala Tyr Ile Ala Cys Lys Leu Ile Gln Glu Ala Gly Phe
        195                 200                 205

Pro Pro Gly Val Ile Asn Val Ile Thr Gly Phe Gly Lys Ile Ala Gly
    210                 215                 220

Ala Ala Met Ser Ala His Met Asp Ile Asp Lys Ile Ala Phe Thr Gly
225                 230                 235                 240

Ser Thr Val Val Gly Arg Gln Ile Met Lys Ser Ala Ala Gly Ser Asn
                245                 250                 255

Leu Lys Lys Val Thr Leu Glu Leu Gly Gly Lys Ser Pro Asn Ile Val
            260                 265                 270

Phe Ala Asp Ala Asp Leu Asp Glu Ala Ile His Trp Val Asn Phe Gly
        275                 280                 285

Ile Tyr Phe Asn His Gly Gln Ala Cys Cys Ala Gly Ser Arg Ile Tyr
    290                 295                 300

Val Gln Glu Glu Ile Tyr Asp Lys Phe Ile Gln Arg Phe Lys Glu Arg
305                 310                 315                 320

Ala Ala Gln Asn Ala Val Gly Asp Pro Phe Ala Thr Leu Gln Gly
                325                 330                 335

Pro Gln Val Ser Gln Leu Gln Phe Asp Arg Ile Met Gly Tyr Ile Glu
            340                 345                 350

Glu Gly Lys Lys Ser Gly Ala Thr Ile Glu Thr Gly Gly Asn Arg Lys
        355                 360                 365

```
Gly Asp Lys Gly Tyr Phe Ile Glu Pro Thr Ile Phe Ser Asn Val Thr
        370                 375                 380

Glu Asp Met Lys Ile Gln Gln Glu Glu Ile Phe Gly Pro Val Cys Thr
385                 390                 395                 400

Ile Ser Lys Phe Lys Thr Lys Ala Asp Val Ile Lys Ile Gly Asn Asn
                405                 410                 415

Thr Thr Tyr Gly Leu Ser Ala Ala Val His Thr Ser Asn Leu Thr Thr
                420                 425                 430

Ala Ile Glu Val Ala Asn Ala Leu Arg Ala Gly Thr Val Trp Val Asn
                435                 440                 445

Ser Tyr Asn Thr Leu His Trp Gln Leu Pro Phe Gly Gly Tyr Lys Glu
                450                 455                 460

Ser Gly Ile Gly Arg Glu Leu Gly Glu Ala Ala Leu Asp Asn Tyr Ile
465                 470                 475                 480

Gln Thr Lys Thr Val Ser Ile Arg Leu Gly Asp Val Leu Phe Gly
                485                 490                 495

<210> SEQ ID NO 12
<211> LENGTH: 110
<212> TYPE: PRT
<213> ORGANISM: Alternaria alternata

<400> SEQUENCE: 12

Met Ser Thr Ser Glu Leu Ala Thr Ser Tyr Ala Ala Leu Ile Leu Ala
1               5                   10                  15

Asp Asp Gly Val Asp Ile Thr Ala Asp Lys Leu Gln Ser Leu Ile Lys
                20                  25                  30

Ala Ala Lys Ile Glu Glu Val Glu Pro Ile Trp Thr Thr Leu Phe Ala
            35                  40                  45

Lys Ala Leu Glu Gly Lys Asp Val Lys Asp Leu Leu Leu Asn Val Gly
        50                  55                  60

Ser Gly Gly Gly Ala Ala Pro Leu Pro Glu Ala Leu Leu Leu Arg Trp
65                  70                  75                  80

Arg Ala Ala Asp Ala Ala Pro Ala Ala Glu Glu Lys Lys Glu Glu Glu
                85                  90                  95

Lys Glu Glu Ser Asp Glu Asp Met Gly Phe Gly Leu Phe Asp
                100                 105                 110

<210> SEQ ID NO 13
<211> LENGTH: 396
<212> TYPE: PRT
<213> ORGANISM: Ambrosia artemisiifolia (Short ragweed)

<400> SEQUENCE: 13

Met Gly Ile Lys His Cys Cys Tyr Ile Leu Tyr Phe Thr Leu Ala Leu
1               5                   10                  15

Val Thr Leu Leu Gln Pro Val Arg Ser Ala Glu Asp Leu Gln Glu Ile
                20                  25                  30

Leu Pro Val Asn Glu Thr Arg Arg Leu Thr Thr Ser Gly Ala Tyr Asn
            35                  40                  45

Ile Ile Asp Gly Cys Trp Arg Gly Lys Ala Asp Trp Ala Glu Asn Arg
        50                  55                  60

Lys Ala Leu Ala Asp Cys Ala Gln Gly Phe Gly Lys Gly Thr Val Gly
65                  70                  75                  80

Gly Lys Asp Gly Asp Ile Tyr Thr Val Thr Ser Glu Leu Asp Asp Asp
                85                  90                  95
```

```
Val Ala Asn Pro Lys Glu Gly Thr Leu Arg Phe Gly Ala Ala Gln Asn
            100                 105                 110

Arg Pro Leu Trp Ile Ile Phe Glu Arg Asp Met Val Ile Arg Leu Asp
        115                 120                 125

Lys Glu Met Val Val Asn Ser Asp Lys Thr Ile Asp Gly Arg Gly Ala
    130                 135                 140

Lys Val Glu Ile Ile Asn Ala Gly Phe Thr Leu Asn Gly Val Lys Asn
145                 150                 155                 160

Val Ile Ile His Asn Ile Asn Met His Asp Val Lys Val Asn Pro Gly
                165                 170                 175

Gly Leu Ile Lys Ser Asn Asp Gly Pro Ala Ala Pro Arg Ala Gly Ser
            180                 185                 190

Asp Gly Asp Ala Ile Ser Ile Ser Gly Ser Ser Gln Ile Trp Ile Asp
        195                 200                 205

His Cys Ser Leu Ser Lys Ser Val Asp Gly Leu Val Asp Ala Lys Leu
    210                 215                 220

Gly Thr Thr Arg Leu Thr Val Ser Asn Ser Leu Phe Thr Gln His Gln
225                 230                 235                 240

Phe Val Leu Leu Phe Gly Ala Gly Asp Glu Asn Ile Glu Asp Arg Gly
                245                 250                 255

Met Leu Ala Thr Val Ala Phe Asn Thr Phe Thr Asp Asn Val Asp Gln
            260                 265                 270

Arg Met Pro Arg Cys Arg His Gly Phe Phe Gln Val Val Asn Asn Asn
        275                 280                 285

Tyr Asp Lys Trp Gly Ser Tyr Ala Ile Gly Gly Ser Ala Ser Pro Thr
    290                 295                 300

Ile Leu Ser Gln Gly Asn Arg Phe Cys Ala Pro Asp Glu Arg Ser Lys
305                 310                 315                 320

Lys Asn Val Leu Gly Arg His Gly Glu Ala Ala Glu Ser Met Lys
                325                 330                 335

Trp Asn Trp Arg Thr Asn Lys Asp Val Leu Glu Asn Gly Ala Ile Phe
        340                 345                 350

Val Ala Ser Gly Val Asp Pro Val Leu Thr Pro Glu Gln Ser Ala Gly
    355                 360                 365

Met Ile Pro Ala Glu Pro Gly Glu Ser Ala Leu Ser Leu Thr Ser Ser
370                 375                 380

Ala Gly Val Leu Ser Cys Gln Pro Gly Ala Pro Cys
385                 390                 395

<210> SEQ ID NO 14
<211> LENGTH: 398
<212> TYPE: PRT
<213> ORGANISM: Ambrosia artemisiifolia (Short ragweed)

<400> SEQUENCE: 14

Met Gly Ile Lys His Cys Cys Tyr Ile Leu Tyr Phe Thr Leu Ala Leu
1               5                   10                  15

Val Thr Leu Leu Gln Pro Val Arg Ser Ala Glu Asp Val Glu Glu Phe
            20                  25                  30

Leu Pro Ser Ala Asn Glu Thr Arg Arg Ser Leu Lys Ala Cys Glu Ala
        35                  40                  45

His Asn Ile Ile Asp Lys Cys Trp Arg Cys Lys Ala Asp Trp Ala Asn
    50                  55                  60

Asn Arg Gln Ala Leu Ala Asp Cys Ala Gln Gly Phe Ala Lys Gly Thr
```

```
                65                  70                  75                  80
Tyr Gly Gly Lys His Gly Asp Val Tyr Thr Val Thr Ser Asp Lys Asp
                    85                  90                  95

Asp Asp Val Ala Asn Pro Lys Glu Gly Thr Leu Arg Phe Ala Ala Ala
                100                 105                 110

Gln Asn Arg Pro Leu Trp Ile Ile Phe Lys Arg Asn Met Val Ile His
                115                 120                 125

Leu Asn Gln Glu Leu Val Val Asn Ser Asp Lys Thr Ile Asp Gly Arg
            130                 135                 140

Gly Val Lys Val Asn Ile Val Asn Ala Gly Leu Thr Leu Met Asn Val
145                 150                 155                 160

Lys Asn Ile Ile Ile His Asn Ile Asn Ile His Asp Ile Lys Val Cys
                165                 170                 175

Pro Gly Gly Met Ile Lys Ser Asn Asp Gly Pro Ile Leu Arg Gln
                180                 185                 190

Gln Ser Asp Gly Asp Ala Ile Asn Val Ala Gly Ser Ser Gln Ile Trp
            195                 200                 205

Ile Asp His Cys Ser Leu Ser Lys Ala Ser Asp Gly Leu Leu Asp Ile
        210                 215                 220

Thr Leu Gly Ser Ser His Val Thr Val Ser Asn Cys Lys Phe Thr Gln
225                 230                 235                 240

His Gln Phe Val Leu Leu Gly Ala Asp Asp Thr His Tyr Gln Asp
                245                 250                 255

Lys Gly Met Leu Ala Thr Val Ala Phe Asn Met Phe Thr Asp His Val
            260                 265                 270

Asp Gln Arg Met Pro Arg Cys Arg Phe Gly Phe Gln Val Val Asn
            275                 280                 285

Asn Asn Tyr Asp Arg Trp Gly Thr Tyr Ala Ile Gly Gly Ser Ser Ala
        290                 295                 300

Pro Thr Ile Leu Ser Gln Gly Asn Arg Phe Phe Ala Pro Asp Asp Ile
305                 310                 315                 320

Ile Lys Lys Asn Val Leu Ala Arg Thr Gly Thr Gly Asn Ala Glu Ser
                325                 330                 335

Met Ser Trp Asn Trp Arg Thr Asp Arg Asp Leu Leu Glu Asn Gly Ala
                340                 345                 350

Ile Phe Leu Pro Ser Gly Ser Asp Pro Val Leu Thr Pro Glu Gln Lys
            355                 360                 365

Ala Gly Met Ile Pro Ala Glu Pro Gly Glu Ala Val Leu Arg Leu Thr
        370                 375                 380

Ser Ser Ala Gly Val Leu Ser Cys His Gln Gly Ala Pro Cys
385                 390                 395

<210> SEQ ID NO 15
<211> LENGTH: 397
<212> TYPE: PRT
<213> ORGANISM: Ambrosia artemisiifolia (Short ragweed)

<400> SEQUENCE: 15

Met Gly Ile Lys Gln Cys Cys Tyr Ile Leu Tyr Phe Thr Leu Ala Leu
1               5                   10                  15

Val Ala Leu Leu Gln Pro Val Arg Ser Ala Glu Gly Val Gly Glu Ile
                20                  25                  30

Leu Pro Ser Val Asn Glu Thr Arg Ser Leu Gln Ala Cys Glu Ala Leu
            35                  40                  45
```

```
Asn Ile Ile Asp Lys Cys Trp Arg Gly Lys Ala Asp Trp Glu Asn Asn
         50                  55                  60

Arg Gln Ala Leu Ala Asp Cys Ala Gln Gly Phe Ala Lys Gly Thr Tyr
 65                  70                  75                  80

Gly Gly Lys Trp Gly Asp Val Tyr Thr Val Thr Ser Asn Leu Asp Asp
                 85                  90                  95

Asp Val Ala Asn Pro Lys Glu Gly Thr Leu Arg Phe Ala Ala Ala Gln
                100                 105                 110

Asn Arg Pro Leu Trp Ile Ile Phe Lys Asn Asp Met Val Ile Asn Leu
                115                 120                 125

Asn Gln Glu Leu Val Val Asn Ser Asp Lys Thr Ile Asp Gly Arg Gly
130                 135                 140

Val Lys Val Glu Ile Ile Asn Gly Gly Leu Thr Leu Met Asn Val Lys
145                 150                 155                 160

Asn Ile Ile Ile His Asn Ile Asn Ile His Asp Val Lys Val Leu Pro
                165                 170                 175

Gly Gly Met Ile Lys Ser Asn Asp Gly Pro Pro Ile Leu Arg Gln Ala
                180                 185                 190

Ser Asp Gly Asp Thr Ile Asn Val Ala Gly Ser Ser Gln Ile Trp Ile
                195                 200                 205

Asp His Cys Ser Leu Ser Lys Ser Phe Asp Gly Leu Val Asp Val Thr
210                 215                 220

Leu Gly Ser Thr His Val Thr Ile Ser Asn Cys Lys Phe Thr Gln Gln
225                 230                 235                 240

Ser Lys Ala Ile Leu Leu Gly Ala Asp Asp Thr His Val Gln Asp Lys
                245                 250                 255

Gly Met Leu Ala Thr Val Ala Phe Asn Met Phe Thr Asp Asn Val Asp
                260                 265                 270

Gln Arg Met Pro Arg Cys Arg Phe Gly Phe Phe Gln Val Val Asn Asn
                275                 280                 285

Asn Tyr Asp Arg Trp Gly Thr Tyr Ala Ile Gly Gly Ser Ser Ala Pro
290                 295                 300

Thr Ile Leu Cys Gln Gly Asn Arg Phe Leu Ala Pro Asp Asp Gln Ile
305                 310                 315                 320

Lys Lys Asn Val Leu Ala Arg Thr Gly Thr Gly Ala Ala Glu Ser Met
                325                 330                 335

Ala Trp Asn Trp Arg Ser Asp Lys Asp Leu Leu Glu Asn Gly Ala Ile
                340                 345                 350

Phe Val Thr Ser Gly Ser Asp Pro Val Leu Thr Pro Val Gln Ser Ala
                355                 360                 365

Gly Met Ile Pro Ala Glu Pro Gly Glu Ala Ala Ile Lys Leu Thr Ser
                370                 375                 380

Ser Ala Gly Val Phe Ser Cys His Pro Gly Ala Pro Cys
385                 390                 395

<210> SEQ ID NO 16
<211> LENGTH: 392
<212> TYPE: PRT
<213> ORGANISM: Ambrosia artemisiifolia (Short ragweed)

<400> SEQUENCE: 16

Met Gly Ile Lys His Cys Cys Tyr Ile Leu Tyr Phe Thr Leu Ala Leu
  1               5                  10                  15

Val Thr Leu Leu Gln Pro Val Arg Ser Ala Glu Asp Leu Gln Gln Ile
                 20                  25                  30
```

```
Leu Pro Ser Ala Asn Glu Thr Arg Ser Leu Thr Thr Cys Gly Thr Tyr
        35                  40                  45
Asn Ile Ile Asp Gly Cys Trp Arg Gly Lys Ala Asp Trp Ala Glu Asn
 50                  55                  60
Arg Lys Ala Leu Ala Asp Cys Ala Gln Gly Phe Ala Lys Gly Thr Ile
 65                  70                  75                  80
Gly Gly Lys Asp Gly Asp Ile Tyr Thr Val Thr Ser Glu Leu Asp Asp
                85                  90                  95
Asp Val Ala Asn Pro Lys Glu Gly Thr Leu Arg Phe Gly Ala Ala Gln
            100                 105                 110
Asn Arg Pro Leu Trp Ile Ile Phe Ala Arg Asp Met Val Ile Arg Leu
        115                 120                 125
Asp Arg Glu Leu Ala Ile Asn Asn Asp Lys Thr Ile Asp Gly Arg Gly
    130                 135                 140
Ala Lys Val Glu Ile Ile Asn Ala Gly Phe Ala Ile Tyr Asn Val Lys
145                 150                 155                 160
Asn Ile Ile Ile His Asn Ile Ile Met His Asp Ile Val Val Asn Pro
                165                 170                 175
Gly Gly Leu Ile Lys Ser His Asp Gly Pro Pro Val Pro Arg Lys Gly
            180                 185                 190
Ser Asp Gly Asp Ala Ile Gly Ile Ser Gly Ser Gln Ile Trp Ile
        195                 200                 205
Asp His Cys Ser Leu Ser Lys Ala Val Asp Gly Leu Ile Asp Ala Lys
    210                 215                 220
His Gly Ser Thr His Phe Thr Val Ser Asn Cys Leu Phe Thr Gln His
225                 230                 235                 240
Gln Tyr Leu Leu Leu Phe Trp Asp Phe Asp Glu Arg Gly Met Leu Cys
                245                 250                 255
Thr Val Ala Phe Asn Lys Phe Thr Asp Asn Val Asp Gln Arg Met Pro
            260                 265                 270
Asn Leu Arg His Gly Phe Val Gln Val Val Asn Asn Tyr Glu Arg
        275                 280                 285
Trp Gly Ser Tyr Ala Leu Gly Gly Ser Ala Gly Pro Thr Ile Leu Ser
    290                 295                 300
Gln Gly Asn Arg Phe Leu Ala Ser Asp Ile Lys Lys Glu Val Val Gly
305                 310                 315                 320
Arg Tyr Gly Glu Ser Ala Met Ser Glu Ser Ile Asn Trp Asn Trp Arg
                325                 330                 335
Ser Tyr Met Asp Val Phe Glu Asn Gly Ala Ile Phe Val Pro Ser Gly
            340                 345                 350
Val Asp Pro Val Leu Thr Pro Glu Gln Asn Ala Gly Met Ile Pro Ala
        355                 360                 365
Glu Pro Gly Glu Ala Val Leu Arg Leu Thr Ser Ser Ala Gly Val Leu
    370                 375                 380
Ser Cys Gln Pro Gly Ala Pro Cys
385                 390

<210> SEQ ID NO 17
<211> LENGTH: 397
<212> TYPE: PRT
<213> ORGANISM: Ambrosia artemisiifolia (Short ragweed)

<400> SEQUENCE: 17

Met Gly Ile Lys His Cys Cys Tyr Ile Leu Tyr Phe Thr Leu Ala Leu
```

-continued

```
  1               5                   10                  15

Val Thr Leu Val Gln Ala Gly Arg Leu Gly Glu Glu Val Asp Ile Leu
                 20                  25                  30

Pro Ser Pro Asn Asp Thr Arg Arg Ser Leu Gln Gly Cys Glu Ala His
             35                  40                  45

Asn Ile Ile Asp Lys Cys Trp Arg Cys Lys Pro Asp Trp Ala Glu Asn
         50                  55                  60

Arg Gln Ala Leu Gly Asn Cys Ala Gln Gly Phe Gly Lys Ala Thr His
 65                  70                  75                  80

Gly Gly Lys Trp Gly Asp Ile Tyr Met Val Thr Ser Asp Gln Asp Asp
                 85                  90                  95

Asp Val Val Asn Pro Lys Glu Gly Thr Leu Arg Phe Gly Ala Thr Gln
             100                 105                 110

Asp Arg Pro Leu Trp Ile Ile Phe Gln Arg Asp Met Ile Ile Tyr Leu
             115                 120                 125

Gln Gln Glu Met Val Val Thr Ser Asp Lys Thr Ile Asp Gly Arg Gly
             130                 135                 140

Ala Lys Val Glu Leu Val Tyr Gly Gly Ile Thr Leu Met Asn Val Lys
145                 150                 155                 160

Asn Val Ile Ile His Asn Ile Asp Ile His Asp Val Arg Val Leu Pro
                 165                 170                 175

Gly Gly Arg Ile Lys Ser Asn Gly Gly Pro Ala Ile Pro Arg His Gln
             180                 185                 190

Ser Asp Gly Asp Ala Ile His Val Thr Gly Ser Ser Ala Ile Trp Ile
             195                 200                 205

Asp His Cys Thr Leu Ser Lys Ser Phe Asp Gly Leu Val Asp Val Asn
             210                 215                 220

Trp Gly Ser Thr Gly Val Thr Ile Ser Asn Cys Lys Phe Thr His His
225                 230                 235                 240

Glu Lys Ala Val Leu Leu Gly Ala Ser Asp Thr His Phe Gln Asp Leu
                 245                 250                 255

Lys Met His Val Thr Leu Ala Tyr Asn Ile Phe Thr Asn Thr Val His
             260                 265                 270

Glu Arg Met Pro Arg Cys Arg Phe Gly Phe Phe Gln Ile Val Asn Asn
             275                 280                 285

Phe Tyr Asp Arg Trp Asp Lys Tyr Ala Ile Gly Gly Ser Ser Asn Pro
             290                 295                 300

Thr Ile Leu Ser Gln Gly Asn Lys Phe Val Ala Pro Asp Phe Ile Tyr
305                 310                 315                 320

Lys Lys Asn Val Cys Leu Arg Thr Gly Ala Gln Glu Pro Glu Trp Met
                 325                 330                 335

Thr Trp Asn Trp Arg Thr Gln Asn Asp Val Leu Glu Asn Gly Ala Ile
             340                 345                 350

Phe Val Ala Ser Gly Ser Asp Pro Val Leu Thr Ala Glu Gln Asn Ala
             355                 360                 365

Gly Met Met Gln Ala Glu Pro Gly Asp Met Val Pro Gln Leu Thr Met
             370                 375                 380

Asn Ala Gly Val Leu Thr Cys Ser Pro Gly Ala Pro Cys
385                 390                 395
```

<210> SEQ ID NO 18
<211> LENGTH: 101
<212> TYPE: PRT
<213> ORGANISM: Ambrosia artemisiifolia var.elatior(Short ragweed)

```
<400> SEQUENCE: 18

Gly Lys Val Tyr Leu Val Gly Gly Pro Glu Leu Gly Trp Lys Leu
1               5                   10                  15

Gln Ser Asp Pro Arg Ala Tyr Ala Leu Trp Ser Ala Arg Gln Gln Phe
            20                  25                  30

Lys Thr Thr Asp Val Leu Trp Phe Asn Phe Thr Thr Gly Glu Asp Ser
                35                  40                  45

Val Ala Glu Val Trp Arg Glu Ala Tyr His Ala Cys Asp Ile Lys
    50                  55                  60

Asp Pro Ile Arg Leu Glu Pro Gly Gly Pro Asp Arg Phe Thr Leu Leu
65                  70                  75                  80

Thr Pro Gly Ser His Phe Ile Cys Thr Lys Asp Gln Lys Phe Val Ala
                85                  90                  95

Cys Val Pro Gly Arg
            100

<210> SEQ ID NO 19
<211> LENGTH: 45
<212> TYPE: PRT
<213> ORGANISM: Ambrosia artemisiifolia var.elatior(Short ragweed)

<400> SEQUENCE: 19

Leu Val Pro Cys Ala Trp Ala Gly Asn Val Cys Gly Glu Lys Arg Ala
1               5                   10                  15

Tyr Cys Cys Ser Asp Pro Gly Arg Tyr Cys Pro Trp Gln Val Val Cys
            20                  25                  30

Tyr Glu Ser Ser Glu Ile Cys Ser Lys Lys Cys Gly Lys
        35                  40                  45

<210> SEQ ID NO 20
<211> LENGTH: 77
<212> TYPE: PRT
<213> ORGANISM: Ambrosia psilostachya (Western ragweed)

<400> SEQUENCE: 20

Met Asn Asn Glu Lys Asn Val Ser Phe Glu Phe Ile Gly Ser Thr Asp
1               5                   10                  15

Glu Val Asp Glu Ile Lys Leu Leu Pro Cys Ala Trp Ala Gly Asn Val
            20                  25                  30

Cys Gly Glu Lys Arg Ala Tyr Cys Cys Ser Asp Pro Gly Arg Tyr Cys
        35                  40                  45

Pro Trp Gln Val Val Cys Tyr Glu Ser Ser Glu Ile Cys Ser Gln Lys
    50                  55                  60

Cys Gly Lys Met Arg Met Asn Val Thr Lys Asn Thr Ile
65                  70                  75

<210> SEQ ID NO 21
<211> LENGTH: 77
<212> TYPE: PRT
<213> ORGANISM: Ambrosia psilostachya (Western ragweed)

<400> SEQUENCE: 21

Met Asn Asn Glu Lys Asn Val Ser Phe Glu Phe Ile Gly Ser Thr Asn
1               5                   10                  15

Glu Val Asp Glu Ile Lys Val Met Ala Cys Tyr Ala Ala Gly Ser Ile
            20                  25                  30

Cys Gly Glu Lys Arg Gly Tyr Cys Ser Ser Asp Pro Gly Arg Tyr Cys
```

```
            35                  40                  45
Pro Trp Gln Val Val Cys Tyr Glu Ser Arg Lys Ile Cys Ala Lys Asn
    50                  55                  60

Ala Ala Lys Met Arg Met Asn Val Thr Lys Asn Thr Ile
65                  70                  75

<210> SEQ ID NO 22
<211> LENGTH: 73
<212> TYPE: PRT
<213> ORGANISM: Ambrosia trifida (Giant ragweed)

<400> SEQUENCE: 22

Met Lys Asn Ile Phe Met Leu Thr Leu Phe Ile Leu Ile Ile Thr Ser
1               5                   10                  15

Thr Ile Lys Ala Ile Gly Ser Thr Asn Glu Val Asp Glu Ile Lys Gln
            20                  25                  30

Glu Asp Asp Gly Leu Cys Tyr Glu Gly Thr Asn Cys Gly Lys Val Gly
        35                  40                  45

Lys Tyr Cys Cys Ser Pro Ile Gly Lys Tyr Cys Val Cys Tyr Asp Ser
    50                  55                  60

Lys Ala Ile Cys Asn Lys Asn Cys Thr
65                  70

<210> SEQ ID NO 23
<211> LENGTH: 154
<212> TYPE: PRT
<213> ORGANISM: um graveolens (Celery)

<400> SEQUENCE: 23

Met Gly Val Gln Thr His Val Leu Glu Leu Thr Ser Ser Val Ser Ala
1               5                   10                  15

Glu Lys Ile Phe Gln Gly Phe Val Ile Asp Val Asp Thr Val Leu Pro
            20                  25                  30

Lys Ala Ala Pro Gly Ala Tyr Lys Ser Val Glu Ile Lys Gly Asp Gly
        35                  40                  45

Gly Pro Gly Thr Leu Lys Ile Ile Thr Leu Pro Asp Gly Gly Pro Ile
    50                  55                  60

Thr Thr Met Thr Leu Arg Ile Asp Gly Val Asn Lys Glu Ala Leu Thr
65                  70                  75                  80

Phe Asp Tyr Ser Val Ile Asp Gly Asp Ile Leu Leu Gly Phe Ile Glu
                85                  90                  95

Ser Ile Glu Asn His Val Val Leu Val Pro Thr Ala Asp Gly Gly Ser
            100                 105                 110

Ile Cys Lys Thr Thr Ala Ile Phe His Thr Lys Gly Asp Ala Val Val
        115                 120                 125

Pro Glu Glu Asn Ile Lys Tyr Ala Asn Glu Gln Asn Thr Ala Leu Phe
    130                 135                 140

Lys Ala Leu Glu Ala Tyr Leu Ile Ala Asn
145                 150

<210> SEQ ID NO 24
<211> LENGTH: 162
<212> TYPE: PRT
<213> ORGANISM: Apis mellifera (Honeybee)

<400> SEQUENCE: 24

Gly Ser Leu Phe Leu Leu Leu Leu Ser Thr Ser His Gly Trp Gln Ile
1               5                   10                  15
```

```
Arg Asp Arg Ile Gly Asp Asn Glu Leu Glu Arg Ile Ile Tyr Pro
            20                  25                  30

Gly Thr Leu Trp Cys Gly His Gly Asn Lys Ser Ser Gly Pro Asn Glu
            35                  40                  45

Leu Gly Arg Phe Lys His Thr Asp Ala Cys Cys Arg Thr His Asp Met
        50                  55                  60

Cys Pro Asp Val Met Ser Ala Gly Glu Ser Lys His Gly Leu Thr Asn
65                  70                  75                  80

Thr Ala Ser His Thr Arg Leu Ser Cys Asp Cys Asp Lys Phe Tyr
                85                  90                  95

Asp Cys Leu Lys Asn Ser Ala Asp Thr Ile Ser Ser Tyr Phe Val Gly
            100                 105                 110

Lys Met Tyr Phe Asn Leu Ile Asp Thr Lys Cys Tyr Lys Leu Glu His
            115                 120                 125

Pro Val Thr Gly Cys Gly Glu Arg Thr Glu Gly Arg Cys Leu His Tyr
        130                 135                 140

Thr Val Asp Lys Ser Lys Pro Lys Val Tyr Gln Trp Phe Asp Leu Arg
145                 150                 155                 160

Lys Tyr

<210> SEQ ID NO 25
<211> LENGTH: 382
<212> TYPE: PRT
<213> ORGANISM: Apis mellifera (Honeybee)

<400> SEQUENCE: 25

Met Ser Arg Pro Leu Val Ile Thr Glu Gly Met Met Ile Gly Val Leu
1               5                   10                  15

Leu Met Leu Ala Pro Ile Asn Ala Leu Leu Leu Gly Phe Val Gln Ser
            20                  25                  30

Thr Pro Asp Asn Asn Lys Thr Val Arg Glu Phe Asn Val Tyr Trp Asn
            35                  40                  45

Val Pro Thr Phe Met Cys His Lys Tyr Gly Leu Arg Phe Glu Glu Val
        50                  55                  60

Ser Glu Lys Tyr Gly Ile Leu Gln Asn Trp Met Asp Lys Phe Arg Gly
65                  70                  75                  80

Glu Glu Ile Ala Ile Leu Tyr Asp Pro Gly Met Phe Pro Ala Leu Leu
                85                  90                  95

Lys Asp Pro Asn Gly Asn Val Val Ala Arg Asn Gly Gly Val Pro Gln
            100                 105                 110

Leu Gly Asn Leu Thr Lys His Leu Gln Val Phe Arg Asp His Leu Ile
            115                 120                 125

Asn Gln Ile Pro Asp Lys Ser Phe Pro Gly Val Gly Val Ile Asp Phe
        130                 135                 140

Glu Ser Trp Arg Pro Ile Phe Arg Gln Asn Trp Ala Ser Leu Gln Pro
145                 150                 155                 160

Tyr Lys Lys Leu Ser Val Glu Val Val Arg Arg Glu His Pro Phe Trp
                165                 170                 175

Asp Asp Gln Arg Val Glu Gln Glu Ala Lys Arg Arg Phe Glu Lys Tyr
            180                 185                 190

Gly Gln Leu Phe Met Glu Glu Thr Leu Lys Ala Ala Lys Arg Met Arg
            195                 200                 205

Pro Ala Ala Asn Trp Gly Tyr Tyr Ala Tyr Pro Tyr Cys Tyr Asn Leu
        210                 215                 220
```

```
Thr Pro Asn Gln Pro Ser Ala Gln Cys Glu Ala Thr Thr Met Gln Glu
225                 230                 235                 240

Asn Asp Lys Met Ser Trp Leu Phe Glu Ser Glu Asp Val Leu Leu Pro
            245                 250                 255

Ser Val Tyr Leu Arg Trp Asn Leu Thr Ser Gly Glu Arg Val Gly Leu
        260                 265                 270

Val Gly Gly Arg Val Lys Glu Ala Leu Arg Ile Ala Arg Gln Met Thr
    275                 280                 285

Thr Ser Arg Lys Lys Val Leu Pro Tyr Tyr Trp Tyr Lys Tyr Gln Asp
290                 295                 300

Arg Arg Asp Thr Asp Leu Ser Arg Ala Asp Leu Glu Ala Thr Leu Arg
305                 310                 315                 320

Lys Ile Thr Asp Leu Gly Ala Asp Gly Phe Ile Ile Trp Gly Ser Ser
                325                 330                 335

Asp Asp Ile Asn Thr Lys Ala Lys Cys Leu Gln Phe Arg Glu Tyr Leu
            340                 345                 350

Asn Asn Glu Leu Gly Pro Ala Val Lys Arg Ile Ala Leu Asn Asn Asn
        355                 360                 365

Ala Asn Asp Arg Leu Thr Val Asp Val Ser Val Asp Gln Val
370                 375                 380

<210> SEQ ID NO 26
<211> LENGTH: 70
<212> TYPE: PRT
<213> ORGANISM: Apis mellifera(Honeybee)Apis cerana(Ind. honeybee)

<400> SEQUENCE: 26

Met Lys Phe Leu Val Asn Val Ala Leu Val Phe Met Val Val Tyr Ile
1               5                   10                  15

Ser Tyr Ile Tyr Ala Ala Pro Glu Pro Glu Pro Ala Pro Glu Pro Glu
            20                  25                  30

Ala Glu Ala Asp Ala Glu Ala Asp Pro Glu Ala Gly Ile Gly Ala Val
        35                  40                  45

Leu Lys Val Leu Thr Thr Gly Leu Pro Ala Leu Ile Ser Trp Ile Lys
    50                  55                  60

Arg Lys Arg Gln Gln Gly
65                  70

<210> SEQ ID NO 27
<211> LENGTH: 614
<212> TYPE: PRT
<213> ORGANISM: Arachis hypogaea (Peanut)

<400> SEQUENCE: 27

Met Arg Gly Arg Val Ser Pro Leu Met Leu Leu Leu Gly Ile Leu Val
1               5                   10                  15

Leu Ala Ser Val Ser Ala Thr Gln Ala Lys Ser Pro Tyr Arg Lys Thr
            20                  25                  30

Glu Asn Pro Cys Ala Gln Arg Cys Leu Gln Ser Cys Gln Gln Glu Pro
        35                  40                  45

Asp Asp Leu Lys Gln Lys Ala Cys Glu Ser Arg Cys Thr Lys Leu Glu
    50                  55                  60

Tyr Asp Pro Arg Cys Val Tyr Asp Thr Gly Ala Thr Asn Gln Arg His
65                  70                  75                  80

Pro Pro Gly Glu Arg Thr Arg Gly Arg Gln Pro Gly Asp Tyr Asp Asp
                85                  90                  95
```

-continued

Asp Arg Arg Gln Pro Arg Arg Glu Glu Gly Gly Arg Trp Gly Pro Ala
            100                 105                 110

Glu Pro Arg Glu Arg Glu Glu Asp Trp Arg Gln Pro Arg Glu
            115                 120                 125

Asp Trp Arg Arg Pro Ser His Gln Gln Pro Arg Lys Ile Arg Pro Glu
130                 135                 140

Gly Arg Glu Gly Glu Gln Glu Trp Gly Thr Pro Gly Ser Glu Val Arg
145                 150                 155                 160

Glu Glu Thr Ser Arg Asn Asn Pro Phe Tyr Phe Pro Ser Arg Arg Phe
                165                 170                 175

Ser Thr Arg Tyr Gly Asn Gln Asn Gly Arg Ile Arg Val Leu Gln Arg
                180                 185                 190

Phe Asp Gln Arg Ser Lys Gln Phe Gln Asn Leu Gln Asn His Arg Ile
            195                 200                 205

Val Gln Ile Glu Ala Arg Pro Asn Thr Leu Val Leu Pro Lys His Ala
210                 215                 220

Asp Ala Asp Asn Ile Leu Val Ile Gln Gly Gln Ala Thr Val Thr
225                 230                 235                 240

Val Ala Asn Gly Asn Asn Arg Lys Ser Phe Asn Leu Asp Glu Gly His
                245                 250                 255

Ala Leu Arg Ile Pro Ser Gly Phe Ile Ser Tyr Ile Leu Asn Arg His
                260                 265                 270

Asp Asn Gln Asn Leu Arg Val Ala Lys Ile Ser Met Pro Val Asn Thr
            275                 280                 285

Pro Gly Gln Phe Glu Asp Phe Phe Pro Ala Ser Ser Arg Asp Gln Ser
290                 295                 300

Ser Tyr Leu Gln Gly Phe Ser Arg Asn Thr Leu Glu Ala Ala Phe Asn
305                 310                 315                 320

Ala Glu Phe Asn Glu Ile Arg Arg Val Leu Leu Glu Glu Asn Ala Gly
                325                 330                 335

Gly Glu Gln Glu Glu Arg Gly Gln Arg Arg Ser Thr Arg Ser Ser
                340                 345                 350

Asp Asn Glu Gly Val Ile Val Lys Val Ser Lys Glu His Val Gln Glu
            355                 360                 365

Leu Thr Lys His Ala Lys Ser Val Ser Lys Lys Gly Ser Glu Glu Glu
            370                 375                 380

Asp Ile Thr Asn Pro Ile Asn Leu Arg Asp Gly Glu Pro Asp Leu Ser
385                 390                 395                 400

Asn Asn Phe Gly Arg Leu Phe Glu Val Lys Pro Asp Lys Lys Asn Pro
                405                 410                 415

Gln Leu Gln Asp Leu Asp Met Met Leu Thr Cys Val Glu Ile Lys Glu
            420                 425                 430

Gly Ala Leu Met Leu Pro His Phe Asn Ser Lys Ala Met Val Ile Val
            435                 440                 445

Val Val Asn Lys Gly Thr Gly Asn Leu Glu Leu Val Ala Val Arg Lys
450                 455                 460

Glu Gln Gln Gln Arg Gly Arg Arg Glu Gln Glu Trp Glu Glu Glu
465                 470                 475                 480

Glu Asp Glu Glu Glu Gly Ser Asn Arg Glu Val Arg Arg Tyr Thr
                485                 490                 495

Ala Arg Leu Lys Glu Gly Asp Val Phe Ile Met Pro Ala Ala His Pro
            500                 505                 510

```
Val Ala Ile Asn Ala Ser Ser Glu Leu His Leu Leu Gly Phe Gly Ile
            515                 520                 525

Asn Ala Glu Asn Asn His Arg Ile Phe Leu Ala Gly Asp Lys Asp Asn
        530                 535                 540

Val Ile Asp Gln Ile Glu Lys Gln Ala Lys Asp Leu Ala Phe Pro Gly
545                 550                 555                 560

Ser Gly Glu Gln Val Glu Lys Leu Ile Lys Asn Gln Arg Glu Ser His
                565                 570                 575

Phe Val Ser Ala Arg Pro Gln Ser Gln Ser Pro Ser Ser Pro Glu Lys
                580                 585                 590

Glu Asp Gln Glu Glu Asn Gln Gly Gly Lys Gly Pro Leu Leu Ser
        595                 600                 605

Ile Leu Lys Ala Phe Asn
        610
```

<210> SEQ ID NO 28
<211> LENGTH: 626
<212> TYPE: PRT
<213> ORGANISM: Arachis hypogaea (Peanut)

<400> SEQUENCE: 28

```
Met Arg Gly Arg Val Ser Pro Leu Met Leu Leu Leu Gly Ile Leu Val
1               5                   10                  15

Leu Ala Ser Val Ser Ala Thr His Ala Lys Ser Ser Pro Tyr Gln Lys
                20                  25                  30

Lys Thr Glu Asn Pro Cys Ala Gln Arg Cys Leu Gln Ser Cys Gln Gln
            35                  40                  45

Glu Pro Asp Asp Leu Lys Gln Lys Ala Cys Glu Ser Arg Cys Thr Lys
        50                  55                  60

Leu Glu Tyr Asp Pro Arg Cys Val Tyr Asp Pro Arg Gly His Thr Gly
65                  70                  75                  80

Thr Thr Asn Gln Arg Ser Pro Pro Gly Glu Arg Thr Arg Gly Arg Gln
                85                  90                  95

Pro Gly Asp Tyr Asp Asp Asp Arg Arg Gln Pro Arg Arg Glu Glu Gly
            100                 105                 110

Gly Arg Trp Gly Pro Ala Gly Pro Arg Glu Arg Glu Arg Glu Glu Asp
        115                 120                 125

Trp Arg Gln Pro Arg Glu Asp Trp Arg Arg Pro Ser His Gln Gln Pro
130                 135                 140

Arg Lys Ile Arg Pro Glu Gly Arg Glu Gly Glu Gln Glu Trp Gly Thr
145                 150                 155                 160

Pro Gly Ser His Val Arg Glu Glu Thr Ser Arg Asn Asn Pro Phe Tyr
                165                 170                 175

Phe Pro Ser Arg Arg Phe Ser Thr Arg Tyr Gly Asn Gln Asn Gly Arg
            180                 185                 190

Ile Arg Val Leu Gln Arg Phe Asp Gln Arg Ser Arg Gln Phe Gln Asn
        195                 200                 205

Leu Gln Asn His Arg Ile Val Gln Ile Glu Ala Lys Pro Asn Thr Leu
    210                 215                 220

Val Leu Pro Lys His Ala Asp Ala Asp Asn Ile Leu Val Ile Gln Gln
225                 230                 235                 240

Gly Gln Ala Thr Val Thr Val Ala Asn Gly Asn Asn Arg Lys Ser Phe
                245                 250                 255

Asn Leu Asp Glu Gly His Ala Leu Arg Ile Pro Ser Gly Phe Ile Ser
            260                 265                 270
```

```
Tyr Ile Leu Asn Arg His Asp Asn Gln Asn Leu Arg Val Ala Lys Ile
            275                 280                 285

Ser Met Pro Val Asn Thr Pro Gly Gln Phe Glu Asp Phe Pro Ala
    290                 295                 300

Ser Ser Arg Asp Gln Ser Ser Tyr Leu Gln Gly Phe Ser Arg Asn Thr
305                 310                 315                 320

Leu Glu Ala Ala Phe Asn Ala Glu Phe Asn Glu Ile Arg Arg Val Leu
                325                 330                 335

Leu Glu Glu Asn Ala Gly Gly Glu Gln Glu Arg Gly Gln Arg Arg
            340                 345                 350

Trp Ser Thr Arg Ser Ser Glu Asn Asn Glu Gly Val Ile Val Lys Val
        355                 360                 365

Ser Lys Glu His Val Glu Glu Leu Thr Lys His Ala Lys Ser Val Ser
    370                 375                 380

Lys Lys Gly Ser Glu Glu Glu Gly Asp Ile Thr Asn Pro Ile Asn Leu
385                 390                 395                 400

Arg Glu Gly Glu Pro Asp Leu Ser Asn Asn Phe Gly Lys Leu Phe Glu
                405                 410                 415

Val Lys Pro Asp Lys Lys Asn Pro Gln Leu Gln Asp Leu Asp Met Met
            420                 425                 430

Leu Thr Cys Val Glu Ile Lys Glu Gly Ala Leu Met Leu Pro His Phe
        435                 440                 445

Asn Ser Lys Ala Met Val Ile Val Val Asn Lys Gly Thr Gly Asn
    450                 455                 460

Leu Glu Leu Val Ala Val Arg Lys Glu Gln Gln Gln Arg Gly Arg Arg
465                 470                 475                 480

Glu Glu Glu Glu Asp Glu Glu Glu Glu Gly Ser Asn Arg Glu
                485                 490                 495

Val Arg Arg Tyr Thr Ala Arg Leu Lys Glu Gly Asp Val Phe Ile Met
            500                 505                 510

Pro Ala Ala His Pro Val Ala Ile Asn Ala Ser Ser Glu Leu His Leu
        515                 520                 525

Leu Gly Phe Gly Ile Asn Ala Glu Asn Asn His Arg Ile Phe Leu Ala
    530                 535                 540

Gly Asp Lys Asp Asn Val Ile Asp Gln Ile Glu Lys Gln Ala Lys Asp
545                 550                 555                 560

Leu Ala Phe Pro Gly Ser Gly Glu Gln Val Glu Lys Leu Ile Lys Asn
                565                 570                 575

Gln Lys Glu Ser His Phe Val Ser Ala Arg Pro Gln Ser Gln Ser Gln
            580                 585                 590

Ser Pro Ser Ser Pro Glu Lys Glu Ser Pro Glu Lys Glu Asp Gln Glu
        595                 600                 605

Glu Glu Asn Gln Gly Gly Lys Gly Pro Leu Leu Ser Ile Leu Lys Ala
    610                 615                 620

Phe Asn
625

<210> SEQ ID NO 29
<211> LENGTH: 131
<212> TYPE: PRT
<213> ORGANISM: Arabidopsis thaliana (Mouse-ear cress)

<400> SEQUENCE: 29

Met Ser Trp Gln Ser Tyr Val Asp Asp His Leu Met Cys Asp Val Glu
```

-continued

```
                1               5                      10                     15
Gly Asn His Leu Thr Ala Ala Ile Leu Gly Gln Asp Gly Ser Val
                        20                      25                      30

Trp Ala Gln Ser Ala Lys Phe Pro Gln Leu Lys Pro Gln Glu Ile Asp
                        35                      40                      45

Gly Ile Lys Lys Asp Phe Glu Glu Pro Gly Phe Leu Ala Pro Thr Gly
                        50                      55                      60

Leu Phe Leu Gly Gly Glu Lys Tyr Met Val Ile Gln Gly Glu Gln Gly
65                              70                      75                      80

Ala Val Ile Arg Gly Lys Lys Gly Pro Gly Gly Val Thr Ile Lys Lys
                        85                      90                      95

Thr Asn Gln Ala Leu Val Phe Gly Phe Tyr Asp Glu Pro Met Thr Gly
                        100                     105                     110

Gly Gln Cys Asn Leu Val Val Glu Arg Leu Gly Asp Tyr Leu Ile Glu
                        115                     120                     125

Ser Glu Leu
        130

<210> SEQ ID NO 30
<211> LENGTH: 176
<212> TYPE: PRT
<213> ORGANISM: Aspergillus restrictus Aspergillus fumigatus

<400> SEQUENCE: 30

Met Val Ala Ile Lys Asn Leu Phe Leu Leu Ala Ala Thr Ala Val Ser
1               5                      10                      15

Val Leu Ala Ala Pro Ser Pro Leu Asp Ala Arg Ala Thr Trp Thr Cys
                        20                      25                      30

Ile Asn Gln Gln Leu Asn Pro Lys Thr Asn Lys Trp Glu Asp Lys Arg
                        35                      40                      45

Leu Leu Tyr Ser Gln Ala Lys Ala Glu Ser Asn Ser His His Ala Pro
                        50                      55                      60

Leu Ser Asp Gly Lys Thr Gly Ser Ser Tyr Pro His Trp Phe Thr Asn
65                              70                      75                      80

Gly Tyr Asp Gly Asn Gly Lys Leu Ile Lys Gly Arg Thr Pro Ile Lys
                        85                      90                      95

Phe Gly Lys Ala Asp Cys Asp Arg Pro Lys His Ser Gln Asn Gly
                        100                     105                     110

Met Gly Lys Asp Asp His Tyr Leu Leu Glu Phe Pro Thr Phe Pro Asp
                        115                     120                     125

Gly His Asp Tyr Lys Phe Asp Ser Lys Lys Pro Lys Glu Asp Pro Gly
                        130                     135                     140

Pro Ala Arg Val Ile Tyr Thr Tyr Pro Asn Lys Val Phe Cys Gly Ile
145                             150                     155                     160

Val Ala His Gln Arg Gly Asn Gln Gly Asp Leu Arg Leu Cys Ser His
                        165                     170                     175

<210> SEQ ID NO 31
<211> LENGTH: 310
<212> TYPE: PRT
<213> ORGANISM: Aspergillus fumigatus (Sartorya fumigata)

<400> SEQUENCE: 31

Met Ala Ala Leu Leu Arg Leu Ala Val Leu Leu Pro Leu Ala Ala Pro
1               5                      10                      15

Leu Val Ala Thr Leu Pro Thr Ser Pro Val Pro Ile Ala Ala Arg Ala
```

```
                    20                  25                  30
Thr Pro His Glu Pro Val Phe Phe Ser Trp Asp Ala Gly Ala Val Thr
             35                  40                  45

Ser Phe Pro Ile His Ser Ser Cys Asn Ala Thr Gln Arg Arg Gln Ile
 50                  55                  60

Glu Ala Gly Leu Asn Glu Ala Val Glu Leu Ala Arg His Ala Lys Ala
 65                  70                  75                  80

His Ile Leu Arg Trp Gly Asn Glu Ser Glu Ile Tyr Arg Lys Tyr Phe
                 85                  90                  95

Gly Asn Arg Pro Thr Met Glu Ala Val Gly Ala Tyr Asp Val Ile Val
             100                 105                 110

Asn Gly Asp Lys Ala Asn Val Leu Phe Arg Cys Asp Asn Pro Asp Gly
             115                 120                 125

Asn Cys Ala Leu Glu Gly Trp Gly Gly His Trp Arg Gly Ala Asn Ala
             130                 135                 140

Thr Ser Glu Thr Val Ile Cys Asp Arg Ser Tyr Thr Thr Arg Arg Trp
145                 150                 155                 160

Leu Val Ser Met Cys Ser Gln Gly Tyr Thr Val Ala Gly Ser Glu Thr
                 165                 170                 175

Asn Thr Phe Trp Ala Ser Asp Leu Met His Arg Leu Tyr His Val Pro
             180                 185                 190

Ala Val Gly Gln Gly Trp Val Asp His Phe Ala Asp Gly Tyr Asp Glu
             195                 200                 205

Val Ile Ala Leu Ala Lys Ser Asn Gly Thr Glu Ser Thr His Asp Ser
210                 215                 220

Glu Ala Phe Glu Tyr Phe Ala Leu Glu Ala Tyr Ala Phe Asp Ile Ala
225                 230                 235                 240

Ala Pro Gly Val Gly Cys Ala Gly Glu Ser His Gly Pro Asp Gln Gly
             245                 250                 255

His Asp Thr Gly Ser Ala Ser Ala Pro Ala Ser Thr Ser Thr Ser Ser
             260                 265                 270

Ser Ser Ser Gly Ser Gly Ser Gly Ala Thr Thr Thr Pro Thr Asp Ser
             275                 280                 285

Pro Ser Ala Thr Ile Asp Val Pro Ser Asn Cys His Thr His Glu Gly
             290                 295                 300

Gly Gln Leu His Cys Thr
305                 310

<210> SEQ ID NO 32
<211> LENGTH: 168
<212> TYPE: PRT
<213> ORGANISM: Aspergillus fumigatus (Sartorya fumigata)

<400> SEQUENCE: 32

Met Ser Gly Leu Lys Ala Gly Asp Ser Phe Pro Ser Asp Val Val Phe
  1               5                  10                  15

Ser Tyr Ile Pro Trp Ser Glu Asp Lys Gly Glu Ile Thr Ala Cys Gly
                 20                  25                  30

Ile Pro Ile Asn Tyr Asn Ala Ser Lys Glu Trp Ala Asp Lys Lys Val
             35                  40                  45

Ile Leu Phe Ala Leu Pro Gly Ala Phe Thr Pro Val Cys Ser Ala Arg
 50                  55                  60

His Val Pro Glu Tyr Ile Glu Lys Leu Pro Glu Ile Arg Ala Lys Gly
 65                  70                  75                  80
```

```
Val Asp Val Val Ala Val Leu Ala Tyr Asn Asp Ala Tyr Val Met Ser
            85                  90                  95

Ala Trp Gly Lys Ala Asn Gln Val Thr Gly Asp Asp Ile Leu Phe Leu
            100                 105                 110

Ser Asp Pro Asp Ala Arg Phe Ser Lys Ser Ile Gly Trp Ala Asp Glu
            115                 120                 125

Glu Gly Arg Thr Lys Arg Tyr Ala Leu Val Ile Asp His Gly Lys Ile
            130                 135                 140

Thr Tyr Ala Ala Leu Glu Pro Ala Lys Asn His Leu Glu Phe Ser Ser
145                 150                 155                 160

Ala Glu Thr Val Leu Lys His Leu
                165

<210> SEQ ID NO 33
<211> LENGTH: 152
<212> TYPE: PRT
<213> ORGANISM: Aspergillus fumigatus (Sartorya fumigata)

<400> SEQUENCE: 33

Met Lys Phe Thr Thr Pro Ile Ser Leu Ile Ser Leu Phe Val Ser Ser
1               5                   10                  15

Ala Leu Ala Ala Pro Thr Pro Glu Asn Glu Ala Arg Asp Ala Ile Pro
            20                  25                  30

Val Ser Val Ser Tyr Asp Pro Arg Tyr Asp Asn Ala Gly Thr Ser Met
            35                  40                  45

Asn Asp Val Ser Cys Ser Asn Gly Val Asn Gly Leu Val Thr Lys Trp
50                  55                  60

Pro Thr Phe Gly Ser Val Pro Gly Phe Ala Arg Ile Gly Gly Ala Pro
65                  70                  75                  80

Thr Ile Pro Gly Trp Asn Ser Pro Asn Cys Gly Lys Cys Tyr Lys Leu
            85                  90                  95

Gln Tyr Glu Gln Asn Thr Ile Tyr Val Thr Ala Ile Asp Ala Ala Pro
            100                 105                 110

Gly Gly Phe Asn Ile Ala Thr Ser Ala Met Asp Gln Leu Thr Asn Gly
            115                 120                 125

Met Ala Val Glu Leu Gly Arg Val Gln Ala Thr Tyr Glu Glu Ala Asp
            130                 135                 140

Pro Ser His Cys Ala Ser Gly Val
145                 150

<210> SEQ ID NO 34
<211> LENGTH: 159
<212> TYPE: PRT
<213> ORGANISM: Betula verrucosa (White birch) (Betula pendula)

<400> SEQUENCE: 34

Gly Val Phe Asn Tyr Glu Thr Glu Thr Thr Ser Val Ile Pro Ala Ala
1               5                   10                  15

Arg Leu Phe Lys Ala Phe Ile Leu Asp Gly Asp Asn Leu Phe Pro Lys
            20                  25                  30

Val Ala Pro Gln Ala Ile Ser Ser Val Glu Asn Ile Glu Gly Asn Gly
            35                  40                  45

Gly Pro Gly Thr Ile Lys Lys Ile Ser Phe Pro Glu Gly Phe Pro Phe
            50                  55                  60

Lys Tyr Val Lys Asp Arg Val Asp Glu Val Asp His Thr Asn Phe Lys
65                  70                  75                  80
```

```
Tyr Asn Tyr Ser Val Ile Glu Gly Gly Pro Ile Gly Asp Thr Leu Glu
                85                  90                  95

Lys Ile Ser Asn Glu Ile Lys Ile Val Ala Thr Pro Asp Gly Gly Ser
            100                 105                 110

Ile Leu Lys Ile Ser Asn Lys Tyr His Thr Lys Gly Asp His Glu Val
        115                 120                 125

Lys Ala Glu Gln Val Lys Ala Ser Lys Glu Met Gly Glu Thr Leu Leu
    130                 135                 140

Arg Ala Val Glu Ser Tyr Leu Leu Ala His Ser Asp Ala Tyr Asn
145                 150                 155

<210> SEQ ID NO 35
<211> LENGTH: 159
<212> TYPE: PRT
<213> ORGANISM: Betula verrucosa (White birch) (Betula pendula)

<400> SEQUENCE: 35

Gly Val Phe Asn Tyr Glu Ser Glu Thr Thr Ser Val Ile Pro Ala Ala
1               5                   10                  15

Arg Leu Phe Lys Ala Phe Ile Leu Glu Gly Asp Thr Leu Ile Pro Lys
            20                  25                  30

Val Ala Pro Gln Ala Ile Ser Ser Val Glu Asn Ile Glu Gly Asn Gly
        35                  40                  45

Gly Pro Gly Thr Ile Lys Lys Ile Thr Phe Pro Glu Gly Ser Pro Phe
    50                  55                  60

Lys Tyr Val Lys Glu Arg Val Asp Glu Val Asp His Ala Asn Phe Lys
65                  70                  75                  80

Tyr Ser Tyr Ser Met Ile Glu Gly Gly Ala Leu Gly Asp Thr Leu Glu
                85                  90                  95

Lys Ile Cys Asn Glu Ile Lys Ile Val Ala Thr Pro Asp Gly Gly Ser
            100                 105                 110

Ile Leu Lys Ile Ser Asn Lys Tyr His Thr Lys Gly Asp Gln Glu Met
        115                 120                 125

Lys Ala Glu His Met Lys Ala Ile Lys Glu Lys Gly Glu Ala Leu Leu
    130                 135                 140

Arg Ala Val Glu Ser Tyr Leu Leu Ala His Ser Asp Ala Tyr Asn
145                 150                 155

<210> SEQ ID NO 36
<211> LENGTH: 159
<212> TYPE: PRT
<213> ORGANISM: Betula verrucosa (White birch) (Betula pendula)

<400> SEQUENCE: 36

Gly Val Phe Asn Tyr Glu Ile Glu Thr Thr Ser Val Ile Pro Ala Ala
1               5                   10                  15

Arg Leu Phe Lys Ala Phe Ile Leu Asp Gly Asp Asn Leu Val Pro Lys
            20                  25                  30

Val Ala Pro Gln Ala Ile Ser Ser Val Glu Asn Ile Glu Gly Asn Gly
        35                  40                  45

Gly Pro Gly Thr Ile Lys Lys Ile Asn Phe Pro Glu Gly Phe Pro Phe
    50                  55                  60

Lys Tyr Val Lys Asp Arg Val Asp Glu Val Asp His Thr Asn Phe Lys
65                  70                  75                  80

Tyr Asn Tyr Ser Val Ile Glu Gly Gly Pro Val Gly Asp Thr Leu Glu
                85                  90                  95
```

```
Lys Ile Ser Asn Glu Ile Lys Ile Val Ala Thr Pro Asp Gly Gly Cys
                100                 105                 110

Val Leu Lys Ile Ser Asn Lys Tyr His Thr Lys Gly Asn His Glu Val
            115                 120                 125

Lys Ala Glu Gln Val Lys Ala Ser Lys Glu Met Gly Thr Leu Leu
        130                 135                 140

Arg Ala Val Glu Ser Tyr Leu Leu Ala His Ser Asp Ala Tyr Asn
145                 150                 155

<210> SEQ ID NO 37
<211> LENGTH: 159
<212> TYPE: PRT
<213> ORGANISM: Betula verrucosa (White birch) (Betula pendula)

<400> SEQUENCE: 37

Gly Val Phe Asn Tyr Glu Thr Glu Ala Thr Ser Val Ile Pro Ala Ala
1               5                   10                  15

Arg Leu Phe Lys Ala Phe Ile Leu Asp Gly Asp Asn Leu Phe Pro Lys
            20                  25                  30

Val Ala Pro Gln Ala Ile Ser Ser Val Glu Asn Ile Glu Gly Asn Gly
        35                  40                  45

Gly Pro Gly Thr Ile Lys Lys Ile Ser Phe Pro Glu Gly Ile Pro Phe
    50                  55                  60

Lys Tyr Val Lys Gly Arg Val Asp Glu Val Asp His Thr Asn Phe Lys
65                  70                  75                  80

Tyr Ser Tyr Ser Val Ile Glu Gly Gly Pro Val Gly Asp Thr Leu Glu
                85                  90                  95

Lys Ile Ser Asn Glu Ile Lys Ile Val Ala Thr Pro Asn Gly Gly Ser
                100                 105                 110

Ile Leu Lys Ile Asn Asn Lys Tyr His Thr Lys Gly Asp His Glu Val
            115                 120                 125

Lys Ala Glu Gln Ile Lys Ala Ser Lys Glu Met Gly Glu Thr Leu Leu
        130                 135                 140

Arg Ala Val Glu Ser Tyr Leu Leu Ala His Ser Asp Ala Tyr Asn
145                 150                 155

<210> SEQ ID NO 38
<211> LENGTH: 159
<212> TYPE: PRT
<213> ORGANISM: Betula verrucosa (White birch) (Betula pendula)

<400> SEQUENCE: 38

Gly Val Phe Asn Tyr Glu Ile Glu Ala Thr Ser Val Ile Pro Ala Ala
1               5                   10                  15

Arg Leu Phe Lys Ala Phe Ile Leu Asp Gly Asp Asn Leu Phe Pro Lys
            20                  25                  30

Val Ala Pro Gln Ala Ile Ser Ser Val Glu Asn Ile Glu Gly Asn Gly
        35                  40                  45

Gly Pro Gly Thr Ile Lys Lys Ile Ser Phe Pro Glu Gly Phe Pro Phe
    50                  55                  60

Lys Tyr Val Lys Asp Arg Val Asp Glu Val Asp His Thr Asn Phe Lys
65                  70                  75                  80

Tyr Ser Tyr Ser Val Ile Glu Gly Gly Pro Val Gly Asp Thr Leu Glu
                85                  90                  95

Lys Ile Ser Asn Glu Ile Lys Ile Val Ala Thr Pro Asn Gly Gly Ser
                100                 105                 110
```

```
Ile Leu Lys Ile Asn Asn Lys Tyr His Thr Lys Gly Asp His Glu Val
        115                 120                 125

Lys Ala Glu Gln Ile Lys Ala Ser Lys Glu Met Gly Glu Thr Leu Leu
130                 135                 140

Arg Ala Val Glu Ser Tyr Leu Leu Ala His Ser Asp Ala Tyr Asn
145                 150                 155

<210> SEQ ID NO 39
<211> LENGTH: 159
<212> TYPE: PRT
<213> ORGANISM: Betula verrucosa (White birch) (Betula pendula)

<400> SEQUENCE: 39

Gly Val Phe Asn Tyr Glu Ser Glu Thr Thr Ser Val Ile Pro Ala Ala
1               5                   10                  15

Arg Leu Phe Lys Ala Phe Ile Leu Glu Gly Asp Asn Leu Ile Pro Lys
            20                  25                  30

Val Ala Pro Gln Ala Ile Ser Ser Val Glu Asn Ile Glu Gly Asn Gly
        35                  40                  45

Gly Pro Gly Thr Ile Lys Lys Ile Asn Phe Pro Glu Gly Phe Pro Phe
    50                  55                  60

Lys Tyr Val Lys Asp Arg Val Asp Glu Val Asp His Thr Asn Phe Lys
65                  70                  75                  80

Tyr Asn Tyr Ser Val Ile Glu Gly Gly Pro Val Gly Asp Thr Leu Glu
                85                  90                  95

Lys Ile Ser Asn Glu Ile Lys Ile Val Ala Thr Pro Gly Gly Cys
            100                 105                 110

Val Leu Lys Ile Ser Asn Lys Tyr His Thr Lys Gly Asn His Glu Val
        115                 120                 125

Lys Ala Glu Gln Val Lys Ala Ser Lys Glu Met Gly Glu Thr Leu Leu
130                 135                 140

Arg Ala Val Glu Ser Tyr Leu Leu Ala His Ser Asp Ala Tyr Asn
145                 150                 155

<210> SEQ ID NO 40
<211> LENGTH: 159
<212> TYPE: PRT
<213> ORGANISM: Betula verrucosa (White birch) (Betula pendula)

<400> SEQUENCE: 40

Gly Val Phe Asn Tyr Glu Thr Glu Ala Thr Ser Val Ile Pro Ala Ala
1               5                   10                  15

Arg Leu Phe Lys Ala Phe Ile Leu Asp Gly Asp Asn Leu Phe Pro Lys
            20                  25                  30

Val Ala Pro Gln Ala Ile Ser Ser Val Glu Asn Ile Glu Gly Asn Gly
        35                  40                  45

Gly Pro Gly Thr Ile Lys Lys Ile Ser Phe Pro Glu Gly Phe Pro Phe
    50                  55                  60

Lys Tyr Val Lys Asp Arg Val Asp Glu Val Asp His Thr Asn Phe Lys
65                  70                  75                  80

Tyr Ser Tyr Ser Val Ile Glu Gly Gly Pro Val Gly Asp Thr Leu Glu
                85                  90                  95

Lys Ile Ser Asn Glu Ile Lys Ile Val Ala Thr Pro Asn Gly Gly Ser
            100                 105                 110

Ile Leu Lys Ile Asn Asn Lys Tyr His Thr Lys Gly Asp His Glu Val
        115                 120                 125
```

```
Lys Ala Glu Gln Ile Lys Ala Ser Lys Glu Met Gly Glu Thr Leu Leu
            130                 135                 140

Arg Ala Val Glu Ser Tyr Leu Leu Ala His Ser Asp Ala Tyr Asn
145                 150                 155
```

<210> SEQ ID NO 41
<211> LENGTH: 159
<212> TYPE: PRT
<213> ORGANISM: Betula verrucosa (White birch) (Betula pendula)

<400> SEQUENCE: 41

```
Gly Val Phe Asn Tyr Glu Ser Glu Thr Thr Ser Val Ile Pro Ala Ala
1               5                   10                  15

Arg Leu Phe Lys Ala Phe Ile Leu Glu Gly Asp Thr Leu Ile Pro Lys
            20                  25                  30

Val Ala Pro Gln Ala Ile Ser Ser Val Glu Asn Ile Glu Gly Asn Gly
            35                  40                  45

Gly Pro Gly Thr Ile Lys Lys Ile Thr Phe Pro Glu Gly Ser Pro Phe
        50                  55                  60

Lys Tyr Val Lys Glu Arg Val Asp Glu Val Asp His Ala Asn Phe Lys
65                  70                  75                  80

Tyr Ser Tyr Ser Met Ile Glu Gly Gly Ala Leu Gly Asp Thr Leu Glu
                85                  90                  95

Lys Ile Cys Asn Glu Ile Lys Ile Val Ala Thr Pro Asp Gly Gly Ser
            100                 105                 110

Ile Leu Lys Ile Ser Asn Lys Tyr His Thr Lys Gly Asp His Glu Met
            115                 120                 125

Lys Ala Glu His Met Lys Ala Ile Lys Glu Lys Gly Glu Ala Leu Leu
            130                 135                 140

Arg Ala Val Glu Ser Tyr Leu Leu Ala His Ser Asp Ala Tyr Asn
145                 150                 155
```

<210> SEQ ID NO 42
<211> LENGTH: 159
<212> TYPE: PRT
<213> ORGANISM: Betula verrucosa (White birch) (Betula pendula)

<400> SEQUENCE: 42

```
Gly Val Phe Asn Tyr Glu Thr Glu Ala Thr Ser Val Ile Pro Ala Ala
1               5                   10                  15

Arg Met Phe Lys Ala Phe Ile Leu Asp Gly Asp Lys Leu Val Pro Lys
            20                  25                  30

Val Ala Pro Gln Ala Ile Ser Ser Val Glu Asn Ile Glu Gly Asn Gly
            35                  40                  45

Gly Pro Gly Thr Ile Lys Lys Ile Asn Phe Pro Glu Gly Phe Pro Phe
        50                  55                  60

Lys Tyr Val Lys Asp Arg Val Asp Glu Val Asp His Thr Asn Phe Lys
65                  70                  75                  80

Tyr Asn Tyr Ser Val Ile Glu Gly Gly Pro Val Gly Asp Thr Leu Glu
                85                  90                  95

Lys Ile Ser Asn Glu Ile Lys Ile Val Ala Thr Pro Asp Gly Gly Cys
            100                 105                 110

Val Leu Lys Ile Ser Asn Lys Tyr His Thr Lys Gly Asn His Glu Val
            115                 120                 125

Lys Ala Glu Gln Val Lys Ala Ser Lys Glu Met Gly Glu Thr Leu Leu
            130                 135                 140
```

-continued

Arg Ala Val Glu Ser Tyr Leu Leu Ala His Ser Asp Ala Tyr Asn
145                 150                 155

<210> SEQ ID NO 43
<211> LENGTH: 159
<212> TYPE: PRT
<213> ORGANISM: Betula verrucosa (White birch) (Betula pendula)

<400> SEQUENCE: 43

Gly Val Phe Asn Tyr Glu Ser Glu Thr Thr Ser Val Ile Pro Ala Ala
1               5                   10                  15

Arg Leu Phe Lys Ala Phe Ile Leu Asp Gly Asp Asn Leu Ile Pro Lys
                20                  25                  30

Val Ala Pro Gln Ala Ile Ser Ser Val Glu Asn Ile Glu Gly Asn Gly
            35                  40                  45

Gly Pro Gly Thr Ile Lys Lys Ile Thr Phe Pro Glu Gly Ser Pro Phe
        50                  55                  60

Lys Tyr Val Lys Glu Arg Val Asp Glu Val Asp His Ala Asn Phe Lys
65                  70                  75                  80

Tyr Ser Tyr Ser Met Ile Glu Gly Gly Ala Leu Gly Asp Thr Leu Glu
                85                  90                  95

Lys Ile Cys Asn Glu Ile Lys Ile Val Ala Thr Pro Asp Gly Gly Ser
                100                 105                 110

Ile Leu Lys Ile Ser Asn Lys Tyr His Thr Lys Gly Asp His Glu Met
            115                 120                 125

Lys Ala Glu His Met Lys Ala Ile Lys Glu Lys Gly Glu Ala Leu Leu
        130                 135                 140

Arg Ala Val Glu Ser Tyr Leu Leu Ala His Ser Asp Ala Tyr Asn
145                 150                 155

<210> SEQ ID NO 44
<211> LENGTH: 133
<212> TYPE: PRT
<213> ORGANISM: Betula verrucosa (White birch) (Betula pendula)

<400> SEQUENCE: 44

Met Ser Trp Gln Thr Tyr Val Asp Glu His Leu Met Cys Asp Ile Asp
1               5                   10                  15

Gly Gln Ala Ser Asn Ser Leu Ala Ser Ala Ile Val Gly His Asp Gly
                20                  25                  30

Ser Val Trp Ala Gln Ser Ser Ser Phe Pro Gln Phe Lys Pro Gln Glu
            35                  40                  45

Ile Thr Gly Ile Met Lys Asp Phe Glu Glu Pro Gly His Leu Ala Pro
        50                  55                  60

Thr Gly Leu His Leu Gly Gly Ile Lys Tyr Met Val Ile Gln Gly Glu
65                  70                  75                  80

Ala Gly Ala Val Ile Arg Gly Lys Gly Ser Gly Gly Ile Thr Ile
                85                  90                  95

Lys Lys Thr Gly Gln Ala Leu Val Phe Gly Ile Tyr Glu Glu Pro Val
                100                 105                 110

Thr Pro Gly Gln Cys Asn Met Val Val Glu Arg Leu Gly Asp Tyr Leu
            115                 120                 125

Ile Asp Gln Gly Leu
        130

<210> SEQ ID NO 45
<211> LENGTH: 205

```
<212> TYPE: PRT
<213> ORGANISM: Betula verrucosa (White birch) (Betula pendula)

<400> SEQUENCE: 45

Met Pro Cys Ser Thr Glu Ala Met Glu Lys Ala Gly His Gly His Ala
1               5                   10                  15

Ser Thr Pro Arg Lys Arg Ser Leu Ser Asn Ser Ser Phe Arg Leu Arg
            20                  25                  30

Ser Glu Ser Leu Asn Thr Leu Arg Leu Arg Arg Ile Phe Asp Leu Phe
        35                  40                  45

Asp Lys Asn Ser Asp Gly Ile Ile Thr Val Asp Glu Leu Ser Arg Ala
    50                  55                  60

Leu Asn Leu Leu Gly Leu Glu Thr Asp Leu Ser Glu Leu Glu Ser Thr
65                  70                  75                  80

Val Lys Ser Phe Thr Arg Glu Gly Asn Ile Gly Leu Gln Phe Glu Asp
                85                  90                  95

Phe Ile Ser Leu His Gln Ser Leu Asn Asp Ser Tyr Phe Ala Tyr Gly
            100                 105                 110

Gly Glu Asp Glu Asp Asp Asn Glu Glu Asp Met Arg Lys Ser Ile Leu
        115                 120                 125

Ser Gln Glu Glu Ala Asp Ser Phe Gly Gly Phe Lys Val Phe Asp Glu
    130                 135                 140

Asp Gly Asp Gly Tyr Ile Ser Ala Arg Glu Leu Gln Met Val Leu Gly
145                 150                 155                 160

Lys Leu Gly Phe Ser Glu Gly Ser Glu Ile Asp Arg Val Glu Lys Met
                165                 170                 175

Ile Val Ser Val Asp Ser Asn Arg Asp Gly Arg Val Asp Phe Phe Glu
            180                 185                 190

Phe Lys Asp Met Met Arg Ser Val Leu Val Arg Ser Ser
        195                 200                 205

<210> SEQ ID NO 46
<211> LENGTH: 352
<212> TYPE: PRT
<213> ORGANISM: Blattella germanica (German cockroach)

<400> SEQUENCE: 46

Met Ile Gly Leu Lys Leu Val Thr Val Leu Phe Ala Val Ala Thr Ile
1               5                   10                  15

Thr His Ala Ala Glu Leu Gln Arg Val Pro Leu Tyr Lys Leu Val His
            20                  25                  30

Val Phe Ile Asn Thr Gln Tyr Ala Gly Ile Thr Lys Ile Gly Asn Gln
        35                  40                  45

Asn Phe Leu Thr Val Phe Asp Ser Thr Ser Cys Asn Val Val Val Ala
    50                  55                  60

Ser Gln Glu Cys Val Gly Gly Ala Cys Val Cys Pro Asn Leu Gln Lys
65                  70                  75                  80

Tyr Glu Lys Leu Lys Pro Lys Tyr Ile Ser Asp Gly Asn Val Gln Val
                85                  90                  95

Lys Phe Phe Asp Thr Gly Ser Ala Val Gly Arg Gly Ile Glu Asp Ser
            100                 105                 110

Leu Thr Ile Ser Asn Leu Thr Thr Ser Gln Gln Asp Ile Val Leu Ala
        115                 120                 125

Asp Glu Leu Ser Gln Glu Val Cys Ile Leu Ser Ala Asp Val Val Val
    130                 135                 140
```

```
Gly Ile Ala Ala Pro Gly Cys Pro Asn Ala Leu Lys Gly Lys Thr Val
145                 150                 155                 160

Leu Glu Asn Phe Val Glu Asn Leu Ile Ala Pro Val Phe Ser Ile
            165                 170                 175

His His Ala Arg Phe Gln Asp Gly Glu His Phe Gly Glu Ile Ile Phe
            180                 185                 190

Gly Gly Ser Asp Trp Lys Tyr Val Asp Gly Glu Phe Thr Tyr Val Pro
            195                 200                 205

Leu Val Gly Asp Asp Ser Trp Lys Phe Arg Leu Asp Gly Val Lys Ile
        210                 215                 220

Gly Asp Thr Thr Val Ala Pro Ala Gly Thr Gln Ala Ile Ile Asp Thr
225                 230                 235                 240

Ser Lys Ala Ile Ile Val Gly Pro Lys Ala Tyr Val Asn Pro Ile Asn
                245                 250                 255

Glu Ala Ile Gly Cys Val Val Glu Lys Thr Thr Thr Arg Arg Ile Cys
            260                 265                 270

Lys Leu Asp Cys Ser Lys Ile Pro Ser Leu Pro Asp Val Thr Phe Val
        275                 280                 285

Ile Asn Gly Arg Asn Phe Asn Ile Ser Ser Gln Tyr Tyr Ile Gln Gln
    290                 295                 300

Asn Gly Asn Leu Cys Tyr Ser Gly Phe Gln Pro Cys Gly His Ser Asp
305                 310                 315                 320

His Phe Phe Ile Gly Asp Phe Val Asp His Tyr Tyr Ser Glu Phe
                325                 330                 335

Asn Trp Glu Asn Lys Thr Met Gly Phe Gly Arg Ser Val Glu Ser Val
            340                 345                 350

<210> SEQ ID NO 47
<211> LENGTH: 182
<212> TYPE: PRT
<213> ORGANISM: Blattella germanica (German cockroach)

<400> SEQUENCE: 47

Ala Val Leu Ala Leu Cys Ala Thr Asp Thr Leu Ala Asn Glu Asp Cys
1               5                   10                  15

Phe Arg His Glu Ser Leu Val Pro Asn Leu Asp Tyr Glu Arg Phe Arg
            20                  25                  30

Gly Ser Trp Ile Ile Ala Ala Gly Thr Ser Glu Ala Leu Thr Gln Tyr
        35                  40                  45

Lys Cys Trp Ile Asp Arg Phe Ser Tyr Asp Asp Ala Leu Val Ser Lys
    50                  55                  60

Tyr Thr Asp Ser Gln Gly Lys Asn Arg Thr Thr Ile Arg Gly Arg Thr
65                  70                  75                  80

Lys Phe Glu Gly Asn Lys Phe Thr Ile Asp Tyr Asn Asp Lys Gly Lys
            85                  90                  95

Ala Phe Ser Ala Pro Tyr Ser Val Leu Ala Thr Asp Tyr Glu Asn Tyr
            100                 105                 110

Ala Ile Val Glu Gly Cys Pro Ala Ala Ala Asn Gly His Val Ile Tyr
        115                 120                 125

Val Gln Ile Arg Phe Ser Val Arg Arg Phe His Pro Lys Leu Gly Asp
    130                 135                 140

Lys Glu Met Ile Gln His Tyr Thr Leu Asp Gln Val Asn Gln His Lys
145                 150                 155                 160

Lys Ala Ile Glu Glu Asp Leu Lys His Phe Asn Leu Lys Tyr Glu Asp
                165                 170                 175
```

-continued

Leu His Ser Thr Cys His
            180

<210> SEQ ID NO 48
<211> LENGTH: 203
<212> TYPE: PRT
<213> ORGANISM: Blattella germanica (German cockroach)

<400> SEQUENCE: 48

Ala Pro Ser Tyr Lys Leu Thr Tyr Cys Pro Val Lys Ala Leu Gly Glu
1               5                   10                  15

Pro Ile Arg Phe Leu Leu Ser Tyr Gly Glu Lys Asp Phe Glu Asp Tyr
            20                  25                  30

Arg Phe Gln Glu Gly Asp Trp Pro Asn Leu Lys Pro Ser Met Pro Phe
        35                  40                  45

Gly Lys Thr Pro Val Leu Glu Ile Asp Gly Lys Gln Thr His Gln Ser
    50                  55                  60

Val Ala Ile Ser Arg Tyr Leu Gly Lys Gln Phe Gly Leu Ser Gly Lys
65                  70                  75                  80

Asp Asp Trp Glu Asn Leu Glu Ile Asp Met Ile Val Asp Thr Ile Ser
                85                  90                  95

Asp Phe Arg Ala Ala Ile Ala Asn Tyr His Tyr Asp Ala Asp Glu Asn
            100                 105                 110

Ser Lys Gln Lys Lys Trp Asp Pro Leu Lys Lys Glu Thr Ile Pro Tyr
        115                 120                 125

Tyr Thr Lys Lys Phe Asp Glu Val Val Lys Ala Asn Gly Gly Tyr Leu
    130                 135                 140

Ala Ala Gly Lys Leu Thr Trp Ala Asp Phe Tyr Phe Val Ala Ile Leu
145                 150                 155                 160

Asp Tyr Leu Asn His Met Ala Lys Glu Asp Leu Val Ala Asn Gln Pro
                165                 170                 175

Asn Leu Lys Ala Leu Arg Glu Lys Val Leu Gly Leu Pro Ala Ile Lys
            180                 185                 190

Ala Trp Val Ala Lys Arg Pro Pro Thr Asp Leu
        195                 200

<210> SEQ ID NO 49
<211> LENGTH: 144
<212> TYPE: PRT
<213> ORGANISM: Blomia tropicalis (Mite)

<400> SEQUENCE: 49

Met Lys Ser Val Leu Ile Phe Leu Val Ala Ile Ala Leu Phe Ser Ala
1               5                   10                  15

Asn Ile Val Ser Ala Asp Glu Gln Thr Thr Arg Gly Arg His Thr Glu
            20                  25                  30

Pro Asp Asp His His Glu Lys Pro Thr Thr Gln Cys Thr His Glu Glu
        35                  40                  45

Thr Thr Ser Thr Gln His His Glu Glu Val Thr Thr Gln Thr
    50                  55                  60

Pro His His Glu Glu Lys Thr Thr Glu Glu Thr His His Ser Asp
65                  70                  75                  80

Asp Leu Ile Val His Glu Gly Gly Lys Thr Tyr His Val Val Cys His
                85                  90                  95

Glu Glu Gly Pro Ile His Ile Gln Glu Met Cys Asn Lys Tyr Ile Ile
            100                 105                 110

```
Cys Ser Lys Ser Gly Ser Leu Trp Tyr Ile Thr Val Met Pro Cys Ser
            115                 120                 125

Ile Gly Thr Lys Phe Asp Pro Ile Ser Arg Asn Cys Val Leu Asp Asn
130                 135                 140
```

<210> SEQ ID NO 50
<211> LENGTH: 172
<212> TYPE: PRT
<213> ORGANISM: Bos taurus (Bovine)

<400> SEQUENCE: 50

```
Met Lys Ala Val Phe Leu Thr Leu Leu Phe Gly Leu Val Cys Thr Ala
  1               5                  10                  15

Gln Glu Thr Pro Ala Glu Ile Asp Pro Ser Lys Ile Pro Gly Glu Trp
             20                  25                  30

Arg Ile Ile Tyr Ala Ala Ala Asp Asn Lys Asp Lys Ile Val Glu Gly
         35                  40                  45

Gly Pro Leu Arg Asn Tyr Tyr Arg Arg Ile Glu Cys Ile Asn Asp Cys
     50                  55                  60

Glu Ser Leu Ser Ile Thr Phe Tyr Leu Lys Asp Gln Gly Thr Cys Leu
65                  70                  75                  80

Leu Leu Thr Glu Val Ala Lys Arg Gln Glu Gly Tyr Val Tyr Val Leu
                 85                  90                  95

Glu Phe Tyr Gly Thr Asn Thr Leu Glu Val Ile His Val Ser Glu Asn
            100                 105                 110

Met Leu Val Thr Tyr Val Glu Asn Tyr Asp Gly Glu Arg Ile Thr Lys
            115                 120                 125

Met Thr Glu Gly Leu Ala Lys Gly Thr Ser Phe Thr Pro Glu Glu Leu
        130                 135                 140

Glu Lys Tyr Gln Gln Leu Asn Ser Glu Arg Gly Val Pro Asn Glu Asn
145                 150                 155                 160

Ile Glu Asn Leu Ile Lys Thr Asp Asn Cys Pro Pro
                165                 170
```

<210> SEQ ID NO 51
<211> LENGTH: 178
<212> TYPE: PRT
<213> ORGANISM: Bos taurus (Bovine)

<400> SEQUENCE: 51

```
Met Lys Cys Leu Leu Leu Ala Leu Ala Leu Thr Cys Gly Ala Gln Ala
  1               5                  10                  15

Leu Ile Val Thr Gln Thr Met Lys Gly Leu Asp Ile Gln Lys Val Ala
             20                  25                  30

Gly Thr Trp Tyr Ser Leu Ala Met Ala Ala Ser Asp Ile Ser Leu Leu
         35                  40                  45

Asp Ala Gln Ser Ala Pro Leu Arg Val Tyr Val Glu Glu Leu Lys Pro
     50                  55                  60

Thr Pro Glu Gly Asp Leu Glu Ile Leu Leu Gln Lys Trp Glu Asn Gly
65                  70                  75                  80

Glu Cys Ala Gln Lys Lys Ile Ile Ala Glu Lys Thr Lys Ile Pro Ala
                 85                  90                  95

Val Phe Lys Ile Asp Ala Leu Asn Glu Asn Lys Val Leu Val Leu Asp
            100                 105                 110

Thr Asp Tyr Lys Lys Tyr Leu Leu Phe Cys Met Glu Asn Ser Ala Glu
            115                 120                 125
```

```
Pro Glu Gln Ser Leu Ala Cys Gln Cys Leu Val Arg Thr Pro Glu Val
            130                 135                 140

Asp Asp Glu Ala Leu Glu Lys Phe Asp Lys Ala Leu Lys Ala Leu Pro
145                 150                 155                 160

Met His Ile Arg Leu Ser Phe Asn Pro Thr Gln Leu Glu Glu Gln Cys
                165                 170                 175

His Ile

<210> SEQ ID NO 52
<211> LENGTH: 129
<212> TYPE: PRT
<213> ORGANISM: Brassica juncea (Leaf mustard) (Indian mustard)

<400> SEQUENCE: 52

Ala Gly Pro Phe Arg Phe Pro Arg Cys Arg Lys Glu Phe Gln Gln Ala
1               5                   10                  15

Gln His Leu Arg Ala Cys Gln Gln Trp Leu His Lys Gln Ala Met Gln
                20                  25                  30

Ser Gly Ser Gly Pro Gln Pro Gln Gly Pro Gln Gln Arg Pro Pro Leu
            35                  40                  45

Leu Gln Gln Cys Cys Asn Glu Leu His Gln Glu Pro Leu Cys Val
50                  55                  60

Cys Pro Thr Leu Lys Gly Ala Ser Lys Ala Val Lys Gln Gln Ile Arg
65                  70                  75                  80

Gln Gln Gly Gln Gln Gly Gln Gly Gln Gln Leu Gln His Glu
                85                  90                  95

Ile Ser Arg Ile Tyr Gln Thr Ala Thr His Leu Pro Arg Val Cys Asn
                100                 105                 110

Ile Pro Arg Val Ser Ile Cys Pro Phe Gln Lys Thr Met Pro Gly Pro
            115                 120                 125

Ser

<210> SEQ ID NO 53
<211> LENGTH: 350
<212> TYPE: PRT
<213> ORGANISM: Candida albicans (Yeast)

<400> SEQUENCE: 53

Met Ser Glu Gln Ile Pro Lys Thr Gln Lys Ala Val Val Phe Asp Thr
1               5                   10                  15

Asn Gly Gly Gln Leu Val Tyr Lys Asp Tyr Pro Val Pro Thr Pro Lys
                20                  25                  30

Pro Asn Glu Leu Leu Ile His Val Lys Tyr Ser Gly Val Cys His Thr
            35                  40                  45

Asp Leu His Ala Arg Lys Gly Asp Trp Pro Leu Ala Thr Lys Leu Pro
50                  55                  60

Leu Val Gly Gly His Glu Gly Ala Gly Val Val Val Gly Met Gly Glu
65                  70                  75                  80

Asn Val Lys Gly Trp Lys Ile Gly Asp Phe Ala Gly Ile Lys Trp Leu
                85                  90                  95

Asn Gly Ser Cys Met Ser Cys Glu Phe Cys Gln Gln Gly Ala Glu Pro
                100                 105                 110

Asn Cys Gly Glu Ala Asp Leu Ser Gly Tyr Thr His Asp Gly Ser Phe
            115                 120                 125

Glu Gln Tyr Ala Thr Ala Asp Ala Val Gln Ala Ala Lys Ile Pro Ala
```

-continued

```
            130                 135                 140
Gly Thr Asp Leu Ala Asn Val Ala Pro Ile Leu Cys Ala Gly Val Thr
145                 150                 155                 160

Val Tyr Lys Ala Leu Lys Thr Ala Asp Leu Ala Ala Gly Gln Trp Val
                165                 170                 175

Ala Ile Ser Gly Ala Gly Gly Leu Gly Ser Leu Ala Val Gln Tyr
            180                 185                 190

Ala Arg Ala Met Gly Leu Arg Val Val Ala Ile Asp Gly Gly Asp Glu
                195                 200                 205

Lys Gly Glu Phe Val Lys Ser Leu Gly Ala Glu Ala Tyr Val Asp Phe
210                 215                 220

Thr Lys Asp Lys Asp Ile Val Glu Ala Val Lys Lys Ala Thr Asp Gly
225                 230                 235                 240

Gly Pro His Gly Ala Ile Asn Val Ser Val Ser Glu Lys Ala Ile Asp
                    245                 250                 255

Gln Ser Val Glu Tyr Val Arg Pro Leu Gly Lys Val Val Leu Val Gly
                260                 265                 270

Leu Pro Ala His Ala Lys Val Thr Ala Pro Val Phe Asp Ala Val Val
            275                 280                 285

Lys Ser Ile Glu Ile Lys Gly Ser Tyr Val Gly Asn Arg Lys Asp Thr
290                 295                 300

Ala Glu Ala Ile Asp Phe Phe Ser Arg Gly Leu Ile Lys Cys Pro Ile
305                 310                 315                 320

Lys Ile Val Gly Leu Ser Asp Leu Pro Glu Val Phe Lys Leu Met Glu
                325                 330                 335

Glu Gly Lys Ile Leu Gly Arg Tyr Val Leu Asp Thr Ser Lys
            340                 345                 350

<210> SEQ ID NO 54
<211> LENGTH: 174
<212> TYPE: PRT
<213> ORGANISM: Canis familiaris (Dog)

<400> SEQUENCE: 54

Met Lys Thr Leu Leu Thr Ile Gly Phe Ser Leu Ile Ala Ile Leu
1               5                   10                  15

Gln Ala Gln Asp Thr Pro Ala Leu Gly Lys Asp Thr Val Ala Val Ser
                20                  25                  30

Gly Lys Trp Tyr Leu Lys Ala Met Thr Ala Asp Gln Glu Val Pro Glu
            35                  40                  45

Lys Pro Asp Ser Val Thr Pro Met Ile Leu Lys Ala Gln Lys Gly Gly
50                  55                  60

Asn Leu Glu Ala Lys Ile Thr Met Leu Thr Asn Gly Gln Cys Gln Asn
65                  70                  75                  80

Ile Thr Val Val Leu His Lys Thr Ser Glu Pro Gly Lys Tyr Thr Ala
                85                  90                  95

Tyr Glu Gly Gln Arg Val Val Phe Ile Gln Pro Ser Pro Val Arg Asp
            100                 105                 110

His Tyr Ile Leu Tyr Cys Glu Gly Glu Leu His Gly Arg Gln Ile Arg
        115                 120                 125

Met Ala Lys Leu Leu Gly Arg Asp Pro Glu Gln Ser Gln Glu Ala Leu
        130                 135                 140

Glu Asp Phe Arg Glu Phe Ser Arg Ala Lys Gly Leu Asn Gln Glu Ile
145                 150                 155                 160
```

```
Leu Glu Leu Ala Gln Ser Glu Thr Cys Ser Pro Gly Gly Gln
            165                 170
```

<210> SEQ ID NO 55
<211> LENGTH: 180
<212> TYPE: PRT
<213> ORGANISM: Canis familiaris (Dog)

<400> SEQUENCE: 55

```
Met Gln Leu Leu Leu Thr Val Gly Leu Ala Leu Ile Cys Gly Leu
 1               5                  10                  15

Gln Ala Gln Glu Gly Asn His Glu Glu Pro Gln Gly Gly Leu Glu Glu
                20                  25                  30

Leu Ser Gly Arg Trp His Ser Val Ala Leu Ala Ser Asn Lys Ser Asp
            35                  40                  45

Leu Ile Lys Pro Trp Gly His Phe Arg Val Phe Ile His Ser Met Ser
 50                  55                  60

Ala Lys Asp Gly Asn Leu His Gly Asp Ile Leu Ile Pro Gln Asp Gly
 65                  70                  75                  80

Gln Cys Glu Lys Val Ser Leu Thr Ala Phe Lys Thr Ala Thr Ser Asn
                85                  90                  95

Lys Phe Asp Leu Glu Tyr Trp Gly His Asn Asp Leu Tyr Leu Ala Glu
                100                 105                 110

Val Asp Pro Lys Ser Tyr Leu Ile Leu Tyr Met Ile Asn Gln Tyr Asn
            115                 120                 125

Asp Asp Thr Ser Leu Val Ala His Leu Met Val Arg Asp Leu Ser Arg
130                 135                 140

Gln Gln Asp Phe Leu Pro Ala Phe Glu Ser Val Cys Glu Asp Ile Gly
145                 150                 155                 160

Leu His Lys Asp Gln Ile Val Val Leu Ser Asp Asp Arg Cys Gln
                165                 170                 175

Gly Ser Arg Asp
            180
```

<210> SEQ ID NO 56
<211> LENGTH: 159
<212> TYPE: PRT
<213> ORGANISM: Carpinus betulus (Hornbeam)

<400> SEQUENCE: 56

```
Gly Val Phe Asn Tyr Glu Ala Glu Thr Pro Ser Val Ile Pro Ala Ala
 1               5                  10                  15

Arg Leu Phe Lys Ser Tyr Val Leu Asp Gly Asp Lys Leu Ile Pro Lys
                20                  25                  30

Val Ala Pro Gln Val Ile Ser Ser Val Glu Asn Val Gly Asn Gly
            35                  40                  45

Gly Pro Gly Thr Ile Lys Asn Ile Thr Phe Ala Glu Gly Ile Pro Phe
 50                  55                  60

Lys Phe Val Lys Glu Arg Val Asp Glu Val Asp Asn Ala Asn Phe Lys
 65                  70                  75                  80

Tyr Asn Tyr Thr Val Ile Glu Gly Asp Val Leu Gly Asp Lys Leu Glu
                85                  90                  95

Lys Val Ser His Glu Leu Lys Ile Val Ala Ala Pro Gly Gly Gly Ser
                100                 105                 110

Ile Val Lys Ile Ser Ser Lys Phe His Ala Lys Gly Tyr His Glu Val
            115                 120                 125
```

-continued

Asn Ala Glu Lys Met Lys Gly Ala Lys Glu Met Ala Glu Lys Leu Leu
    130                 135                 140

Arg Ala Val Glu Ser Tyr Leu Leu Ala His Thr Ala Glu Tyr Asn
145                 150                 155

<210> SEQ ID NO 57
<211> LENGTH: 159
<212> TYPE: PRT
<213> ORGANISM: Carpinus betulus (Hornbeam)

<400> SEQUENCE: 57

Gly Val Phe Asn Tyr Glu Ala Glu Thr Thr Ser Val Ile Pro Ala Ala
1               5                   10                  15

Arg Leu Phe Lys Ala Phe Ile Leu Asp Gly Asn Lys Leu Ile Pro Lys
            20                  25                  30

Val Ser Pro Gln Ala Val Ser Ser Val Glu Asn Val Glu Gly Asn Gly
        35                  40                  45

Gly Pro Gly Thr Ile Lys Lys Ile Thr Phe Ser Glu Gly Ser Pro Val
    50                  55                  60

Lys Tyr Val Lys Glu Arg Val Glu Glu Ile Asp His Thr Asn Phe Lys
65                  70                  75                  80

Tyr Asn Tyr Thr Val Ile Glu Gly Asp Val Leu Gly Asp Lys Leu Glu
                85                  90                  95

Lys Val Ser His Glu Leu Lys Ile Val Ala Ala Pro Gly Gly Gly Ser
            100                 105                 110

Ile Val Lys Ile Ser Ser Lys Phe His Ala Lys Gly Tyr His Glu Val
        115                 120                 125

Asn Ala Glu Glu Met Lys Gly Ala Lys Glu Met Ala Glu Lys Leu Leu
    130                 135                 140

Arg Ala Val Glu Ser Tyr Leu Leu Ala His Thr Ala Glu Tyr Asn
145                 150                 155

<210> SEQ ID NO 58
<211> LENGTH: 375
<212> TYPE: PRT
<213> ORGANISM: Chamaecyparis obtusa (Japanese cypress)

<400> SEQUENCE: 58

Met Ala Ser Cys Thr Leu Leu Ala Val Leu Val Phe Leu Cys Ala Ile
1               5                   10                  15

Val Ser Cys Phe Ser Asp Asn Pro Ile Asp Ser Cys Trp Arg Gly Asp
            20                  25                  30

Ala Asn Trp Asp Gln Asn Arg Met Lys Leu Ala Asp Cys Ala Val Gly
        35                  40                  45

Phe Gly Ser Ser Ala Met Gly Gly Lys Gly Gly Ala Phe Tyr Thr Val
    50                  55                  60

Thr Ser Ser Asp Asp Pro Val Asn Pro Ala Pro Gly Thr Leu Arg
65                  70                  75                  80

Tyr Gly Ala Thr Arg Glu Arg Ser Leu Trp Ile Ile Phe Ser Lys Asn
                85                  90                  95

Leu Asn Ile Lys Leu Asn Met Pro Leu Tyr Ile Ala Gly Asn Lys Thr
            100                 105                 110

Ile Asp Gly Arg Gly Ala Glu Val His Ile Gly Asn Gly Gly Pro Cys
        115                 120                 125

Leu Phe Met Arg Thr Val Ser His Val Ile Leu His Gly Leu Asn Ile
    130                 135                 140

```
His Gly Cys Asn Thr Ser Val Ser Gly Asn Val Leu Ile Ser Glu Ala
145                 150                 155                 160

Ser Gly Val Val Pro Val His Ala Gln Asp Gly Asp Ala Ile Thr Met
            165                 170                 175

Arg Asn Val Thr Asp Val Trp Ile Asp His Asn Ser Leu Ser Asp Ser
        180                 185                 190

Ser Asp Gly Leu Val Asp Val Thr Leu Ala Ser Thr Gly Val Thr Ile
    195                 200                 205

Ser Asn Asn His Phe Phe Asn His His Lys Val Met Leu Leu Gly His
210                 215                 220

Ser Asp Ile Tyr Ser Asp Asp Lys Ser Met Lys Val Thr Val Ala Phe
225                 230                 235                 240

Asn Gln Phe Gly Pro Asn Ala Gly Gln Arg Met Pro Arg Ala Arg Tyr
                245                 250                 255

Gly Leu Ile His Val Ala Asn Asn Tyr Asp Pro Trp Ser Ile Tyr
                260                 265                 270

Ala Ile Gly Gly Ser Ser Asn Pro Thr Ile Leu Ser Glu Gly Asn Ser
        275                 280                 285

Phe Thr Ala Pro Asn Asp Ser Asp Lys Lys Glu Val Thr Arg Arg Val
    290                 295                 300

Gly Cys Glu Ser Pro Ser Thr Cys Ala Asn Trp Val Trp Arg Ser Thr
305                 310                 315                 320

Gln Asp Ser Phe Asn Asn Gly Ala Tyr Phe Val Ser Ser Gly Lys Asn
                325                 330                 335

Glu Gly Thr Asn Ile Tyr Asn Asn Glu Ala Phe Lys Val Glu Asn
                340                 345                 350

Gly Ser Ala Ala Pro Gln Leu Thr Lys Asn Ala Gly Val Leu Thr Cys
        355                 360                 365

Ile Leu Ser Lys Pro Cys Ser
    370                 375

<210> SEQ ID NO 59
<211> LENGTH: 496
<212> TYPE: PRT
<213> ORGANISM: Cladosporium herbarum

<400> SEQUENCE: 59

Met Thr Ser Val Gln Leu Glu Thr Pro His Ser Gly Lys Tyr Glu Gln
1               5                   10                  15

Pro Thr Gly Leu Phe Ile Asn Asn Glu Phe Val Lys Gly Gln Glu Gly
            20                  25                  30

Lys Thr Phe Asp Val Ile Asn Pro Ser Asp Glu Ser Val Ile Thr Gln
        35                  40                  45

Val His Glu Ala Thr Glu Lys Asp Val Asp Ile Ala Val Ala Ala Ala
    50                  55                  60

Arg Gln Ala Phe Glu Gly Ser Trp Arg Leu Thr Pro Glu Asn Arg
65              70                  75                  80

Gly Lys Leu Leu Asn Asn Leu Ala Asn Leu Phe Glu Lys Asn Thr Asp
                85                  90                  95

Leu Leu Ala Ala Val Glu Ser Leu Asp Asn Gly Lys Ala Thr Ser Met
            100                 105                 110

Ala Arg Val Thr Ser Ala Cys Ala Ser Gly Cys Leu Arg Tyr Tyr Gly
        115                 120                 125

Gly Trp Ala Asp Lys Ile Thr Gly Lys Val Ile Asp Thr Thr Pro Asp
    130                 135                 140
```

```
Thr Phe Asn Tyr Val Lys Lys Glu Pro Ile Gly Val Cys Arg Ser Asp
145                 150                 155                 160

His Ser Leu Glu Leu Pro Leu Leu Met Trp Ala Trp Lys Ile Gly Pro
            165                 170                 175

Ala Ile Ala Cys Gly Asn Thr Val Val Leu Lys Thr Ala Glu Gln Thr
            180                 185                 190

Pro Leu Gly Gly Leu Val Ala Ala Ser Leu Val Lys Glu Ala Gly Phe
            195                 200                 205

Pro Pro Gly Val Ile Asn Val Ile Ser Gly Phe Gly Lys Val Ala Gly
210                 215                 220

Ala Ala Leu Ser Ser His Met Asp Val Asp Lys Val Ala Phe Thr Gly
225                 230                 235                 240

Ser Thr Val Val Gly Arg Thr Ile Leu Lys Ala Ala Ser Ser Asn
                245                 250                 255

Leu Lys Lys Val Thr Leu Glu Leu Gly Gly Lys Ser Pro Asn Ile Val
            260                 265                 270

Phe Glu Asp Ala Asp Ile Asp Asn Ala Ile Ser Trp Val Asn Phe Gly
275                 280                 285

Ile Phe Phe Asn His Gly Gln Cys Cys Cys Ala Gly Ser Arg Val Tyr
290                 295                 300

Val Gln Glu Ser Ile Tyr Asp Lys Phe Val Gln Lys Phe Lys Glu Arg
305                 310                 315                 320

Ala Gln Lys Asn Val Val Gly Asp Pro Phe Ala Ala Asp Thr Phe Gln
                325                 330                 335

Gly Pro Gln Val Ser Lys Val Gln Phe Asp Arg Ile Met Glu Tyr Ile
            340                 345                 350

Gln Ala Gly Lys Asp Ala Gly Ala Thr Val Glu Thr Gly Gly Ser Arg
            355                 360                 365

Lys Gly Asp Lys Gly Tyr Phe Ile Glu Pro Thr Ile Phe Ser Asn Val
370                 375                 380

Thr Glu Asp Met Lys Ile Val Lys Glu Ile Phe Gly Pro Val Cys
385                 390                 395                 400

Ser Ile Ala Lys Phe Lys Thr Lys Glu Asp Ala Ile Lys Leu Gly Asn
            405                 410                 415

Ala Ser Thr Tyr Gly Leu Ala Ala Val His Thr Lys Asn Leu Asn
            420                 425                 430

Thr Ala Ile Glu Val Ser Asn Ala Leu Lys Ala Gly Thr Val Trp Val
            435                 440                 445

Asn Thr Tyr Asn Thr Leu His His Gln Met Pro Phe Gly Gly Tyr Lys
450                 455                 460

Glu Ser Gly Ile Gly Arg Glu Leu Gly Glu Asp Ala Leu Ala Asn Tyr
465                 470                 475                 480

Thr Gln Thr Lys Thr Val Ser Ile Arg Leu Gly Asp Ala Leu Phe Gly
            485                 490                 495

<210> SEQ ID NO 60
<211> LENGTH: 111
<212> TYPE: PRT
<213> ORGANISM: Cladosporium herbarum

<400> SEQUENCE: 60

Met Lys Tyr Met Ala Ala Tyr Leu Leu Leu Gly Leu Ala Gly Asn Ser
 1               5                  10                  15

Ser Pro Ser Ala Glu Asp Ile Lys Thr Val Leu Ser Ser Val Gly Ile
```

-continued

```
                    20                  25                  30
Asp Ala Asp Glu Glu Arg Leu Ser Ser Leu Leu Lys Glu Leu Glu Gly
            35                  40                  45
Lys Asp Ile Asn Glu Leu Ile Ser Ser Gly Ser Gln Lys Leu Ala Ser
        50                  55                  60
Val Pro Ser Gly Ser Gly Ala Ala Pro Ser Ala Gly Gly Ala Ala
65                  70                  75                  80
Ala Ala Gly Gly Ala Thr Glu Ala Ala Pro Glu Ala Ala Lys Glu Glu
                85                  90                  95
Glu Lys Glu Glu Ser Asp Asp Met Gly Phe Gly Leu Phe Asp
            100                 105                 110

<210> SEQ ID NO 61
<211> LENGTH: 643
<212> TYPE: PRT
<213> ORGANISM: Cladosporium herbarum

<400> SEQUENCE: 61

Met Ala Pro Ala Ile Gly Ile Asp Leu Gly Thr Thr Tyr Ser Cys Val
1               5                   10                  15
Gly Ile Tyr Arg Asp Asp Arg Ile Glu Ile Ala Asn Asp Gln Gly
            20                  25                  30
Asn Arg Thr Thr Pro Ser Phe Val Ala Phe Thr Asp Thr Glu Arg Leu
        35                  40                  45
Ile Gly Asp Ser Ala Lys Asn Gln Val Ala Ile Asn Pro His Asn Thr
    50                  55                  60
Val Phe Asp Ala Lys Arg Leu Ile Gly Arg Lys Phe Gln Asp Ala Glu
65                  70                  75                  80
Val Gln Ala Asp Met Lys His Phe Pro Phe Lys Val Ile Glu Lys Ala
                85                  90                  95
Gly Lys Pro Val Thr Gln Val Glu Phe Lys Gly Glu Thr Lys Asp Phe
            100                 105                 110
Thr Pro Glu Glu Ile Ser Ser Met Ile Leu Thr Lys Met Arg Glu Thr
        115                 120                 125
Ala Glu Ser Tyr Leu Gly Gly Thr Val Asn Asn Ala Val Ile Thr Val
    130                 135                 140
Pro Ala Tyr Phe Asn Asp Ser Gln Arg Gln Ala Thr Lys Asp Ala Gly
145                 150                 155                 160
Leu Ile Ala Gly Leu Asn Val Leu Arg Ile Ile Asn Glu Pro Thr Ala
                165                 170                 175
Ala Ala Ile Ala Tyr Gly Leu Asp Lys Lys Gln Glu Gly Glu Lys Asn
            180                 185                 190
Val Leu Ile Phe Asp Leu Gly Gly Gly Thr Phe Asp Val Ser Phe Leu
        195                 200                 205
Thr Ile Glu Glu Gly Ile Phe Glu Val Lys Ser Thr Ala Gly Asp Thr
    210                 215                 220
His Leu Gly Gly Glu Asp Phe Asp Asn Arg Leu Val Asn His Phe Ser
225                 230                 235                 240
Asn Glu Phe Lys Arg Lys His Lys Lys Asp Leu Ser Asp Asn Ala Arg
                245                 250                 255
Ala Leu Arg Arg Leu Arg Thr Ala Cys Glu Arg Ala Lys Arg Thr Leu
            260                 265                 270
Ser Ser Ser Ala Gln Thr Ser Ile Glu Ile Asp Ser Leu Phe Glu Gly
        275                 280                 285
```

```
Ile Asp Phe Phe Thr Ser Asn Thr Arg Ala Arg Phe Glu Val Gly
    290                 295                 300

Gln Asp Leu Phe Arg Gly Asn Met Glu Pro Gly Glu Arg Thr Leu Arg
305                 310                 315                 320

Asp Asp Lys Ile Asp Lys Ser Ser Val His Glu Ile Val Leu Gly Gly
                325                 330                 335

Gly Ser Thr Arg Ile Pro Lys Val Gln Lys Leu Val Ser Asp Phe Phe
            340                 345                 350

Asn Gly Lys Glu Pro Cys Lys Ser Ile Asn Pro Asp Glu Ala Val Ala
        355                 360                 365

Tyr Gly Ala Ala Val Gln Ala Ala Ile Leu Ser Gly Asp Thr Ser Ser
370                 375                 380

Lys Ser Thr Lys Glu Ile Leu Leu Asp Val Ala Pro Leu Ser Leu
385                 390                 395                 400

Gly Ile Glu Thr Ala Gly Gly Val Met Thr Ala Leu Ile Lys Arg Asn
                405                 410                 415

Thr Thr Ile Pro Thr Lys Lys Ser Glu Thr Phe Ser Thr Phe Ser Asp
            420                 425                 430

Asn Gln Pro Gly Val Leu Ile Gln Val Phe Glu Gly Gly Arg Ala Arg
        435                 440                 445

Thr Lys Asp Ile Asn Leu Met Gly Lys Phe Glu Leu Ser Gly Ile Arg
450                 455                 460

Pro Ala Pro Arg Gly Val Pro Gln Ile Glu Val Thr Phe Asp Leu Asp
465                 470                 475                 480

Ala Asn Gly Ile Met Asn Val Ser Ala Leu Glu Lys Gly Thr Gly Lys
                485                 490                 495

Thr Asn Lys Ile Val Ile Thr Asn Asp Lys Gly Arg Leu Ser Lys Glu
            500                 505                 510

Glu Ile Glu Arg Met Leu Ala Asp Ala Glu Lys Tyr Lys Glu Glu Asp
        515                 520                 525

Glu Ala Glu Ala Gly Arg Ile Gln Ala Lys Asn Gly Leu Glu Ser Tyr
530                 535                 540

Ala Tyr Ser Leu Lys Asn Thr Val Ser Asp Pro Lys Val Glu Glu Lys
545                 550                 555                 560

Leu Ser Ala Glu Asp Lys Glu Thr Leu Thr Gly Ala Ile Asp Lys Thr
                565                 570                 575

Val Ala Trp Ile Asp Glu Asn Gln Thr Ala Thr Lys Glu Glu Tyr Glu
            580                 585                 590

Ala Glu Gln Lys Gln Leu Glu Ser Val Ala Asn Pro Val Met Met Lys
        595                 600                 605

Ile Tyr Gly Ala Glu Gly Gly Ala Pro Gly Gly Met Pro Gly Gln Gly
610                 615                 620

Ala Gly Ala Pro Pro Gly Ala Gly Asp Asp Gly Pro Thr Val Glu
625                 630                 635                 640

Glu Val Asp

<210> SEQ ID NO 62
<211> LENGTH: 112
<212> TYPE: PRT
<213> ORGANISM: Cladosporium herbarum

<400> SEQUENCE: 62

Met Lys Tyr Leu Ala Ala Phe Leu Leu Leu Gly Leu Ala Gly Asn Ser
1               5                   10                  15
```

-continued

```
Ser Pro Ser Ala Glu Asp Ile Lys Thr Val Leu Ser Ser Val Gly Ile
            20                  25                  30

Asp Ala Asp Glu Glu Arg Leu Ser Ser Leu Leu Lys Glu Leu Glu Gly
        35                  40                  45

Lys Asp Ile Asn Glu Leu Ile Ser Ser Gly Ser Glu Lys Leu Ala Ser
    50                  55                  60

Val Pro Ser Gly Gly Ala Gly Ala Ala Ser Ala Gly Gly Ala Ala Ala
65                  70                  75                  80

Ala Gly Gly Ala Ala Glu Ala Ala Pro Glu Ala Glu Arg Ala Glu Glu
                85                  90                  95

Glu Lys Glu Glu Ser Asp Asp Asp Met Gly Phe Gly Leu Phe Asp Glx
            100                 105                 110
```

<210> SEQ ID NO 63
<211> LENGTH: 204
<212> TYPE: PRT
<213> ORGANISM: Cladosporium herbarum

<400> SEQUENCE: 63

```
Met Ala Pro Lys Ile Ala Ile Ile Phe Tyr Ser Thr Trp Gly His Val
 1               5                  10                  15

Gln Thr Leu Ala Glu Ala Glu Ala Lys Gly Ile Arg Glu Ala Gly Gly
            20                  25                  30

Ser Val Asp Leu Tyr Arg Val Pro Glu Thr Leu Thr Gln Glu Val Leu
        35                  40                  45

Thr Lys Met His Ala Pro Pro Lys Asp Asp Ser Ile Pro Glu Ile Thr
    50                  55                  60

Asp Pro Phe Ile Leu Glu Gln Tyr Asp Arg Phe Pro His Gly His Pro
65                  70                  75                  80

Thr Arg Tyr Gly Asn Phe Pro Ala Gln Trp Arg Thr Phe Trp Asp Arg
                85                  90                  95

Thr Gly Gly Gln Trp Gln Thr Gly Ala Phe Trp Gly Lys Tyr Ala Gly
            100                 105                 110

Leu Phe Ile Ser Thr Gly Thr Gln Gly Gly Gly Gln Glu Ser Thr Ala
        115                 120                 125

Leu Ala Ala Met Ser Thr Leu Ser His His Gly Ile Ile Tyr Val Pro
    130                 135                 140

Leu Gly Tyr Lys Thr Thr Phe His Leu Leu Gly Asp Asn Ser Glu Val
145                 150                 155                 160

Arg Gly Ala Ala Val Trp Gly Ala Gly Thr Phe Ser Gly Gly Asp Gly
                165                 170                 175

Ser Arg Gln Pro Ser Gln Lys Glu Leu Glu Leu Thr Ala Gln Gly Lys
            180                 185                 190

Ala Phe Tyr Glu Ala Val Ala Lys Val Asn Phe Gln
        195                 200
```

<210> SEQ ID NO 64
<211> LENGTH: 440
<212> TYPE: PRT
<213> ORGANISM: Cladosporium herbarum

<400> SEQUENCE: 64

```
Met Pro Ile Ser Lys Ile His Ser Arg Tyr Val Tyr Asp Ser Arg Gly
 1               5                  10                  15

Asn Pro Thr Val Glu Val Asp Ile Val Thr Glu Thr Gly Leu His Arg
            20                  25                  30
```

-continued

```
Ala Ile Val Pro Ser Gly Ala Ser Thr Gly Ser His Glu Ala Cys Glu
            35                  40                  45

Leu Arg Asp Gly Asp Lys Ser Lys Trp Ala Gly Lys Gly Val Thr Lys
        50                  55                  60

Ala Val Ala Asn Val Asn Glu Ile Ile Ala Pro Ala Leu Ile Lys Glu
65                  70                  75                  80

Asn Leu Asp Val Lys Asp Gln Ala Ala Val Asp Ala Phe Leu Asn Lys
                85                  90                  95

Leu Asp Gly Thr Thr Asn Lys Thr Lys Ile Gly Ala Asn Ala Ile Leu
            100                 105                 110

Gly Val Ser Met Ala Val Ala Lys Ala Ala Ala Glu Lys Arg Val
        115                 120                 125

Pro Leu Tyr Ala His Ile Ser Asp Leu Ser Gly Thr Lys Lys Pro Phe
        130                 135                 140

Val Leu Pro Val Pro Phe Met Asn Val Val Asn Gly Gly Ser His Ala
145                 150                 155                 160

Gly Gly Arg Leu Ala Phe Gln Glu Phe Met Ile Val Pro Ser Gly Ala
                165                 170                 175

Pro Ser Phe Thr Glu Ala Met Arg Gln Gly Ala Glu Val Tyr Gln Lys
            180                 185                 190

Leu Lys Ser Leu Thr Lys Lys Arg Tyr Gly Gln Ser Ala Gly Asn Val
        195                 200                 205

Gly Asp Glu Gly Gly Val Ala Pro Asp Ile Gln Thr Ala Glu Glu Ala
        210                 215                 220

Leu Asp Leu Ile Thr Asp Ala Ile Glu Glu Ala Gly Tyr Thr Gly Gln
225                 230                 235                 240

Ile Lys Ile Ala Met Asp Val Ala Ser Ser Glu Phe Tyr Lys Ala Asp
                245                 250                 255

Glu Lys Lys Tyr Asp Leu Asp Phe Lys Asn Pro Asp Ser Asp Lys Ser
            260                 265                 270

Lys Trp Ile Thr Tyr Glu Gln Leu Ala Asp Gln Tyr Lys Gln Leu Ala
        275                 280                 285

Ala Lys Tyr Pro Ile Val Ser Ile Glu Asp Pro Phe Ala Glu Asp Asp
        290                 295                 300

Trp Glu Ala Trp Ser Tyr Phe Tyr Lys Thr Ser Gly Ser Asp Phe Gln
305                 310                 315                 320

Ile Val Gly Asp Asp Leu Thr Val Thr Asn Pro Glu Phe Ile Lys Lys
                325                 330                 335

Ala Ile Glu Thr Lys Ala Cys Asn Ala Leu Leu Leu Lys Val Asn Gln
            340                 345                 350

Ile Gly Thr Ile Thr Glu Ala Ile Asn Ala Ala Lys Asp Ser Phe Ala
        355                 360                 365

Ala Gly Trp Gly Val Met Val Ser His Arg Ser Gly Glu Thr Glu Asp
        370                 375                 380

Val Thr Ile Ala Asp Ile Val Val Gly Leu Arg Ala Gly Gln Ile Lys
385                 390                 395                 400

Thr Gly Ala Pro Ala Arg Ser Glu Arg Leu Ala Lys Leu Asn Gln Ile
                405                 410                 415

Leu Arg Ile Glu Glu Glu Leu Gly Asp Lys Ala Val Tyr Ala Gly Asp
            420                 425                 430

Asn Phe Arg Thr Ala Ile Asn Leu
        435                 440
```

-continued

<210> SEQ ID NO 65
<211> LENGTH: 110
<212> TYPE: PRT
<213> ORGANISM: Cladosporium herbarum

<400> SEQUENCE: 65

```
Met Ser Ala Ala Glu Leu Ala Ser Ser Tyr Ala Ala Leu Ile Leu Ala
 1               5                  10                  15

Asp Glu Gly Leu Glu Ile Thr Ala Asp Lys Leu Gln Ala Leu Ile Ser
            20                  25                  30

Ala Ala Lys Val Pro Glu Ile Glu Pro Ile Trp Thr Ser Leu Phe Ala
        35                  40                  45

Lys Ala Leu Glu Gly Lys Asp Val Lys Asp Leu Leu Leu Asn Val Gly
    50                  55                  60

Ser Gly Gly Gly Ala Ala Pro Ala Ala Gly Gly Ala Ala Ala Gly Gly
65                  70                  75                  80

Ala Ala Ala Val Leu Asp Ala Pro Ala Glu Glu Lys Ala Glu Glu Glu
                85                  90                  95

Lys Glu Glu Ser Asp Asp Asp Met Gly Phe Gly Leu Phe Asp
            100                 105                 110
```

<210> SEQ ID NO 66
<211> LENGTH: 159
<212> TYPE: PRT
<213> ORGANISM: Corylus avellana (European hazel)

<400> SEQUENCE: 66

```
Gly Val Phe Asn Tyr Glu Val Glu Thr Pro Ser Val Ile Pro Ala Ala
 1               5                  10                  15

Arg Leu Phe Lys Ser Tyr Val Leu Asp Gly Asp Lys Leu Ile Pro Lys
            20                  25                  30

Val Ala Pro Gln Ala Ile Thr Ser Val Glu Asn Val Glu Gly Asn Gly
        35                  40                  45

Gly Pro Gly Thr Ile Lys Asn Ile Thr Phe Gly Glu Gly Ser Arg Tyr
    50                  55                  60

Lys Tyr Val Lys Glu Arg Val Asp Glu Val Asp Asn Thr Asn Phe Thr
65                  70                  75                  80

Tyr Ser Tyr Thr Val Ile Glu Gly Asp Val Leu Gly Asp Lys Leu Glu
                85                  90                  95

Lys Val Cys His Glu Leu Lys Ile Val Ala Ala Pro Gly Gly Gly Ser
            100                 105                 110

Ile Leu Lys Ile Ser Ser Lys Phe His Ala Lys Gly Asp His Glu Ile
        115                 120                 125

Asn Ala Glu Glu Met Lys Gly Ala Lys Glu Met Ala Glu Lys Leu Leu
    130                 135                 140

Arg Ala Val Glu Thr Tyr Leu Leu Ala His Ser Ala Glu Tyr Asn
145                 150                 155
```

<210> SEQ ID NO 67
<211> LENGTH: 346
<212> TYPE: PRT
<213> ORGANISM: Cupressus arizonica

<400> SEQUENCE: 67

```
Asp Asn Pro Ile Asp Ser Cys Trp Arg Gly Asp Ser Asn Trp Asp Gln
 1               5                  10                  15

Asn Arg Met Lys Leu Ala Asp Cys Val Val Gly Phe Gly Ser Ser Thr
            20                  25                  30
```

```
Met Gly Gly Lys Gly Gly Glu Ile Tyr Thr Val Thr Ser Ser Glu Asp
            35                  40                  45

Asn Pro Val Asn Pro Thr Pro Gly Thr Leu Arg Tyr Gly Ala Thr Arg
 50                  55                  60

Glu Lys Ala Leu Trp Ile Ile Phe Ser Gln Asn Met Asn Ile Lys Leu
 65                  70                  75                  80

Gln Met Pro Leu Tyr Val Ala Gly Tyr Lys Thr Ile Asp Gly Arg Gly
                 85                  90                  95

Ala Val Val His Leu Gly Asn Gly Gly Pro Cys Leu Phe Met Arg Lys
                100                 105                 110

Ala Ser His Val Ile Leu His Gly Leu His Ile His Gly Cys Asn Thr
            115                 120                 125

Ser Val Leu Gly Asp Val Leu Val Ser Glu Ser Ile Gly Val Glu Pro
130                 135                 140

Val His Ala Gln Asp Gly Asp Ala Ile Thr Met Arg Asn Val Thr Asn
145                 150                 155                 160

Ala Trp Ile Asp His Asn Ser Leu Ser Asp Cys Ser Asp Gly Leu Ile
                165                 170                 175

Asp Val Thr Leu Gly Ser Thr Gly Ile Thr Ile Ser Asn Asn His Phe
                180                 185                 190

Phe Asn His His Lys Val Met Leu Leu Gly His Asp Asp Thr Tyr Asp
            195                 200                 205

Asp Asp Lys Ser Met Lys Val Thr Val Ala Phe Asn Gln Phe Gly Pro
210                 215                 220

Asn Ala Gly Gln Arg Met Pro Arg Ala Arg Tyr Gly Leu Val His Val
225                 230                 235                 240

Ala Asn Asn Asn Tyr Asp Gln Trp Asn Ile Tyr Ala Ile Gly Gly Ser
                245                 250                 255

Ser Asn Pro Thr Ile Leu Ser Glu Gly Asn Ser Phe Thr Ala Pro Asn
            260                 265                 270

Glu Ser Tyr Lys Lys Glu Val Thr Lys Arg Ile Gly Cys Glu Thr Thr
            275                 280                 285

Ser Ala Cys Ala Asn Trp Val Trp Arg Ser Thr Arg Asp Ala Phe Thr
290                 295                 300

Asn Gly Ala Tyr Phe Val Ser Ser Gly Lys Ala Glu Asp Thr Asn Ile
305                 310                 315                 320

Tyr Asn Ser Asn Glu Ala Phe Lys Val Glu Asn Gly Asn Ala Ala Pro
                325                 330                 335

Gln Leu Thr Gln Asn Ala Gly Val Val Ala
            340                 345

<210> SEQ ID NO 68
<211> LENGTH: 374
<212> TYPE: PRT
<213> ORGANISM: Cryptomeria japonica (Japanese cedar)

<400> SEQUENCE: 68

Met Asp Ser Pro Cys Leu Val Ala Leu Leu Val Leu Ser Phe Val Ile
 1               5                  10                  15

Gly Ser Cys Phe Ser Asp Asn Pro Ile Asp Ser Cys Trp Arg Gly Asp
                20                  25                  30

Ser Asn Trp Ala Gln Asn Arg Met Lys Leu Ala Asp Cys Ala Val Gly
            35                  40                  45

Phe Gly Ser Ser Thr Met Gly Gly Lys Gly Gly Asp Leu Tyr Thr Val
```

```
                50                  55                  60
Thr Asn Ser Asp Asp Pro Val Asn Pro Ala Pro Gly Thr Leu Arg
 65                  70                  75                  80

Tyr Gly Ala Thr Arg Asp Arg Pro Leu Trp Ile Ile Phe Ser Gly Asn
                 85                  90                  95

Met Asn Ile Lys Leu Lys Met Pro Met Tyr Ile Ala Gly Tyr Lys Thr
                100                 105                 110

Phe Asp Gly Arg Gly Ala Gln Val Tyr Ile Gly Asn Gly Gly Pro Cys
                115                 120                 125

Val Phe Ile Lys Arg Val Ser Asn Val Ile Ile His Gly Leu His Leu
130                 135                 140

Tyr Gly Cys Ser Thr Ser Val Leu Gly Asn Val Leu Ile Asn Glu Ser
145                 150                 155                 160

Phe Gly Val Glu Pro Val His Pro Gln Asp Gly Asp Ala Leu Thr Leu
                165                 170                 175

Arg Thr Ala Thr Asn Ile Trp Ile Asp His Asn Ser Phe Ser Asn Ser
                180                 185                 190

Ser Asp Gly Leu Val Asp Val Thr Leu Ser Ser Thr Gly Val Thr Ile
                195                 200                 205

Ser Asn Asn Leu Phe Phe Asn His His Lys Val Met Leu Leu Gly His
210                 215                 220

Asp Asp Ala Tyr Ser Asp Asp Lys Ser Met Lys Val Thr Val Ala Phe
225                 230                 235                 240

Asn Gln Phe Gly Pro Asn Cys Gly Gln Arg Met Pro Arg Ala Arg Tyr
                245                 250                 255

Gly Leu Val His Val Ala Asn Asn Asn Tyr Asp Pro Trp Thr Ile Tyr
                260                 265                 270

Ala Ile Gly Gly Ser Ser Asn Pro Thr Ile Leu Ser Glu Gly Asn Ser
                275                 280                 285

Phe Thr Ala Pro Asn Glu Ser Tyr Lys Lys Gln Val Thr Ile Arg Ile
                290                 295                 300

Gly Cys Lys Thr Ser Ser Ser Cys Ser Asn Trp Val Trp Gln Ser Thr
305                 310                 315                 320

Gln Asp Val Phe Tyr Asn Gly Ala Tyr Phe Val Ser Ser Gly Lys Tyr
                325                 330                 335

Glu Gly Gly Asn Ile Tyr Thr Lys Lys Glu Ala Phe Asn Val Glu Asn
                340                 345                 350

Gly Asn Ala Thr Pro Gln Leu Thr Lys Asn Ala Gly Val Leu Thr Cys
                355                 360                 365

Ser Leu Ser Lys Arg Cys
    370

<210> SEQ ID NO 69
<211> LENGTH: 514
<212> TYPE: PRT
<213> ORGANISM: Cryptomeria japonica (Japanese cedar)

<400> SEQUENCE: 69

Met Ala Met Lys Phe Ile Ala Pro Met Ala Phe Val Ala Met Gln Leu
 1               5                  10                  15

Ile Ile Met Ala Ala Ala Glu Asp Gln Ser Ala Gln Ile Met Leu Asp
                20                  25                  30

Ser Asp Ile Glu Gln Tyr Leu Arg Ser Asn Arg Ser Leu Arg Lys Val
                35                  40                  45
```

```
Glu His Ser Arg His Asp Ala Ile Asn Ile Phe Asn Val Glu Lys Tyr
 50                  55                  60

Gly Ala Val Gly Asp Gly Lys His Asp Cys Thr Glu Ala Phe Ser Thr
 65                  70                  75                  80

Ala Trp Gln Ala Ala Cys Lys Lys Pro Ser Ala Met Leu Leu Val Pro
                 85                  90                  95

Gly Asn Lys Lys Phe Val Val Asn Asn Leu Phe Phe Asn Gly Pro Cys
            100                 105                 110

Gln Pro His Phe Thr Phe Lys Val Asp Gly Ile Ile Ala Ala Tyr Gln
        115                 120                 125

Asn Pro Ala Ser Trp Lys Asn Arg Ile Trp Leu Gln Phe Ala Lys
    130                 135                 140

Leu Thr Gly Phe Thr Leu Met Gly Lys Gly Val Ile Asp Gly Gln Gly
145                 150                 155                 160

Lys Gln Trp Trp Ala Gly Gln Cys Lys Trp Val Asn Gly Arg Glu Ile
                165                 170                 175

Cys Asn Asp Arg Asp Arg Pro Thr Ala Ile Lys Phe Asp Phe Ser Thr
            180                 185                 190

Gly Leu Ile Ile Gln Gly Leu Lys Leu Met Asn Ser Pro Glu Phe His
        195                 200                 205

Leu Val Phe Gly Asn Cys Glu Gly Val Lys Ile Ile Gly Ile Ser Ile
    210                 215                 220

Thr Ala Pro Arg Asp Ser Pro Asn Thr Asp Gly Ile Asp Ile Phe Ala
225                 230                 235                 240

Ser Lys Asn Phe His Leu Gln Lys Asn Thr Ile Gly Thr Gly Asp Asp
                245                 250                 255

Cys Val Ala Ile Gly Thr Gly Ser Ser Asn Ile Val Ile Glu Asp Leu
            260                 265                 270

Ile Cys Gly Pro Gly His Gly Ile Ser Ile Gly Ser Leu Gly Arg Glu
        275                 280                 285

Asn Ser Arg Ala Glu Val Ser Tyr Val His Val Asn Gly Ala Lys Phe
    290                 295                 300

Ile Asp Thr Gln Asn Gly Leu Arg Ile Lys Thr Trp Gln Gly Gly Ser
305                 310                 315                 320

Gly Met Ala Ser His Ile Ile Tyr Glu Asn Val Glu Met Ile Asn Ser
                325                 330                 335

Glu Asn Pro Ile Leu Ile Asn Gln Phe Tyr Cys Thr Ser Ala Ser Ala
            340                 345                 350

Cys Gln Asn Gln Arg Ser Ala Val Gln Ile Gln Asp Val Thr Tyr Lys
        355                 360                 365

Asn Ile Arg Gly Thr Ser Ala Thr Ala Ala Ala Ile Gln Leu Lys Cys
    370                 375                 380

Ser Asp Ser Met Pro Cys Lys Asp Ile Lys Leu Ser Asp Ile Ser Leu
385                 390                 395                 400

Lys Leu Thr Ser Gly Lys Ile Ala Ser Cys Leu Asn Asp Asn Ala Asn
                405                 410                 415

Gly Tyr Phe Ser Gly His Val Ile Pro Ala Cys Lys Asn Leu Ser Pro
            420                 425                 430

Ser Ala Lys Arg Lys Glu Ser Lys Ser His Lys His Pro Lys Thr Val
        435                 440                 445

Met Val Lys Asn Met Gly Ala Tyr Asp Lys Gly Asn Arg Thr Arg Ile
    450                 455                 460

Leu Leu Gly Ser Arg Pro Pro Asn Cys Thr Asn Lys Cys His Gly Cys
```

```
                         465                 470                 475                 480
Ser Pro Cys Lys Ala Lys Leu Val Ile Val His Arg Ile Met Pro Gln
                        485                 490                 495

Glu Tyr Tyr Pro Gln Arg Trp Met Cys Ser Arg His Gly Lys Ile Tyr
                500                 505                 510

His Pro

<210> SEQ ID NO 70
<211> LENGTH: 131
<212> TYPE: PRT
<213> ORGANISM: Cynodon dactylon (Bermuda grass)

<400> SEQUENCE: 70

Met Ser Trp Gln Ala Tyr Val Asp Asp His Leu Met Cys Glu Ile Glu
  1               5                  10                  15

Gly His His Leu Thr Ser Ala Ala Ile Ile Gly His Asp Gly Thr Val
                 20                  25                  30

Trp Ala Gln Ser Ala Ala Phe Pro Ala Phe Lys Pro Glu Glu Met Ala
             35                  40                  45

Asn Ile Met Lys Asp Phe Asp Glu Pro Gly Phe Leu Ala Pro Thr Gly
         50                  55                  60

Leu Phe Leu Gly Pro Thr Lys Tyr Met Val Ile Gln Gly Glu Pro Gly
 65                  70                  75                  80

Ala Val Ile Arg Gly Lys Lys Gly Ser Gly Gly Val Thr Val Lys Lys
                 85                  90                  95

Thr Gly Gln Ala Leu Val Ile Gly Ile Tyr Asp Glu Pro Met Thr Pro
            100                 105                 110

Gly Gln Cys Asn Met Val Ile Glu Lys Leu Gly Asp Tyr Leu Ile Glu
        115                 120                 125

Gln Gly Met
        130

<210> SEQ ID NO 71
<211> LENGTH: 36
<212> TYPE: PRT
<213> ORGANISM: Dactylis glomerata(Orchard grass)(Cocksfoot grass)

<400> SEQUENCE: 71

Glu Ala Pro Val Thr Phe Thr Val Glu Lys Gly Ser Asp Glu Lys Asn
  1               5                  10                  15

Leu Ala Leu Ser Ile Lys Tyr Asn Lys Glu Gly Asp Ser Met Ala Glu
                 20                  25                  30

Val Glu Leu Lys
         35

<210> SEQ ID NO 72
<211> LENGTH: 154
<212> TYPE: PRT
<213> ORGANISM: Daucus carota (Carrot)

<400> SEQUENCE: 72

Met Gly Ala Gln Ser His Ser Leu Glu Ile Thr Ser Ser Val Ser Ala
  1               5                  10                  15

Glu Lys Ile Phe Ser Gly Ile Val Leu Asp Val Asp Thr Val Ile Pro
                 20                  25                  30

Lys Ala Ala Pro Gly Ala Tyr Lys Ser Val Glu Val Lys Gly Asp Gly
             35                  40                  45
```

```
Gly Ala Gly Thr Val Arg Ile Ile Thr Leu Pro Glu Gly Ser Pro Ile
 50                  55                  60

Thr Ser Met Thr Val Arg Thr Asp Ala Val Asn Lys Glu Ala Leu Thr
 65                  70                  75                  80

Tyr Asp Ser Thr Val Ile Asp Gly Asp Ile Leu Leu Gly Phe Ile Glu
                 85                  90                  95

Ser Ile Glu Thr His Leu Val Val Pro Thr Ala Asp Gly Gly Ser
            100                 105                 110

Ile Thr Lys Thr Thr Ala Ile Phe His Thr Lys Gly Asp Ala Val Val
            115                 120                 125

Pro Glu Glu Asn Ile Lys Phe Ala Asp Ala Gln Asn Thr Ala Leu Phe
130                 135                 140

Lys Ala Ile Glu Ala Tyr Leu Ile Ala Asn
145                 150

<210> SEQ ID NO 73
<211> LENGTH: 321
<212> TYPE: PRT
<213> ORGANISM: Dermatophagoides farinae (House-dust mite)

<400> SEQUENCE: 73

Met Lys Phe Val Leu Ala Ile Ala Ser Leu Leu Val Leu Ser Thr Val
 1               5                  10                  15

Tyr Ala Arg Pro Ala Ser Ile Lys Thr Phe Glu Glu Phe Lys Lys Ala
            20                  25                  30

Phe Asn Lys Asn Tyr Ala Thr Val Glu Glu Glu Val Ala Arg Lys
        35                  40                  45

Asn Phe Leu Glu Ser Leu Lys Tyr Val Glu Ala Asn Lys Gly Ala Ile
 50                  55                  60

Asn His Leu Ser Asp Leu Ser Leu Asp Glu Phe Lys Asn Arg Tyr Leu
 65                  70                  75                  80

Met Ser Ala Glu Ala Phe Glu Gln Leu Lys Thr Gln Phe Asp Leu Asn
                 85                  90                  95

Ala Glu Thr Ser Ala Cys Arg Ile Asn Ser Val Asn Val Pro Ser Glu
            100                 105                 110

Leu Asp Leu Arg Ser Leu Arg Thr Val Thr Pro Ile Arg Met Gln Gly
            115                 120                 125

Gly Cys Gly Ser Cys Trp Ala Phe Ser Gly Val Ala Ala Thr Glu Ser
130                 135                 140

Ala Tyr Leu Ala Tyr Arg Asn Thr Ser Leu Asp Leu Ser Glu Gln Glu
145                 150                 155                 160

Leu Val Asp Cys Ala Ser Gln His Gly Cys His Gly Asp Thr Ile Pro
                165                 170                 175

Arg Gly Ile Glu Tyr Ile Gln Gln Asn Gly Val Val Glu Glu Arg Ser
            180                 185                 190

Tyr Pro Tyr Val Ala Arg Glu Gln Arg Cys Arg Arg Pro Asn Ser Gln
        195                 200                 205

His Tyr Gly Ile Ser Asn Tyr Cys Gln Ile Tyr Pro Pro Asp Val Lys
    210                 215                 220

Gln Ile Arg Glu Ala Leu Thr Gln Thr His Thr Ala Ile Ala Val Ile
225                 230                 235                 240

Ile Gly Ile Lys Asp Leu Arg Ala Phe Gln His Tyr Asp Gly Arg Thr
                245                 250                 255

Ile Ile Gln His Asp Asn Gly Tyr Gln Pro Asn Tyr His Ala Val Asn
            260                 265                 270
```

```
Ile Val Gly Tyr Gly Ser Thr Gln Gly Asp Asp Tyr Trp Ile Val Arg
            275                 280                 285

Asn Ser Trp Asp Thr Thr Trp Gly Asp Ser Gly Tyr Gly Tyr Phe Gln
            290                 295                 300

Ala Gly Asn Asn Leu Met Met Ile Glu Gln Tyr Pro Tyr Val Val Ile
305                 310                 315                 320

Met

<210> SEQ ID NO 74
<211> LENGTH: 146
<212> TYPE: PRT
<213> ORGANISM: Dermatophagoides farinae (House-dust mite)

<400> SEQUENCE: 74

Met Ile Ser Lys Ile Leu Cys Leu Ser Leu Leu Val Ala Ala Val Val
1               5                   10                  15

Ala Asp Gln Val Asp Val Lys Asp Cys Ala Asn Asn Glu Ile Lys Lys
            20                  25                  30

Val Met Val Asp Gly Cys His Gly Ser Asp Pro Cys Ile Ile His Arg
        35                  40                  45

Gly Lys Pro Phe Thr Leu Glu Ala Leu Phe Asp Ala Asn Gln Asn Thr
    50                  55                  60

Lys Thr Ala Lys Ile Glu Ile Lys Ala Ser Leu Asp Gly Leu Glu Ile
65                  70                  75                  80

Asp Val Pro Gly Ile Asp Thr Asn Ala Cys His Phe Met Lys Cys Pro
                85                  90                  95

Leu Val Lys Gly Gln Gln Tyr Asp Ile Lys Tyr Thr Trp Asn Val Pro
            100                 105                 110

Lys Ile Ala Pro Lys Ser Glu Asn Val Val Val Thr Val Lys Leu Ile
        115                 120                 125

Gly Asp Asn Gly Val Leu Ala Cys Ala Ile Ala Thr His Gly Lys Ile
    130                 135                 140

Arg Asp
145

<210> SEQ ID NO 75
<211> LENGTH: 259
<212> TYPE: PRT
<213> ORGANISM: Dermatophagoides farinae (House-dust mite)

<400> SEQUENCE: 75

Met Met Ile Leu Thr Ile Val Val Leu Leu Ala Ala Asn Ile Leu Ala
1               5                   10                  15

Thr Pro Ile Leu Pro Ser Ser Pro Asn Ala Thr Ile Val Gly Gly Val
            20                  25                  30

Lys Ala Gln Ala Gly Asp Cys Pro Tyr Gln Ile Ser Leu Gln Ser Ser
            35                  40                  45

Ser His Phe Cys Gly Gly Ser Ile Leu Asp Glu Tyr Trp Ile Leu Thr
    50                  55                  60

Ala Ala His Cys Val Asn Gly Gln Ser Ala Lys Lys Leu Ser Ile Arg
65                  70                  75                  80

Tyr Asn Thr Leu Lys His Ala Ser Gly Gly Glu Lys Ile Gln Val Ala
                85                  90                  95

Glu Ile Tyr Gln His Glu Asn Tyr Asp Ser Met Thr Ile Asp Asn Asp
            100                 105                 110
```

```
Val Ala Leu Ile Lys Leu Lys Thr Pro Met Thr Leu Asp Gln Thr Asn
        115                 120                 125

Ala Lys Pro Val Pro Leu Pro Ala Gln Gly Ser Asp Val Lys Val Gly
130                 135                 140

Asp Lys Ile Arg Val Ser Gly Trp Gly Tyr Leu Gln Glu Gly Ser Tyr
145                 150                 155                 160

Ser Leu Pro Ser Glu Leu Gln Arg Val Asp Ile Asp Val Val Ser Arg
                165                 170                 175

Glu Gln Cys Asp Gln Leu Tyr Ser Lys Ala Gly Ala Asp Val Ser Glu
            180                 185                 190

Asn Met Ile Cys Gly Gly Asp Val Ala Asn Gly Gly Val Asp Ser Cys
        195                 200                 205

Gln Gly Asp Ser Gly Gly Pro Val Val Asp Val Ala Thr Lys Gln Ile
210                 215                 220

Val Gly Ile Val Ser Trp Gly Tyr Gly Cys Ala Arg Lys Gly Tyr Pro
225                 230                 235                 240

Gly Val Tyr Thr Arg Val Gly Asn Phe Val Asp Trp Ile Glu Ser Lys
                245                 250                 255

Arg Ser Gln

<210> SEQ ID NO 76
<211> LENGTH: 20
<212> TYPE: PRT
<213> ORGANISM: Dermatophagoides farinae (House-dust mite)

<400> SEQUENCE: 76

Ala Val Gly Gly Gln Asp Ala Asp Leu Ala Glu Ala Pro Phe Gln Ile
1               5                   10                  15

Ser Leu Leu Lys
            20

<210> SEQ ID NO 77
<211> LENGTH: 213
<212> TYPE: PRT
<213> ORGANISM: Dermatophagoides farinae (House-dust mite)

<400> SEQUENCE: 77

Met Met Lys Phe Leu Leu Ile Ala Ala Val Ala Phe Val Ala Val Ser
1               5                   10                  15

Ala Asp Pro Ile His Tyr Asp Lys Ile Thr Glu Glu Ile Asn Lys Ala
            20                  25                  30

Ile Asp Asp Ala Ile Ala Ala Ile Glu Gln Ser Glu Thr Ile Asp Pro
        35                  40                  45

Met Lys Val Pro Asp His Ala Asp Lys Phe Glu Arg His Val Gly Ile
    50                  55                  60

Val Asp Phe Lys Gly Glu Leu Ala Met Arg Asn Ile Glu Ala Arg Gly
65                  70                  75                  80

Leu Lys Gln Met Lys Arg Gln Gly Asp Ala Asn Val Lys Gly Glu Glu
                85                  90                  95

Gly Ile Val Lys Ala His Leu Leu Ile Gly Val His Asp Asp Ile Val
            100                 105                 110

Ser Met Glu Tyr Asp Leu Ala Tyr Lys Leu Gly Asp Leu His Pro Thr
        115                 120                 125

Thr His Val Ile Ser Asp Ile Gln Asp Phe Val Ala Leu Ser Leu
    130                 135                 140

Glu Ile Ser Asp Glu Gly Asn Ile Thr Met Thr Ser Phe Glu Val Arg
```

```
145                 150                 155                 160
Gln Phe Ala Asn Val Val Asn His Ile Gly Gly Leu Ser Ile Leu Asp
                165                 170                 175
Pro Ile Phe Gly Val Leu Ser Asp Val Leu Thr Ala Ile Phe Gln Asp
            180                 185                 190
Thr Val Arg Lys Glu Met Thr Lys Val Leu Ala Pro Ala Phe Lys Arg
        195                 200                 205
Glu Leu Glu Lys Asn
    210

<210> SEQ ID NO 78
<211> LENGTH: 30
<212> TYPE: PRT
<213> ORGANISM: Dermatophagoides microceras (House-dust mite)

<400> SEQUENCE: 78

Thr Gln Ala Cys Arg Ile Asn Ser Gly Asn Val Pro Ser Glu Leu Asp
1               5                   10                  15
Leu Arg Ser Leu Arg Thr Val Thr Pro Ile Arg Met Gln Gly
            20                  25                  30

<210> SEQ ID NO 79
<211> LENGTH: 320
<212> TYPE: PRT
<213> ORGANISM: Dermatophagoides pteronyssinus (House-dust mite)

<400> SEQUENCE: 79

Met Lys Ile Val Leu Ala Ile Ala Ser Leu Leu Ala Leu Ser Ala Val
1               5                   10                  15
Tyr Ala Arg Pro Ser Ser Ile Lys Thr Phe Glu Glu Tyr Lys Lys Ala
            20                  25                  30
Phe Asn Lys Ser Tyr Ala Thr Phe Glu Asp Glu Glu Ala Ala Arg Lys
        35                  40                  45
Asn Phe Leu Glu Ser Val Lys Tyr Val Gln Ser Asn Gly Gly Ala Ile
    50                  55                  60
Asn His Leu Ser Asp Leu Ser Leu Asp Glu Phe Lys Asn Arg Phe Leu
65                  70                  75                  80
Met Ser Ala Glu Ala Phe Glu His Leu Lys Thr Gln Phe Asp Leu Asn
                85                  90                  95
Ala Glu Thr Asn Ala Cys Ser Ile Asn Gly Asn Ala Pro Ala Glu Ile
            100                 105                 110
Asp Leu Arg Gln Met Arg Thr Val Thr Pro Ile Arg Met Gln Gly Gly
        115                 120                 125
Cys Gly Ser Cys Trp Ala Phe Ser Gly Val Ala Ala Thr Glu Ser Ala
    130                 135                 140
Tyr Leu Ala Tyr Arg Asn Gln Ser Leu Asp Leu Ala Glu Gln Glu Leu
145                 150                 155                 160
Val Asp Cys Ala Ser Gln His Gly Cys His Gly Asp Thr Ile Pro Arg
                165                 170                 175
Gly Ile Glu Tyr Ile Gln His Asn Gly Val Val Gln Glu Ser Tyr Tyr
            180                 185                 190
Arg Tyr Val Ala Arg Glu Gln Ser Cys Arg Arg Pro Asn Ala Gln Arg
        195                 200                 205
Phe Gly Ile Ser Asn Tyr Cys Gln Ile Tyr Pro Pro Asn Val Asn Lys
    210                 215                 220
Ile Arg Glu Ala Leu Ala Gln Thr His Ser Ala Ile Ala Val Ile Ile
```

```
                225                 230                 235                 240
Gly Ile Lys Asp Leu Asp Ala Phe Arg His Tyr Asp Gly Arg Thr Ile
                245                 250                 255
Ile Gln Arg Asp Asn Gly Tyr Gln Pro Asn Tyr His Ala Val Asn Ile
                260                 265                 270
Val Gly Tyr Ser Asn Ala Gln Gly Val Asp Tyr Trp Ile Val Arg Asn
                275                 280                 285
Ser Trp Asp Thr Asn Trp Gly Asp Asn Gly Tyr Gly Tyr Phe Ala Ala
                290                 295                 300
Asn Ile Asp Leu Met Met Ile Glu Glu Tyr Pro Tyr Val Val Ile Leu
305                 310                 315                 320

<210> SEQ ID NO 80
<211> LENGTH: 146
<212> TYPE: PRT
<213> ORGANISM: Dermatophagoides pteronyssinus (House-dust mite)

<400> SEQUENCE: 80

Met Met Tyr Lys Ile Leu Cys Leu Ser Leu Leu Val Ala Ala Val Ala
1               5                   10                  15
Arg Asp Gln Val Asp Val Lys Asp Cys Ala Asn His Glu Ile Lys Lys
                20                  25                  30
Val Leu Val Pro Gly Cys His Gly Ser Glu Pro Cys Ile Ile His Arg
            35                  40                  45
Gly Lys Pro Phe Gln Leu Glu Ala Val Phe Glu Ala Asn Gln Asn Thr
        50                  55                  60
Lys Thr Ala Lys Ile Glu Ile Lys Ala Ser Ile Asp Gly Leu Glu Val
65                  70                  75                  80
Asp Val Pro Gly Ile Asp Pro Asn Ala Cys His Tyr Met Lys Cys Pro
                85                  90                  95
Leu Val Lys Gly Gln Gln Tyr Asp Ile Lys Tyr Thr Trp Asn Val Pro
            100                 105                 110
Lys Ile Ala Pro Lys Ser Glu Asn Val Val Thr Val Lys Val Met
        115                 120                 125
Gly Asp Asp Gly Val Leu Ala Cys Ala Ile Ala Thr His Ala Lys Ile
    130                 135                 140
Arg Asp
145

<210> SEQ ID NO 81
<211> LENGTH: 261
<212> TYPE: PRT
<213> ORGANISM: Dermatophagoides pteronyssinus (House-dust mite)

<400> SEQUENCE: 81

Met Ile Ile Tyr Asn Ile Leu Ile Val Leu Leu Leu Ala Ile Asn Thr
1               5                   10                  15
Leu Ala Asn Pro Ile Leu Pro Ala Ser Pro Asn Ala Thr Ile Val Gly
                20                  25                  30
Gly Glu Lys Ala Leu Ala Gly Glu Cys Pro Tyr Gln Ile Ser Leu Gln
            35                  40                  45
Ser Ser Ser His Phe Cys Gly Gly Thr Ile Leu Asp Glu Tyr Trp Ile
        50                  55                  60
Leu Thr Ala Ala His Cys Val Ala Gly Gln Thr Ala Ser Lys Leu Ser
65                  70                  75                  80
Ile Arg Tyr Asn Ser Leu Lys His Ser Leu Gly Gly Glu Lys Ile Ser
```

```
                85                  90                  95
Val Ala Lys Ile Phe Ala His Glu Lys Tyr Asp Ser Tyr Gln Ile Asp
            100                 105                 110

Asn Asp Ile Ala Leu Ile Lys Leu Lys Ser Pro Met Lys Leu Asn Gln
            115                 120                 125

Lys Asn Ala Lys Ala Val Gly Leu Pro Ala Lys Gly Ser Asp Val Lys
        130                 135                 140

Val Gly Asp Gln Val Arg Val Ser Gly Trp Gly Tyr Leu Glu Glu Gly
145                 150                 155                 160

Ser Tyr Ser Leu Pro Ser Glu Leu Arg Arg Val Asp Ile Ala Val Val
                165                 170                 175

Ser Arg Lys Glu Cys Asn Glu Leu Tyr Ser Lys Ala Asn Ala Glu Val
            180                 185                 190

Thr Asp Asn Met Ile Cys Gly Gly Asp Val Ala Asn Gly Gly Lys Asp
            195                 200                 205

Ser Cys Gln Gly Asp Ser Gly Gly Pro Val Val Asp Val Lys Asn Asn
        210                 215                 220

Gln Val Val Gly Ile Val Ser Trp Gly Tyr Gly Cys Ala Arg Lys Gly
225                 230                 235                 240

Tyr Pro Gly Val Tyr Thr Arg Val Gly Asn Phe Ile Asp Trp Ile Glu
                245                 250                 255

Ser Lys Arg Ser Gln
            260

<210> SEQ ID NO 82
<211> LENGTH: 19
<212> TYPE: PRT
<213> ORGANISM: Dermatophagoides pteronyssinus (House-dust mite)
<220> FEATURE:
<221> NAME/KEY: UNSURE
<222> LOCATION: 3, 16
<223> OTHER INFORMATION: Xaa = any amino acid

<400> SEQUENCE: 82

Lys Tyr Xaa Asn Pro His Phe Ile Gly Xaa Arg Ser Val Ile Thr Xaa
1               5                   10                  15

Leu Met Glu

<210> SEQ ID NO 83
<211> LENGTH: 132
<212> TYPE: PRT
<213> ORGANISM: Dermatophagoides pteronyssinus (House-dust mite)

<400> SEQUENCE: 83

Met Lys Phe Ile Ile Ala Phe Phe Val Ala Thr Leu Ala Val Met Thr
1               5                   10                  15

Val Ser Gly Glu Asp Lys Lys His Asp Tyr Gln Asn Glu Phe Asp Phe
            20                  25                  30

Leu Leu Met Glu Arg Ile His Glu Gln Ile Lys Lys Gly Glu Leu Ala
        35                  40                  45

Leu Phe Tyr Leu Gln Glu Gln Ile Asn His Phe Glu Glu Lys Pro Thr
    50                  55                  60

Lys Glu Met Lys Asp Lys Ile Val Ala Glu Met Asp Thr Ile Ile Ala
65                  70                  75                  80

Met Ile Asp Gly Val Arg Gly Val Leu Asp Arg Leu Met Gln Arg Lys
                85                  90                  95

Asp Leu Asp Ile Phe Glu Gln Tyr Asn Leu Glu Met Ala Lys Lys Ser
```

-continued

```
                100                 105                 110
Gly Asp Ile Leu Glu Arg Asp Leu Lys Lys Glu Glu Ala Arg Val Lys
        115                 120                 125

Lys Ile Glu Val
    130

<210> SEQ ID NO 84
<211> LENGTH: 20
<212> TYPE: PRT
<213> ORGANISM: Dermatophagoides pteronyssinus (House-dust mite)
<220> FEATURE:
<221> NAME/KEY: UNSURE
<222> LOCATION: 4
<223> OTHER INFORMATION: Xaa = any amino acid

<400> SEQUENCE: 84

Ala Ile Gly Xaa Gln Pro Ala Ala Glu Ala Glu Ala Pro Phe Gln Ile
1               5                   10                  15

Ser Leu Met Lys
        20

<210> SEQ ID NO 85
<211> LENGTH: 215
<212> TYPE: PRT
<213> ORGANISM: Dermatophagoides pteronyssinus (House-dust mite)

<400> SEQUENCE: 85

Met Met Lys Leu Leu Leu Ile Ala Ala Ala Ala Phe Val Ala Val Ser
1               5                   10                  15

Ala Asp Pro Ile His Tyr Asp Lys Ile Thr Glu Glu Ile Asn Lys Ala
            20                  25                  30

Val Asp Glu Ala Val Ala Ala Ile Glu Lys Ser Glu Thr Phe Asp Pro
        35                  40                  45

Met Lys Val Pro Asp His Ser Asp Lys Phe Glu Arg His Ile Gly Ile
    50                  55                  60

Ile Asp Leu Lys Gly Glu Leu Asp Met Arg Asn Ile Gln Val Arg Gly
65                  70                  75                  80

Leu Lys Gln Met Lys Arg Val Gly Asp Ala Asn Val Lys Ser Glu Asp
                85                  90                  95

Gly Val Val Lys Ala His Leu Leu Val Gly Val His Asp Asp Val Val
            100                 105                 110

Ser Met Glu Tyr Asp Leu Ala Tyr Lys Leu Gly Asp Leu His Pro Asn
        115                 120                 125

Thr His Val Ile Ser Asp Ile Gln Asp Phe Val Val Glu Leu Ser Leu
    130                 135                 140

Glu Val Ser Glu Glu Gly Asn Met Thr Leu Thr Ser Phe Glu Val Arg
145                 150                 155                 160

Gln Phe Ala Asn Val Val Asn His Ile Gly Gly Leu Ser Ile Leu Asp
                165                 170                 175

Pro Ile Phe Ala Val Leu Ser Asp Val Leu Thr Ala Ile Phe Gln Asp
            180                 185                 190

Thr Val Arg Ala Glu Met Thr Lys Val Leu Ala Pro Ala Phe Lys Lys
        195                 200                 205

Glu Leu Glu Arg Asn Asn Gln
    210                 215

<210> SEQ ID NO 86
<211> LENGTH: 203
```

-continued

```
<212> TYPE: PRT
<213> ORGANISM: Dolichovespula arenaria (Yellow hornet)

<400> SEQUENCE: 86

Asn Asn Tyr Cys Lys Ile Cys Pro Lys Gly Thr His Thr Leu Cys Lys
 1               5                  10                  15

Tyr Gly Thr Ser Met Lys Pro Asn Cys Gly Gly Lys Ile Val Lys Ser
            20                  25                  30

Tyr Gly Val Thr Asn Asp Glu Lys Asn Glu Ile Val Lys Arg His Asn
        35                  40                  45

Glu Phe Arg Gln Lys Val Ala Gln Gly Leu Glu Thr Arg Gly Asn Pro
 50                  55                  60

Gly Pro Gln Pro Pro Ala Lys Asn Met Asn Leu Leu Val Trp Asn Asp
65                  70                  75                  80

Glu Leu Ala Lys Ile Ala Gln Thr Trp Ala Asn Gln Cys Asn Phe Gly
                85                  90                  95

His Asp Gln Cys Arg Asn Thr Ala Lys Tyr Pro Val Gly Gln Asn Val
            100                 105                 110

Ala Ile Ala Ser Thr Thr Gly Asn Ser Tyr Gln Thr Met Ser Tyr Leu
        115                 120                 125

Ile Lys Met Trp Glu Asp Glu Val Lys Asp Tyr Asn Pro His Lys Asp
130                 135                 140

Leu Met His Asn Asn Phe Ser Lys Val Gly His Tyr Thr Gln Met Val
145                 150                 155                 160

Trp Gly Lys Thr Lys Glu Ile Gly Cys Gly Ser Val Lys Tyr Ile Glu
                165                 170                 175

Asn Lys Trp His Thr His Tyr Leu Val Cys Asn Tyr Gly Pro Ala Gly
            180                 185                 190

Asn Tyr Met Asn Gln Pro Val Tyr Glu Arg Lys
        195                 200

<210> SEQ ID NO 87
<211> LENGTH: 317
<212> TYPE: PRT
<213> ORGANISM: Dolichovespula maculata (White-face hornet)

<400> SEQUENCE: 87

Arg Leu Ile Met Phe Val Gly Asp Pro Ser Ser Asn Glu Leu Asp
 1               5                  10                  15

Arg Phe Ser Val Cys Pro Phe Ser Asn Asp Thr Val Lys Met Ile Phe
            20                  25                  30

Leu Thr Arg Glu Asn Arg Lys His Asp Phe Tyr Thr Leu Asp Thr Met
        35                  40                  45

Asn Arg His Asn Glu Phe Lys Lys Ser Ile Ile Lys Arg Pro Val Val
 50                  55                  60

Phe Ile Thr His Gly Phe Thr Ser Ser Ala Thr Glu Lys Asn Phe Val
65                  70                  75                  80

Ala Met Ser Glu Ala Leu Met His Thr Gly Asp Phe Leu Ile Ile Met
                85                  90                  95

Val Asp Trp Arg Met Ala Ala Cys Thr Asp Glu Tyr Pro Gly Leu Lys
            100                 105                 110

Tyr Met Phe Tyr Lys Ala Ala Val Gly Asn Thr Arg Leu Val Gly Asn
        115                 120                 125

Phe Ile Ala Met Ile Ala Lys Lys Leu Val Glu Gln Tyr Lys Val Pro
130                 135                 140
```

```
Met Thr Asn Ile Arg Leu Val Gly His Ser Leu Gly Ala His Ile Ser
145                 150                 155                 160

Gly Phe Ala Gly Lys Arg Val Gln Glu Leu Lys Leu Gly Lys Phe Ser
                165                 170                 175

Glu Ile Ile Gly Leu Asp Pro Ala Gly Pro Ser Phe Lys Lys Asn Asp
            180                 185                 190

Cys Ser Glu Arg Ile Cys Glu Thr Asp Ala His Tyr Val Gln Ile Leu
        195                 200                 205

His Thr Ser Ser Asn Leu Gly Thr Glu Arg Thr Leu Gly Thr Val Asp
    210                 215                 220

Phe Tyr Ile Asn Asn Gly Ser Asn Gln Pro Gly Cys Arg Tyr Ile Ile
225                 230                 235                 240

Gly Glu Thr Cys Ser His Thr Arg Ala Val Lys Tyr Phe Thr Glu Cys
                245                 250                 255

Ile Arg Arg Glu Cys Cys Leu Ile Gly Val Pro Gln Ser Lys Asn Pro
            260                 265                 270

Gln Pro Val Ser Lys Cys Thr Arg Asn Glu Cys Val Cys Val Gly Leu
        275                 280                 285

Asn Ala Lys Lys Tyr Pro Lys Arg Gly Ser Phe Tyr Val Pro Val Glu
    290                 295                 300

Ala Glu Ala Pro Tyr Cys Asn Asn Asn Gly Lys Ile Ile
305                 310                 315

<210> SEQ ID NO 88
<211> LENGTH: 303
<212> TYPE: PRT
<213> ORGANISM: Dolichovespula maculata (White-face hornet)

<400> SEQUENCE: 88

Gly Ile Leu Pro Glu Cys Lys Leu Val Pro Glu Ile Ser Phe Val
1               5                   10                  15

Leu Ser Thr Arg Glu Asn Arg Asp Gly Val Tyr Leu Thr Leu Gln Lys
                20                  25                  30

Leu Lys Asn Gly Lys Met Phe Lys Asn Ser Asp Leu Ser Ser Lys Lys
            35                  40                  45

Val Pro Phe Leu Ile His Gly Phe Ile Ser Ser Ala Thr Asn Lys Asn
        50                  55                  60

Tyr Ala Asp Met Thr Arg Ala Leu Leu Asp Lys Asp Ile Met Val
65                  70                  75                  80

Ile Ser Ile Asp Trp Arg Asp Gly Ala Cys Ser Asn Glu Phe Ala Leu
                85                  90                  95

Leu Lys Phe Ile Gly Tyr Pro Lys Ala Val Glu Asn Thr Arg Ala Val
            100                 105                 110

Gly Lys Tyr Ile Ala Asp Phe Ser Lys Ile Leu Ile Gln Lys Tyr Lys
        115                 120                 125

Val Leu Leu Glu Asn Ile Arg Leu Ile Gly His Ser Leu Gly Ala Gln
    130                 135                 140

Ile Ala Gly Phe Ala Gly Lys Glu Phe Gln Arg Phe Lys Leu Gly Lys
145                 150                 155                 160

Tyr Pro Glu Ile Ile Gly Leu Asp Pro Ala Gly Pro Ser Phe Lys Lys
                165                 170                 175

Lys Asp Cys Pro Glu Arg Ile Cys Glu Thr Asp Ala His Tyr Val Gln
            180                 185                 190

Ile Leu His Thr Ser Ser Asn Leu Gly Thr Glu Arg Thr Leu Gly Thr
        195                 200                 205
```

```
Val Asp Phe Tyr Ile Asn Asp Gly Ser Asn Gln Pro Gly Cys Thr Tyr
    210                 215                 220

Ile Ile Gly Glu Thr Cys Ser His Thr Arg Ala Val Lys Tyr Leu Thr
225                 230                 235                 240

Glu Cys Ile Arg Arg Glu Cys Cys Leu Ile Gly Val Pro Gln Ser Lys
                245                 250                 255

Asn Pro Gln Pro Val Ser Lys Cys Thr Arg Asn Glu Cys Val Cys Val
            260                 265                 270

Gly Leu Asn Ala Lys Glu Tyr Pro Lys Lys Gly Ser Phe Tyr Val Pro
            275                 280                 285

Val Glu Ala Lys Ala Pro Phe Cys Asn Asn Asn Gly Lys Ile Ile
            290                 295                 300
```

<210> SEQ ID NO 89
<211> LENGTH: 331
<212> TYPE: PRT
<213> ORGANISM: Dolichovespula maculata (White-face hornet)

<400> SEQUENCE: 89

```
Ser Glu Arg Pro Lys Arg Val Phe Asn Ile Tyr Trp Asn Val Pro Thr
1               5                   10                  15

Phe Met Cys His Gln Tyr Gly Leu Tyr Phe Asp Glu Val Thr Asn Phe
                20                  25                  30

Asn Ile Lys His Asn Ser Lys Asp Asp Phe Gln Gly Asp Lys Ile Ser
            35                  40                  45

Ile Phe Tyr Asp Pro Gly Glu Phe Pro Ala Leu Leu Pro Leu Lys Glu
        50                  55                  60

Gly Asn Tyr Lys Ile Arg Asn Gly Gly Val Pro Gln Glu Gly Asn Ile
65                  70                  75                  80

Thr Ile His Leu Gln Arg Phe Ile Glu Asn Leu Asp Lys Thr Tyr Pro
                85                  90                  95

Asn Arg Asn Phe Asn Gly Ile Gly Val Ile Asp Phe Glu Arg Trp Arg
                100                 105                 110

Pro Ile Phe Arg Gln Asn Trp Gly Asn Met Met Ile His Lys Lys Phe
            115                 120                 125

Ser Ile Asp Leu Val Arg Asn Glu His Pro Phe Trp Asp Lys Lys Met
130                 135                 140

Ile Glu Leu Glu Ala Ser Lys Arg Phe Glu Lys Tyr Ala Arg Leu Phe
145                 150                 155                 160

Met Glu Glu Thr Leu Lys Leu Ala Lys Lys Thr Arg Lys Gln Ala Asp
                165                 170                 175

Trp Gly Tyr Tyr Gly Tyr Pro Tyr Cys Phe Asn Met Ser Pro Asn Asn
            180                 185                 190

Leu Val Pro Asp Cys Asp Ala Thr Ala Met Leu Glu Asn Asp Lys Met
        195                 200                 205

Ser Trp Leu Phe Asn Asn Gln Asn Val Leu Leu Pro Ser Val Tyr Ile
    210                 215                 220

Arg His Glu Leu Thr Pro Asp Gln Arg Val Gly Leu Val Gln Gly Arg
225                 230                 235                 240

Val Lys Glu Ala Val Arg Ile Ser Asn Asn Leu Lys His Ser Pro Lys
                245                 250                 255

Val Leu Ser Tyr Trp Trp Tyr Val Tyr Gln Asp Asp Thr Asn Thr Phe
            260                 265                 270

Leu Thr Glu Thr Asp Val Lys Lys Thr Phe Gln Glu Ile Ala Ile Asn
```

-continued

```
                275                 280                 285
Gly Gly Asp Gly Ile Ile Ile Trp Gly Ser Ser Asp Val Asn Ser
            290                 295                 300

Leu Ser Lys Cys Lys Arg Leu Arg Glu Tyr Leu Leu Thr Val Leu Gly
305                 310                 315                 320

Pro Ile Thr Val Asn Val Thr Glu Thr Val Asn
                325                 330

<210> SEQ ID NO 90
<211> LENGTH: 227
<212> TYPE: PRT
<213> ORGANISM: Dolichovespula maculata (White-face hornet)

<400> SEQUENCE: 90

Met Glu Ile Gly Gly Leu Val Tyr Leu Ile Leu Ile Ile Thr Ile Ile
1               5                   10                  15

Asn Leu Ser Phe Gly Glu Thr Asn Asn Tyr Cys Lys Ile Lys Cys Arg
            20                  25                  30

Lys Gly Ile His Thr Leu Cys Lys Phe Gly Thr Ser Met Lys Pro Asn
        35                  40                  45

Cys Gly Arg Asn Val Val Lys Ala Tyr Gly Leu Thr Asn Asp Glu Lys
    50                  55                  60

Asn Glu Ile Leu Lys Arg His Asn Asp Phe Arg Gln Asn Val Ala Lys
65                  70                  75                  80

Gly Leu Glu Thr Arg Gly Lys Pro Gly Pro Gln Pro Pro Ala Lys Asn
                85                  90                  95

Met Asn Val Leu Val Trp Asn Asp Glu Leu Ala Lys Ile Ala Gln Thr
            100                 105                 110

Trp Ala Asn Gln Cys Asp Phe Asn His Asp Asp Cys Arg Asn Thr Ala
        115                 120                 125

Lys Tyr Gln Val Gly Gln Asn Ile Ala Ile Ser Ser Thr Thr Ala Thr
    130                 135                 140

Gln Phe Asp Arg Pro Ser Lys Leu Ile Lys Gln Trp Glu Asp Glu Val
145                 150                 155                 160

Thr Glu Phe Asn Tyr Lys Val Gly Leu Gln Asn Ser Asn Phe Arg Lys
                165                 170                 175

Val Gly His Tyr Thr Gln Met Val Trp Gly Lys Thr Lys Glu Ile Gly
            180                 185                 190

Cys Gly Ser Ile Lys Tyr Ile Glu Asp Asn Trp Tyr Thr His Tyr Leu
        195                 200                 205

Val Cys Asn Tyr Gly Pro Gly Gly Asn Asp Phe Asn Gln Pro Ile Tyr
    210                 215                 220

Glu Arg Lys
225

<210> SEQ ID NO 91
<211> LENGTH: 215
<212> TYPE: PRT
<213> ORGANISM: Dolichovespula maculata (White-face hornet)

<400> SEQUENCE: 91

Pro Ile Ile Asn Leu Ser Phe Gly Glu Ala Asn Asn Tyr Cys Lys Ile
1               5                   10                  15

Lys Cys Ser Arg Gly Ile His Thr Leu Cys Lys Phe Gly Thr Ser Met
            20                  25                  30

Lys Pro Asn Cys Gly Ser Lys Leu Val Lys Val His Gly Val Ser Asn
```

-continued

```
                35                  40                  45

Asp Glu Lys Asn Glu Ile Val Asn Arg His Asn Gln Phe Arg Gln Lys
             50                  55                  60

Val Ala Lys Gly Leu Glu Thr Arg Gly Asn Pro Gly Pro Gln Pro Pro
 65                  70                  75                  80

Ala Lys Asn Met Asn Val Leu Val Trp Asn Asp Glu Leu Ala Lys Ile
                 85                  90                  95

Ala Gln Thr Trp Ala Asn Gln Cys Ser Phe Gly His Asp Gln Cys Arg
            100                 105                 110

Asn Thr Glu Lys Tyr Gln Val Gly Gln Asn Val Ala Ile Ala Ser Thr
        115                 120                 125

Thr Gly Asn Ser Tyr Ala Thr Met Ser Lys Leu Ile Glu Met Trp Glu
    130                 135                 140

Asn Glu Val Lys Asp Phe Asn Pro Lys Lys Gly Thr Met Gly Asp Asn
145                 150                 155                 160

Asn Phe Ser Lys Val Gly His Tyr Thr Gln Met Val Trp Gly Lys Thr
                165                 170                 175

Lys Glu Ile Gly Cys Gly Ser Val Lys Tyr Ile Glu Asn Asn Trp His
            180                 185                 190

Thr His Tyr Leu Val Cys Asn Tyr Gly Pro Ala Gly Asn Tyr Met Asp
        195                 200                 205

Gln Pro Ile Tyr Glu Arg Lys
    210                 215

<210> SEQ ID NO 92
<211> LENGTH: 187
<212> TYPE: PRT
<213> ORGANISM: Equus caballus (Horse)

<400> SEQUENCE: 92

Met Lys Leu Leu Leu Leu Cys Leu Gly Leu Ile Leu Val Cys Ala Gln
 1               5                  10                  15

Gln Glu Glu Asn Ser Asp Val Ala Ile Arg Asn Phe Asp Ile Ser Lys
             20                  25                  30

Ile Ser Gly Glu Trp Tyr Ser Ile Phe Leu Ala Ser Asp Val Lys Glu
         35                  40                  45

Lys Ile Glu Glu Asn Gly Ser Met Arg Val Phe Val Asp Val Ile Arg
     50                  55                  60

Ala Leu Asp Asn Ser Ser Leu Tyr Ala Glu Tyr Gln Thr Lys Val Asn
 65                  70                  75                  80

Gly Glu Cys Thr Glu Phe Pro Met Val Phe Asp Lys Thr Glu Glu Asp
                 85                  90                  95

Gly Val Tyr Ser Leu Asn Tyr Asp Gly Tyr Asn Val Phe Arg Ile Ser
            100                 105                 110

Glu Phe Glu Asn Asp Glu His Ile Ile Leu Tyr Leu Val Asn Phe Asp
        115                 120                 125

Lys Asp Arg Pro Phe Gln Leu Phe Glu Phe Tyr Ala Arg Glu Pro Asp
    130                 135                 140

Val Ser Pro Glu Ile Lys Glu Glu Phe Val Lys Ile Val Gln Lys Arg
145                 150                 155                 160

Gly Ile Val Lys Glu Asn Ile Ile Asp Leu Thr Lys Ile Asp Arg Cys
                165                 170                 175

Phe Gln Leu Arg Gly Asn Gly Val Ala Gln Ala
            180                 185
```

```
<210> SEQ ID NO 93
<211> LENGTH: 29
<212> TYPE: PRT
<213> ORGANISM: Equus caballus (Horse)
<220> FEATURE:
<221> NAME/KEY: UNSURE
<222> LOCATION: 3, 28
<223> OTHER INFORMATION: Xaa = any amino acid

<400> SEQUENCE: 93

Ser Gln Xaa Pro Gln Ser Glu Thr Asp Tyr Ser Gln Leu Ser Gly Glu
 1               5                  10                  15

Trp Asn Thr Ile Tyr Gly Ala Ala Ser Asn Ile Xaa Lys
            20                  25

<210> SEQ ID NO 94
<211> LENGTH: 19
<212> TYPE: PRT
<213> ORGANISM: Equus caballus (Horse)
<220> FEATURE:
<221> NAME/KEY: UNSURE
<222> LOCATION: 1
<223> OTHER INFORMATION: Xaa = any amino acid

<400> SEQUENCE: 94

Xaa Gln Asp Pro Gln Ser Glu Thr Asp Tyr Ser Gln Leu Ser Gly Glu
 1               5                  10                  15

Trp Asn Thr

<210> SEQ ID NO 95
<211> LENGTH: 211
<212> TYPE: PRT
<213> ORGANISM: Euroglyphus maynei (House-dust mite)

<400> SEQUENCE: 95

Thr Tyr Ala Cys Ser Ile Asn Ser Val Ser Leu Pro Ser Glu Leu Asp
 1               5                  10                  15

Leu Arg Ser Leu Arg Thr Val Thr Pro Ile Arg Met Gln Gly Gly Cys
            20                  25                  30

Gly Ser Cys Trp Ala Phe Ser Gly Val Ala Ser Thr Glu Ser Ala Tyr
        35                  40                  45

Leu Ala Tyr Arg Asn Met Ser Leu Asp Leu Ala Glu Gln Glu Leu Val
    50                  55                  60

Asp Cys Ala Ser Gln Asn Gly Cys His Gly Asp Thr Ile Pro Arg Gly
65                  70                  75                  80

Ile Glu Tyr Ile Gln Gln Asn Gly Val Val Gln Glu His Tyr Tyr Pro
                85                  90                  95

Tyr Val Ala Arg Glu Gln Ser Cys His Arg Pro Asn Ala Gln Arg Tyr
            100                 105                 110

Gly Leu Lys Asn Tyr Cys Gln Ile Ser Pro Pro Asp Ser Asn Lys Ile
        115                 120                 125

Arg Gln Ala Leu Thr Gln Thr His Thr Ala Val Ala Val Ile Ile Gly
    130                 135                 140

Ile Lys Asp Leu Asn Ala Phe Arg His Tyr Asp Gly Arg Thr Ile Met
145                 150                 155                 160

Gln His Asp Asn Gly Tyr Gln Pro Asn Tyr His Ala Val Asn Ile Val
                165                 170                 175

Gly Tyr Gly Asn Thr Gln Gly Val Asp Tyr Trp Ile Val Arg Asn Ser
            180                 185                 190
```

```
Trp Asp Thr Thr Trp Gly Asp Asn Gly Tyr Gly Tyr Phe Ala Ala Asn
        195                 200                 205

Ile Asn Leu
    210

<210> SEQ ID NO 96
<211> LENGTH: 92
<212> TYPE: PRT
<213> ORGANISM: Felis silvestris catus (Cat)

<400> SEQUENCE: 96

Met Lys Gly Ala Cys Val Leu Val Leu Leu Trp Ala Ala Leu Leu Leu
1               5                   10                  15

Ile Ser Gly Gly Asn Cys Glu Ile Cys Pro Ala Val Lys Arg Asp Val
            20                  25                  30

Asp Leu Phe Leu Thr Gly Thr Pro Asp Glu Tyr Val Glu Gln Val Ala
        35                  40                  45

Gln Tyr Lys Ala Leu Pro Val Val Leu Glu Asn Ala Arg Ile Leu Lys
    50                  55                  60

Asn Cys Val Asp Ala Lys Met Thr Glu Glu Asp Lys Glu Asn Ala Leu
65                  70                  75                  80

Ser Val Leu Asp Lys Ile Tyr Thr Ser Pro Leu Cys
                85                  90

<210> SEQ ID NO 97
<211> LENGTH: 88
<212> TYPE: PRT
<213> ORGANISM: Felis silvestris catus (Cat)

<400> SEQUENCE: 97

Met Leu Asp Ala Ala Leu Pro Pro Cys Pro Thr Val Ala Ala Thr Ala
1               5                   10                  15

Asp Cys Glu Ile Cys Pro Ala Val Lys Arg Asp Val Asp Leu Phe Leu
            20                  25                  30

Thr Gly Thr Pro Asp Glu Tyr Val Glu Gln Val Ala Gln Tyr Lys Ala
        35                  40                  45

Leu Pro Val Val Leu Glu Asn Ala Arg Ile Leu Lys Asn Cys Val Asp
    50                  55                  60

Ala Lys Met Thr Glu Glu Asp Lys Glu Asn Ala Leu Ser Val Leu Asp
65                  70                  75                  80

Lys Ile Tyr Thr Ser Pro Leu Cys
                85

<210> SEQ ID NO 98
<211> LENGTH: 109
<212> TYPE: PRT
<213> ORGANISM: Felis silvestris catus (Cat)

<400> SEQUENCE: 98

Met Arg Gly Ala Leu Leu Val Leu Ala Leu Leu Val Thr Gln Ala Leu
1               5                   10                  15

Gly Val Lys Met Ala Glu Thr Cys Pro Ile Phe Tyr Asp Val Phe Phe
            20                  25                  30

Ala Val Ala Asn Gly Asn Glu Leu Leu Leu Asp Leu Ser Leu Thr Lys
        35                  40                  45

Val Asn Ala Thr Glu Pro Glu Arg Thr Ala Met Lys Lys Ile Gln Asp
    50                  55                  60

Cys Tyr Val Glu Asn Gly Leu Ile Ser Arg Val Leu Asp Gly Leu Val
```

```
                65                  70                  75                  80
Met Thr Thr Ile Ser Ser Ser Lys Asp Cys Met Gly Glu Ala Val Gln
                    85                  90                  95

Asn Thr Val Glu Asp Leu Lys Leu Asn Thr Leu Gly Arg
            100                 105

<210> SEQ ID NO 99
<211> LENGTH: 113
<212> TYPE: PRT
<213> ORGANISM: Gadus callarias (Baltic cod)

<400> SEQUENCE: 99

Ala Phe Lys Gly Ile Leu Ser Asn Ala Asp Ile Lys Ala Ala Glu Ala
1               5                   10                  15

Ala Cys Phe Lys Glu Gly Ser Phe Asp Glu Asp Gly Phe Tyr Ala Lys
                20                  25                  30

Val Gly Leu Asp Ala Phe Ser Ala Asp Glu Leu Lys Lys Leu Phe Lys
            35                  40                  45

Ile Ala Asp Glu Asp Lys Glu Gly Phe Ile Glu Glu Asp Glu Leu Lys
        50                  55                  60

Leu Phe Leu Ile Ala Phe Ala Ala Asp Leu Arg Ala Leu Thr Asp Ala
65                  70                  75                  80

Glu Thr Lys Ala Phe Leu Lys Ala Gly Asp Ser Asp Gly Asp Gly Lys
                85                  90                  95

Ile Gly Val Asp Glu Phe Gly Ala Leu Val Asp Lys Trp Gly Ala Lys
            100                 105                 110

Gly

<210> SEQ ID NO 100
<211> LENGTH: 210
<212> TYPE: PRT
<213> ORGANISM: Gallus gallus (Chicken)

<400> SEQUENCE: 100

Met Ala Met Ala Gly Val Phe Val Leu Phe Ser Phe Val Leu Cys Gly
1               5                   10                  15

Phe Leu Pro Asp Ala Ala Phe Gly Ala Glu Val Asp Cys Ser Arg Phe
                20                  25                  30

Pro Asn Ala Thr Asp Lys Glu Gly Lys Asp Val Leu Val Cys Asn Lys
            35                  40                  45

Asp Leu Arg Pro Ile Cys Gly Thr Asp Gly Val Thr Tyr Thr Asn Asp
        50                  55                  60

Cys Leu Leu Cys Ala Tyr Ser Ile Glu Phe Gly Thr Asn Ile Ser Lys
65                  70                  75                  80

Glu His Asp Gly Glu Cys Lys Glu Thr Val Pro Met Asn Cys Ser Ser
                85                  90                  95

Tyr Ala Asn Thr Thr Ser Glu Asp Gly Lys Val Met Val Leu Cys Asn
            100                 105                 110

Arg Ala Phe Asn Pro Val Cys Gly Thr Asp Gly Val Thr Tyr Asp Asn
        115                 120                 125

Glu Cys Leu Leu Cys Ala His Lys Val Glu Gln Gly Ala Ser Val Asp
    130                 135                 140

Lys Arg His Asp Gly Gly Cys Arg Lys Glu Leu Ala Ala Val Ser Val
145                 150                 155                 160

Asp Cys Ser Glu Tyr Pro Lys Pro Asp Cys Thr Ala Glu Asp Arg Pro
                165                 170                 175
```

```
Leu Cys Gly Ser Asp Asn Lys Thr Tyr Gly Asn Lys Cys Asn Phe Cys
            180                 185                 190

Asn Ala Val Val Glu Ser Asn Gly Thr Leu Thr Leu Ser His Phe Gly
        195                 200                 205

Lys Cys
    210

<210> SEQ ID NO 101
<211> LENGTH: 385
<212> TYPE: PRT
<213> ORGANISM: Gallus gallus (Chicken)

<400> SEQUENCE: 101

Gly Ser Ile Gly Ala Ala Ser Met Glu Phe Cys Phe Asp Val Phe Lys
1               5                   10                  15

Glu Leu Lys Val His His Ala Asn Glu Asn Ile Phe Tyr Cys Pro Ile
            20                  25                  30

Ala Ile Met Ser Ala Leu Ala Met Val Tyr Leu Gly Ala Lys Asp Ser
        35                  40                  45

Thr Arg Thr Gln Ile Asn Lys Val Val Arg Phe Asp Lys Leu Pro Gly
    50                  55                  60

Phe Gly Asp Ser Ile Glu Ala Gln Cys Gly Thr Ser Val Asn Val His
65                  70                  75                  80

Ser Ser Leu Arg Asp Ile Leu Asn Gln Ile Thr Lys Pro Asn Asp Val
                85                  90                  95

Tyr Ser Phe Ser Leu Ala Ser Arg Leu Tyr Ala Glu Glu Arg Tyr Pro
            100                 105                 110

Ile Leu Pro Glu Tyr Leu Gln Cys Val Lys Glu Leu Tyr Arg Gly Gly
        115                 120                 125

Leu Glu Pro Ile Asn Phe Gln Thr Ala Ala Asp Gln Ala Arg Glu Leu
    130                 135                 140

Ile Asn Ser Trp Val Glu Ser Gln Thr Asn Gly Ile Ile Arg Asn Val
145                 150                 155                 160

Leu Gln Pro Ser Ser Val Asp Ser Gln Thr Ala Met Val Leu Val Asn
                165                 170                 175

Ala Ile Val Phe Lys Gly Leu Trp Glu Lys Ala Phe Lys Asp Glu Asp
            180                 185                 190

Thr Gln Ala Met Pro Phe Arg Val Thr Glu Gln Glu Ser Lys Pro Val
        195                 200                 205

Gln Met Met Tyr Gln Ile Gly Leu Phe Arg Val Ala Ser Met Ala Ser
    210                 215                 220

Glu Lys Met Lys Ile Leu Glu Leu Pro Phe Ala Ser Gly Thr Met Ser
225                 230                 235                 240

Met Leu Val Leu Leu Pro Asp Glu Val Ser Gly Leu Glu Gln Leu Glu
                245                 250                 255

Ser Ile Ile Asn Phe Glu Lys Leu Thr Glu Trp Thr Ser Ser Asn Val
            260                 265                 270

Met Glu Glu Arg Lys Ile Lys Val Tyr Leu Pro Arg Met Lys Met Glu
        275                 280                 285

Glu Lys Tyr Asn Leu Thr Ser Val Leu Met Ala Met Gly Ile Thr Asp
    290                 295                 300

Val Phe Ser Ser Ala Asn Leu Ser Gly Ile Ser Ser Ala Glu Ser
305                 310                 315                 320

Leu Lys Ile Ser Gln Ala Val His Ala Ala His Ala Glu Ile Asn Glu
```

```
                       325                 330                 335
Ala Gly Arg Glu Val Val Gly Ser Ala Glu Ala Gly Val Asp Ala Ala
                340                 345                 350

Ser Val Ser Glu Glu Phe Arg Ala Asp His Pro Phe Leu Phe Cys Ile
            355                 360                 365

Lys His Ile Ala Thr Asn Ala Val Leu Phe Phe Gly Arg Cys Val Ser
        370                 375                 380

Pro
385

<210> SEQ ID NO 102
<211> LENGTH: 705
<212> TYPE: PRT
<213> ORGANISM: Gallus gallus (Chicken)

<400> SEQUENCE: 102

Met Lys Leu Ile Leu Cys Thr Val Leu Ser Leu Gly Ile Ala Ala Val
 1               5                  10                  15

Cys Phe Ala Ala Pro Pro Lys Ser Val Ile Arg Trp Cys Thr Ile Ser
                20                  25                  30

Ser Pro Glu Glu Lys Lys Cys Asn Asn Leu Arg Asp Leu Thr Gln Gln
            35                  40                  45

Glu Arg Ile Ser Leu Thr Cys Val Gln Lys Ala Thr Tyr Leu Asp Cys
        50                  55                  60

Ile Lys Ala Ile Ala Asn Asn Glu Ala Asp Ala Ile Ser Leu Asp Gly
65                  70                  75                  80

Gly Gln Ala Phe Glu Ala Gly Leu Ala Pro Tyr Lys Leu Lys Pro Ile
                85                  90                  95

Ala Ala Glu Val Tyr Glu His Thr Glu Gly Ser Thr Thr Ser Tyr Tyr
            100                 105                 110

Ala Val Ala Val Val Lys Lys Gly Thr Glu Phe Thr Val Asn Asp Leu
        115                 120                 125

Gln Gly Lys Thr Ser Cys His Thr Gly Leu Gly Arg Ser Ala Gly Trp
130                 135                 140

Asn Ile Pro Ile Gly Thr Leu Leu His Arg Gly Ala Ile Glu Trp Glu
145                 150                 155                 160

Gly Ile Glu Ser Gly Ser Val Glu Gln Ala Val Ala Lys Phe Phe Ser
                165                 170                 175

Ala Ser Cys Val Pro Gly Ala Thr Ile Glu Gln Lys Leu Cys Arg Gln
            180                 185                 190

Cys Lys Gly Asp Pro Lys Thr Lys Cys Ala Arg Asn Ala Pro Tyr Ser
        195                 200                 205

Gly Tyr Ser Gly Ala Phe His Cys Leu Lys Asp Gly Lys Gly Asp Val
    210                 215                 220

Ala Phe Val Lys His Thr Thr Val Asn Glu Asn Ala Pro Asp Gln Lys
225                 230                 235                 240

Asp Glu Tyr Glu Leu Leu Cys Leu Asp Gly Ser Arg Gln Pro Val Asp
                245                 250                 255

Asn Tyr Lys Thr Cys Asn Trp Ala Arg Val Ala Ala His Ala Val Val
            260                 265                 270

Ala Arg Asp Asp Asn Lys Val Glu Asp Ile Trp Ser Phe Leu Ser Lys
        275                 280                 285

Ala Gln Ser Asp Phe Gly Val Asp Thr Lys Ser Asp Phe His Leu Phe
    290                 295                 300
```

-continued

```
Gly Pro Pro Gly Lys Lys Asp Pro Val Leu Lys Asp Leu Leu Phe Lys
305                 310                 315                 320

Asp Ser Ala Ile Met Leu Lys Arg Val Pro Ser Leu Met Asp Ser Gln
            325                 330                 335

Leu Tyr Leu Gly Phe Glu Tyr Tyr Ser Ala Ile Gln Ser Met Arg Lys
            340                 345                 350

Asp Gln Leu Thr Pro Ser Pro Arg Glu Asn Arg Ile Gln Trp Cys Ala
            355                 360                 365

Val Gly Lys Asp Glu Lys Ser Lys Cys Asp Arg Trp Ser Val Val Ser
    370                 375                 380

Asn Gly Asp Val Glu Cys Thr Val Val Asp Glu Thr Lys Asp Cys Ile
385                 390                 395                 400

Ile Lys Ile Met Lys Gly Glu Ala Asp Ala Val Ala Leu Asp Gly Gly
                405                 410                 415

Leu Val Tyr Thr Ala Gly Val Cys Gly Leu Val Pro Val Met Ala Glu
            420                 425                 430

Arg Tyr Asp Asp Glu Ser Gln Cys Ser Lys Thr Asp Glu Arg Pro Ala
            435                 440                 445

Ser Tyr Phe Ala Val Ala Val Ala Arg Lys Asp Ser Asn Val Asn Trp
    450                 455                 460

Asn Asn Leu Lys Gly Lys Lys Ser Cys His Thr Ala Val Gly Arg Thr
465                 470                 475                 480

Ala Gly Trp Val Ile Pro Met Gly Leu Ile His Asn Arg Thr Gly Thr
                485                 490                 495

Cys Asn Phe Asp Glu Tyr Phe Ser Glu Gly Cys Ala Pro Gly Ser Pro
            500                 505                 510

Pro Asn Ser Arg Leu Cys Gln Leu Cys Gln Gly Ser Gly Gly Ile Pro
            515                 520                 525

Pro Glu Lys Cys Val Ala Ser Ser His Glu Lys Tyr Phe Gly Tyr Thr
    530                 535                 540

Gly Ala Leu Arg Cys Leu Val Glu Lys Gly Asp Val Ala Phe Ile Gln
545                 550                 555                 560

His Ser Thr Val Glu Glu Asn Thr Gly Gly Lys Asn Lys Ala Asp Trp
                565                 570                 575

Ala Lys Asn Leu Gln Met Asp Asp Phe Glu Leu Leu Cys Thr Asp Gly
            580                 585                 590

Arg Arg Ala Asn Val Met Asp Tyr Arg Glu Cys Asn Leu Ala Glu Val
            595                 600                 605

Pro Thr His Ala Val Val Arg Pro Glu Lys Ala Asn Lys Ile Arg
    610                 615                 620

Asp Leu Leu Glu Arg Gln Glu Lys Arg Phe Gly Val Asn Gly Ser Glu
625                 630                 635                 640

Lys Ser Lys Phe Met Met Phe Glu Ser Gln Asn Lys Asp Leu Leu Phe
                645                 650                 655

Lys Asp Leu Thr Lys Cys Leu Phe Lys Val Arg Glu Gly Thr Thr Tyr
            660                 665                 670

Lys Glu Phe Leu Gly Asp Lys Phe Tyr Thr Val Ile Ser Ser Leu Lys
            675                 680                 685

Thr Cys Asn Pro Ser Asp Ile Leu Gln Met Cys Ser Phe Leu Glu Gly
            690                 695                 700

Lys
705
```

<210> SEQ ID NO 103
<211> LENGTH: 147
<212> TYPE: PRT
<213> ORGANISM: Gallus gallus (Chicken)

<400> SEQUENCE: 103

Met Arg Ser Leu Leu Ile Leu Val Leu Cys Phe Leu Pro Leu Ala Ala
1               5                   10                  15

Leu Gly Lys Val Phe Gly Arg Cys Glu Leu Ala Ala Ala Met Lys Arg
            20                  25                  30

His Gly Leu Asp Asn Tyr Arg Gly Tyr Ser Leu Gly Asn Trp Val Cys
        35                  40                  45

Ala Ala Lys Phe Glu Ser Asn Phe Asn Thr Gln Ala Thr Asn Arg Asn
    50                  55                  60

Thr Asp Gly Ser Thr Asp Tyr Gly Ile Leu Gln Ile Asn Ser Arg Trp
65                  70                  75                  80

Trp Cys Asn Asp Gly Arg Thr Pro Gly Ser Arg Asn Leu Cys Asn Ile
                85                  90                  95

Pro Cys Ser Ala Leu Leu Ser Ser Asp Ile Thr Ala Ser Val Asn Cys
            100                 105                 110

Ala Lys Lys Ile Val Ser Asp Gly Asn Gly Met Asn Ala Trp Val Ala
        115                 120                 125

Trp Arg Asn Arg Cys Lys Gly Thr Asp Val Gln Ala Trp Ile Arg Gly
    130                 135                 140

Cys Arg Leu
145

<210> SEQ ID NO 104
<211> LENGTH: 133
<212> TYPE: PRT
<213> ORGANISM: Helianthus annuus (Common sunflower)

<400> SEQUENCE: 104

Met Ser Trp Gln Ala Tyr Val Asp Glu His Leu Met Cys Asp Ile Glu
1               5                   10                  15

Gly Thr Gly Gln His Leu Thr Ser Ala Ala Ile Leu Gly Leu Asp Gly
            20                  25                  30

Thr Val Trp Ala Gln Ser Ala Lys Phe Pro Gln Phe Lys Pro Glu Glu
        35                  40                  45

Met Lys Gly Ile Ile Lys Glu Phe Asp Glu Ala Gly Thr Leu Ala Pro
    50                  55                  60

Thr Gly Met Phe Ile Ala Gly Ala Lys Tyr Met Val Leu Gln Gly Glu
65                  70                  75                  80

Pro Gly Ala Val Ile Arg Gly Lys Lys Gly Ala Gly Gly Ile Cys Ile
                85                  90                  95

Lys Lys Thr Gly Gln Ala Met Ile Met Gly Ile Tyr Asp Glu Pro Val
            100                 105                 110

Ala Pro Gly Gln Cys Asn Met Val Val Glu Arg Leu Gly Asp Tyr Leu
        115                 120                 125

Leu Glu Gln Gly Met
    130

<210> SEQ ID NO 105
<211> LENGTH: 137
<212> TYPE: PRT
<213> ORGANISM: Hevea brasiliensis (Para rubber tree)

<400> SEQUENCE: 105

```
Ala Glu Asp Glu Asp Asn Gln Gln Gly Gln Gly Glu Gly Leu Lys Tyr
  1               5                  10                  15

Leu Gly Phe Val Gln Asp Ala Ala Thr Tyr Ala Val Thr Thr Phe Ser
              20                  25                  30

Asn Val Tyr Leu Phe Ala Lys Asp Lys Ser Gly Pro Leu Gln Pro Gly
              35                  40                  45

Val Asp Ile Ile Glu Gly Pro Val Lys Asn Val Ala Val Pro Leu Tyr
 50                  55                  60

Asn Arg Phe Ser Tyr Ile Pro Asn Gly Ala Leu Lys Phe Val Asp Ser
65                   70                  75                  80

Thr Val Val Ala Ser Val Thr Ile Ile Asp Arg Ser Leu Pro Pro Ile
              85                  90                  95

Val Lys Asp Ala Ser Ile Gln Val Val Ser Ala Ile Arg Ala Ala Pro
             100                 105                 110

Glu Ala Ala Arg Ser Leu Ala Ser Ser Leu Pro Gly Gln Thr Lys Ile
             115                 120                 125

Leu Ala Lys Val Phe Tyr Gly Glu Asn
         130                 135

<210> SEQ ID NO 106
<211> LENGTH: 150
<212> TYPE: PRT
<213> ORGANISM: Hevea brasiliensis (Para rubber tree)

<400> SEQUENCE: 106

Ala Ser Val Glu Val Glu Ser Ala Ala Thr Ala Leu Pro Lys Asn Glu
  1               5                  10                  15

Thr Pro Glu Val Thr Lys Ala Glu Glu Thr Lys Thr Glu Glu Pro Ala
              20                  25                  30

Ala Pro Pro Ala Ser Glu Gln Glu Thr Ala Asp Ala Thr Pro Glu Lys
              35                  40                  45

Glu Glu Pro Thr Ala Ala Pro Ala Gly Pro Glu Ala Pro Ala Pro Glu
 50                  55                  60

Thr Glu Lys Ala Glu Glu Val Glu Lys Ile Glu Lys Thr Glu Glu Pro
65                   70                  75                  80

Ala Pro Glu Ala Asp Gln Thr Thr Pro Glu Glu Lys Pro Ala Glu Pro
              85                  90                  95

Glu Pro Val Ala Glu Glu Pro Lys His Glu Thr Lys Glu Thr Glu
             100                 105                 110

Thr Glu Ala Pro Ala Ala Pro Ala Glu Gly Glu Lys Pro Ala Glu Glu
             115                 120                 125

Glu Lys Pro Ile Thr Glu Ala Ala Glu Thr Ala Thr Thr Glu Val Pro
         130                 135                 140

Val Glu Lys Thr Glu Glu
145                 150

<210> SEQ ID NO 107
<211> LENGTH: 265
<212> TYPE: PRT
<213> ORGANISM: Holcus lanatus (Velvet grass)

<400> SEQUENCE: 107

Met Ala Ser Ser Ser Arg Ser Val Leu Leu Leu Val Ala Ala Leu Phe
  1               5                  10                  15

Ala Val Phe Leu Gly Ser Ala His Gly Ile Ala Lys Val Pro Pro Gly
              20                  25                  30
```

```
Pro Asn Ile Thr Ala Thr Tyr Gly Asp Glu Trp Leu Asp Ala Lys Ser
            35                  40                  45

Thr Trp Tyr Gly Lys Pro Thr Gly Ala Gly Pro Lys Asp Asn Gly Gly
 50                  55                  60

Ala Cys Gly Tyr Lys Asp Val Asp Lys Pro Pro Phe Ser Gly Met Thr
 65                  70                  75                  80

Gly Cys Gly Asn Thr Pro Ile Phe Lys Asp Gly Arg Gly Cys Gly Ser
                 85                  90                  95

Cys Phe Glu Ile Lys Cys Thr Lys Pro Glu Ser Cys Ser Gly Glu Pro
            100                 105                 110

Val Thr Val His Ile Thr Asp Asp Asn Glu Glu Pro Ile Ala Pro Tyr
            115                 120                 125

His Phe Asp Leu Ser Gly His Ala Phe Gly Ser Met Ala Lys Lys Gly
            130                 135                 140

Glu Glu Gln Lys Leu Arg Ser Ala Gly Glu Leu Glu Leu Lys Phe Arg
145                 150                 155                 160

Arg Val Lys Cys Lys Tyr Pro Asp Gly Thr Lys Pro Thr Phe His Val
                165                 170                 175

Glu Lys Gly Ser Asn Pro Asn Tyr Leu Ala Leu Leu Val Lys Tyr Ile
                180                 185                 190

Asp Gly Asp Gly Asp Val Val Ala Val Asp Ile Lys Glu Lys Gly Lys
            195                 200                 205

Asp Lys Trp Ile Glu Leu Lys Glu Ser Trp Gly Ala Val Trp Arg Val
210                 215                 220

Asp Thr Pro Asp Lys Leu Thr Gly Pro Phe Thr Val Arg Tyr Thr Thr
225                 230                 235                 240

Glu Gly Gly Thr Lys Gly Glu Ala Glu Asp Val Ile Pro Glu Gly Trp
                245                 250                 255

Lys Ala Asp Thr Ala Tyr Glu Ala Lys
                260                 265

<210> SEQ ID NO 108
<211> LENGTH: 146
<212> TYPE: PRT
<213> ORGANISM: Hordeum vulgare (Barley)

<400> SEQUENCE: 108

Pro Thr Ser Val Ala Val Asp Gln Gly Ser Met Val Ser Asn Ser Pro
 1               5                  10                  15

Gly Glu Trp Cys Trp Pro Gly Met Gly Tyr Pro Val Tyr Pro Phe Pro
                 20                  25                  30

Arg Cys Arg Ala Leu Val Lys Ser Gln Cys Ala Gly Gly Gln Val Val
            35                  40                  45

Glu Ser Ile Gln Lys Asp Cys Cys Arg Gln Ile Ala Ala Ile Gly Asp
 50                  55                  60

Glu Trp Cys Ile Cys Gly Ala Leu Gly Ser Met Arg Gly Ser Met Tyr
 65                  70                  75                  80

Lys Glu Leu Gly Val Ala Leu Ala Asp Lys Ala Thr Val Ala Glu
                 85                  90                  95

Val Phe Pro Gly Cys Arg Thr Glu Val Met Asp Arg Ala Val Ala Ser
            100                 105                 110

Leu Pro Ala Val Cys Asn Gln Tyr Ile Pro Asn Thr Asn Gly Thr Asp
            115                 120                 125

Gly Val Cys Tyr Trp Leu Ser Tyr Tyr Gln Pro Pro Arg Gln Met Ser
```

```
            130                 135                 140
Ser Arg
145

<210> SEQ ID NO 109
<211> LENGTH: 367
<212> TYPE: PRT
<213> ORGANISM: Juniperus ashei (Ozark white cedar)

<400> SEQUENCE: 109

Met Ala Ser Pro Cys Leu Ile Ala Val Leu Val Phe Leu Cys Ala Ile
1               5                   10                  15

Val Ser Cys Tyr Ser Asp Asn Pro Ile Asp Ser Cys Trp Arg Gly Asp
            20                  25                  30

Ser Asn Trp Asp Gln Asn Arg Met Lys Leu Ala Asp Cys Ala Val Gly
        35                  40                  45

Phe Gly Ser Ser Thr Met Gly Gly Lys Gly Asp Phe Tyr Thr Val
    50                  55                  60

Thr Ser Thr Asp Asp Asn Pro Val Asn Pro Thr Pro Gly Thr Leu Arg
65                  70                  75                  80

Tyr Gly Ala Thr Arg Glu Lys Ala Leu Trp Ile Ile Phe Ser Gln Asn
                85                  90                  95

Met Asn Ile Lys Leu Lys Met Pro Leu Tyr Val Ala Gly His Lys Thr
            100                 105                 110

Ile Asp Gly Arg Gly Ala Asp Val His Leu Gly Asn Gly Gly Pro Cys
        115                 120                 125

Leu Phe Met Arg Lys Val Ser His Val Ile Leu His Ser Leu His Ile
    130                 135                 140

His Gly Cys Asn Thr Ser Val Leu Gly Asp Val Leu Val Ser Glu Ser
145                 150                 155                 160

Ile Gly Val Glu Pro Val His Ala Gln Asp Gly Asp Ala Ile Thr Met
                165                 170                 175

Arg Asn Val Thr Asn Ala Trp Ile Asp His Asn Ser Leu Ser Asp Cys
            180                 185                 190

Ser Asp Gly Leu Ile Asp Val Thr Leu Gly Ser Thr Gly Ile Thr Ile
        195                 200                 205

Ser Asn Asn His Phe Phe Asn His His Lys Val Met Leu Leu Gly His
    210                 215                 220

Asp Asp Thr Tyr Asp Asp Lys Ser Met Lys Val Thr Val Ala Phe
225                 230                 235                 240

Asn Gln Phe Gly Pro Asn Ala Gly Gln Arg Met Pro Arg Ala Arg Tyr
                245                 250                 255

Gly Leu Val His Val Ala Asn Asn Tyr Asp Pro Trp Asn Ile Tyr
            260                 265                 270

Ala Ile Gly Gly Ser Ser Asn Pro Thr Ile Leu Ser Glu Gly Asn Ser
        275                 280                 285

Phe Thr Ala Pro Ser Glu Ser Tyr Lys Lys Glu Val Thr Lys Arg Ile
    290                 295                 300

Gly Cys Glu Ser Pro Ser Ala Cys Ala Asn Trp Val Trp Arg Ser Thr
305                 310                 315                 320

Arg Asp Ala Phe Ile Asn Gly Ala Tyr Phe Val Ser Ser Gly Lys Thr
                325                 330                 335

Glu Glu Thr Asn Ile Tyr Asn Ser Asn Glu Ala Phe Lys Val Glu Asn
            340                 345                 350
```

-continued

Gly Asn Ala Ala Pro Gln Leu Thr Lys Asn Ala Gly Val Val Thr
            355                 360                 365

<210> SEQ ID NO 110
<211> LENGTH: 225
<212> TYPE: PRT
<213> ORGANISM: Juniperus ashei (Ozark white cedar)

<400> SEQUENCE: 110

Met Ala Arg Val Ser Glu Leu Ala Phe Leu Leu Ala Ala Thr Leu Ala
 1               5                  10                  15

Ile Ser Leu His Met Gln Glu Ala Gly Val Val Lys Phe Asp Ile Lys
            20                  25                  30

Asn Gln Cys Gly Tyr Thr Val Trp Ala Ala Gly Leu Pro Gly Gly Gly
        35                  40                  45

Lys Arg Leu Asp Gln Gly Gln Thr Trp Thr Val Asn Leu Ala Ala Gly
    50                  55                  60

Thr Ala Ser Ala Arg Phe Trp Gly Arg Thr Gly Cys Thr Phe Asp Ala
65                  70                  75                  80

Ser Gly Lys Gly Ser Cys Gln Thr Gly Asp Cys Gly Gly Gln Leu Ser
                85                  90                  95

Cys Thr Val Ser Gly Ala Val Pro Ala Thr Leu Ala Glu Tyr Thr Gln
            100                 105                 110

Ser Asp Gln Asp Tyr Tyr Asp Val Ser Leu Val Asp Gly Phe Asn Ile
        115                 120                 125

Pro Leu Ala Ile Asn Pro Thr Asn Ala Gln Cys Thr Ala Pro Ala Cys
    130                 135                 140

Lys Ala Asp Ile Asn Ala Val Cys Pro Ser Glu Leu Lys Val Asp Gly
145                 150                 155                 160

Gly Cys Asn Ser Ala Cys Asn Val Phe Lys Thr Asp Gln Tyr Cys Cys
                165                 170                 175

Arg Asn Ala Tyr Val Asp Asn Cys Pro Ala Thr Asn Tyr Ser Lys Ile
            180                 185                 190

Phe Lys Asn Gln Cys Pro Gln Ala Tyr Ser Tyr Ala Lys Asp Asp Thr
        195                 200                 205

Ala Thr Phe Ala Cys Ala Ser Gly Thr Asp Tyr Ser Ile Val Phe Cys
    210                 215                 220

Pro
225

<210> SEQ ID NO 111
<211> LENGTH: 141
<212> TYPE: PRT
<213> ORGANISM: Lepidoglyphus destructor (Storage mite)

<400> SEQUENCE: 111

Met Met Lys Phe Ile Ala Leu Phe Ala Leu Val Ala Val Ala Ser Ala
 1               5                  10                  15

Gly Lys Met Thr Phe Lys Asp Cys Gly His Gly Glu Val Thr Glu Leu
            20                  25                  30

Asp Ile Thr Gly Cys Ser Gly Asp Thr Cys Val Ile His Arg Gly Glu
        35                  40                  45

Lys Met Thr Leu Glu Ala Lys Phe Ala Ala Asn Gln Asp Thr Ala Lys
    50                  55                  60

Val Thr Ile Lys Val Leu Ala Lys Val Ala Gly Thr Thr Ile Gln Val
65                  70                  75                  80

```
Pro Gly Leu Glu Thr Asp Gly Cys Lys Phe Ile Lys Cys Pro Val Lys
                85                  90                  95

Lys Gly Glu Ala Leu Asp Phe Ile Tyr Ser Gly Thr Ile Pro Ala Ile
            100                 105                 110

Thr Pro Lys Val Lys Ala Asp Val Thr Ala Glu Leu Ile Gly Asp His
        115                 120                 125

Gly Val Met Ala Cys Gly Thr Val His Gly Gln Val Glu
    130                 135                 140

<210> SEQ ID NO 112
<211> LENGTH: 263
<212> TYPE: PRT
<213> ORGANISM: Lolium perenne (Perennial ryegrass)

<400> SEQUENCE: 112

Met Ala Ser Ser Ser Val Leu Leu Val Ala Leu Phe Ala Val
  1               5                  10                  15

Phe Leu Gly Ser Ala His Gly Ile Ala Lys Val Pro Pro Gly Pro Asn
                20                  25                  30

Ile Thr Ala Glu Tyr Gly Asp Lys Trp Leu Asp Ala Lys Ser Thr Trp
            35                  40                  45

Tyr Gly Lys Pro Thr Gly Ala Gly Pro Lys Asn Gly Ala Cys
 50                  55                  60

Gly Tyr Lys Asn Val Asp Lys Ala Pro Phe Asn Gly Met Thr Gly Cys
 65                  70                  75                  80

Gly Asn Thr Pro Ile Phe Lys Asp Gly Arg Gly Cys Gly Ser Cys Phe
                85                  90                  95

Glu Ile Lys Cys Thr Lys Pro Glu Ser Cys Ser Gly Glu Ala Val Thr
            100                 105                 110

Val Thr Ile Thr Asp Asp Asn Glu Glu Pro Ile Ala Pro Tyr His Phe
        115                 120                 125

Asp Leu Ser Gly His Ala Phe Gly Ser Met Ala Lys Lys Gly Glu Glu
    130                 135                 140

Gln Asn Val Arg Ser Ala Gly Glu Leu Glu Leu Gln Phe Arg Arg Val
145                 150                 155                 160

Lys Cys Lys Tyr Pro Asp Asp Thr Lys Pro Thr Phe His Val Glu Lys
                165                 170                 175

Ala Ser Asn Pro Asn Tyr Leu Ala Ile Leu Val Lys Tyr Val Asp Gly
            180                 185                 190

Asp Gly Asp Val Val Ala Val Asp Ile Lys Glu Lys Gly Lys Asp Lys
        195                 200                 205

Trp Ile Glu Leu Lys Glu Ser Trp Gly Ala Val Trp Arg Ile Asp Thr
    210                 215                 220

Pro Asp Lys Leu Thr Gly Pro Phe Thr Val Arg Tyr Thr Thr Glu Gly
225                 230                 235                 240

Gly Thr Lys Ser Glu Phe Glu Asp Val Ile Pro Glu Gly Trp Lys Ala
                245                 250                 255

Asp Thr Ser Tyr Ser Ala Lys
            260

<210> SEQ ID NO 113
<211> LENGTH: 97
<212> TYPE: PRT
<213> ORGANISM: Lolium perenne (Perennial ryegrass)

<400> SEQUENCE: 113
```

```
Ala Ala Pro Val Glu Phe Thr Val Glu Lys Gly Ser Asp Glu Lys Asn
1               5                   10                  15

Leu Ala Leu Ser Ile Lys Tyr Asn Lys Glu Gly Asp Ser Met Ala Glu
            20                  25                  30

Val Glu Leu Lys Glu His Gly Ser Asn Glu Trp Leu Ala Leu Lys Lys
                35                  40                  45

Asn Gly Asp Gly Val Trp Glu Ile Lys Ser Asp Lys Pro Leu Lys Gly
    50                  55                  60

Pro Phe Asn Phe Arg Phe Val Ser Glu Lys Gly Met Arg Asn Val Phe
65                  70                  75                  80

Asp Asp Val Val Pro Ala Asp Phe Lys Val Gly Thr Thr Tyr Lys Pro
                85                  90                  95

Glu
```

<210> SEQ ID NO 114
<211> LENGTH: 97
<212> TYPE: PRT
<213> ORGANISM: Lolium perenne (Perennial ryegrass)

<400> SEQUENCE: 114

```
Thr Lys Val Asp Leu Thr Val Glu Lys Gly Ser Asp Ala Lys Thr Leu
1               5                   10                  15

Val Leu Asn Ile Lys Tyr Thr Arg Pro Gly Asp Thr Leu Ala Glu Val
            20                  25                  30

Glu Leu Arg Gln His Gly Ser Glu Glu Trp Glu Pro Met Thr Lys Lys
                35                  40                  45

Gly Asn Leu Trp Glu Val Lys Ser Ala Lys Pro Leu Thr Gly Pro Met
    50                  55                  60

Asn Phe Arg Phe Leu Ser Lys Gly Gly Met Lys Asn Val Phe Asp Glu
65                  70                  75                  80

Val Ile Pro Thr Ala Phe Thr Val Gly Lys Thr Tyr Thr Pro Glu Tyr
                85                  90                  95

Asn
```

<210> SEQ ID NO 115
<211> LENGTH: 308
<212> TYPE: PRT
<213> ORGANISM: Lolium perenne (Perennial ryegrass)

<400> SEQUENCE: 115

```
Met Ala Val Gln Lys Tyr Thr Val Ala Leu Phe Leu Arg Arg Gly Pro
1               5                   10                  15

Arg Gly Gly Pro Gly Arg Ser Tyr Ala Ala Asp Ala Gly Tyr Thr Pro
            20                  25                  30

Ala Ala Ala Ala Thr Pro Ala Thr Pro Ala Ala Thr Pro Ala Gly Gly
                35                  40                  45

Trp Arg Glu Gly Asp Asp Arg Ala Glu Ala Gly Gly Arg Gln
    50                  55                  60

Arg Leu Ala Ser Arg Gln Pro Trp Pro Leu Pro Thr Pro Leu Arg
65                  70                  75                  80

Arg Thr Ser Ser Arg Ser Ser Arg Pro Pro Ser Pro Ser Pro Arg
                85                  90                  95

Ala Ser Ser Pro Thr Ser Ala Ala Lys Ala Pro Gly Leu Ile Pro Lys
                100                 105                 110

Leu Asp Thr Ala Tyr Asp Val Ala Tyr Lys Ala Ala Glu Ala His Pro
            115                 120                 125
```

```
Arg Gly Gln Val Arg Arg Leu Arg His Cys Pro His Arg Ser Leu Arg
        130                 135                 140

Val Ile Ala Gly Ala Leu Glu Val His Ala Val Lys Pro Ala Thr Glu
145                 150                 155                 160

Glu Val Leu Ala Ala Lys Ile Pro Thr Gly Glu Leu Gln Ile Val Asp
                165                 170                 175

Lys Ile Asp Ala Ala Phe Lys Ile Ala Ala Thr Ala Ala Asn Ala Ala
                180                 185                 190

Pro Thr Asn Asp Lys Phe Thr Val Phe Glu Ser Ala Phe Asn Lys Ala
                195                 200                 205

Leu Asn Glu Cys Thr Gly Gly Ala Met Arg Pro Thr Ser Ser Ser Pro
        210                 215                 220

Pro Ser Arg Pro Arg Ser Ser Arg Pro Thr Pro Pro Ser Pro Ala
225                 230                 235                 240

Ala Pro Glu Val Lys Tyr Ala Val Phe Glu Ala Ala Leu Thr Lys Ala
                245                 250                 255

Ile Thr Ala Met Thr Gln Ala Gln Lys Ala Gly Lys Pro Ala Ala Ala
                260                 265                 270

Ala Ala Thr Ala Ala Ala Thr Val Ala Thr Ala Ala Thr Ala Ala
        275                 280                 285

Ala Val Leu Pro Pro Leu Leu Val Val Gln Ser Leu Ile Ser Leu
        290                 295                 300

Leu Ile Tyr Tyr
305

<210> SEQ ID NO 116
<211> LENGTH: 339
<212> TYPE: PRT
<213> ORGANISM: Lolium perenne (Perennial ryegrass)

<400> SEQUENCE: 116

Met Ala Val Gln Lys His Thr Val Ala Leu Phe Leu Ala Val Ala Leu
1               5                   10                  15

Val Ala Gly Pro Ala Ala Ser Tyr Ala Ala Asp Ala Gly Tyr Ala Pro
                20                  25                  30

Ala Thr Pro Ala Thr Pro Ala Ala Pro Ala Thr Ala Ala Thr Pro Ala
            35                  40                  45

Thr Pro Ala Thr Pro Ala Thr Pro Ala Ala Val Pro Ser Gly Lys Ala
50                  55                  60

Thr Thr Glu Glu Gln Lys Leu Ile Glu Lys Ile Asn Ala Gly Phe Lys
65                  70                  75                  80

Ala Ala Val Ala Ala Ala Val Val Pro Pro Ala Asp Lys Tyr Lys
                85                  90                  95

Thr Phe Val Glu Thr Phe Gly Thr Ala Thr Asn Lys Ala Phe Val Glu
                100                 105                 110

Gly Leu Ala Ser Gly Tyr Ala Asp Gln Ser Lys Asn Gln Leu Thr Ser
        115                 120                 125

Lys Leu Asp Ala Ala Leu Lys Leu Ala Tyr Glu Ala Gln Gly Ala
        130                 135                 140

Thr Pro Glu Ala Lys Tyr Asp Ala Tyr Val Ala Thr Leu Thr Glu Ala
145                 150                 155                 160

Leu Arg Val Ile Ala Gly Thr Leu Glu Val His Ala Val Lys Pro Ala
                165                 170                 175

Ala Glu Glu Val Lys Val Gly Ala Ile Pro Ala Ala Glu Val Gln Leu
```

-continued

```
            180                 185                 190
Ile Asp Lys Val Asp Ala Ala Tyr Arg Thr Ala Thr Ala Ala Asn
        195                 200                 205
Ala Ala Pro Ala Asn Asp Lys Phe Thr Val Phe Glu Asn Thr Phe Asn
    210                 215                 220
Asn Ala Ile Lys Val Ser Leu Gly Ala Ala Tyr Asp Ser Tyr Lys Phe
225                 230                 235                 240
Ile Pro Thr Leu Val Ala Ala Val Lys Gln Ala Tyr Ala Ala Lys Gln
                245                 250                 255
Ala Thr Ala Pro Glu Val Lys Tyr Thr Val Ser Glu Thr Ala Leu Lys
            260                 265                 270
Lys Ala Val Thr Ala Met Ser Glu Ala Glu Lys Glu Ala Thr Pro Ala
        275                 280                 285
Ala Ala Ala Thr Ala Thr Pro Thr Pro Ala Ala Thr Ala Thr Ala
    290                 295                 300
Thr Pro Ala Ala Ala Tyr Ala Thr Ala Thr Pro Ala Ala Ala Thr Ala
305                 310                 315                 320
Thr Ala Thr Pro Ala Ala Ala Thr Ala Thr Pro Ala Ala Ala Gly Gly
                325                 330                 335
Tyr Lys Val
```

<210> SEQ ID NO 117
<211> LENGTH: 158
<212> TYPE: PRT
<213> ORGANISM: Malus domestica (Apple) (Malus sylvestris)

<400> SEQUENCE: 117

```
Gly Val Tyr Thr Phe Glu Asn Glu Phe Thr Ser Glu Ile Pro Pro Ser
1               5                   10                  15
Arg Leu Phe Lys Ala Phe Val Leu Asp Ala Asp Asn Leu Ile Pro Lys
            20                  25                  30
Ile Ala Pro Gln Ala Ile Lys Gln Ala Glu Ile Leu Glu Gly Asn Gly
        35                  40                  45
Gly Pro Gly Thr Ile Lys Lys Ile Thr Phe Gly Glu Gly Ser Gln Tyr
    50                  55                  60
Gly Tyr Val Lys His Arg Ile Asp Ser Ile Asp Glu Ala Ser Tyr Ser
65                  70                  75                  80
Tyr Ser Tyr Thr Leu Ile Glu Gly Asp Ala Leu Thr Asp Thr Ile Glu
                85                  90                  95
Lys Ile Ser Tyr Glu Thr Lys Leu Val Ala Cys Gly Ser Gly Ser Thr
            100                 105                 110
Ile Lys Ser Ile Ser His Tyr His Thr Lys Gly Asn Ile Glu Ile Lys
        115                 120                 125
Glu Glu His Val Lys Val Gly Lys Glu Lys Ala His Gly Leu Phe Lys
    130                 135                 140
Leu Ile Glu Ser Tyr Leu Lys Asp His Pro Asp Ala Tyr Asn
145                 150                 155
```

<210> SEQ ID NO 118
<211> LENGTH: 133
<212> TYPE: PRT
<213> ORGANISM: Mercurialis annua (Annual mercury)

<400> SEQUENCE: 118

```
Met Ser Trp Gln Thr Tyr Val Asp Asp His Leu Met Cys Asp Ile Asp
1               5                   10                  15
```

```
Gly Gln Gly Gln His Leu Ala Ala Ser Ile Val Gly His Asp Gly
            20                  25                  30

Ser Ile Trp Ala Gln Ser Ala Ser Phe Pro Gln Leu Lys Pro Glu Glu
        35                  40                  45

Ile Thr Gly Ile Met Lys Asp Phe Asp Glu Pro Gly His Leu Ala Pro
    50                  55                  60

Thr Gly Leu Tyr Ile Ala Gly Thr Lys Tyr Met Val Ile Gln Gly Glu
65                  70                  75                  80

Ser Gly Ala Val Ile Arg Gly Lys Gly Ser Gly Gly Ile Thr Ile
                85                  90                  95

Lys Lys Thr Gly Gln Ala Leu Val Phe Gly Ile Tyr Glu Glu Pro Val
                100                 105                 110

Thr Pro Gly Gln Cys Asn Met Val Val Glu Arg Leu Gly Asp Tyr Leu
            115                 120                 125

Ile Glu Gln Gly Met
            130

<210> SEQ ID NO 119
<211> LENGTH: 274
<212> TYPE: PRT
<213> ORGANISM: Metapenaeus ensis (Greasyback shrimp) (Sand shrim

<400> SEQUENCE: 119

Met Lys Leu Glu Lys Asp Asn Ala Met Asp Arg Ala Asp Thr Leu Glu
1               5                   10                  15

Gln Gln Asn Lys Glu Ala Asn Asn Arg Ala Glu Lys Ser Glu Glu Glu
            20                  25                  30

Val His Asn Leu Gln Lys Arg Met Gln Gln Leu Glu Asn Asp Leu Asp
        35                  40                  45

Gln Val Gln Glu Ser Leu Leu Lys Ala Asn Asn Gln Leu Val Glu Lys
    50                  55                  60

Asp Lys Ala Leu Ser Asn Ala Glu Gly Glu Val Ala Ala Leu Asn Arg
65                  70                  75                  80

Arg Ile Gln Leu Leu Glu Glu Asp Leu Glu Arg Ser Glu Glu Arg Leu
                85                  90                  95

Asn Thr Ala Thr Thr Lys Leu Ala Glu Ala Ser Gln Ala Ala Asp Glu
                100                 105                 110

Ser Glu Arg Met Arg Lys Val Leu Glu Asn Arg Ser Leu Ser Asp Glu
            115                 120                 125

Glu Arg Met Asp Ala Leu Glu Asn Gln Leu Lys Glu Ala Arg Phe Leu
        130                 135                 140

Ala Glu Glu Ala Asp Arg Lys Tyr Asp Glu Val Ala Arg Lys Leu Ala
145                 150                 155                 160

Met Val Glu Ala Asp Leu Glu Arg Ala Glu Arg Ala Glu Thr Gly
                165                 170                 175

Glu Ser Lys Ile Val Glu Leu Glu Glu Leu Arg Val Val Gly Asn
            180                 185                 190

Asn Leu Lys Ser Leu Glu Val Ser Glu Lys Ala Asn Gln Arg Glu
        195                 200                 205

Glu Ala Tyr Lys Glu Gln Ile Lys Thr Leu Thr Asn Lys Leu Lys Ala
    210                 215                 220

Ala Glu Ala Arg Ala Glu Phe Ala Glu Arg Ser Val Gln Lys Leu Gln
225                 230                 235                 240

Lys Glu Val Asp Arg Leu Glu Asp Glu Leu Val Asn Glu Lys Glu Lys
```

```
                       245                 250                 255
Tyr Lys Ser Ile Thr Asp Glu Leu Asp Gln Thr Phe Ser Glu Leu Ser
            260                 265                 270

Gly Tyr

<210> SEQ ID NO 120
<211> LENGTH: 180
<212> TYPE: PRT
<213> ORGANISM: Mus musculus (Mouse)

<400> SEQUENCE: 120

Met Lys Met Leu Leu Leu Cys Leu Gly Leu Thr Leu Val Cys Val
 1               5                  10                  15

His Ala Glu Glu Ala Ser Ser Thr Gly Arg Asn Phe Asn Val Glu Lys
             20                  25                  30

Ile Asn Gly Glu Trp His Thr Ile Ile Leu Ala Ser Asp Lys Arg Glu
         35                  40                  45

Lys Ile Glu Asp Asn Gly Asn Phe Arg Leu Phe Leu Glu Gln Ile His
     50                  55                  60

Val Leu Glu Asn Ser Leu Val Leu Lys Phe His Thr Val Arg Asp Glu
 65                  70                  75                  80

Glu Cys Ser Glu Leu Ser Met Val Ala Asp Lys Thr Glu Lys Ala Gly
                 85                  90                  95

Glu Tyr Ser Val Thr Tyr Asp Gly Phe Asn Thr Phe Thr Ile Pro Lys
            100                 105                 110

Thr Asp Tyr Asp Asn Phe Leu Met Ala His Leu Ile Asn Glu Lys Asp
        115                 120                 125

Gly Glu Thr Phe Gln Leu Met Gly Leu Tyr Gly Arg Glu Pro Asp Leu
    130                 135                 140

Met Ser Asp Ile Lys Glu Arg Phe Ala Gln Leu Cys Glu Glu His Gly
145                 150                 155                 160

Ile Leu Arg Glu Asn Ile Ile Asp Leu Ser Asn Ala Asn Arg Cys Leu
                165                 170                 175

Gln Ala Arg Glu
            180

<210> SEQ ID NO 121
<211> LENGTH: 112
<212> TYPE: PRT
<213> ORGANISM: Myrmecia pilosula (Bulldog ant) (Australian jumpe

<400> SEQUENCE: 121

Met Lys Leu Ser Cys Leu Leu Leu Thr Leu Thr Ile Ile Phe Val Leu
 1               5                  10                  15

Thr Ile Val His Ala Pro Asn Val Glu Ala Lys Asp Leu Ala Asp Pro
             20                  25                  30

Glu Ser Glu Ala Val Gly Phe Ala Asp Ala Phe Gly Glu Ala Asp Ala
         35                  40                  45

Val Gly Glu Ala Asp Pro Asn Ala Gly Leu Gly Ser Val Phe Gly Arg
     50                  55                  60

Leu Ala Arg Ile Leu Gly Arg Val Ile Pro Lys Val Ala Lys Lys Leu
 65                  70                  75                  80

Gly Pro Lys Val Ala Lys Val Leu Pro Lys Val Met Lys Glu Ala Ile
                 85                  90                  95

Pro Met Ala Val Glu Met Ala Lys Ser Gln Glu Glu Gln Gln Pro Gln
            100                 105                 110
```

<210> SEQ ID NO 122
<211> LENGTH: 75
<212> TYPE: PRT
<213> ORGANISM: Myrmecia pilosula (Bulldog ant) (Australian jumpe

<400> SEQUENCE: 122

Met Lys Leu Ser Cys Leu Leu Leu Thr Leu Ala Ile Ile Phe Val Leu
1               5                   10                  15

Thr Ile Val His Ala Pro Asn Val Glu Ala Lys Ala Leu Ala Asp Pro
            20                  25                  30

Glu Ser Asp Ala Val Gly Phe Ala Asp Ala Val Gly Glu Ala Asp Pro
        35                  40                  45

Ile Asp Trp Lys Lys Val Asp Trp Lys Lys Val Ser Lys Lys Thr Cys
    50                  55                  60

Lys Val Met Leu Lys Ala Cys Lys Phe Leu Gly
65                  70                  75

<210> SEQ ID NO 123
<211> LENGTH: 145
<212> TYPE: PRT
<213> ORGANISM: Olea europaea (Common olive)

<400> SEQUENCE: 123

Glu Asp Ile Pro Gln Pro Pro Val Ser Gln Phe His Ile Gln Gly Gln
1               5                   10                  15

Val Tyr Cys Asp Thr Cys Arg Ala Gly Phe Ile Thr Glu Leu Ser Glu
            20                  25                  30

Phe Ile Pro Gly Ala Ser Leu Arg Leu Gln Cys Lys Asp Lys Glu Asn
        35                  40                  45

Gly Asp Val Thr Phe Thr Glu Val Gly Tyr Thr Arg Ala Glu Gly Leu
    50                  55                  60

Tyr Ser Met Leu Val Glu Arg Asp His Lys Asn Glu Phe Cys Glu Ile
65                  70                  75                  80

Thr Leu Ile Ser Ser Gly Arg Lys Asp Cys Asn Glu Ile Pro Thr Glu
            85                  90                  95

Gly Trp Ala Lys Pro Ser Leu Lys Phe Lys Leu Asn Thr Val Asn Gly
        100                 105                 110

Thr Thr Arg Thr Val Asn Pro Leu Gly Phe Phe Lys Lys Glu Ala Leu
    115                 120                 125

Pro Lys Cys Ala Gln Val Tyr Asn Lys Leu Gly Met Tyr Pro Pro Asn
    130                 135                 140

Met
145

<210> SEQ ID NO 124
<211> LENGTH: 24
<212> TYPE: PRT
<213> ORGANISM: Olea europaea (Common olive)

<400> SEQUENCE: 124

Ala Phe Ala Asn Thr Gly Val Glu Ile Val Ser Ile Asp Thr Tyr Leu
1               5                   10                  15

Phe Ser Leu Tyr Asp Glu Asp Lys
            20

<210> SEQ ID NO 125
<211> LENGTH: 29

```
<212> TYPE: PRT
<213> ORGANISM: Olea europaea (Common olive)

<400> SEQUENCE: 125

Val Lys Ala Val Thr Val Leu Asn Ser Ser Glu Gly Pro His Gly Ile
 1               5                  10                  15

Val Tyr Phe Ala Gln Glu Gly Asp Gly Pro Thr Thr Val
            20                  25

<210> SEQ ID NO 126
<211> LENGTH: 19
<212> TYPE: PRT
<213> ORGANISM: Olea europaea (Common olive)
<220> FEATURE:
<221> NAME/KEY: UNSURE
<222> LOCATION: 14, 16
<223> OTHER INFORMATION: Xaa = any amino acid

<400> SEQUENCE: 126

Ala Pro Ser Gln Gly Thr Val Thr Ala Lys Leu Thr Ser Xaa Val Xaa
 1               5                  10                  15

Tyr Lys Asp

<210> SEQ ID NO 127
<211> LENGTH: 263
<212> TYPE: PRT
<213> ORGANISM: Oryza sativa (Rice)

<400> SEQUENCE: 127

Met Ala Ser Ser Ser Leu Leu Leu Ala Cys Val Val Ala Ala Met
 1               5                  10                  15

Val Ser Pro Ser Pro Ala Gly His Pro Lys Val Pro Pro Gly Pro Asn
            20                  25                  30

Ile Thr Thr Ser Tyr Gly Asp Lys Trp Leu Glu Ala Arg Pro Pro Gly
        35                  40                  45

Met Val Arg Pro Arg Val Leu Ala Pro Lys Asp Asn Gly Gly Ala Cys
    50                  55                  60

Gly Tyr Lys Asp Val Asp Lys Ala Pro Phe Leu Gly Met Asn Ser Cys
65                  70                  75                  80

Gly Asn Asp Pro Ile Phe Lys Asp Gly Lys Gly Cys Gly Ser Cys Phe
                85                  90                  95

Glu Ile Lys Cys Ser Lys Pro Glu Ala Cys Ser Asp Lys Pro Ala Leu
            100                 105                 110

Ile His Val Thr Asp Met Asn Asp Glu Pro Ile Ala Ala Tyr His Phe
        115                 120                 125

Asp Leu Ser Gly Leu Ala Met Ala Lys Asp Gly Lys Asp Glu Glu Leu
    130                 135                 140

Arg Lys Ala Gly Ile Ile Asp Thr Gln Phe Arg Arg Val Lys Cys Lys
145                 150                 155                 160

Tyr Pro Ala Asp Thr Lys Ile Thr Phe His Ile Glu Lys Ala Ser Asn
                165                 170                 175

Pro Asn Tyr Leu Ala Leu Leu Val Lys Tyr Val Ala Gly Asp Gly Asp
            180                 185                 190

Val Val Glu Val Glu Ile Lys Glu Lys Gly Ser Glu Gly Trp Lys Ala
        195                 200                 205

Leu Lys Glu Ser Trp Gly Ala Ile Trp Arg Ile Asp Thr Pro Lys Pro
    210                 215                 220

Leu Lys Gly Pro Phe Ser Val Arg Val Thr Thr Glu Gly Ala Arg Arg
```

```
                225                 230                 235                 240
Ser Ser Ala Glu Asp Ala Ile Pro Asp Pro Gly Arg Arg Gln Arg Val
                        245                 250                 255

Gln Val Asn Val Gln Ala Lys
            260

<210> SEQ ID NO 128
<211> LENGTH: 139
<212> TYPE: PRT
<213> ORGANISM: Parietaria judaica

<400> SEQUENCE: 128

Gln Glu Thr Cys Gly Thr Met Val Arg Ala Leu Met Pro Cys Leu Pro
 1               5                  10                  15

Phe Val Gln Gly Lys Glu Lys Glu Pro Ser Lys Gly Cys Cys Ser Gly
             20                  25                  30

Ala Lys Arg Leu Asp Gly Glu Thr Lys Thr Gly Pro Gln Arg Val His
         35                  40                  45

Ala Cys Glu Cys Ile Gln Thr Ala Met Lys Thr Tyr Ser Asp Ile Asp
     50                  55                  60

Gly Lys Leu Val Ser Glu Val Pro Lys His Cys Gly Ile Val Asp Ser
 65                  70                  75                  80

Lys Leu Pro Pro Ile Asp Val Asn Met Asp Cys Lys Thr Val Gly Val
                 85                  90                  95

Val Pro Arg Gln Pro Gln Leu Pro Val Ser Leu Arg His Gly Pro Val
            100                 105                 110

Thr Gly Pro Ser Asp Pro Ala His Lys Ala Arg Leu Glu Arg Pro Gln
        115                 120                 125

Ile Arg Val Pro Pro Pro Ala Pro Glu Lys Ala
    130                 135

<210> SEQ ID NO 129
<211> LENGTH: 176
<212> TYPE: PRT
<213> ORGANISM: Parietaria judaica

<400> SEQUENCE: 129

Met Arg Thr Val Ser Ala Pro Ser Ala Val Ala Leu Val Val Ile Val
 1               5                  10                  15

Ala Ala Gly Leu Ala Trp Thr Ser Leu Ala Ser Val Ala Pro Pro Ala
             20                  25                  30

Pro Ala Pro Gly Ser Glu Glu Thr Cys Gly Thr Val Arg Ala Leu
         35                  40                  45

Met Pro Cys Leu Pro Phe Val Gln Gly Lys Glu Lys Glu Pro Ser Lys
     50                  55                  60

Gly Cys Cys Ser Gly Ala Lys Arg Leu Asp Gly Glu Thr Lys Thr Gly
 65                  70                  75                  80

Leu Gln Arg Val His Ala Cys Glu Cys Ile Gln Thr Ala Met Lys Thr
                 85                  90                  95

Tyr Ser Asp Ile Asp Gly Lys Leu Val Ser Glu Val Pro Lys His Cys
            100                 105                 110

Gly Ile Val Asp Ser Lys Leu Pro Pro Ile Asp Val Asn Met Asp Cys
        115                 120                 125

Lys Thr Leu Gly Val Val Pro Arg Gln Pro Gln Leu Pro Val Ser Leu
    130                 135                 140

Arg His Gly Pro Val Thr Gly Pro Ser Asp Pro Ala His Lys Ala Arg
```

```
                145                 150                 155                 160
Leu Glu Arg Pro Gln Ile Arg Val Pro Pro Ala Pro Glu Lys Ala
                    165                 170                 175

<210> SEQ ID NO 130
<211> LENGTH: 138
<212> TYPE: PRT
<213> ORGANISM: Parietaria judaica

<400> SEQUENCE: 130

Met Arg Thr Val Ser Ala Arg Ser Ser Val Ala Leu Val Val Ile Val
 1               5                  10                  15

Ala Ala Val Leu Val Trp Thr Ser Ser Ala Ser Val Ala Pro Ala Pro
                20                  25                  30

Ala Pro Gly Ser Glu Glu Thr Cys Gly Thr Val Val Gly Ala Leu Met
                35                  40                  45

Pro Cys Leu Pro Phe Val Gln Gly Lys Glu Lys Glu Pro Ser Lys Gly
        50                  55                  60

Cys Cys Ser Gly Ala Lys Arg Leu Asp Gly Glu Thr Lys Thr Gly Pro
 65                  70                  75                  80

Gln Arg Val His Ala Cys Glu Cys Ile Gln Thr Ala Met Lys Thr Tyr
                 85                  90                  95

Ser Asp Ile Asp Gly Lys Leu Val Ser Glu Val Pro Lys His Cys Gly
                100                 105                 110

Ile Val Asp Ser Lys Leu Pro Pro Ile Asp Val Asn Met Asp Cys Lys
            115                 120                 125

Thr Leu Gly Val Leu His Tyr Lys Gly Asn
        130                 135

<210> SEQ ID NO 131
<211> LENGTH: 133
<212> TYPE: PRT
<213> ORGANISM: Parietaria judaica

<400> SEQUENCE: 131

Met Arg Thr Val Ser Met Ala Ala Leu Val Val Ile Ala Ala Ala Leu
 1               5                  10                  15

Ala Trp Thr Ser Ser Ala Glu Pro Ala Pro Ala Pro Gly Glu
                20                  25                  30

Glu Ala Cys Gly Lys Val Val Gln Asp Ile Met Pro Cys Leu His Phe
                35                  40                  45

Val Lys Gly Glu Glu Lys Glu Pro Ser Lys Glu Cys Cys Ser Gly Thr
        50                  55                  60

Lys Lys Leu Ser Glu Glu Val Lys Thr Thr Glu Gln Lys Arg Glu Ala
 65                  70                  75                  80

Cys Lys Cys Ile Val Arg Ala Thr Lys Gly Ile Ser Gly Ile Lys Asn
                 85                  90                  95

Glu Leu Val Ala Glu Val Pro Lys Lys Cys Asp Ile Lys Thr Thr Leu
                100                 105                 110

Pro Pro Ile Thr Ala Asp Phe Asp Cys Ser Lys Ile Gln Ser Thr Ile
            115                 120                 125

Phe Arg Gly Tyr Tyr
        130

<210> SEQ ID NO 132
<211> LENGTH: 133
<212> TYPE: PRT
```

<213> ORGANISM: Parietaria judaica

<400> SEQUENCE: 132

| Met | Arg | Thr | Val | Ser | Met | Ala | Ala | Leu | Val | Val | Ile | Ala | Ala | Leu |
|---|---|---|---|---|---|---|---|---|---|---|---|---|---|---|
| 1 | | | | 5 | | | | | 10 | | | | | 15 |

Ala Trp Thr Ser Ser Ala Glu Leu Ala Ser Ala Pro Ala Pro Gly Glu
                20                  25                  30

Gly Pro Cys Gly Lys Val Val His His Ile Met Pro Cys Leu Lys Phe
            35                  40                  45

Val Lys Gly Glu Glu Lys Glu Pro Ser Lys Ser Cys Cys Ser Gly Thr
    50                  55                  60

Lys Lys Leu Ser Glu Glu Val Lys Thr Thr Glu Gln Lys Arg Glu Ala
65                  70                  75                  80

Cys Lys Cys Ile Val Ala Ala Thr Lys Gly Ile Ser Gly Ile Lys Asn
                85                  90                  95

Glu Leu Val Ala Glu Val Pro Lys Lys Cys Gly Ile Thr Thr Thr Leu
            100                 105                 110

Pro Pro Ile Thr Ala Asp Phe Asp Cys Ser Lys Ile Glu Ser Thr Ile
        115                 120                 125

Phe Arg Gly Tyr Tyr
        130

<210> SEQ ID NO 133
<211> LENGTH: 269
<212> TYPE: PRT
<213> ORGANISM: Phalaris aquatica (Canary grass)

<400> SEQUENCE: 133

Met Met Lys Met Val Cys Ser Ser Ser Ser Ser Leu Leu Val Val
1               5                   10                  15

Ala Ala Leu Leu Ala Val Phe Val Gly Ser Ala Gln Gly Ile Ala Lys
                20                  25                  30

Val Pro Pro Gly Pro Asn Ile Thr Ala Glu Tyr Gly Asp Lys Trp Leu
            35                  40                  45

Asp Ala Lys Ser Thr Trp Tyr Gly Lys Pro Thr Gly Ala Gly Pro Lys
    50                  55                  60

Asp Asn Gly Gly Ala Cys Gly Tyr Lys Asp Val Asp Lys Ala Pro Phe
65                  70                  75                  80

Asn Gly Met Thr Gly Cys Gly Asn Thr Pro Ile Phe Lys Asp Gly Arg
                85                  90                  95

Gly Cys Gly Ser Cys Phe Glu Leu Lys Cys Ser Lys Pro Glu Ser Cys
            100                 105                 110

Ser Gly Glu Pro Ile Thr Val His Ile Thr Asp Asp Asn Glu Glu Pro
        115                 120                 125

Ile Ala Pro Tyr His Phe Asp Leu Ser Gly His Ala Phe Gly Ser Met
    130                 135                 140

Ala Lys Lys Gly Glu Glu Glu Asn Val Arg Gly Ala Gly Glu Leu Glu
145                 150                 155                 160

Leu Gln Phe Arg Arg Val Lys Cys Lys Tyr Pro Asp Gly Thr Lys Pro
                165                 170                 175

Thr Phe His Val Glu Lys Gly Ser Asn Pro Asn Tyr Leu Ala Leu Leu
            180                 185                 190

Val Lys Tyr Val Asp Gly Asp Gly Asp Val Val Ala Val Asp Ile Lys
        195                 200                 205

Glu Lys Gly Lys Asp Lys Trp Ile Glu Leu Lys Glu Ser Trp Gly Ala

```
                    210                 215                 220
Ile Trp Arg Ile Asp Thr Pro Asp Lys Leu Thr Gly Pro Phe Thr Val
225                 230                 235                 240

Arg Tyr Thr Thr Glu Gly Gly Thr Lys Ala Glu Phe Glu Asp Val Ile
                245                 250                 255

Pro Glu Gly Trp Lys Ala Asp Thr His Asp Ala Ser Lys
                260                 265

<210> SEQ ID NO 134
<211> LENGTH: 320
<212> TYPE: PRT
<213> ORGANISM: Phalaris aquatica (Canary grass)

<400> SEQUENCE: 134

Met Ala Val Gln Lys Tyr Thr Met Ala Leu Phe Leu Ala Val Ala Leu
1               5                   10                  15

Val Ala Gly Pro Ala Ala Pro Thr Pro Pro Thr Pro Arg Thr Pro Pro
                20                  25                  30

Leu Leu Pro Pro Pro Arg Ala Arg Asp Lys Ala Thr Leu Thr Ser Arg
            35                  40                  45

Ser Val Glu Asp Ile Asn Ala Ala Ser Arg Arg Pro Trp Trp Ala Ser
        50                  55                  60

Val Pro Pro Ala Asp Lys Phe Lys Thr Phe Ala Asp His Val Leu Cys
65                  70                  75                  80

Val Pro Asn Ala Asp Val Thr Ser Ala Ala Thr Lys Ala Pro Gln Leu
                85                  90                  95

Lys Ala Lys Leu Asp Ala Ala Tyr Arg Val Ala Tyr Glu Ala Ala Glu
            100                 105                 110

Gly Ser Thr Pro Glu Ala Lys Tyr Asp Ala Phe Ile Ala Ala Leu Thr
        115                 120                 125

Glu Ala Leu Arg Val Ile Ala Gly Ala Phe Glu Val His Ala Val Lys
130                 135                 140

Pro Ala Thr Glu Glu Val Val Ala Asp Pro Val Gly Glu Leu Gln Ile
145                 150                 155                 160

Val Asp Lys Ile Asp Ala Ala Phe Lys Ile Ala Ala Thr Ala Ala Asn
                165                 170                 175

Ser Ala Pro Ala Asn Asp Lys Phe Thr Val Phe Glu Gly Ala Phe Asn
            180                 185                 190

Lys Ala Ile Lys Glu Ser Thr Ala Gly Ala Tyr Glu Thr Tyr Lys Phe
        195                 200                 205

Ile Pro Ser Leu Glu Ala Ala Val Lys Gln Ala Tyr Gly Ala Thr Val
    210                 215                 220

Ala Arg Ala Pro Glu Val Lys Tyr Ala Val Phe Glu Ala Gly Leu Thr
225                 230                 235                 240

Lys Ala Ile Thr Ala Met Ser Glu Ala Gln Lys Val Ala Lys Pro Pro
                245                 250                 255

Leu Ser Pro Gln Pro Pro Gln Val Leu Pro Leu Ala Ala Gly Gly Ala
            260                 265                 270

Ala Thr Val Ala Ala Ala Ser Asp Val Arg Val Cys Arg Ser His Gly
        275                 280                 285

Thr Leu Gln Asp Ala Cys Leu Leu Arg Cys Arg Gly Gly Cys Gln Pro
    290                 295                 300

Val Val Trp Arg Gly Gly Ser His Arg Ala Arg Gly Gly Tyr Lys Val
305                 310                 315                 320
```

```
<210> SEQ ID NO 135
<211> LENGTH: 305
<212> TYPE: PRT
<213> ORGANISM: Phalaris aquatica (Canary grass)

<400> SEQUENCE: 135

Met Ala Val Gln Lys Tyr Thr Val Ala Leu Phe Leu Ala Val Ala Leu
  1               5                  10                  15

Val Ala Gly Pro Ala Ala Leu Tyr Ala Gly Asp Gly Tyr Ala Pro Ala
                 20                  25                  30

Thr Pro Ala Ala Ser Ala Thr Leu Ala Thr Pro Ala Thr Pro Ala Ala
             35                  40                  45

Ser Pro Gln His Ala Gly Thr Thr Glu Tyr His Ile Val Arg Lys Ala
 50                  55                  60

Gly Leu Asn Glu Glu Lys Asn Ala Ala Arg Gln Thr Asp Asp Glu Gln
 65                  70                  75                  80

Lys Arg Ser Asp Glu Ile Asn Cys Pro Asp Phe Asn Lys Ser Val His
                 85                  90                  95

Cys Arg Ala Asp Arg Leu Pro Val Cys Ser Ser Thr Ala His Ser
                100                 105                 110

Ser Lys Gln Asp Val Ala Trp Met Leu Gly Tyr Gly Ser Ile Gln Gly
            115                 120                 125

Phe Ser Met Asp Asp Ala Ser Val Gly Ser Val Ser Ser Glu Phe His
130                 135                 140

Val Ile Glu Ser Ala Ile Glu Val Ile Thr Tyr Ile Gly Glu Glu Val
145                 150                 155                 160

Lys Val Ile Pro Ala Gly Glu Val Glu Val Ile Asn Lys Val Lys Ala
                165                 170                 175

Ala Phe Ser Thr Ala Ala Thr Ala Ala Asp Glu Ala Pro Ala Asn Asp
            180                 185                 190

Lys Phe Thr Val Phe Val Ser Ser Phe Asn Lys Ala Ile Lys Glu Thr
        195                 200                 205

Thr Gly Gly Ala Tyr Ala Gly Tyr Lys Phe Ile Pro Thr Leu Glu Ala
    210                 215                 220

Ala Val Lys Gln Ala Tyr Ala Ala Ser Ser Ala Thr Ala Pro Glu Val
225                 230                 235                 240

Lys Tyr Ala Val Phe Glu Thr Ala Leu Lys Lys Ala Ile Ser Ala Met
                245                 250                 255

Ser Glu Ala Gln Lys Glu Ala Lys Pro Ala Ala Ala Ile Ser Ala Ala
            260                 265                 270

Thr Thr Thr Ile Ser Ala Ser Thr Ala Thr Pro Ala Ala Pro Pro Pro
        275                 280                 285

Pro Gln Leu Gly Thr Ala Thr Pro Ala Val Ala Gly Gly Tyr Lys
    290                 295                 300

Val
305

<210> SEQ ID NO 136
<211> LENGTH: 294
<212> TYPE: PRT
<213> ORGANISM: Phalaris aquatica (Canary grass)

<400> SEQUENCE: 136

Met Ala Val Gln Lys Tyr Thr Val Ala Leu Phe Leu Ala Met Ala Leu
  1               5                  10                  15
```

```
Val Ala Gly Pro Ala Ala Ser Tyr Ala Asp Ala Gly Thr Pro Pro
            20                  25                  30

Thr Pro Ala Thr Pro Ala Val Pro Gly Ala Ala Ala Gly Lys Ala Thr
        35                  40                  45

Thr His Glu Gln Lys Leu Ile Glu Asp Ile Asn Ala Ala Phe Lys Trp
 50                  55                  60

Trp Pro Ala Ser Ala Pro Pro Ala Asp Lys Tyr Lys Thr Phe Glu Thr
 65                  70                  75                  80

Ala Phe Ser Lys Ala Asn Ile Ala Gly Ala Ser Thr Lys Gly Leu Asp
                 85                  90                  95

Ala Ala Tyr Ser Val Val Tyr Asn Thr Ala Ala Gly Ala Thr Pro Glu
            100                 105                 110

Ala Lys Tyr Asp Ser Phe Val Thr Ala Leu Thr Glu Ala Leu Arg Ile
        115                 120                 125

Met Ala Gly Thr Leu Glu Val His Ala Val Lys Pro Ala Thr Glu Glu
130                 135                 140

Glu Val Pro Ser Ala Lys Ile Leu Arg Ala Asn Ser Arg Ser Ser Thr
145                 150                 155                 160

Arg Ser Ser Arg Phe Lys Ile Ala Ala Thr Val Ala Thr Pro Leu Ser
                165                 170                 175

His Ser Thr Ala Ala Asn Ser Ala Pro Ala Asn Asp Lys Phe Thr Val
            180                 185                 190

Phe Glu Gly Ala Phe Asn Lys Ala Ile Lys Glu Arg His Gly Gly Pro
        195                 200                 205

Thr Glu Thr Tyr Lys Phe Ile Pro Ser Leu Glu Ala Ala Val Lys Gln
210                 215                 220

Ala Tyr Gly Ala Thr Val Ala Arg Ala Pro Glu Val Lys Tyr Ala Val
225                 230                 235                 240

Phe Glu Ala Gly Leu Thr Lys Ala Ile Thr Ala Met Ser Glu Ala Gln
                245                 250                 255

Lys Val Ala Lys Pro Val Arg Leu Ser Pro Gln Pro Pro Gln Val Leu
            260                 265                 270

Pro Leu Ala Ala Gly Gly Ala Ala Thr Val Ala Ala Ser Asp Ser
        275                 280                 285

Arg Gly Gly Tyr Lys Val
    290

<210> SEQ ID NO 137
<211> LENGTH: 175
<212> TYPE: PRT
<213> ORGANISM: Phalaris aquatica (Canary grass)

<400> SEQUENCE: 137

Ala Lys Tyr Asp Ala Phe Ile Ala Ala Leu Thr Glu Ala Leu Arg Val
 1               5                   10                  15

Ile Ala Gly Ala Phe Glu Val His Ala Val Lys Pro Ala Thr Glu Glu
            20                  25                  30

Val Pro Ala Ala Lys Ile Pro Ala Gly Glu Leu Gln Ile Val Asp Lys
        35                  40                  45

Ile Asp Ala Ala Phe Lys Ile Ala Ala Thr Ala Ala Asn Ser Ala Pro
 50                  55                  60

Ala Asn Asp Lys Phe Thr Val Phe Glu Gly Ala Phe Asn Lys Ala Ile
 65                  70                  75                  80

Lys Glu Arg His Gly Gly Ala Tyr Glu Thr Tyr Lys Phe Ile Pro Ser
                 85                  90                  95
```

-continued

```
Leu Glu Ala Ser Arg Ser Lys Gln Ala Tyr Gly Ala Thr Val Ala Arg
            100                 105                 110

Ala Pro Glu Val Lys Tyr Ala Val Phe Glu Ala Gly Leu Thr Lys Ala
        115                 120                 125

Ile Thr Ala Met Ser Glu Ala Gln Lys Val Ala Lys Pro Val Arg Ser
    130                 135                 140

Val Thr Ala Ala Ala Gly Ala Ala Thr Ala Ala Gly Gly Ala Ala
145                 150                 155                 160

Thr Val Ala Ala Ser Arg Pro Thr Ser Ala Gly Gly Tyr Lys Val
                165                 170                 175

<210> SEQ ID NO 138
<211> LENGTH: 263
<212> TYPE: PRT
<213> ORGANISM: Phleum pratense (Common timothy)

<400> SEQUENCE: 138

Met Ala Ser Ser Ser Val Leu Leu Val Val Leu Phe Ala Val
1               5                   10                  15

Phe Leu Gly Ser Ala Tyr Gly Ile Pro Lys Val Pro Pro Gly Pro Asn
            20                  25                  30

Ile Thr Ala Thr Tyr Gly Asp Lys Trp Leu Asp Ala Lys Ser Thr Trp
        35                  40                  45

Tyr Gly Lys Pro Thr Gly Ala Gly Pro Lys Asp Asn Gly Gly Ala Cys
    50                  55                  60

Gly Tyr Lys Asp Val Asp Lys Pro Pro Phe Ser Gly Met Thr Gly Cys
65                  70                  75                  80

Gly Asn Thr Pro Ile Phe Lys Ser Gly Arg Gly Cys Gly Ser Cys Phe
                85                  90                  95

Glu Ile Lys Cys Thr Lys Pro Glu Ala Cys Ser Gly Glu Pro Val Val
            100                 105                 110

Val His Ile Thr Asp Asp Asn Glu Glu Pro Ile Ala Pro Tyr His Phe
        115                 120                 125

Asp Leu Ser Gly His Ala Phe Gly Ala Met Ala Lys Lys Gly Asp Glu
    130                 135                 140

Gln Lys Leu Arg Ser Ala Gly Glu Leu Glu Leu Gln Phe Arg Arg Val
145                 150                 155                 160

Lys Cys Lys Tyr Pro Glu Gly Thr Lys Val Thr Phe His Val Glu Lys
                165                 170                 175

Gly Ser Asn Pro Asn Tyr Leu Ala Leu Leu Val Lys Tyr Val Asn Gly
            180                 185                 190

Asp Gly Asp Val Val Ala Val Asp Ile Lys Glu Lys Gly Lys Asp Lys
        195                 200                 205

Trp Ile Glu Leu Lys Glu Ser Trp Gly Ala Ile Trp Arg Ile Asp Thr
    210                 215                 220

Pro Asp Lys Leu Thr Gly Pro Phe Thr Val Arg Tyr Thr Thr Glu Gly
225                 230                 235                 240

Gly Thr Lys Thr Glu Ala Glu Asp Val Ile Pro Glu Gly Trp Lys Ala
                245                 250                 255

Asp Thr Ser Tyr Glu Ser Lys
            260

<210> SEQ ID NO 139
<211> LENGTH: 122
<212> TYPE: PRT
```

<213> ORGANISM: Phleum pratense (Common timothy)

<400> SEQUENCE: 139

```
Met Ser Met Ala Ser Ser Ser Ser Leu Leu Ala Met Ala Val
 1               5                  10                  15

Leu Ala Ala Leu Phe Ala Gly Ala Trp Cys Val Pro Lys Val Thr Phe
             20                  25                  30

Thr Val Glu Lys Gly Ser Asn Glu Lys His Leu Ala Val Leu Val Lys
         35                  40                  45

Tyr Glu Gly Asp Thr Met Ala Glu Val Glu Leu Arg Glu His Gly Ser
     50                  55                  60

Asp Glu Trp Val Ala Met Thr Lys Gly Glu Gly Val Trp Thr Phe
 65                  70                  75                  80

Asp Ser Glu Glu Pro Leu Gln Gly Pro Phe Asn Phe Arg Phe Leu Thr
                 85                  90                  95

Glu Lys Gly Met Lys Asn Val Phe Asp Asp Val Val Pro Glu Lys Tyr
             100                 105                 110

Thr Ile Gly Ala Thr Tyr Ala Pro Glu Glu
         115                 120
```

<210> SEQ ID NO 140
<211> LENGTH: 286
<212> TYPE: PRT
<213> ORGANISM: Phleum pratense (Common timothy)

<400> SEQUENCE: 140

```
Ala Asp Leu Gly Tyr Gly Pro Ala Thr Pro Ala Ala Pro Ala Ala Gly
 1               5                  10                  15

Tyr Thr Pro Ala Thr Pro Ala Ala Pro Ala Gly Ala Asp Ala Ala Gly
             20                  25                  30

Lys Ala Thr Thr Glu Glu Gln Lys Leu Ile Glu Lys Ile Asn Ala Gly
         35                  40                  45

Phe Lys Ala Ala Leu Ala Gly Ala Gly Val Gln Pro Ala Asp Lys Tyr
     50                  55                  60

Arg Thr Phe Val Ala Thr Phe Gly Pro Ala Ser Asn Lys Ala Phe Ala
 65                  70                  75                  80

Glu Gly Leu Ser Gly Glu Pro Lys Gly Ala Ala Glu Ser Ser Ser Lys
                 85                  90                  95

Ala Ala Leu Thr Ser Lys Leu Asp Ala Ala Tyr Lys Leu Ala Tyr Lys
             100                 105                 110

Thr Ala Glu Gly Ala Thr Pro Glu Ala Lys Tyr Asp Ala Tyr Val Ala
         115                 120                 125

Thr Leu Ser Glu Ala Leu Arg Ile Ile Ala Gly Thr Leu Glu Val His
     130                 135                 140

Ala Val Lys Pro Ala Ala Glu Glu Val Lys Val Ile Pro Ala Gly Glu
145                 150                 155                 160

Leu Gln Val Ile Glu Lys Val Asp Ala Ala Phe Lys Val Ala Ala Thr
                 165                 170                 175

Ala Ala Asn Ala Ala Pro Ala Asn Asp Lys Phe Thr Val Phe Glu Ala
             180                 185                 190

Ala Phe Asn Asp Glu Ile Lys Ala Ser Thr Gly Gly Ala Tyr Glu Ser
         195                 200                 205

Tyr Lys Phe Ile Pro Ala Leu Glu Ala Ala Val Lys Gln Ala Tyr Ala
     210                 215                 220

Ala Thr Val Ala Thr Ala Pro Glu Val Lys Tyr Thr Val Phe Glu Thr
```

```
                225                 230                 235                 240
Ala Leu Lys Lys Ala Ile Thr Ala Met Ser Glu Ala Gln Lys Ala Ala
                245                 250                 255

Lys Pro Ala Ala Ala Thr Ala Thr Ala Thr Ala Ala Val Gly Ala
            260                 265                 270

Ala Thr Gly Ala Ala Thr Ala Ala Thr Gly Gly Tyr Lys Val
        275                 280                 285

<210> SEQ ID NO 141
<211> LENGTH: 284
<212> TYPE: PRT
<213> ORGANISM: Phleum pratense (Common timothy)

<400> SEQUENCE: 141

Ala Ala Ala Ala Val Pro Arg Arg Gly Pro Arg Gly Gly Pro Gly Arg
  1               5                  10                  15

Ser Tyr Thr Ala Asp Ala Gly Tyr Ala Pro Ala Thr Pro Ala Ala Ala
             20                  25                  30

Gly Ala Ala Ala Gly Lys Ala Thr Thr Glu Glu Gln Lys Leu Ile Glu
         35                  40                  45

Asp Ile Asn Val Gly Phe Lys Ala Val Ala Ala Ala Ser Val
         50                  55                  60

Pro Ala Ala Asp Lys Phe Lys Thr Phe Glu Ala Ala Phe Thr Ser Ser
 65                  70                  75                  80

Ser Lys Ala Ala Ala Lys Ala Pro Gly Leu Val Pro Lys Leu Asp
                 85                  90                  95

Ala Ala Tyr Ser Val Ala Tyr Lys Ala Ala Val Gly Ala Thr Pro Glu
            100                 105                 110

Ala Lys Phe Asp Ser Phe Val Ala Ser Leu Thr Glu Ala Leu Arg Val
            115                 120                 125

Ile Ala Gly Ala Leu Glu Val His Ala Val Lys Pro Val Thr Glu Glu
            130                 135                 140

Pro Gly Met Ala Lys Ile Pro Ala Gly Glu Leu Gln Ile Ile Asp Lys
145                 150                 155                 160

Ile Asp Ala Ala Phe Lys Val Ala Ala Thr Ala Ala Thr Ala Pro
                165                 170                 175

Ala Asp Asp Lys Phe Thr Val Phe Glu Ala Ala Phe Asn Lys Ala Ile
            180                 185                 190

Lys Glu Ser Thr Gly Gly Ala Tyr Asp Thr Tyr Lys Cys Ile Pro Ser
            195                 200                 205

Leu Glu Ala Ala Val Lys Gln Ala Tyr Ala Ala Thr Val Ala Ala Ala
            210                 215                 220

Pro Gln Val Lys Tyr Ala Val Phe Glu Ala Ala Leu Thr Lys Ala Ile
225                 230                 235                 240

Thr Ala Met Ser Glu Val Gln Lys Val Ser Gln Pro Ala Thr Gly Ala
                245                 250                 255

Ala Thr Val Ala Ala Gly Ala Ala Thr Thr Ala Ala Gly Ala Ala Ser
            260                 265                 270

Gly Ala Ala Thr Val Ala Ala Gly Gly Tyr Lys Val
            275                 280

<210> SEQ ID NO 142
<211> LENGTH: 132
<212> TYPE: PRT
<213> ORGANISM: Phleum pratense (Common timothy)
```

-continued

```
<400> SEQUENCE: 142

Met Val Ala Met Phe Leu Ala Val Ala Val Leu Gly Leu Ala Thr
1               5                   10                  15

Ser Pro Thr Ala Glu Gly Gly Lys Ala Thr Thr Glu Glu Gln Lys Leu
            20                  25                  30

Ile Glu Asp Val Asn Ala Ser Phe Arg Ala Ala Met Ala Thr Thr Ala
                35                  40                  45

Asn Val Pro Pro Ala Asp Lys Tyr Lys Thr Phe Glu Ala Ala Phe Thr
    50                  55                  60

Val Ser Ser Lys Arg Asn Leu Ala Asp Ala Val Ser Lys Ala Pro Gln
65                  70                  75                  80

Leu Val Pro Lys Leu Asp Glu Val Tyr Asn Ala Ala Tyr Asn Ala Ala
                85                  90                  95

Asp His Ala Ala Pro Glu Asp Lys Tyr Glu Ala Phe Val Leu His Phe
            100                 105                 110

Ser Glu Ala Leu Arg Ile Ile Ala Gly Thr Pro Glu Val His Ala Val
                115                 120                 125

Lys Pro Gly Ala
    130

<210> SEQ ID NO 143
<211> LENGTH: 131
<212> TYPE: PRT
<213> ORGANISM: Phleum pratense (Common timothy)

<400> SEQUENCE: 143

Met Ser Trp Gln Thr Tyr Val Asp Glu His Leu Met Cys Glu Ile Glu
1               5                   10                  15

Gly His His Leu Ala Ser Ala Ala Ile Leu Gly His Asp Gly Thr Val
            20                  25                  30

Trp Ala Gln Ser Ala Asp Phe Pro Gln Phe Lys Pro Glu Glu Ile Thr
                35                  40                  45

Gly Ile Met Lys Asp Phe Asp Glu Pro Gly His Leu Ala Pro Thr Gly
    50                  55                  60

Met Phe Val Ala Gly Ala Lys Tyr Met Val Ile Gln Gly Glu Pro Gly
65                  70                  75                  80

Arg Val Ile Arg Gly Lys Lys Gly Ala Gly Gly Ile Thr Ile Lys Lys
                85                  90                  95

Thr Gly Gln Ala Leu Val Val Gly Ile Tyr Asp Glu Pro Met Thr Pro
            100                 105                 110

Gly Gln Cys Asn Met Val Val Glu Arg Leu Gly Asp Tyr Leu Val Glu
                115                 120                 125

Gln Gly Met
    130

<210> SEQ ID NO 144
<211> LENGTH: 131
<212> TYPE: PRT
<213> ORGANISM: Phleum pratense (Common timothy)

<400> SEQUENCE: 144

Met Ser Trp Gln Thr Tyr Val Asp Glu His Leu Met Cys Glu Ile Glu
1               5                   10                  15

Gly His His Leu Ala Ser Ala Ala Ile Leu Gly His Asp Gly Thr Val
            20                  25                  30

Trp Ala Gln Ser Ala Asp Phe Pro Gln Phe Lys Pro Glu Glu Ile Thr
```

```
                35                  40                  45
Gly Ile Met Lys Asp Phe Asp Glu Pro Gly His Leu Ala Pro Thr Gly
 50                  55                  60

Met Phe Val Ala Gly Ala Lys Tyr Met Val Ile Gln Gly Glu Pro Gly
 65                  70                  75                  80

Ala Val Ile Arg Gly Lys Lys Gly Ala Gly Gly Ile Thr Ile Lys Lys
                 85                  90                  95

Thr Gly Gln Ala Leu Val Val Gly Ile Tyr Asp Glu Pro Met Thr Pro
            100                 105                 110

Gly Gln Cys Asn Met Val Val Glu Arg Leu Gly Asp Tyr Leu Val Glu
        115                 120                 125

Gln Gly Met
        130

<210> SEQ ID NO 145
<211> LENGTH: 131
<212> TYPE: PRT
<213> ORGANISM: Phleum pratense (Common timothy)

<400> SEQUENCE: 145

Met Ser Trp Gln Thr Tyr Val Asp Glu His Leu Met Cys Glu Ile Glu
  1               5                  10                  15

Gly His His Leu Ala Ser Ala Ala Ile Phe Gly His Asp Gly Thr Val
                 20                  25                  30

Trp Ala Gln Ser Ala Asp Phe Pro Gln Phe Lys Pro Glu Glu Ile Thr
            35                  40                  45

Gly Ile Met Lys Asp Leu Asp Glu Pro Gly His Leu Ala Pro Thr Gly
 50                  55                  60

Met Phe Val Ala Ala Lys Tyr Met Val Ile Gln Gly Glu Pro Gly
 65                  70                  75                  80

Ala Val Ile Arg Gly Lys Lys Gly Ala Gly Gly Ile Thr Ile Lys Lys
                 85                  90                  95

Thr Gly Gln Ala Leu Val Val Gly Ile Tyr Asp Glu Pro Met Thr Pro
            100                 105                 110

Gly Gln Cys Asn Met Val Val Glu Arg Leu Gly Asp Tyr Leu Val Glu
        115                 120                 125

Gln Gly Met
        130

<210> SEQ ID NO 146
<211> LENGTH: 373
<212> TYPE: PRT
<213> ORGANISM: Poa pratensis (Kentucky bluegrass)

<400> SEQUENCE: 146

Met Asp Lys Ala Asn Gly Ala Tyr Lys Thr Ala Leu Lys Ala Ala Ser
  1               5                  10                  15

Ala Val Ala Pro Ala Glu Lys Phe Pro Val Phe Gln Ala Thr Phe Asp
                 20                  25                  30

Lys Asn Leu Lys Glu Gly Leu Ser Gly Pro Asp Ala Val Gly Phe Ala
            35                  40                  45

Lys Lys Leu Asp Ala Phe Ile Gln Thr Ser Tyr Leu Ser Thr Lys Ala
 50                  55                  60

Ala Glu Pro Lys Glu Lys Phe Asp Leu Phe Val Leu Ser Leu Thr Glu
 65                  70                  75                  80

Val Leu Arg Phe Met Ala Gly Ala Val Lys Ala Pro Pro Ala Ser Lys
```

-continued

```
                85                  90                  95
Phe Pro Ala Lys Pro Ala Pro Lys Val Ala Ala Tyr Thr Pro Ala Ala
            100                 105                 110
Pro Ala Gly Ala Ala Pro Lys Ala Thr Thr Asp Glu Gln Lys Leu Ile
        115                 120                 125
Glu Lys Ile Asn Val Gly Phe Lys Ala Ala Val Ala Ala Ala Ala Gly
    130                 135                 140
Val Pro Ala Ala Ser Lys Tyr Lys Thr Phe Val Ala Thr Phe Gly Ala
145                 150                 155                 160
Ala Ser Asn Lys Ala Phe Ala Glu Ala Leu Ser Thr Glu Pro Lys Gly
                165                 170                 175
Ala Ala Val Ala Ser Ser Lys Ala Val Leu Thr Ser Lys Leu Asp Ala
            180                 185                 190
Ala Tyr Lys Leu Ala Tyr Lys Ser Ala Glu Gly Ala Thr Pro Glu Ala
        195                 200                 205
Lys Tyr Asp Ala Tyr Val Ala Thr Leu Ser Glu Ala Leu Arg Ile Ile
    210                 215                 220
Ala Gly Thr Leu Glu Val His Gly Val Lys Pro Ala Ala Glu Glu Val
225                 230                 235                 240
Lys Ala Ile Pro Ala Gly Glu Leu Gln Val Ile Asp Lys Val Asp Ala
                245                 250                 255
Ala Phe Lys Val Ala Ala Thr Ala Ala Asn Ala Ala Pro Ala Asn Asp
            260                 265                 270
Lys Phe Thr Val Phe Glu Ala Ala Phe Asn Asp Ala Ile Lys Ala Ser
        275                 280                 285
Thr Gly Gly Ala Tyr Gln Ser Tyr Lys Phe Ile Pro Ala Leu Glu Ala
    290                 295                 300
Ala Val Lys Gln Ser Tyr Ala Ala Thr Val Ala Thr Ala Pro Ala Val
305                 310                 315                 320
Lys Tyr Thr Val Phe Glu Thr Ala Leu Lys Lys Ala Ile Thr Ala Met
                325                 330                 335
Ser Gln Ala Gln Lys Ala Ala Lys Pro Ala Ala Ala Val Thr Gly Thr
            340                 345                 350
Ala Thr Ser Ala Val Gly Ala Ala Thr Gly Ala Ala Thr Ala Ala Ala
        355                 360                 365
Gly Gly Tyr Lys Val
    370

<210> SEQ ID NO 147
<211> LENGTH: 333
<212> TYPE: PRT
<213> ORGANISM: Poa pratensis (Kentucky bluegrass)

<400> SEQUENCE: 147

Met Ala Val His Gln Tyr Thr Val Ala Leu Phe Leu Ala Val Ala Leu
1               5                   10                  15
Val Ala Gly Pro Ala Ala Ser Tyr Ala Ala Asp Val Gly Tyr Gly Ala
            20                  25                  30
Pro Ala Thr Leu Ala Thr Pro Ala Thr Pro Ala Ala Pro Ala Ala Gly
        35                  40                  45
Tyr Thr Pro Ala Ala Pro Ala Gly Ala Ala Pro Lys Ala Thr Thr Asp
    50                  55                  60
Glu Gln Lys Leu Ile Glu Lys Ile Asn Ala Gly Phe Lys Ala Ala Val
65                  70                  75                  80
```

Ala Ala Ala Ala Gly Val Pro Ala Val Asp Lys Tyr Lys Thr Phe Val
            85                  90                  95

Ala Thr Phe Gly Thr Ala Ser Asn Lys Ala Phe Ala Glu Ala Leu Ser
            100                 105                 110

Thr Glu Pro Lys Gly Ala Ala Ala Ser Ser Asn Ala Val Leu Thr
            115                 120                 125

Ser Lys Leu Asp Ala Ala Tyr Lys Leu Ala Tyr Lys Ser Ala Glu Gly
        130                 135                 140

Ala Thr Pro Glu Ala Lys Tyr Asp Ala Tyr Val Ala Thr Leu Ser Glu
145                 150                 155                 160

Ala Leu Arg Ile Ile Ala Gly Thr Leu Glu Val His Ala Val Lys Pro
                165                 170                 175

Ala Gly Glu Glu Val Lys Ala Ile Pro Ala Gly Glu Leu Gln Val Ile
            180                 185                 190

Asp Lys Val Asp Ala Ala Phe Lys Val Ala Thr Ala Ala Asn Ala
        195                 200                 205

Ala Pro Ala Asn Asp Lys Phe Thr Val Phe Glu Ala Ala Phe Asn Asp
        210                 215                 220

Ala Ile Lys Ala Ser Thr Gly Gly Ala Tyr Gln Ser Tyr Lys Phe Ile
225                 230                 235                 240

Pro Ala Leu Glu Ala Ala Val Lys Gln Ser Tyr Ala Ala Thr Val Ala
                245                 250                 255

Thr Ala Pro Ala Val Lys Tyr Thr Val Phe Glu Thr Ala Leu Lys Lys
            260                 265                 270

Ala Ile Thr Ala Met Ser Gln Ala Gln Lys Ala Ala Lys Pro Ala Ala
            275                 280                 285

Ala Val Thr Ala Thr Ala Thr Gly Ala Val Gly Ala Ala Thr Gly Ala
            290                 295                 300

Val Gly Ala Ala Thr Gly Ala Ala Thr Ala Ala Ala Gly Gly Tyr Lys
305                 310                 315                 320

Thr Gly Ala Ala Thr Pro Thr Ala Gly Gly Tyr Lys Val
                325                 330

<210> SEQ ID NO 148
<211> LENGTH: 307
<212> TYPE: PRT
<213> ORGANISM: Poa pratensis (Kentucky bluegrass)

<400> SEQUENCE: 148

Met Ala Val Gln Lys Tyr Thr Val Ala Leu Phe Leu Val Ala Leu Val
1               5                   10                  15

Val Gly Pro Ala Ala Ser Tyr Ala Ala Asp Leu Ser Tyr Gly Ala Pro
            20                  25                  30

Ala Thr Pro Ala Ala Pro Ala Ala Gly Tyr Thr Pro Ala Ala Pro Ala
            35                  40                  45

Gly Ala Ala Pro Lys Ala Thr Thr Asp Glu Gln Lys Met Ile Glu Lys
        50                  55                  60

Ile Asn Val Gly Phe Lys Ala Ala Val Ala Ala Ala Gly Gly Val Pro
65                  70                  75                  80

Ala Ala Asn Lys Tyr Lys Thr Phe Val Ala Thr Phe Gly Ala Ala Ser
                85                  90                  95

Asn Lys Ala Phe Ala Glu Ala Leu Ser Thr Glu Pro Lys Gly Ala Ala
            100                 105                 110

Val Asp Ser Ser Lys Ala Ala Leu Thr Ser Lys Leu Asp Ala Ala Tyr
        115                 120                 125

```
Lys Leu Ala Tyr Lys Ser Ala Glu Gly Ala Thr Pro Glu Ala Lys Tyr
            130                 135                 140

Asp Asp Tyr Val Ala Thr Leu Ser Glu Ala Leu Arg Ile Ile Ala Gly
145                 150                 155                 160

Thr Leu Glu Val His Gly Val Lys Pro Ala Ala Glu Val Lys Ala
                165                 170                 175

Thr Pro Ala Gly Glu Leu Gln Val Ile Asp Lys Val Asp Ala Ala Phe
                180                 185                 190

Lys Val Ala Ala Thr Ala Ala Asn Ala Ala Pro Ala Asn Asp Lys Phe
                195                 200                 205

Thr Val Phe Glu Ala Ala Phe Asn Asp Ala Ile Lys Ala Ser Thr Gly
                210                 215                 220

Gly Ala Tyr Gln Ser Tyr Lys Phe Ile Pro Ala Leu Glu Ala Ala Val
225                 230                 235                 240

Lys Gln Ser Tyr Ala Ala Thr Val Ala Thr Ala Pro Ala Val Lys Tyr
                245                 250                 255

Thr Val Phe Glu Thr Ala Leu Lys Lys Ala Ile Thr Ala Met Ser Gln
                260                 265                 270

Ala Gln Lys Ala Ala Lys Pro Ala Ala Ala Thr Gly Thr Ala Thr
                275                 280                 285

Ala Ala Val Gly Ala Ala Thr Gly Ala Ala Thr Ala Ala Ala Gly Gly
                290                 295                 300

Tyr Lys Val
305

<210> SEQ ID NO 149
<211> LENGTH: 209
<212> TYPE: PRT
<213> ORGANISM: Polistes annularis (Paper wasp)

<400> SEQUENCE: 149

Ser Ser Gln Gly Val Asp Tyr Cys Lys Ile Lys Cys Pro Ser Gly Ile
1               5                   10                  15

His Thr Val Cys Gln Tyr Gly Glu Ser Thr Lys Pro Ser Lys Asn Cys
                20                  25                  30

Ala Gly Lys Val Ile Lys Ser Val Gly Pro Thr Glu Glu Lys Lys
            35                  40                  45

Leu Ile Val Ser Glu His Asn Arg Phe Arg Gln Lys Val Ala Gln Gly
    50                  55                  60

Leu Glu Thr Arg Gly Asn Pro Gly Pro Gln Pro Ala Ala Ser Asp Met
65                  70                  75                  80

Asn Asp Leu Val Trp Asn Asp Glu Leu Ala His Ile Ala Gln Val Trp
                85                  90                  95

Ala Ser Gln Cys Gln Phe Leu His Asp Lys Cys Arg Asn Thr Ala
                100                 105                 110

Lys Tyr Pro Val Gly Gln Asn Ile Ala Tyr Ala Gly Ser Asn Leu
    115                 120                 125

Pro Asp Val Val Ser Leu Ile Lys Leu Trp Glu Asn Glu Val Lys Asp
    130                 135                 140

Phe Asn Tyr Asn Thr Gly Ile Thr Lys Gln Asn Phe Ala Lys Ile Gly
145                 150                 155                 160

His Tyr Thr Gln Met Val Trp Gly Lys Thr Lys Glu Ile Gly Cys Gly
                165                 170                 175

Ser Leu Lys Tyr Met Glu Asn Asn Met Gln Asn His Tyr Leu Ile Cys
```

180                 185                 190
Asn Tyr Gly Pro Ala Gly Asn Tyr Leu Gly Gln Leu Pro Tyr Thr Lys
        195                 200                 205

Lys

<210> SEQ ID NO 150
<211> LENGTH: 206
<212> TYPE: PRT
<213> ORGANISM: Polistes dominulus (European paper wasp)

<400> SEQUENCE: 150

Asn Asp Tyr Cys Lys Ile Lys Cys Ser Ser Gly Val His Thr Val Cys
1               5                   10                  15

Gln Tyr Gly Glu Ser Thr Lys Pro Ser Lys Asn Cys Ala Gly Lys Leu
            20                  25                  30

Ile Lys Ser Val Gly Pro Thr Glu Glu Lys Lys Leu Ile Val Glu
        35                  40                  45

Glu His Asn Arg Phe Arg Gln Lys Val Ala Lys Gly Leu Glu Thr Arg
    50                  55                  60

Gly Asn Pro Gly Pro Gln Pro Ala Ala Ser Asn Met Asn Asn Leu Val
65                  70                  75                  80

Trp Asn Asp Glu Leu Ala Lys Ile Ala Gln Val Trp Ala Ser Gln Cys
                85                  90                  95

Gln Ile Leu Val His Asp Lys Cys Arg Asn Thr Glu Lys Tyr Gln Val
            100                 105                 110

Gly Gln Asn Ile Ala Tyr Ala Gly Ser Ser Asn His Phe Pro Ser Val
        115                 120                 125

Thr Lys Leu Ile Gln Leu Trp Glu Asn Glu Val Lys Asp Phe Asn Tyr
    130                 135                 140

Asn Thr Gly Ile Thr Asn Lys Asn Phe Gly Lys Val Gly His Tyr Thr
145                 150                 155                 160

Gln Met Val Trp Gly Asn Thr Lys Glu Val Gly Cys Gly Ser Leu Lys
                165                 170                 175

Tyr Val Glu Lys Asn Met Gln Ile His Tyr Leu Ile Cys Asn Tyr Gly
            180                 185                 190

Pro Ala Gly Asn Tyr Leu Gly Gln Pro Ile Tyr Thr Lys Lys
        195                 200                 205

<210> SEQ ID NO 151
<211> LENGTH: 205
<212> TYPE: PRT
<213> ORGANISM: Polistes exclamans (Paper wasp)

<400> SEQUENCE: 151

Val Asp Tyr Cys Lys Ile Lys Cys Pro Ser Gly Ile His Thr Val Cys
1               5                   10                  15

Gln Tyr Gly Glu Ser Thr Lys Pro Ser Lys Asn Cys Ala Gly Lys Val
            20                  25                  30

Ile Lys Ser Val Gly Pro Thr Glu Glu Lys Lys Leu Ile Val Ser
        35                  40                  45

Glu His Asn Arg Phe Arg Gln Lys Val Ala Gln Gly Leu Glu Thr Arg
    50                  55                  60

Gly Asn Pro Gly Pro Gln Pro Ala Ala Ser Asp Met Asn Asp Leu Val
65                  70                  75                  80

Trp Asn Asp Glu Leu Ala His Ile Ala Gln Val Trp Ala Ser Gln Cys
                85                  90                  95

```
Gln Phe Leu Val His Asp Lys Cys Arg Asn Thr Ala Lys Tyr Pro Val
                100                 105                 110

Gly Gln Asn Ile Ala Tyr Ala Gly Gly Ser Lys Leu Pro Asp Val Val
            115                 120                 125

Ser Leu Ile Lys Leu Trp Glu Asn Glu Val Lys Asp Phe Asn Tyr Asn
        130                 135                 140

Thr Gly Ile Thr Lys Gln Asn Phe Ala Lys Ile Gly His Tyr Thr Gln
145                 150                 155                 160

Met Val Trp Gly Lys Thr Lys Glu Ile Gly Cys Gly Ser Leu Lys Tyr
                165                 170                 175

Ile Glu Asn Lys Met Gln Asn His Tyr Leu Ile Cys Asn Tyr Gly Pro
            180                 185                 190

Ala Gly Asn Tyr Leu Gly Gln Leu Pro Tyr Thr Lys Lys
        195                 200                 205

<210> SEQ ID NO 152
<211> LENGTH: 205
<212> TYPE: PRT
<213> ORGANISM: Polistes fuscatus (Paper wasp)

<400> SEQUENCE: 152

Val Asp Tyr Cys Lys Ile Lys Cys Ser Ser Gly Ile His Thr Val Cys
1               5                   10                  15

Gln Tyr Gly Glu Ser Thr Lys Pro Ser Lys Asn Cys Ala Asp Lys Val
            20                  25                  30

Ile Lys Ser Val Gly Pro Thr Glu Glu Lys Lys Leu Ile Val Asn
        35                  40                  45

Glu His Asn Arg Phe Arg Gln Lys Val Ala Gln Gly Leu Glu Thr Arg
    50                  55                  60

Gly Asn Pro Gly Pro Gln Pro Ala Ala Ser Asp Met Asn Asn Leu Val
65                  70                  75                  80

Trp Asn Asp Glu Leu Ala His Ile Ala Gln Val Trp Ala Ser Gln Cys
                85                  90                  95

Gln Ile Leu Val His Asp Lys Cys Arg Asn Thr Ala Lys Tyr Gln Val
                100                 105                 110

Gly Gln Asn Ile Ala Tyr Ala Gly Gly Ser Lys Leu Pro Asp Val Val
            115                 120                 125

Ser Leu Ile Lys Leu Trp Glu Asn Glu Val Lys Asp Phe Asn Tyr Asn
        130                 135                 140

Lys Gly Ile Thr Lys Gln Asn Phe Gly Lys Val Gly His Tyr Thr Gln
145                 150                 155                 160

Met Ile Trp Ala Lys Thr Lys Glu Ile Gly Cys Gly Ser Leu Lys Tyr
                165                 170                 175

Met Lys Asn Asn Met Gln His His Tyr Leu Ile Cys Asn Tyr Gly Pro
            180                 185                 190

Ala Gly Asn Tyr Leu Gly Gln Leu Pro Tyr Thr Lys Lys
        195                 200                 205

<210> SEQ ID NO 153
<211> LENGTH: 160
<212> TYPE: PRT
<213> ORGANISM: Prunus avium (Cherry)

<400> SEQUENCE: 153

Met Gly Val Phe Thr Tyr Glu Ser Glu Phe Thr Ser Glu Ile Pro Pro
1               5                   10                  15
```

```
Pro Arg Leu Phe Lys Ala Phe Val Leu Asp Ala Asp Asn Leu Val Pro
        20                  25                  30

Lys Ile Ala Pro Gln Ala Ile Lys His Ser Glu Ile Leu Glu Gly Asp
    35                  40                  45

Gly Gly Pro Gly Thr Ile Lys Lys Ile Thr Phe Gly Glu Gly Ser Gln
50                  55                  60

Tyr Gly Tyr Val Lys His Lys Ile Asp Ser Ile Asp Lys Glu Asn Tyr
65                  70                  75                  80

Ser Tyr Ser Tyr Thr Leu Ile Glu Gly Asp Ala Leu Gly Asp Thr Leu
            85                  90                  95

Glu Lys Ile Ser Tyr Glu Thr Lys Leu Val Ala Ser Pro Ser Gly Gly
        100                 105                 110

Ser Ile Ile Lys Ser Thr Ser His Tyr His Thr Lys Gly Asn Val Glu
        115                 120                 125

Ile Lys Glu Glu His Val Lys Ala Gly Lys Lys Ala Ser Asn Leu
130                 135                 140

Phe Lys Leu Ile Glu Thr Tyr Leu Lys Gly His Pro Asp Ala Tyr Asn
145                 150                 155                 160

<210> SEQ ID NO 154
<211> LENGTH: 181
<212> TYPE: PRT
<213> ORGANISM: Rattus norvegicus (Rat)

<400> SEQUENCE: 154

Met Lys Leu Leu Leu Leu Leu Cys Leu Gly Leu Thr Leu Val Cys
1               5                   10                  15

Gly His Ala Glu Glu Ala Ser Ser Thr Arg Gly Asn Leu Asp Val Ala
        20                  25                  30

Lys Leu Asn Gly Asp Trp Phe Ser Ile Val Ala Ser Asn Lys Arg
    35                  40                  45

Glu Lys Ile Glu Glu Asn Gly Ser Met Arg Val Phe Met Gln His Ile
50                  55                  60

Asp Val Leu Glu Asn Ser Leu Gly Phe Lys Phe Arg Ile Lys Glu Asn
65                  70                  75                  80

Gly Glu Cys Arg Glu Leu Tyr Leu Val Ala Tyr Lys Thr Pro Glu Asp
            85                  90                  95

Gly Glu Tyr Phe Val Glu Tyr Asp Gly Gly Asn Thr Phe Thr Ile Leu
        100                 105                 110

Lys Thr Asp Tyr Asp Arg Tyr Val Met Phe His Leu Ile Asn Phe Lys
        115                 120                 125

Asn Gly Glu Thr Phe Gln Leu Met Val Leu Tyr Gly Arg Thr Lys Asp
        130                 135                 140

Leu Ser Ser Asp Ile Lys Glu Lys Phe Ala Lys Leu Cys Glu Ala His
145                 150                 155                 160

Gly Ile Thr Arg Asp Asn Ile Ile Asp Leu Thr Lys Thr Asp Arg Cys
                165                 170                 175

Leu Gln Ala Arg Gly
            180

<210> SEQ ID NO 155
<211> LENGTH: 138
<212> TYPE: PRT
<213> ORGANISM: Solenopsis invicta (Red imported fire ant)

<400> SEQUENCE: 155
```

```
Met Lys Ser Phe Val Leu Ala Thr Cys Leu Leu Gly Phe Ala Gln Ile
1               5                   10                  15

Ile Tyr Ala Asp Asn Lys Glu Leu Lys Ile Ile Arg Lys Asp Val Ala
            20                  25                  30

Glu Cys Leu Arg Thr Leu Pro Lys Cys Gly Asn Gln Pro Asp Asp Pro
        35                  40                  45

Leu Ala Arg Val Asp Val Trp His Cys Ala Met Ala Lys Arg Gly Val
    50                  55                  60

Tyr Asp Asn Pro Asp Pro Ala Val Ile Lys Glu Arg Ser Met Lys Met
65                  70                  75                  80

Cys Thr Lys Ile Ile Thr Asp Pro Ala Asn Val Glu Asn Cys Lys Lys
                85                  90                  95

Val Ala Ser Arg Cys Val Asp Arg Glu Thr Gln Gly Pro Lys Ser Asn
            100                 105                 110

Arg Gln Lys Ala Val Asn Ile Ile Gly Cys Ala Leu Arg Ala Gly Val
        115                 120                 125

Ala Glu Thr Thr Val Leu Ala Arg Lys Lys
    130                 135

<210> SEQ ID NO 156
<211> LENGTH: 212
<212> TYPE: PRT
<213> ORGANISM: Solenopsis invicta (Red imported fire ant)

<400> SEQUENCE: 156

Thr Asn Tyr Cys Asn Leu Gln Ser Cys Lys Arg Asn Asn Ala Ile His
1               5                   10                  15

Thr Met Cys Gln Tyr Thr Ser Pro Thr Pro Gly Pro Met Cys Leu Glu
            20                  25                  30

Tyr Ser Asn Val Gly Phe Thr Asp Ala Glu Lys Asp Ala Ile Val Asn
        35                  40                  45

Lys His Asn Glu Leu Arg Gln Arg Val Ala Ser Gly Lys Glu Met Arg
    50                  55                  60

Gly Thr Asn Gly Pro Gln Pro Pro Ala Val Lys Met Pro Asn Leu Thr
65                  70                  75                  80

Trp Asp Pro Glu Leu Ala Thr Ile Ala Gln Arg Trp Ala Asn Gln Cys
                85                  90                  95

Thr Phe Glu His Asp Ala Cys Arg Asn Val Glu Arg Phe Ala Val Gly
            100                 105                 110

Gln Asn Ile Ala Ala Thr Ser Ser Ser Gly Lys Asn Lys Ser Thr Pro
        115                 120                 125

Asn Glu Met Ile Leu Leu Trp Tyr Asn Glu Val Lys Asp Phe Asp Asn
    130                 135                 140

Arg Trp Ile Ser Ser Phe Pro Ser Asp Asp Asn Ile Leu Met Lys Val
145                 150                 155                 160

Glu His Tyr Thr Gln Ile Val Trp Ala Lys Thr Ser Lys Ile Gly Cys
                165                 170                 175

Ala Arg Ile Met Phe Lys Glu Pro Asp Asn Trp Thr Lys His Tyr Leu
            180                 185                 190

Val Cys Asn Tyr Gly Pro Ala Gly Asn Val Leu Gly Ala Pro Ile Tyr
        195                 200                 205

Glu Ile Lys Lys
    210
```

```
<210> SEQ ID NO 157
<211> LENGTH: 117
<212> TYPE: PRT
<213> ORGANISM: Solenopsis invicta (Red imported fire ant)

<400> SEQUENCE: 157

Leu Asp Ile Lys Glu Ile Ser Ile Met Asn Arg Ile Leu Glu Lys Cys
1               5                   10                  15

Ile Arg Thr Val Pro Lys Arg Glu Asn Asp Pro Ile Asn Pro Leu Lys
            20                  25                  30

Asn Val Asn Val Leu Tyr Cys Ala Phe Thr Lys Arg Gly Ile Phe Thr
        35                  40                  45

Pro Lys Gly Val Asn Thr Lys Gln Tyr Ile Asn Tyr Cys Glu Lys Thr
    50                  55                  60

Ile Ile Ser Pro Ala Asp Ile Lys Leu Cys Lys Ile Ala Ser Lys
65                  70                  75                  80

Cys Val Lys Lys Val Tyr Asp Arg Pro Gly Pro Val Ile Glu Arg Ser
                85                  90                  95

Lys Asn Leu Leu Ser Cys Val Leu Lys Lys Gly Leu Leu Glu Leu Thr
            100                 105                 110

Val Tyr Gly Lys Asn
        115

<210> SEQ ID NO 158
<211> LENGTH: 119
<212> TYPE: PRT
<213> ORGANISM: Solenopsis richteri (Black imported fire ant)

<400> SEQUENCE: 158

Asp Ile Glu Ala Gln Arg Val Leu Arg Lys Asp Ile Ala Glu Cys Ala
1               5                   10                  15

Arg Thr Leu Pro Lys Cys Val Asn Gln Pro Asp Asp Pro Leu Ala Arg
            20                  25                  30

Val Asp Val Trp His Cys Ala Met Ser Lys Arg Gly Val Tyr Asp Asn
        35                  40                  45

Pro Asp Pro Ala Val Val Lys Glu Lys Asn Ser Lys Met Cys Pro Lys
    50                  55                  60

Ile Ile Thr Asp Pro Ala Asp Val Glu Asn Cys Lys Lys Val Val Ser
65                  70                  75                  80

Arg Cys Val Asp Arg Glu Thr Gln Arg Pro Arg Ser Asn Arg Gln Lys
                85                  90                  95

Ala Ile Asn Ile Thr Gly Cys Ile Leu Arg Ala Gly Val Val Glu Ala
            100                 105                 110

Thr Val Leu Ala Arg Glu Lys
        115

<210> SEQ ID NO 159
<211> LENGTH: 211
<212> TYPE: PRT
<213> ORGANISM: Solenopsis richteri (Black imported fire ant)

<400> SEQUENCE: 159

Thr Asn Tyr Cys Asn Leu Gln Ser Cys Lys Arg Asn Asn Ala Ile His
1               5                   10                  15

Thr Met Cys Gln Tyr Thr Ser Pro Thr Pro Gly Pro Met Cys Leu Glu
            20                  25                  30

Tyr Ser Asn Val Gly Phe Thr Asp Ala Glu Lys Asp Ala Ile Val Asn
        35                  40                  45
```

-continued

```
Lys His Asn Glu Leu Arg Gln Arg Val Ala Ser Gly Lys Glu Met Arg
 50                  55                  60

Gly Thr Asn Gly Pro Gln Pro Pro Ala Val Lys Met Pro Asn Leu Thr
 65                  70                  75                  80

Trp Asp Pro Glu Leu Ala Thr Ile Ala Gln Arg Trp Ala Asn Gln Cys
                 85                  90                  95

Thr Phe Glu His Asp Ala Cys Arg Asn Val Glu Arg Phe Ala Val Gly
            100                 105                 110

Gln Asn Ile Ala Ala Thr Ser Ser Gly Lys Asn Lys Ser Thr Leu
            115                 120                 125

Ser Asp Met Ile Leu Leu Trp Tyr Asn Glu Val Lys Asp Phe Asp Asn
130                 135                 140

Arg Trp Ile Ser Ser Phe Pro Ser Asp Gly Asn Ile Leu Met His Val
145                 150                 155                 160

Gly His Tyr Thr Gln Ile Val Trp Ala Lys Thr Lys Ile Gly Cys
                165                 170                 175

Gly Arg Ile Met Phe Lys Glu Asp Asn Trp Asn Lys His Tyr Leu Val
            180                 185                 190

Cys Asn Tyr Gly Pro Ala Gly Asn Val Leu Gly Ala Gln Ile Tyr Glu
            195                 200                 205

Ile Lys Lys
    210

<210> SEQ ID NO 160
<211> LENGTH: 202
<212> TYPE: PRT
<213> ORGANISM: Vespa crabro (European hornet)

<400> SEQUENCE: 160

Asn Asn Tyr Cys Lys Ile Lys Cys Arg Ser Gly Ile His Thr Leu Cys
 1               5                  10                  15

Lys Tyr Gly Thr Ser Thr Lys Pro Asn Cys Gly Lys Asn Val Val Lys
                20                  25                  30

Ala Ser Gly Leu Thr Lys Gln Glu Asn Leu Glu Ile Leu Lys Gln His
            35                  40                  45

Asn Glu Phe Arg Gln Lys Val Ala Arg Gly Leu Glu Thr Arg Gly Asn
 50                  55                  60

Pro Gly Pro Gln Pro Pro Ala Lys Ser Met Asn Thr Leu Val Trp Asn
 65                  70                  75                  80

Asp Glu Leu Ala Gln Ile Ala Gln Val Trp Ala Asn Gln Cys Asn Tyr
                 85                  90                  95

Gly His Asp Asn Cys Arg Asn Ser Ala Lys Tyr Ser Val Gly Gln Asn
            100                 105                 110

Ile Ala Glu Gly Ser Thr Thr Ala Asp Asn Phe Gly Ser Val Ser Asn
            115                 120                 125

Met Val Lys Met Trp Glu Asp Glu Val Lys Asp Tyr Gln Tyr Gly Ser
130                 135                 140

Pro Lys Asn Lys Leu Asn Lys Val Gly His Tyr Thr Gln Met Val Trp
145                 150                 155                 160

Ala Lys Thr Lys Glu Ile Gly Cys Gly Ser Ile Lys Tyr Ile Glu Asn
                165                 170                 175

Gly Trp His Arg His Tyr Leu Val Cys Asn Tyr Gly Pro Ala Gly Asn
            180                 185                 190

Val Gly Asn Glu Pro Ile Tyr Glu Arg Lys
```

195                 200

<210> SEQ ID NO 161
<211> LENGTH: 202
<212> TYPE: PRT
<213> ORGANISM: Vespa crabro (European hornet)

<400> SEQUENCE: 161

Asn Asn Tyr Cys Lys Ile Lys Cys Arg Ser Gly Ile His Thr Leu Cys
 1               5                  10                  15

Lys Tyr Gly Thr Ser Thr Lys Pro Asn Cys Gly Lys Asn Val Val Lys
            20                  25                  30

Ala Ser Gly Leu Thr Lys Gln Glu Asn Leu Glu Ile Leu Lys Gln His
        35                  40                  45

Asn Glu Phe Arg Gln Lys Val Ala Arg Gly Leu Glu Thr Arg Gly Asn
    50                  55                  60

Pro Gly Pro Gln Pro Pro Ala Lys Ser Met Asn Thr Leu Val Trp Asn
65                  70                  75                  80

Asp Glu Leu Ala Gln Ile Ala Gln Val Trp Ala Asn Gln Cys Asn Tyr
                85                  90                  95

Gly His Asp Asn Cys Arg Asn Ser Ala Lys Tyr Ser Val Gly Gln Asn
            100                 105                 110

Ile Ala Glu Gly Ser Thr Ser Ala Asp Asn Phe Val Asn Val Ser Asn
        115                 120                 125

Met Val Lys Met Trp Glu Asp Glu Val Lys Asp Tyr Gln Tyr Gly Ser
    130                 135                 140

Pro Lys Asn Lys Leu Asn Lys Val Gly His Tyr Thr Gln Met Val Trp
145                 150                 155                 160

Ala Lys Thr Lys Glu Ile Gly Cys Gly Ser Glu Asp Tyr Ile Glu Asp
                165                 170                 175

Gly Trp His Arg His Tyr Leu Val Cys Asn Tyr Gly Pro Ala Gly Asn
            180                 185                 190

Val Gly Asn Glu Pro Ile Tyr Glu Arg Lys
        195                 200

<210> SEQ ID NO 162
<211> LENGTH: 204
<212> TYPE: PRT
<213> ORGANISM: Vespula flavopilosa (Yellow jacket) (Wasp)

<400> SEQUENCE: 162

Asn Asn Tyr Cys Lys Ile Lys Cys Leu Lys Gly Gly Val His Thr Ala
 1               5                  10                  15

Cys Lys Tyr Gly Ser Leu Lys Pro Asn Cys Gly Asn Lys Val Val Val
            20                  25                  30

Ser Tyr Gly Leu Thr Lys Gln Glu Lys Gln Asp Ile Leu Lys Glu His
        35                  40                  45

Asn Asp Phe Arg Gln Lys Ile Ala Arg Gly Leu Glu Thr Arg Gly Asn
    50                  55                  60

Pro Gly Pro Gln Pro Pro Ala Lys Asn Met Lys Asn Leu Val Trp Asn
65                  70                  75                  80

Asp Glu Leu Ala Tyr Val Ala Gln Val Trp Ala Asn Gln Cys Gln Tyr
                85                  90                  95

Gly His Asp Thr Cys Arg Asp Ile Ala Lys Tyr Gln Val Gly Gln Asn
            100                 105                 110

Val Ala Leu Thr Gly Ser Thr Ala Ala Lys Tyr Asp Asp Pro Val Lys

```
            115                 120                 125
Leu Val Lys Met Trp Glu Asp Glu Val Lys Asp Tyr Asn Pro Lys Lys
        130                 135                 140

Lys Phe Ser Gly Asn Asn Phe Leu Lys Thr Gly His Tyr Thr Gln Met
145                 150                 155                 160

Val Trp Ala Asn Thr Lys Glu Val Gly Cys Gly Ser Ile Lys Phe Ile
                165                 170                 175

Gln Glu Lys Trp His Lys His Tyr Leu Val Cys Asn Tyr Gly Pro Ser
            180                 185                 190

Gly Asn Phe Gln Asn Glu Glu Leu Tyr Gln Thr Lys
        195                 200

<210> SEQ ID NO 163
<211> LENGTH: 204
<212> TYPE: PRT
<213> ORGANISM: Vespula germanica (Yellow jacket) (Wasp)

<400> SEQUENCE: 163

Asn Asn Tyr Cys Lys Ile Lys Cys Leu Lys Gly Gly Val His Thr Ala
1               5                   10                  15

Cys Lys Tyr Glu Ser Leu Lys Pro Asn Cys Ala Asn Lys Lys Val Val
            20                  25                  30

Ala Tyr Gly Leu Thr Lys Gln Glu Lys Gln Asp Ile Leu Lys Glu His
        35                  40                  45

Asn Asp Phe Arg Gln Lys Ile Ala Arg Gly Leu Glu Thr Arg Gly Asn
    50                  55                  60

Pro Gly Pro Gln Pro Ala Lys Asn Met Lys Asn Leu Val Trp Ser
65                  70                  75                  80

Asp Glu Leu Ala Tyr Ile Ala Gln Val Trp Ala Asn Gln Cys Gln Tyr
                85                  90                  95

Gly His Asp Thr Cys Arg Asp Val Ala Lys Tyr Pro Val Gly Gln Asn
            100                 105                 110

Val Ala Leu Thr Gly Ser Thr Ala Ala Lys Tyr Asp Asn Pro Val Lys
        115                 120                 125

Leu Val Lys Met Trp Glu Asp Glu Val Lys Asp Tyr Asn Pro Lys Lys
    130                 135                 140

Lys Phe Ser Glu Asn Asn Phe Leu Lys Ile Gly His Tyr Thr Gln Met
145                 150                 155                 160

Val Trp Ala Asn Thr Lys Glu Val Gly Cys Gly Ser Ile Lys Tyr Ile
                165                 170                 175

Gln Asp Lys Trp His Lys His Tyr Leu Val Cys Asn Tyr Gly Pro Ser
            180                 185                 190

Gly Asn Phe Gly Asn Glu Glu Leu Tyr Gln Thr Lys
        195                 200

<210> SEQ ID NO 164
<211> LENGTH: 300
<212> TYPE: PRT
<213> ORGANISM: Vespula maculifrons (Eastern yellow jacket)(Wasp)

<400> SEQUENCE: 164

Gly Pro Lys Cys Pro Phe Asn Ser Asp Thr Val Ser Ile Ile Glu
1               5                   10                  15

Thr Arg Glu Asn Arg Asn Arg Asp Leu Tyr Thr Leu Gln Thr Leu Gln
            20                  25                  30

Asn His Pro Glu Phe Lys Lys Lys Thr Ile Thr Arg Pro Val Val Phe
```

-continued

```
                35                  40                  45
Ile Thr His Gly Phe Thr Ser Ser Ala Ser Glu Lys Asn Phe Ile Asn
 50                  55                  60

Leu Ala Lys Ala Leu Val Asp Lys Asp Asn Tyr Met Val Ile Ser Ile
 65                  70                  75                  80

Asp Trp Gln Thr Ala Ala Cys Thr Asn Glu Tyr Pro Gly Leu Lys Tyr
                 85                  90                  95

Ala Tyr Tyr Pro Thr Ala Ala Ser Asn Thr Arg Leu Val Gly Gln Tyr
                100                 105                 110

Ile Ala Thr Ile Thr Gln Lys Leu Val Lys Asp Tyr Lys Ile Ser Met
                115                 120                 125

Ala Asn Ile Arg Leu Ile Gly His Ser Leu Gly Ala His Val Ser Gly
                130                 135                 140

Phe Ala Gly Lys Arg Val Gln Glu Leu Lys Leu Gly Lys Tyr Ser Glu
145                 150                 155                 160

Ile Ile Gly Leu Asp Pro Ala Arg Pro Ser Phe Asp Ser Asn His Cys
                165                 170                 175

Ser Glu Arg Leu Cys Glu Thr Asp Ala Glu Tyr Val Gln Ile Ile His
                180                 185                 190

Thr Ser Asn Tyr Leu Gly Thr Glu Lys Ile Leu Gly Thr Val Asp Phe
                195                 200                 205

Tyr Met Asn Asn Gly Lys Asn Asn Pro Gly Cys Gly Arg Phe Phe Ser
                210                 215                 220

Glu Val Cys Ser His Thr Arg Ala Val Ile Tyr Met Ala Glu Cys Ile
225                 230                 235                 240

Lys His Glu Cys Cys Leu Ile Gly Ile Pro Arg Ser Lys Ser Ser Gln
                245                 250                 255

Pro Ile Ser Arg Cys Thr Lys Gln Glu Cys Val Cys Val Gly Leu Asn
                260                 265                 270

Ala Lys Lys Tyr Pro Ser Arg Gly Ser Phe Tyr Val Pro Val Glu Ser
                275                 280                 285

Thr Ala Pro Phe Cys Asn Asn Lys Gly Lys Ile Ile
                290                 295                 300

<210> SEQ ID NO 165
<211> LENGTH: 204
<212> TYPE: PRT
<213> ORGANISM: Vespula maculifrons (Eastern yellow jacket)(Wasp)

<400> SEQUENCE: 165

Asn Asn Tyr Cys Lys Ile Lys Cys Leu Lys Gly Gly Val His Thr Ala
 1               5                  10                  15

Cys Lys Tyr Gly Ser Leu Lys Pro Asn Cys Gly Asn Lys Lys Val Val
                20                  25                  30

Ser Tyr Gly Leu Thr Lys Gln Glu Lys Gln Asp Ile Leu Lys Glu His
                35                  40                  45

Asn Asp Phe Arg Gln Lys Ile Ala Arg Gly Leu Glu Thr Arg Gly Asn
 50                  55                  60

Pro Gly Pro Gln Pro Pro Ala Lys Asn Met Lys Asn Leu Val Trp Ser
 65                  70                  75                  80

Asp Glu Leu Ala Tyr Ile Ala Gln Val Trp Ala Asn Gln Cys Gln Tyr
                 85                  90                  95

Gly His Asp Thr Cys Arg Asp Val Ala Lys Tyr Gln Val Gly Gln Asn
                100                 105                 110
```

```
Val Ala Leu Thr Gly Ser Thr Ala Val Tyr Asn Asp Pro Val Lys
        115                 120                 125

Leu Val Lys Met Trp Glu Asp Glu Val Lys Asp Tyr Asn Pro Lys Lys
130                 135                 140

Lys Phe Ser Glu Asn Asn Phe Leu Lys Ile Gly His Tyr Thr Gln Met
145                 150                 155                 160

Val Trp Ala Asn Thr Lys Glu Val Gly Cys Gly Ser Ile Lys Tyr Ile
                165                 170                 175

Gln Glu Asn Trp His Lys His Tyr Leu Val Cys Asn Tyr Gly Pro Ser
                180                 185                 190

Gly Asn Phe Gln Asn Glu Glu Leu Tyr Gln Thr Lys
        195                 200
```

<210> SEQ ID NO 166
<211> LENGTH: 204
<212> TYPE: PRT
<213> ORGANISM: Vespula pensylvanica (Western yellow jacket)(Wasp)

<400> SEQUENCE: 166

```
Asn Asn Tyr Cys Lys Ile Lys Cys Leu Lys Gly Gly Val His Thr Ala
1               5                   10                  15

Cys Lys Tyr Gly Ser Leu Lys Pro Asn Cys Gly Asn Lys Ile Val Val
                20                  25                  30

Ser Tyr Gly Leu Thr Lys Glu Glu Lys Gln Asp Ile Leu Lys Glu His
        35                  40                  45

Asn Asp Phe Arg Gln Lys Ile Ala Arg Gly Leu Glu Thr Arg Gly Asn
    50                  55                  60

Pro Gly Pro Gln Pro Ala Lys Asn Met Lys Asn Leu Val Trp Asn
65                  70                  75                  80

Asp Glu Leu Ala Tyr Val Ala Gln Val Trp Ala Asn Gln Cys Gln Tyr
                85                  90                  95

Gly His Asp Thr Cys Arg Asp Val Ala Lys Tyr Pro Val Gly Gln Asn
                100                 105                 110

Val Ala Leu Thr Gly Ser Thr Ala Asp Lys Tyr Asp Asn Pro Val Lys
        115                 120                 125

Leu Val Lys Met Trp Glu Asp Glu Val Lys Asp Tyr Asn Pro Lys Lys
130                 135                 140

Lys Phe Ser Glu Asn Asn Phe Asn Lys Ile Gly His Tyr Thr Gln Met
145                 150                 155                 160

Val Trp Ala Asn Thr Lys Glu Ile Gly Cys Gly Ser Ile Lys Tyr Ile
                165                 170                 175

Gln Asn Glu Trp His Lys His Tyr Leu Val Cys Asn Tyr Gly Pro Ser
                180                 185                 190

Gly Asn Phe Gly Asn Glu Glu Leu Tyr Gln Thr Lys
        195                 200
```

<210> SEQ ID NO 167
<211> LENGTH: 205
<212> TYPE: PRT
<213> ORGANISM: Vespula squamosa (Southern yellow jacket)(Wasp)

<400> SEQUENCE: 167

```
Val Asp Tyr Cys Lys Ile Lys Cys Leu Lys Gly Gly Val His Thr Ala
1               5                   10                  15

Cys Lys Tyr Gly Thr Ser Thr Leu Pro Asn Cys Gly Asn Met Val Val
                20                  25                  30
```

```
Lys Ser Tyr Gly Val Thr Gln Ala Glu Lys Gln Glu Ile Leu Lys Ile
            35                  40                  45

His Asn Asp Phe Arg Asn Lys Val Ala Arg Gly Leu Glu Thr Arg Gly
 50                  55                  60

Asn Pro Gly Pro Gln Pro Pro Ala Lys Asn Met Asn Asn Leu Val Trp
 65                  70                  75                  80

Asn Asn Glu Leu Ala Asn Ile Ala Gln Ile Trp Ala Ser Gln Cys Lys
                 85                  90                  95

Tyr Gly His Asp Thr Cys Lys Asp Thr Thr Lys Tyr Asn Val Gly Gln
            100                 105                 110

Asn Ile Ala Val Ser Ser Thr Ala Ala Val Tyr Glu Asn Val Gly
            115                 120                 125

Asn Leu Val Lys Ala Trp Glu Asn Glu Val Lys Asp Phe Asn Pro Thr
130                 135                 140

Ile Ser Trp Glu Gln Asn Glu Phe Lys Lys Ile Gly His Tyr Thr Gln
145                 150                 155                 160

Met Val Trp Ala Lys Thr Lys Glu Ile Gly Cys Gly Ser Ile Lys Tyr
                165                 170                 175

Val Asp Asn Asn Trp Tyr Thr His Tyr Leu Val Cys Asn Tyr Gly Pro
            180                 185                 190

Ala Gly Asn Phe Gly Asn Gln Glu Val Tyr Glu Arg Lys
            195                 200                 205

<210> SEQ ID NO 168
<211> LENGTH: 336
<212> TYPE: PRT
<213> ORGANISM: Vespula vulgaris (Yellow jacket) (Wasp)

<400> SEQUENCE: 168

Met Glu Glu Asn Met Asn Leu Lys Tyr Leu Leu Phe Val Tyr Phe
 1               5                  10                  15

Val Gln Val Leu Asn Cys Cys Tyr Gly His Gly Asp Pro Leu Ser Tyr
                 20                  25                  30

Glu Leu Asp Arg Gly Pro Lys Cys Pro Phe Asn Ser Asp Thr Val Ser
            35                  40                  45

Ile Ile Ile Glu Thr Arg Glu Asn Arg Asn Arg Asp Leu Tyr Thr Leu
 50                  55                  60

Gln Thr Leu Gln Asn His Pro Glu Phe Lys Lys Lys Thr Ile Thr Arg
 65                  70                  75                  80

Pro Val Val Phe Ile Thr His Gly Phe Thr Ser Ser Ala Ser Glu Thr
                 85                  90                  95

Asn Phe Ile Asn Leu Ala Lys Ala Leu Val Asp Lys Asp Asn Tyr Met
            100                 105                 110

Val Ile Ser Ile Asp Trp Gln Thr Ala Ala Cys Thr Asn Glu Ala Ala
            115                 120                 125

Gly Leu Lys Tyr Leu Tyr Pro Thr Ala Ala Arg Asn Thr Arg Leu
130                 135                 140

Val Gly Gln Tyr Ile Ala Thr Ile Thr Gln Lys Leu Val Lys His Tyr
145                 150                 155                 160

Lys Ile Ser Met Ala Asn Ile Arg Leu Ile Gly His Ser Leu Gly Ala
                165                 170                 175

His Ala Ser Gly Phe Ala Gly Lys Lys Val Gln Glu Leu Lys Leu Gly
            180                 185                 190

Lys Tyr Ser Glu Ile Ile Gly Leu Asp Pro Ala Arg Pro Ser Phe Asp
            195                 200                 205
```

Ser Asn His Cys Ser Glu Arg Leu Cys Glu Thr Asp Ala Glu Tyr Val
210                 215                 220

Gln Ile Ile His Thr Ser Asn Tyr Leu Gly Thr Glu Lys Thr Leu Gly
225                 230                 235                 240

Thr Val Asp Phe Tyr Met Asn Asn Gly Lys Asn Gln Pro Gly Cys Gly
                245                 250                 255

Arg Phe Phe Ser Glu Val Cys Ser His Ser Arg Ala Val Ile Tyr Met
            260                 265                 270

Ala Glu Cys Ile Lys His Glu Cys Cys Leu Ile Gly Ile Pro Lys Ser
            275                 280                 285

Lys Ser Ser Gln Pro Ile Ser Ser Cys Thr Lys Gln Glu Cys Val Cys
290                 295                 300

Val Gly Leu Asn Ala Lys Lys Tyr Pro Ser Arg Gly Ser Phe Tyr Val
305                 310                 315                 320

Pro Val Glu Ser Thr Ala Pro Phe Cys Asn Asn Lys Gly Lys Ile Ile
                325                 330                 335

<210> SEQ ID NO 169
<211> LENGTH: 331
<212> TYPE: PRT
<213> ORGANISM: Vespula vulgaris (Yellow jacket) (Wasp)

<400> SEQUENCE: 169

Ser Glu Arg Pro Lys Arg Val Phe Asn Ile Tyr Trp Asn Val Pro Thr
1               5                   10                  15

Phe Met Cys His Gln Tyr Asp Leu Tyr Phe Asp Glu Val Thr Asn Phe
                20                  25                  30

Asn Ile Lys Arg Asn Ser Lys Asp Asp Phe Gln Gly Asp Lys Ile Ala
            35                  40                  45

Ile Phe Tyr Asp Pro Gly Glu Phe Pro Ala Leu Leu Ser Leu Lys Asp
50                  55                  60

Gly Lys Tyr Lys Lys Arg Asn Gly Gly Val Pro Gln Glu Gly Asn Ile
65                  70                  75                  80

Thr Ile His Leu Gln Lys Phe Ile Glu Asn Leu Asp Lys Ile Tyr Pro
                85                  90                  95

Asn Arg Asn Phe Ser Gly Ile Gly Val Ile Asp Phe Glu Arg Trp Arg
            100                 105                 110

Pro Ile Phe Arg Gln Asn Trp Gly Asn Met Lys Ile His Lys Asn Phe
        115                 120                 125

Ser Ile Asp Leu Val Arg Asn Glu His Pro Thr Trp Asn Lys Lys Met
130                 135                 140

Ile Glu Leu Glu Ala Ser Lys Arg Phe Glu Lys Tyr Ala Arg Phe Phe
145                 150                 155                 160

Met Glu Glu Thr Leu Lys Leu Ala Lys Lys Thr Arg Lys Gln Ala Asp
                165                 170                 175

Trp Gly Tyr Tyr Gly Tyr Pro Tyr Cys Phe Asn Met Ser Pro Asn Asn
            180                 185                 190

Leu Val Pro Glu Cys Asp Val Thr Ala Met His Glu Asn Asp Lys Met
        195                 200                 205

Ser Trp Leu Phe Asn Asn Gln Asn Val Leu Leu Pro Ser Val Tyr Val
210                 215                 220

Arg Gln Glu Leu Thr Pro Asp Gln Arg Ile Gly Leu Val Gln Gly Arg
225                 230                 235                 240

Val Lys Glu Ala Val Arg Ile Ser Asn Asn Leu Lys His Ser Pro Lys

```
                        245                 250                 255
Val Leu Ser Tyr Trp Trp Tyr Val Tyr Gln Asp Glu Thr Asn Thr Phe
            260                 265                 270

Leu Thr Glu Thr Asp Val Lys Lys Thr Phe Gln Glu Ile Val Ile Asn
            275                 280                 285

Gly Gly Asp Gly Ile Ile Trp Gly Ser Ser Asp Val Asn Ser
            290                 295                 300

Leu Ser Lys Cys Lys Arg Leu Gln Asp Tyr Leu Leu Thr Val Leu Gly
305                 310                 315                 320

Pro Ile Ala Ile Asn Val Thr Glu Ala Val Asn
                325                 330

<210> SEQ ID NO 170
<211> LENGTH: 227
<212> TYPE: PRT
<213> ORGANISM: Vespula vulgaris (Yellow jacket) (Wasp)

<400> SEQUENCE: 170

Met Glu Ile Ser Gly Leu Val Tyr Leu Ile Ile Val Thr Ile Ile
1               5                   10                  15

Asp Leu Pro Tyr Gly Lys Ala Asn Asn Tyr Cys Lys Ile Lys Cys Leu
            20                  25                  30

Lys Gly Gly Val His Thr Ala Cys Lys Tyr Gly Ser Leu Lys Pro Asn
        35                  40                  45

Cys Gly Asn Lys Val Val Ser Tyr Gly Leu Thr Lys Gln Glu Lys
    50                  55                  60

Gln Asp Ile Leu Lys Glu His Asn Asp Phe Arg Gln Lys Ile Ala Arg
65                  70                  75                  80

Gly Leu Glu Thr Arg Gly Asn Pro Gly Pro Gln Pro Ala Lys Asn
                85                  90                  95

Met Lys Asn Leu Val Trp Asn Asp Glu Leu Ala Tyr Val Ala Gln Val
            100                 105                 110

Trp Ala Asn Gln Cys Gln Tyr Gly His Asp Thr Cys Arg Asp Val Ala
        115                 120                 125

Lys Tyr Gln Val Gly Gln Asn Val Ala Leu Thr Gly Ser Thr Ala Ala
    130                 135                 140

Lys Tyr Asp Asp Pro Val Lys Leu Val Lys Met Trp Glu Asp Glu Val
145                 150                 155                 160

Lys Asp Tyr Asn Pro Lys Lys Phe Ser Gly Asn Asp Phe Leu Lys
                165                 170                 175

Thr Gly His Tyr Thr Gln Met Val Trp Ala Asn Thr Lys Glu Val Gly
            180                 185                 190

Cys Gly Ser Ile Lys Tyr Ile Gln Glu Lys Trp His Lys His Tyr Leu
        195                 200                 205

Val Cys Asn Tyr Gly Pro Ser Gly Asn Phe Met Asn Glu Glu Leu Tyr
    210                 215                 220

Gln Thr Lys
225

<210> SEQ ID NO 171
<211> LENGTH: 206
<212> TYPE: PRT
<213> ORGANISM: Vespula vidua (Yellow jacket) (Wasp)

<400> SEQUENCE: 171

Lys Val Asn Tyr Cys Lys Ile Lys Cys Leu Lys Gly Gly Val His Thr
```

```
             1               5                  10                 15
Ala Cys Lys Tyr Gly Thr Ser Thr Lys Pro Asn Cys Gly Lys Met Val
                    20                  25                 30

Val Lys Ala Tyr Gly Leu Thr Glu Ala Glu Lys Gln Glu Ile Leu Lys
                    35                  40                 45

Val His Asn Asp Phe Arg Gln Lys Val Ala Lys Gly Leu Glu Thr Arg
            50                  55                  60

Gly Asn Pro Gly Pro Gln Pro Pro Ala Lys Asn Met Asn Asn Leu Val
65                          70                  75                  80

Trp Asn Asp Glu Leu Ala Asn Ile Ala Gln Val Trp Ala Ser Gln Cys
                    85                  90                  95

Asn Tyr Gly His Asp Thr Cys Lys Asp Thr Glu Lys Tyr Pro Val Gly
                    100                 105                110

Gln Asn Ile Ala Lys Arg Ser Thr Thr Ala Ala Leu Phe Asp Ser Pro
                    115                 120                125

Gly Lys Leu Val Lys Met Trp Glu Asn Glu Val Lys Asp Phe Asn Pro
            130                 135                 140

Asn Ile Glu Trp Ser Lys Asn Asn Leu Lys Lys Thr Gly His Tyr Thr
145                         150                 155                 160

Gln Met Val Trp Ala Lys Thr Lys Glu Ile Gly Cys Gly Ser Val Lys
                    165                 170                 175

Tyr Val Lys Asp Glu Trp Tyr Thr His Tyr Leu Val Cys Asn Tyr Gly
                    180                 185                 190

Pro Ser Gly Asn Phe Arg Asn Glu Lys Leu Tyr Glu Lys Lys
            195                 200                 205

<210> SEQ ID NO 172
<211> LENGTH: 202
<212> TYPE: PRT
<213> ORGANISM: Vespa mandarinia (Hornet)

<400> SEQUENCE: 172

Asn Asn Tyr Cys Lys Ile Lys Cys Arg Ser Gly Ile His Thr Leu Cys
1               5                   10                  15

Lys Phe Gly Ile Ser Thr Lys Pro Asn Cys Gly Lys Asn Val Val Lys
                    20                  25                  30

Ala Ser Gly Leu Thr Lys Ala Glu Lys Leu Glu Ile Leu Lys Gln His
                    35                  40                  45

Asn Glu Phe Arg Gln Lys Val Ala Arg Gly Leu Glu Thr Arg Gly Lys
            50                  55                  60

Pro Gly Pro Gln Pro Pro Ala Lys Ser Met Asn Thr Leu Val Trp Asn
65                          70                  75                  80

Asp Glu Leu Ala Gln Ile Ala Gln Val Trp Ala Gly Gln Cys Asp Tyr
                    85                  90                  95

Gly His Asp Val Cys Arg Asn Thr Ala Lys Tyr Ser Val Gly Gln Asn
                    100                 105                 110

Ile Ala Glu Asn Gly Ser Thr Ala Ala Ser Phe Ala Ser Val Ser Asn
            115                 120                 125

Met Val Gln Met Trp Ala Asp Glu Val Lys Asn Tyr Gln Tyr Gly Ser
            130                 135                 140

Thr Lys Asn Lys Leu Ile Glu Val Gly His Tyr Thr Gln Met Val Trp
145                         150                 155                 160

Ala Lys Thr Lys Glu Ile Gly Cys Gly Ser Ile Lys Tyr Ile Glu Asn
                    165                 170                 175
```

Gly Trp His Arg His Tyr Leu Val Cys Asn Tyr Gly Pro Ala Gly Asn
            180                 185                 190

Ile Gly Asn Glu Pro Ile Tyr Glu Arg Lys
        195                 200

<210> SEQ ID NO 173
<211> LENGTH: 191
<212> TYPE: PRT
<213> ORGANISM: Zea mays (Maize)

<400> SEQUENCE: 173

Met Thr Ala Cys Gly Asn Val Pro Ile Phe Lys Asp Gly Lys Gly Cys
 1               5                  10                  15

Gly Ser Cys Tyr Glu Val Arg Cys Lys Glu Lys Pro Glu Cys Ser Gly
            20                  25                  30

Asn Pro Val Thr Val Phe Ile Thr Asp Met Asn Tyr Glu Pro Ile Ala
        35                  40                  45

Pro Tyr His Phe Asp Leu Ser Gly Lys Ala Phe Gly Ser Leu Ala Lys
    50                  55                  60

Pro Gly Leu Asn Asp Lys Leu Arg His Cys Gly Ile Met Asp Val Glu
65                  70                  75                  80

Phe Arg Arg Val Arg Cys Lys Tyr Pro Ala Gly Gln Lys Ile Val Phe
                85                  90                  95

His Ile Glu Lys Gly Cys Asn Pro Asn Tyr Val Ala Val Leu Val Lys
            100                 105                 110

Phe Val Ala Asp Asp Gly Asp Ile Val Leu Met Glu Ile Gln Asp Lys
        115                 120                 125

Leu Ser Ala Glu Trp Lys Pro Met Lys Leu Ser Trp Gly Ala Ile Trp
    130                 135                 140

Arg Met Asp Thr Ala Lys Ala Leu Lys Gly Pro Phe Ser Ile Arg Leu
145                 150                 155                 160

Thr Ser Glu Ser Gly Lys Lys Val Ile Ala Lys Asp Ile Ile Pro Ala
                165                 170                 175

Asn Trp Arg Pro Asp Ala Val Tyr Thr Ser Asn Val Gln Phe Tyr
            180                 185                 190

<210> SEQ ID NO 174
<211> LENGTH: 73
<212> TYPE: DNA
<213> ORGANISM: Unknown
<220> FEATURE:
<223> OTHER INFORMATION: Primer sequence

<400> SEQUENCE: 174
gctcgagggt ggaggcggtt caggcggagg tggctctggc ggtggcggat cgttcacccc      60
gcccaccgtg aag                                                        73

<210> SEQ ID NO 175
<211> LENGTH: 33
<212> TYPE: DNA
<213> ORGANISM: Unknown
<220> FEATURE:
<223> OTHER INFORMATION: Primer sequence

<400> SEQUENCE: 175
ggcggccgct catttaccgg gatttacaga cac                                  33

<210> SEQ ID NO 176
<211> LENGTH: 32

-continued

```
<212> TYPE: PRT
<213> ORGANISM: Arachis hypogaea (peanut)
<220> FEATURE:
<221> NAME/KEY: UNSURE
<222> LOCATION: 1, 4, 11, 12, 27, 30
<223> OTHER INFORMATION: Xaa = any amino acid

<400> SEQUENCE: 176

Xaa Gln Gln Xaa Glu Leu Gln Asp Leu Glu Xaa Xaa Gln Ser Gln Leu
 1               5                  10                  15

Glu Asp Ala Asn Leu Arg Pro Arg Glu Gln Xaa Leu Met Xaa Lys Ile
            20                  25                  30

<210> SEQ ID NO 177
<211> LENGTH: 32
<212> TYPE: PRT
<213> ORGANISM: Arachis hypogaea (peanut)
<220> FEATURE:
<221> NAME/KEY: UNSURE
<222> LOCATION: 1, 4, 8, 10, 11, 12, 27, 30
<223> OTHER INFORMATION: Xaa = any amino acid

<400> SEQUENCE: 177

Xaa Gln Gln Xaa Glu Leu Gln Xaa Asp Xaa Xaa Xaa Gln Ser Gln Leu
 1               5                  10                  15

Glu Arg Ala Asp Leu Arg Pro Gly Glu Gln Xaa Leu Met Xaa Lys Ile
            20                  25                  30
```

FUSION MOLECULES AND TREATMENT OF IGE-MEDIATED ALLERGIC DISEASES

RELATED APPLICATIONS

This application is a continuation of, and claims priority under 35 USC §120 to, U.S. application Ser. No. 09/847,208 filed May 1, 2001 now U.S. Pat. No. 7,265,208, the entire disclosure which is hereby incorporated by reference.

This invention was made with Government support under Grant No. AI15251, awarded by the National Institutes of Health. The Government has certain rights in this invention.

BACKGROUND OF THE INVENTION

1. Field of the Invention

The invention concerns a new approach for the management of IgE-mediated allergic diseases and other disorders mediated through IgE receptors (FcεRs) using novel fusion molecules that are able to complex with an FcεR and an inhibitory receptor expressed on mast cells, basophils, or B cells, including inhibitory receptors having an immune receptor tyrosine-based inhibitory (ITIM) motif.

2. Description of the Related Art

Immunoglobulin receptors (also referred to as Fc receptors) are cell-surface receptors binding the constant region of immunoglobulins, and mediate various immunoglobulin functions other than antigen binding.

Fc receptors for IgE molecules are found on many cell types of the immune system (Fridman, W., *FASEB J.*, 5(12): 2684-90 (1991)). There are two different receptors currently known for IgE. IgE mediates its biological responses as an antibody through the multichain high-affinity receptor, FcεRI, and the low-affinity receptor, FcεRII. The high-affinity FcεRI, expressed on the surface of mast cells, basophils, and Langerhans cells, belongs to the immunoglobulin gene superfamily, and has a tetrameric structure composed of an α-chain, a β-chain and two disulfide-linked γ-chains (Adamczewski, M., and Kinet, J. P., *Chemical Immun.*, 59:173-190 (1994)) that are required for receptor expression and signal transduction (Tunon de Lara, *Rev. Mal. Respir.*, 13(1):27-36 (1996)). The α-chain of the receptor interacts with the distal portion of the third constant domain of the IgE heavy chain. The specific amino acids of human IgE involved in binding to human FcεRI have been identified as including Arg-408, Ser-411, Lys-415, Glu-452, Arg-465, and Met-469 (Presta et al., *J. Biol. Chem.* 269:26368-73 (1994)). The interaction is highly specific with a binding constant of about $10^{10}M^{-1}$.

The low-affinity FcεRII receptor, represented on the surface of inflammatory cells, including eosinophils, leukocytes, B lymphocytes, and platelets, did not evolve from the immunoglobulin superfamily but has substantial homology with several animal lectins (Yodoi et al., *Ciba Found. Symp.*, 147: 133-148 (1989)) and is made up of a transmembrane chain with an intracytoplasmic NH2 terminus. The low-affinity receptor, FcεRII (CD23) is currently known to have two forms (FcεRIIa and FcεRIIb), both of which have been cloned and sequenced. They differ only in the N-terminal cytoplasmic region, the extracellular domains being identical. FcεRIIa is normally expressed on B cells, while FcεRIIb is expressed on T cells, B cells, monocytes and eosinophils upon induction by the cytokine IL-4.

Through the high-affinity IgE receptor, FcεRI, IgE plays key roles in an array of acute and chronic allergic reactions, including asthma, allergic rhinitis, atopic dermatitis, severe food allergies, chronic urticaria and angioedema, as well as the serious physiological condition of anaphylactic shock as results, for example, from bee stings or penicillin allergy. Binding of a multivalent antigen (allergen) to antigen specifically bound to FcεRI on the surface of mast cells and basophils stimulates a complex series of signaling events that culminate in the release of host vasoactive and proinflammatory mediators contributing to both acute and late-phase allergic responses (Metcalfe et al. *Physiol. Rev.* 77:1033-1079 (1997)).

The function of the low affinity IgE receptor, FcεRII (also referred to as CD23), found on the surface of B lymphocytes, is much less well established than that of FcεRI. FcεRII, in a polymeric state, binds IgE, and this binding may play a role in controlling the type (class) of antibody produced by B cells.

Three groups of receptors that bind the constant region of human IgG have so far been identified on cell surfaces: FcγRI (CD64), FcγRII (CD32), and FcγRIII (CD16), all of which belong to the immunoglobulin gene superfamily. The three Fcγreceptors have a large number of various isoforms.

Along with the stimulatory FcεRI, mast cells and basophils co-express an immunoreceptor tyrosine-based inhibition motif (ITIM)-containing inhibitory low-affinity receptor, FcγRIIb, that acts as a negative regulator of antibody function. FcγRIIb represents a growing family of structurally and functionally similar inhibitory receptors, the inhibitory receptor superfamily (IRS), that negatively regulate ITAM-containing immune receptors (Ott and Cambier, *J. Allergy Clin. Immunol.*, 106:429-440 (2000)) and a diverse array of cellular responses. Coaggregation of an IRS member with an activating receptor leads to phosphorylation of the characteristic ITIM tyrosine and subsequent recruitment of the SH2 domain-containing protein tyrosine phosphatates, SHP-1 and SHP-2, and the SH2 domain-containing phospholipases, SHIP and SHIP2 (Cambier, J. C., *Proc. Natl. Acad. Sci. USA*, 94:5993-5995 (1997)). Possible outcomes of the coaggregation include inhibition of cellular activation, as demonstrated by the coaggregation of FcγRIIb and B-cell receptors, T-cell receptors, activating receptors, including FcεRI, or cytokine receptors (Malbec et al., *Curr. Top. Microbiolo. Immunol.*, 244:13-27 (1999)).

Most studies have so far concentrated on elucidating the mechanisms of FcγRII, in particular FcγRIIb, function. The three alternatively spliced isoforms of the FcγIIb receptor, of which FcγRIIb1' is only found in mice, and FcγRIIb1 and FcγRIIb2 are expressed in both humans and mice, have Ig-like loops and a conserved ITIM, but differ in their cytoplasmic domains. Co-crosslinking of the high-affinity FcεRI receptor and the inhibitory low-affinity receptor FcγRII blocks a number of processes, including FcεRI-mediated secretion, IL-4 production, $Ca^{2+}$ mobilization, Syk phosphorylation, and FcεRI-mediated basophil and mast cell activation. In B cells, co-crosslinking of the B-cell receptor and FcγRIIb inhibits B-cell receptor-mediated cell activation (Cambier, J. C., *Proc. Natl. Acad. Sci.*, 94:5993-5995 (1997); Daeron, M., *Annu. Rev. Immunol.*, 5:203-234 (1997)), and specifically, inhibits B-cell receptor-induced blastogenesis and proliferation (Chan et al., *Immunology*, 21:967-981 (1971); Phillips and Parker, *J. Immunol.*, 132:627-632 (1984)) and stimulates apoptosis (Ashman et al., *J. Immunol*, 157:5-11 (1996)). Coaggregation of FcγRIIb1 or FcγRIIb2 with FcεRI in rat basophilic leukemia cells, inhibits FcεRI-mediated release of serotonin and TNF-α (Daeron et al., *J. Clin. Invest.*, 95:577-85 (1995); Daeron et al., *Immunity*, 3:635-646 (1995)).

Another ITIM-containing receptor expressed on mast cells that has been described to prevent IgE-mediated mast cell activation when coligated with FcεRI, is a 49 kDa glycoprotein member of the immunoglobulin superfamily, termed gp49b1 (gp91) (see, e.g. Wagtmann et al., *Current Top. Micobiol. Immunol.* 244:107-113 (1999); Katz, H. R., Int. Arch Allergy Immunol. 118:177-179 (1999); and Lu-Kuo et al., *J. Biol. Chem.* 274:5791-96 (1999)). Gp49b1 was originally identified in mice, while human counterparts of the gp49 family, including gp49b1, have been cloned by Arm et al., *J. Immunol.* 15:2342-2349 (1997). Further ITIM-containing receptors, several expressed in mast cells, basophils or B cells are reviewed by Sinclair N R, *Scand. J. Immunol.* 50:10-13 (1999).

Despite advances in understanding the cellular and molecular mechanisms that control allergic responses and improved therapies, the incidence of allergic diseases, especially asthma, has increased dramatically in recent years in both developed and developing countries (Beasley et al., *J. Allergy Clin. Immunol.* 105:466-472 (2000); Peat and Li, *J. Allergy Clin. Immunol.* 103:1-10 (1999). Allergic diseases can be treated, for example, by allergen-based vaccination, in which increasing doses of allergen are given by injection over years. This approach is costly, time consuming, poorly or not efficacious in many allergic conditions, and has serious side-effects, including death in some instances. Mild asthma can usually be controlled in most patients by relatively low doses of inhaled corticosteroids, while moderate asthma is usually managed by the additional administration of inhaled long-acting β-antagonists or leukotriene inhibitors. The treatment of severe asthma is still a serious medical problem. In addition, many of the therapeutics currently used in allergy treatment have serious side-effects. Although an anti-IgE antibody currently in clinical trials (rhuMAb-E25, Genentech, Inc.) and other experimental therapies (e.g. antagonists of IL-4) show promising results, there is need for the development of additional therapeutic strategies and agents to control allergic disease, such as asthma, severe food allergy, and chronic urticaria and angioedema.

The object of this invention is to provide a novel therapeutic strategy designed to cross-link inhibitory receptors expressed on mast cells, basophils and/or B cells, such as an ITIM-containing FcγRIIb or gp49b1 receptor, or p91/PIR-B receptor, with FcεRI or FcεRII, for the treatment of conditions associated with anaphylactic hypersensitivity and atopic allergies, such as, for example, asthma, allergic rhinitis, atopic dermatitis, severe food allergies, some forms of chronic urticaria and angioedema, as well as the serious physiological condition of anaphylactic shock as results, for example, from bee stings or penicillin allergy.

SUMMARY OF THE INVENTION

The present invention provides novel bi-functional compounds that co-crosslink inhibitory receptors with Fcε receptors and block Fcε receptor-mediated biological activities, as well as methods of making and using such compounds, and compositions and articles of manufacture comprising them.

In one aspect the invention concerns an isolated fusion molecule comprising a first polypeptide sequence capable of specific binding, to a native inhibitory receptor comprising an immune receptor tyrosine-based inhibitory motif (ITIM), expressed on mast cells, basophils and/or B cells, functionally connected to a second polypeptide sequence capable of specific binding, directly or indirectly, to a native IgE receptor (FcεR). Preferably, the inhibitory receptor is a type I transmembrane molecule with an Ig-like domain, such as, for example, a low-affinity IgG receptor FcγRIIb, an inhibitory receptor of the gp49 family, e.g. gp49b1, p91/PIR-B, leukocyte-associated immunoglobulin-like receptor-1 (LAIR-1), LIR-1, or CD22.

The IgE receptor may be a high-affinity FcεRI receptor, or a low-affinity FcεRII receptor (CD23).

More preferably, the inhibitory receptor is a low-affinity FcγRIIb receptor, most preferably native human FcγRIIb, and the IgE receptor is a high-affinity FcεRI receptor, most preferably native human FcεRI, although fusion molecules including sequences capable of specific binding, directly or indirectly, to the low-affinity IgE receptor FcεRII are also within the scope of the invention.

In a particularly preferred embodiment, the two receptors are both of human origin, and the first and second polypeptide sequences present in the fusion molecules are human IgG, e.g. $IgG_1$, and IgE heavy chain constant region sequences, respectively.

In a preferred embodiment, the second polypeptide sequence comprises a sequence of an allergen protein, which is capable of indirect binding to a high- or low-affinity IgE receptor via an allergen-specific IgE molecule. In this embodiment, the second polypeptide sequence may comprise part or whole of a native or variant allergen protein, such as a food or pollen allergen.

The first and second polypeptide sequences may be connected via a linker, e.g. a polypeptide linker or a non-polypeptide bifunctional linker, or may be directly fused to each other. The length of the polypeptide linker typically is about 5 to 25 amino acid residues, preferably about 10 to 25 amino acid residues, most preferably about 15 to 25 amino acid residues.

In a particular embodiment, the first polypeptide sequence in the fusion molecule retains the residues from a native IgG heavy chain constant region that are required to bind to the targeted IgG inhibitory receptor, e.g. FcγRIIb. Similarly, in a particular embodiment, the second polypeptide sequence in the fusion molecule retains the residues from a native IgE heavy chain constant region that are required for binding to the targeted IgE receptor, such as FcεRI or FcεRII.

In another embodiment, the first polypeptide sequence comprises an amino acid sequence having at least about 80%, preferably at least about 85%, more preferably at least about 90%, even more preferably at least about 95%, most preferably at least about 99% sequence identity with the hinge-CH2-CH3 portion of a native IgG immunoglobulin heavy chain constant region. The IgG preferably is, but does not need to be, $IgG_1$. Indeed, the IgG portion of the molecule can derive from the heavy chain constant region of any IgG subclass, including $IgG_1$, $IgG_2$, $IgG_3$ and $IgG_4$.

In yet another embodiment, the first polypeptide sequence comprises an amino acid sequence having at least about 80%, preferably at least about 85%, more preferably at least about 90%, even more preferably at least about 95%, most preferably at least about 99% sequence identity with the receptor-binding domain of a ligand of another native ITIM-containing inhibitory receptor expressed on mast cells, basophils, or B cells, such as, without limitation, a native gp49b1, p91/PIR-B, LAIR-1, LIR-1, or CD11 receptor.

In another particular embodiment, the second polypeptide sequence in the fusion molecule comprises an amino acid sequence having at least about 80%, preferably at least about 85%, more preferably at least about 90%, even more preferably at least about 95%, most preferably at least about 99% sequence identity with the CH2-CH3-CH4 portion of a native IgE immunoglobulin heavy chain constant region.

In yet another embodiment, the second polypeptide sequence in the fusion molecule comprises an amino acid sequence having at least about 80%, preferably at least about 85%, more preferably at least about 90%, even more preferably at least about 95%, most preferably at least about 99% sequence identity with a native allergen protein or a fragment thereof.

In a further embodiment, the first polypeptide sequence in the fusion molecule comprises an amino acid sequence encoded by nucleic acid hybridizing under stringent conditions to the complement of the coding sequence of the hinge-CH2-CH3 portion of a native IgG immunoglobulin heavy chain constant region, and retains the ability to bind an IgG inhibitory receptor, preferably human FcγRIIb. The IgG preferably is, but does not need to be, $IgG_1$.

In a still further preferred embodiment, the second polypeptide sequence in the fusion molecule comprises an amino acid sequence encoded by nucleic acid hybridizing under stringent conditions to the complement of the coding sequence of the CH2-CH3-CH4 portion of a native IgE immunoglobulin heavy chain constant region, and retains the ability to bind a high-affinity IgE receptor, preferably human FcεRI.

In yet another embodiment, the second polypeptide sequence in the fusion molecule comprises an amino acid sequence encoded by nucleic acid hybridizing under stringent conditions to the complement of the coding sequence of all or part of a native allergen protein.

A particularly preferred molecule of the invention comprises the hinge-CH2-CH3 portion of an IgG, such as $IgG_1$, immunoglobulin heavy chain constant region functionally linked to the CH2-CH3-CH4 portion of an IgE immunoglobulin heavy chain constant region via a 15 amino acids polypeptide linker. In a preferred embodiment, the $IgG_1$ hinge-CH2-CH3 sequence is connected at its C-terminus to the N-terminus of the IgE CH2-CH3-CH4 sequence via the 15 amino acids polypeptide linker. Preferably both immunoglobulin heavy chain sequences are of human origin.

In another aspect, the invention concerns isolated nucleic acid molecules encoding polypeptide fusions of the present invention. The invention also concerns vectors comprising such nucleic acid molecules, and recombinant host cells transformed with such vectors.

In a further aspect, the invention concerns a pharmaceutical composition comprising a fusion molecule as hereinabove defined in admixture with a pharmaceutically acceptable ingredient. The pharmaceutical composition is preferably used for the treatment of an IgE-mediated response, such as an acute or late phase allergic reaction, including, without limitation, immediate hypersensitivity reactions. In a preferred embodiment, the pharmaceutical composition is for the treatment of a condition associated with anaphylactic hypersensitivity or an atopic allergy, such as asthma, allergic rhinitis, atopic dermatitis, severe food allergies, chronic urticaria, angioedema, and/or anaphylactic shock.

In a still further aspect, the invention concerns an article of manufacture comprising a container, a fusion molecule as hereinabove defined within the container, and a label or package insert on or associated with the container. The label or package insert preferably comprises instructions for the treatment of a condition associated with an IgE-mediated biological response, such as a condition associated with anaphylactic hypersensitivity or an atopic allergy, e.g. asthma, allergic rhinitis, atopic dermatitis, severe food allergies, chronic urticaria, angioedema, and/or anaphylactic shock.

In yet another aspect, the invention concerns a method for the treatment of a condition associated with an IgE-mediated biological response, comprising administering an effective amount of a fusion molecule as hereinabove defined to a subject in need. The subject preferably is a human patient, and the condition to be treated (including prevention), preferably is asthma, allergic rhinitis, atopic dermatitis, severe food allergies, chronic urticaria, angioedema, and/or anaphylactic shock.

In addition to the aspects discussed above, the present invention also contemplates fusion molecules suitable for coaggregation of other inhibitory receptors with IgE receptors, such as FcεRI or FcεRII. For example, a fusion molecule comprising a c-kit ligand sequence, capable of specific binding the receptor PTK c-Kit, fused to a polypeptide sequence capable of specific binding, directly or indirectly, to an IgE receptor, such as FcεRI or FcεRII, is also contemplated. Such fusion molecules are expected to negatively regulate the expression of mast cells, and find utility in the treatment of conditions associated with anaphylactic hypersensitivity and atopic allergies.

BRIEF DESCRIPTION OF THE FIGURES

FIG. 1 shows the nucleotide sequence encoding the human $IgG_1$ heavy chain constant region (SEQ ID NO: 1).

FIG. 2 shows the amino acid sequence of the human $IgG_1$ heavy chain constant region (SEQ ID NO: 2). In the sequence, the CH1 domain extends from amino acid position 122 to amino acid position 219, the hinge region extends from amino acid position 220 to amino acid position 231, the CH2 domain extends from amino acid position 232 to amino acid position 344, and the CH3 domain extends from amino acid position 345 to amino acid 451 (the C-terminus).

FIG. 3 shows the amino acid sequence of the hinge-CH2-CH3 portion of the human $IgG_1$ heavy chain constant region (SEQ ID NO: 3).

FIG. 4 shows the nucleotide sequence encoding the human IgE heavy chain constant region (SEQ ID NO: 4).

FIG. 5 shows the amino acid sequence of the human IgE heavy chain constant region (SEQ ID NO: 5).

FIG. 6 shows the amino acid sequence of the CH2-CH3-CH4 portion of the human IgE heavy chain constant region (SEQ ID NO: 6).

FIG. 7 shows the amino acid sequence of the γhinge-CHγ2-CHγ3-$(Gly_4Ser)_3$-CHε2-CHε3-CHε3 fusion molecule (GE2) of the invention (SEQ ID NO: 7).

FIG. 10 illustrates GE2 binding to HMC-1 cells that express FcγRIIb but not FcεRIa.

FIG. 11 illustrates GE2 binding to 3D10 cells that express FcεRIa but not FcγRIIb.

DETAILED DESCRIPTION OF THE PREFERRED EMBODIMENT

I. Definitions

Figure 8:
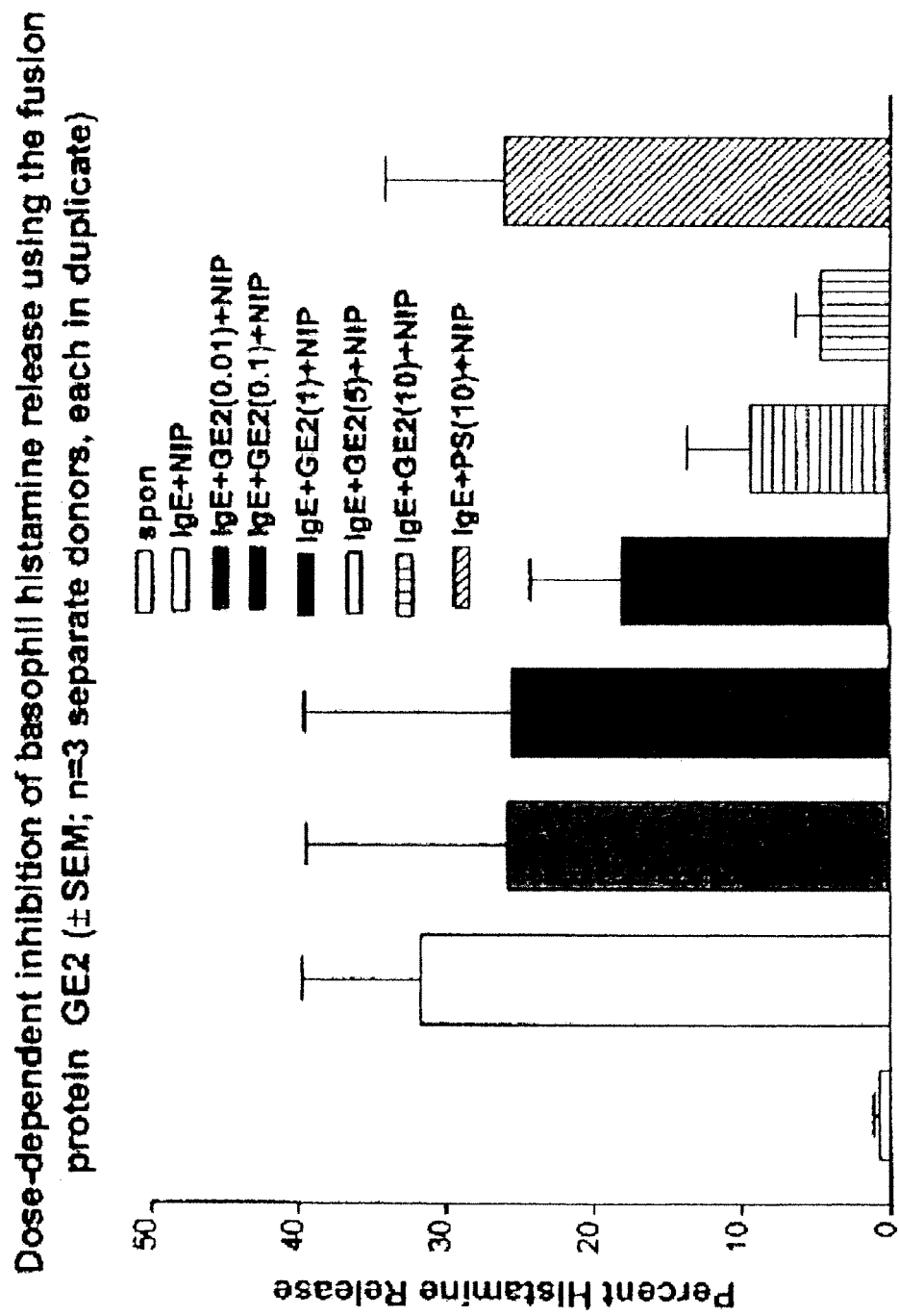
FIG. 8 illustrates the dose-dependent inhibition of basophil histamine release using the fusion protein GE2 (±SEM; n=3 separate donors, each in duplicate). Purified human blood basophils were acid stripped and then sensitized with humanized anti-NP IgE, labeled as IgE, alone or in the presence of GE2 protein or PS that is a purified human IgE myeloma protein. One hour later, cells were challenged with NP-BSA and the resulting level of histamine release measured.

Unless defined otherwise, technical and scientific terms used herein have the same meaning as commonly understood by one of ordinary skill in the art to which this invention belongs. One skilled in the art will recognize many methods and materials similar or equivalent to those described herein, which could be used in the practice of the present invention. Indeed, the present invention is in no way limited to the methods and materials described. For purposes of the present invention, the following terms are defined below.

The term "functionally connected" with reference to the first and second polypeptide sequences included in the fusion molecules herein, is used to indicate that such first and second polypeptide sequences retain the ability to bind to the respective receptors. Thus, after being connected to a second polypeptide sequence, the first polypeptide sequence retains the ability of specific binding to a native IgG inhibitory receptor, such as a low-affinity FcγRIIb receptor. Similarly, after being connected to a first polypeptide sequence, the second polypeptide sequence retains the ability of specific binding, directly or indirectly, i.e. through a third polypeptide sequence, to a native IgE receptor, such as a native high-affinity IgE receptor, e.g. native human FcεRI, or a native low-affinity IgE receptor, e.g. FcεRII. As a result, the fusion molecule, comprising the first and second polypeptide sequences functionally connected to each other, is capable of cross-linking the respective native receptors, such as, for example, FcγRIIb and FcεRI or FcεRII. In order to achieve a functional connection between the two binding sequences within the fusion molecules of the invention, it is preferred that they retain the ability to bind to the corresponding receptor with a binding affinity similar to that of a native immunoglobulin heavy chain or other native polypeptide binding to that receptor.

The binding is "specific" when the binding affinity of a molecule for a binding target, e.g. an IgG or IgE receptor, is significantly higher (preferably at least about 2-times, more preferably at least about 4-times, most preferably at least about 6-times higher) than the binding affinity of that molecule to any other known native polypeptide. Since you do not define how one determines the universe of "other known native polypeptide(s)", this definition could be considered indefinite. What about defining specific binding as preferential binding in the presence of a competitor (you could even name possible competitors).

The term "inhibitory receptor" is used in the broadest sense and refers to a receptor capable of down-regulating a biological response mediated by another receptor, regardless of the mechanism by which the down-regulation occurs.

The terms "receptor comprising an immune receptor tyrosine-based inhibitory motif (ITIM)" and "ITIM-containing receptor" is used to refer to a receptor containing one or more immune receptor tyrosine-based inhibitory motifs, ITIMs. The ITIM motif can be generally represented by the formula Val/Ile-Xaa-PTyr-Xaa-Xaa-Leu/Val (where Xaa represents any amino acid). ITIM-containing receptors include, without limitation, FcγRIIb, gp49b1/gp91 (Arm et al., *J. Biol. Chem.* 266:15966-73 (1991)), p91/PIR-B (Hayami et al., *J. Biol. Chem.* 272:7320-7 (1997)), LIR1-3, 5, 8, LAIR-1; CD22 (van Rossenberg et al., *J. Biol. Chem.* Jan. 4, 2001); CTL-4, CD5, p58/70/140 KIR, PIRB2-5; NKB1, Ly49 A/C/E/F/G, NKG2-A/B, APC-R, CD66, CD72, PD-1, SHPS-1, SIRP-α1, IL T1-5, MIR7, 10, hMIR(HM18), hMIR(HM9), Fas (CD95), TGFβ-R, TNF-R1, IFN-γ-R (α- and β-chains), mast cell function Ag, H2-M, HLA-DM, CD1, CD1-d, CD46, c-cbl, Pyk2/FADK2, P130 Ca rel prot, PGDF-R, LIF, LIR-R, CIS, SOCS13 and 3, as reviewed in Sinclair N R et al., supra. Ligands for many of these receptors are also known, such as, e.g. the ligand for CD95 is called CD95 ligand, the ligands for CTLA-4 are CD80 and CD86, the ligands of IFN-γ receptor is IFN-γ, etc. Ligands for CD22 comprise the basic binding motif Nau5Ac-a(2,6)-Lac, and are discussed, for example in van Rossenberg et al., 2001, supra.

The term "IgG inhibitory receptor" is used to define a member of the inhibitory receptor superfamily (IRS), now know or hereinafter discovered, that is capable of attenuating an FcεR-mediated response, regardless of whether it is mediated via IgE acting through a high-affinity IgE receptor, e.g. FcεRI, or a low-affinity IgE receptor, or by another mechanism such as an autoantibody to the FcεR. The response preferably is an IgE-mediated allergic response, such as a type I (immediate hypersensitivity) reaction but could include autoimmune reactions due to anti-FcεRI α-chain antibodies that have been reported in about half of the cases of chronic idiopathic urticaria.

The term "native" or "native sequence" refers to a polypeptide having the same amino acid sequence as a polypeptide that occurs in nature. A polypeptide is considered to be "native" in accordance with the present invention regardless of its mode of preparation. Thus, such native sequence polypeptide can be isolated from nature or can be produced by recombinant and/or synthetic means. The terms "native" and "native sequence" specifically encompass naturally-occurring truncated or secreted forms (e.g., an extracellular domain sequence), naturally-occurring variant forms (e.g., alternatively spliced forms) and naturally-occurring allelic variants of a polypeptide.

The terms "native FcγRIIb," "native sequence FcγRIIb," "native low-affinity IgG inhibitory receptor FcγRIIb," and "native sequence low-affinity IgG inhibitory receptor FcγRIIb" are used interchangeably, and refer to FcγRIIb receptors of any species, including any mammalian species, as occurring in nature. Preferably, the mammal is human. FcγRIIb is an isoform of the low-affinity IgG receptor FcγRII containing an immunoreceptor tyrosine-based inhibition motif (ITIM). This receptor is the principal FcγRII species in human peripheral blood basophils and cord blood-derived mast cells. For further details see, for example, Malbec and Fridman, *Curr. Top. Microbiol. Immunol.* 244:13-27 (1999); Cambier, J. C., *Proc. Natl. Acad. Sci. USA* 94:5993-5995 (1997); and Ott and Cambier, *J. Allergy Clin. Immunol.* 106 (3):429-440 (2000). FcγRIIb has three alternatively spliced forms designated FcγRIIb1, FcγRIIb1', and FcγRIIb2, which differ only in their cytoplasmic domain sequences. All three alternatively spliced isoforms contain two extracellular Ig-like loops and a single conserved ITIM motif within their cytoplasmic tails, and are specifically included within the definition of FcγRIIb, along with other splice variants that might be identified in the future.

The terms "native FcεRI," "native sequence FcεRI," "native high-affinity IgE receptor FcεRI," and "native sequence high-affinity IgE receptor FcεRI" are used interchangeably and refer to FcεRI receptors of any species, including any mammalian species, that occurs in nature. FcεRI is a member of the multi-subunit immune response receptor (MIRR) family of cell surface receptors that lack intrinsic enzymatic activity but transduce intracellular signals through association with cytoplasmic tyrosine kinases. For further details see, for example, Kinet, J. P., *Annu. Rev. Immunol.* 17:931-972 (1999) and Ott and Cambier, *J. Allergy Clin. Immunol.*, 106:429-440 (2000).

The terms "native FcεRII (CD23)," "native sequence FcεRII (CD23)," native low-affinity IgE receptor FcεRII (CD23)," "native sequence low-affinity IgE receptor FcεRII (CD23)" are used interchangeably and refer to FcεRII (CD23) receptors of any species, including any mammalian species, that occur in nature. Several groups have cloned and expressed low-affinity IgE receptors of various species. The cloning and expression of a human low-affinity IgE receptor is reported, for example, by Kikutani et al., *Cell* 47:657-665 (1986), and Ludin et al., *EMBO J.* 6:109-114 (1987). The cloning and expression of corresponding mouse receptors is disclosed, for example, by Gollnick et al., *J. Immunol.* 144: 1974-82 (1990), and Kondo et al., *Int. Arch. Allergy Immunol.* 105:38-48 (1994). The molecular cloning and sequencing of CD23 for horse and cattle has been recently reported by Watson et al., *Vet. Immunol. Immunopathol.* 73:323-9 (2000). For an earlier review of the low-affinity IgE receptor see also Delespesse et al., *Immunol. Rev.* 125:77-97 (1992).

The term "mammal" or "mammalian species" refers to any animal classified as a mammal, including humans, domestic and farm animals, and zoo, sports, or pet animals, such as dogs, cats, cattle, horses, sheep, pigs, goats, rabbits, as well as rodents such as mice and rats, etc. Preferably, the mammal is human.

The term "polypeptide", in singular or plural, is used herein to refer to any peptide or protein comprising two or more amino acids joined to each other in a linear chain by peptide bonds. As used herein, the term refers to both short chains, which also commonly are referred to in the art as peptides, oligopeptides and oligomers, and to longer chains, commonly referred to in the art as proteins. Polypeptides, as defined herein, may contain amino acids other than the 20 naturally occurring amino acids, and may include modified amino acids. The modification can be anywhere within the polypeptide molecule, such as, for example, at the terminal amino acids, and may be due to natural processes, such as processing and other post-translational modifications, or may result from chemical and/or enzymatic modification techniques which are well known to the art. The known modifications include, without limitation, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Such modifications are well known to those of skill and have been described in great detail in the scientific literature, such as, for instance, Creighton, T. E., Proteins—Structure And Molecular Properties, 2nd Ed., W.H. Freeman and Company, New York (1993); Wold, F., "Posttranslational Protein Modifications: Perspectives and Prospects," in Posttranslational Covalent Modification of Proteins, Johnson, B. C., ed., Academic Press, New York (1983), pp. 1-12; Seifter et al., "Analysis for protein modifications and nonprotein cofactors," *Meth. Enzymol.* 182:626-646 (1990), and Rattan et al., *Ann. N.Y. Acad. Sci.* 663:48-62 (1992).

Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli*, prior to proteolytic processing, almost invariably will be N-formylmethionine. Accordingly, when glycosylation is desired, a polypeptide is expressed in a glycosylating host, generally eukaryotic host cells. Insect cells often carry out the same post-translational glycosylations as mammalian cells and, for this reason, insect cell expression systems have been developed to express efficiently mammalian proteins having native patterns of glycosylation.

It will be appreciated that polypeptides are not always entirely linear. For instance, polypeptides may be branched as a result of ubiquitination, and they may be circular, with or without branching, generally as a result of post-translational events, including natural processing and events brought about by human manipulation which do not occur naturally. Circular, branched and branched circular polypeptides may be synthesized by non-translation natural process and by entirely synthetic methods, as well. Such structures are within the scope of the polypeptides as defined herein.

Amino acids are represented by their common one- or three-letter codes, as is common practice in the art. Accordingly, the designations of the twenty naturally occurring amino acids are as follows: Alanine=Ala (A); Arginine=Arg (R); Aspartic Acid=Asp (D); Asparagine=Asn (N); Cysteine=Cys (C); Glutamic Acid=Glu (E); Glutamine=Gln (O); Glycine=Gly (G); Histidine=His (H); Isoleucine=Ile (I); Leucine=Leu (L); Lysine=Lys (K); Methionine=Met (M); Phenylalanine=Phe (F); Proline=Pro (P); Serine=Ser (S); Threonine=Thr (T); Tryptophan=Trp (W); Tyrosine=Tyr (Y); Valine=Val (V). The polypeptides herein may include all L-amino acids, all D-amino acids or a mixture thereof. The polypeptides comprised entirely of D-amino acids may be advantageous in that they are expected to be resistant to proteases naturally found within the human body, and may have longer half-lives.

The term "amino acid sequence variant" refers to molecules with some differences in their amino acid sequences as compared to a reference (e.g. native sequence) polypeptide. The amino acid alterations may be substitutions, insertions, deletions or any desired combinations of such changes in a native amino acid sequence.

Substitutional variants are those that have at least one amino acid residue in a native sequence removed and a different amino acid inserted in its place at the same position. The substitutions may be single, where only one amino acid in the molecule has been substituted, or they may be multiple, where two or more amino acids have been substituted in the same molecule.

Insertional variants are those with one or more amino acids inserted immediately adjacent to an amino acid at a particular position in a native amino acid sequence. Immediately adjacent to an amino acid means connected to either the α-carboxy or α-amino functional group of the amino acid.

Deletional variants are those with one or more amino acids in the native amino acid sequence removed. Ordinarily, deletional variants will have at least one amino acid deleted in a particular region of the molecule.

"Sequence identity" is defined as the percentage of amino acid residues in a candidate sequence that are identical with the amino acid residues in a reference polypeptide sequence (e.g., a native polypeptide sequence), after aligning the sequences and introducing gaps, if necessary, to achieve the maximum percent sequence identity, and not considering any conservative substitutions as part of the sequence identity. The % sequence identity values are generated by the NCBI BLAST2.0 software as defined by Altschul et al., (1997), "Gapped BLAST and PSI-BLAST: a new generation of protein database search programs", *Nucleic Acids Res.*, 25:3389-

3402. The parameters are set to default values, with the exception of the Penalty for mismatch, which is set to −1.

"Stringent" hybridization conditions are sequence dependent and will be different with different environmental parameters (e.g., salt concentrations, and presence of organics). Generally, stringent conditions are selected to be about 5° C. to 20° C. lower than the thermal melting point ($T_m$) for the specific nucleic acid sequence at a defined ionic strength and pH. Preferably, stringent conditions are about 5° C. to 10° C. lower than the thermal melting point for a specific nucleic acid bound to a perfectly complementary nucleic acid. The $T_m$ is the temperature (under defined ionic strength and pH) at which 50% of a nucleic acid (e.g., tag nucleic acid) hybridizes to a perfectly matched probe.

"Stringent" wash conditions are ordinarily determined empirically for hybridization of each set of tags to a corresponding probe array. The arrays are first hybridized (typically under stringent hybridization conditions) and then washed with buffers containing successively lower concentrations of salts, or higher concentrations of detergents, or at increasing temperatures until the signal to noise ratio for specific to non-specific hybridization is high enough to facilitate detection of specific hybridization. Stringent temperature conditions will usually include temperatures in excess of about 30° C., more usually in excess of about 37° C., and occasionally in excess of about 45° C. Stringent salt conditions will ordinarily be less than about 1000 mM, usually less than about 500 mM, more usually less than about 400 mM, typically less than about 300 mM, preferably less than about 200 mM, and more preferably less than about 150 mM. However, the combination of parameters is more important than the measure of any single parameter. See, e.g., Wetmur et al., *J. Mol. Biol.* 31:349-70 (1966), and Wetmur, *Critical Reviews in Biochemistry and Molecular Biology* 26(34):227-59 (1991).

In a preferred embodiment, "stringent conditions" or "high stringency conditions," as defined herein, may be hybridization in 50% formamide, 6×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (100 µg/ml), 0.5% SDS, and 10% dextran sulfate at 42° C., with washes at 42° C. in 2×SSC (sodium chloride/sodium citrate) and 0.1% SDS at 55° C., followed by a high-stringency wash consisting of 0.2×SSC containing 0.1% SDS at 42° C.

The term "immunoglobulin" (Ig) is used to refer to the immunity-conferring portion of the globulin proteins of serum, and to other glycoproteins, which may not occur in nature but have the same functional characteristics. The term "immunoglobulin" or "Ig" specifically includes "antibodies" (Abs). While antibodies exhibit binding specificity to a specific antigen, immunoglobulins include both antibodies and other antibody-like molecules that lack antigen specificity. Native immunoglobulins are secreted by differentiated B cells termed plasma cells, and immunoglobulins without any known antigen specificity are produced at low levels by the immune system and at increased levels by myelomas. As used herein, the terms "immunoglobulin," "Ig," and grammatical variants thereof are used to include antibodies, and Ig molecules without known antigen specificity, or without antigen binding regions.

Native immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

The main Ig isotypes (classes) found in serum, and the corresponding Ig heavy chains, shown in parentheses, are listed below:

IgG (γ chain): the principal Ig in serum, the main antibody raised in response to an antigen, has four major subtypes, several of which cross the placenta;

IgE (ε chain): this Ig binds tightly to mast cells and basophils, and when additionally bound to antigen, causes release of histamine and other mediators of immediate hypersensitivity; plays a primary role in allergic reactions, including hay fever, asthma and anaphylaxis; and may serve a protective role against parasites;

IgA (α chain): this Ig is present in external secretions, such as saliva, tears, mucous, and colostrum;

IgM (µ chain): the Ig first induced in response to an antigen; it has lower affinity than antibodies produced later and is pentameric; and IgD (δ chain): this Ig is found in relatively high concentrations in umbilical cord blood, serves primarily as an early cell receptor for antigen, and is the main lymphocyte cell surface molecule.

Antibodies of the IgG, IgE, IgA, IgM, and IgD isotypes may have the same variable regions, i.e. the same antigen binding cavities, even though they differ in the constant region of their heavy chains. The constant regions of an immunoglobulin, e.g. antibody are not involved directly in binding the antibody to an antigen, but correlate with the different effector functions mediated by antibodies, such as complement activation or binding to one or more of the antibody Fc receptors expressed on basophils, mast cells, lymphocytes, monocytes and granulocytes.

Some of the main antibody isotypes (classes) are divided into further sub-classes. IgG has four known subclasses: $IgG_1$ ($γ_1$), $IgG_2$ ($γ_2$), $IgG_3$ ($γ_3$), and $IgG_4$ ($γ_4$), while IgA has two known sub-classes: $IgA_1$ ($α_1$) and $IgA_2$ ($α_2$).

A light chain of an Ig molecule is either a κ or a λ chain.

The constant region of an immunoglobulin heavy chain is further divided into globular, structurally discrete domains, termed heavy chain constant domains. For example, the constant region of an $IgG_1$ immunoglobulin heavy chain comprises three constant domains, CH1, CH2 and CH3, and a hinge region between the CH1 and CH2 domains. The IgE immunoglobulin heavy chain comprises four constant domains: CH1, CH2, CH3 and CH4 and does not have a hinge region.

Immunoglobulin sequences, including sequences of immunoglobulin heavy chain constant regions are well known in the art and are disclosed, for example, in Kabat et al., *Sequences of Proteins of Immunological Interest*, 5th Ed. Public Health Service, National Institute of Health, Bethesda, Md. (1991). For a discussion of the human $IgG_1$ heavy chain constant region ($γ_1$), see also Ellison et al., *Nucl. Acid Res.* 10:4071-4079 (1982); and Takahashi et al., *Cell* 29:671-679 (1982). For a discussion of the human $IgG_2$ constant region ($γ_2$), see also Krawinkel et al., *EMBO J.* 1:403-407 (1982); Ellison et al., *Proc. Nat. Acad. Sci. USA* 79:1984-1988 (1982); and Takahashi et al. (1982), supra. For a discussion of human IgG$_3$ heavy chain constant region ($\gamma_3$), see also Krawinkel et al., (1982), supra, and Takahashi et al. (1982), supra. For a discussion of human IgG$_4$ heavy chain constant region ($\gamma_4$), see also Ellison et al., *DNA* 1:11-18 (1982), Krawinkel et al. (1982), supra, and Takahashi et al. (1982), supra. For a discussion of the human IgE heavy chain constant region ($\epsilon$), see also Max et al., *Cell* 29:691-699 (1982). IgE isoforms are described in Saxon et al., *J. Immunol.* 147:4000 (1991); Peng et al., *J. Immunol.* 148:129-136 (1992); Zhang et al., *J. Exp. Med.* 176:233-243 (1992); and Hellman, *Eur. J. Immunol.* 23:159-167 (1992).

The term "allergen," and grammatical variants thereof, are used to refer to special antigens that are capable of inducing IgE-mediated allergies. An allergen can be almost anything that acts as an antigen and stimulates an IgE-mediated allergic reaction. Common allergens can be found, for example, in food, pollen, mold, house dust which may contain mites as well as dander from house pets, venom from insects such as bees, wasps and mosquitoes.

A "Type I" allergic reaction or "immediate hypersensitivity" or "atopic allergy" occurs when an antigen entering the body encounters mast cells or basophils which have been sensitized by IgE attached to its high-affinity receptor, Fc$\epsilon$RI on these cells. When an allergen reaches the sensitized mast cell or basophil, it cross-links surface-bound IgE, causing an increase in intracellular calcium (Ca$^{2+}$) that triggers the release of pre-formed mediators, such as histamine and proteases, and newly synthesized, lipid-derived mediators such as leukotrienes and prostaglandins. These autocoids produce the clinical symptoms of allergy. In addition, cytokines, e.g. IL-4, TNF-alpha, are released from degranulating basophils and mast cells, and serve to augment the inflammatory response that accompanies an IgE reaction (see, e.g. Immunology, Fifth Edition, Roitt et al., eds., 1998, pp. 302-317).

The terms "vector", "polynucleotide vector", "construct" and "polynucleotide construct" are used interchangeably herein. A polynucleotide vector of this invention may be in any of several forms, including, but not limited to, RNA, DNA, RNA encapsulated in a retroviral coat, DNA encapsulated in an adenovirus coat, DNA packaged in another viral or viral-like form (such as herpes simplex, and adeno-associated virus (AAV)), DNA encapsulated in liposomes, DNA complexed with polylysine, complexed with synthetic polycationic molecules, conjugated with transferrin, complexed with compounds such as polyethylene glycol (PEG) to immunologically "mask" the molecule and/or increase half-life, or conjugated to a non-viral protein. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

A "host cell" includes an individual cell or cell culture which can be or has been a recipient of any vector of this invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo with a vector comprising a nucleic acid of the present invention.

The term "promoter" means a nucleotide sequence that, when operably linked to a DNA sequence of interest, promotes transcription of that DNA sequence.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accord with conventional practice.

The term "IgE-mediated biological response" is used to refer to a condition or disease which is characterized by signal transduction through an IgE receptor, including the high-affinity IgE receptor, Fc$\epsilon$RI, and the low-affinity IgE receptor Fc$\epsilon$RII. The definition includes, without limitation, conditions associated with anaphylactic hypersensitivity and atopic allergies, such as, for example, asthma, allergic rhinitis, atopic dermatitis, food allergies, chronic urticaria and angioedema, as well as the serious physiological condition of anaphylactic shock, usually caused by bee stings or medications such as penicillin.

The terms "treat" or "treatment" refer to both therapeutic treatment and prophylactic or preventative measures, wherein the object is to prevent or slow down (lessen) an undesired physiological change or disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. Those in need of treatment include those already with the condition or disorder as well as those prone to have the condition or disorder or those in which the condition or disorder is to be prevented.

"Chronic" administration refers to administration of the agent(s) in a continuous mode as opposed to an acute mode, so as to maintain a desired effect or level of agent(s) for an extended period of time.

"Intermittent" administration is treatment that is not consecutively done without interruption, but rather is periodic in nature.

Administration "in combination with" one or more further therapeutic agents includes simultaneous (concurrent) and consecutive administration in any order.

An "effective amount" is an amount sufficient to effect beneficial or desired therapeutic (including preventative) results. An effective amount can be administered in one or more administrations.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™

II. Description of Certain Preferred Embodiments

1. Design of the Fusion Molecules

In one embodiment, the present invention provides fusion molecules that are capable of attenuating a biological response mediated by an FcεR, such as conditions associated with anaphylactic hypersensitivity and atopic allergies, by cross-linking an inhibitory receptor expressed on mast cells and/or basophils with an IgE receptor. The actual sequence of the fusion molecule will depend on the targeted inhibitory receptor, such as an ITIM-containing receptor, e.g. various forms of FcγRIIb, inhibitory members of the gp49 family, especially gp49b1, p91/PIR-B, LAIR-1, LIR-1, or CD22, and on the targeted IgE receptors, e.g. FcεRI or FcεRII.

In a preferred embodiment, the inhibitory receptor is a native low-affinity FcγRIIb receptor, and the IgE receptor is a native high-affinity or low-affinity IgE receptor, i.e. FcεRI or FcεRII, more preferably FcεRI. Accordingly, the first polypeptide sequence present in the fusion molecules binds to the native low-affinity FcγRIIb receptor, while the second polypeptide sequence, which is functionally connected to the first polypeptide sequence, binds to a native FcεRI or FcεRII, preferably FcεRI. When the goal is to cross-link a native FcγRIIb receptor with a native FcεRI receptor by direct binding of the first and second polypeptide sequences present in the single-chain fusion molecules of the invention to the respective receptors, the first and second polypeptide sequences, which are functionally connected, are preferably designed to bind to the respective receptors at essentially the same region(s) as native IgG and IgE, respectively. It has been reported that the CH2-CH3 interface of the IgG Fc domain contains the binding sites for a number of Fc receptors, including the FcγRIIb low-affinity receptor (Wines et al., *J. Immunol.* 164(10):5313-5318 (2000)). Based on FcϵRI binding studies, Presta et al., *J. Biol. Chem.* 269:26368-26373 (1994) proposed that six amino acid residues (Arg-408, Ser-411, Lys-415, Glu-452, Arg-465, and Met-469) located in three loops, C-D, E-F, and F-G, computed to form the outer ridge on the most exposed side of the human IgE heavy chain CH3 domain, are involved in binding to the high-affinity receptor FcϵRI, mostly by electrostatic interactions. Helm et al., *J. Cell Biol.* 271(13):7494-7500 (1996), reported that the high-affinity receptor binding site in the IgE molecule includes the Pro343-Ser353 peptide sequence within the CH3 domain of the IgE heavy chain, but sequences N- or C-terminal to this core peptide are also necessary to provide structural scaffolding for the maintenance of a receptor binding conformation. In particular, they found that residues, including His, in the C-terminal region of the ϵ-chain make an important contribution toward the maintenance of the high-affinity of interaction between IgE and FcϵRI. The first and second polypeptide sequences within the fusion molecules of the invention are preferably designed to bind to residues within such binding regions.

In another class of the fusion molecules of the invention, the first polypeptide sequence will bind to an ITIM-containing receptor, other than FcγRIIb, expressed on mast cells, basophils and/or B cells. For example, the first polypeptide sequence may contain a region capable of specific binding to an inhibitory member of the gp49 family, such as gp49b1, which is a member of the immunoglobulin superfamily, is preferentially expressed on mast cells and mononuclear macrophages, and contains two ITIM motifs in its cytoplasmic domain. Another ITIM-containing inhibitory receptor is p91, also referred to as PIR-B, which is known to be expressed on B cells and myeloid lineage cells. Further ITIM-containing receptors that might be targeted by the fusion molecules of the invention include, without limitation, LAIR-1, expressed on B cells, in addition to NK cells, T cells and monocytes; LIR-1, expressed on B cells and monocytes; and CD22 expressed on B cells. For review of ITIM-containing receptors and related art see, e.g. Mustelin et al., *Front. Biosci.* 3:d1060-1096 (1998), and Sinclair et al., 1999, supra.

When the second polypeptide sequence comprises part or whole of a native allergen protein, or a variant thereof, binding between the second polypeptide sequence and an IgE receptor occurs indirectly. The allergen-containing sequence will bind to an allergen-specific IgE molecule bound to a high-affinity IgE receptor (FcϵRI) on mast cells or basophils and/or to a low-affinity IgE receptor (FcϵRII, CD23) on B lymphocytes. The first, inhibitory receptor-binding, sequence is designed as discussed above. In a preferred embodiment, the allergen part of the molecule is a fragment that contains only a single IgE binding site, in order to avoid antigen cross-linking of IgE on the mast cell surface.

In a preferred embodiment, the first polypeptide sequence present in the fusion molecules of the invention has at least about 80%, more preferably at least about 85%, even more preferably at least about 90%, yet more preferably at least about 95%, most preferably at least about 99% sequence identity with the amino acid sequence of the hinge-CH2-CH3 region of a native IgG, e.g. $IgG_1$ immunoglobulin, preferably native human $IgG_1$. In a particularly preferred embodiment, the sequence identity is defined with reference to the human γhinge-CHγ2-CHγ3 sequence of SEQ ID NO: 3.

In another preferred embodiment, the first polypeptide sequence present in the fusion molecules of the invention has at least about 80%, more preferably at least about 85%, even more preferably at least about 90%, yet more preferably at least about 95%, most preferably at least about 99% sequence identity with the amino acid sequence of a native ligand of another ITIM-containing receptor expressed on mast cells, basophils and/or B cells, such as gp49b1 or p91/PIR-B (a cytoplasmic signaling protein activated by IFN-α, IFN-γ, and IL-6), or mast cell function Ag.

In yet another preferred embodiment, the first polypeptide sequence present in the fusion molecules of the invention has at least about 80%, more preferably at least about 85%, even more preferably at least about 90%, yet more preferably at least about 95%, most preferably at least about 99% sequence identity with the amino acid sequence of c-Kit (see, e.g. Yarden et al., *EMBO J.* 6:3341-51 (1987)).

The second polypeptide sequence present in the fusion molecules of the invention preferably has at least about 80%, more preferably at least about 85%, even more preferably at least about 90%, yet more preferably at least about 95%, most preferably at least about 99% sequence identity with the amino acid sequence of the CH2-CH3-CH4 region of a native IgE immunoglobulin, preferably native human IgE, or with the sequence of a native allergen protein. In a particularly preferred embodiment, the sequence identity is defined with reference to the human CHϵ2-CHϵ3-CHϵ4 sequence of SEQ ID NO: 6 or with regard to one of the allergen sequences listed in Table 1 below (SEQ ID NOS: 7 through 173), or, in a preferred embodiment, one of two Ara h2 clones represented by SEQ ID NOs: 174 and 175, respectively.

Alternatively, the first polypeptide sequence present in the fusion molecules of the invention may comprise a sequence encoded by nucleic acid hybridizing under stringent conditions to the complement of the coding sequence of a native γhinge-CHγ2-CHγ3 sequence, preferably the γhinge-CHγ2-

CHγ3 coding sequence from within SEQ ID NO: 1, or with the coding sequence of another immunoglobulin heavy chain constant region sequence required for IgG binding.

When the first polypeptide sequence binds specifically to an ITIM-containing receptor expressed on mast cells, basophils or B cells, it is preferably encoded by nucleic acid hybridizing under stringent conditions to the complement of the coding sequence of a native ligand of that receptor.

Similarly, the second polypeptide sequence present in the fusion molecules of the invention may comprise a sequence encoded by nucleic acid hybridizing under stringent conditions to the complement of the coding sequence of a native CHε2-CHε3-CHε4 sequence, preferably the CHϵ2-CHϵ3-CHϵ4 coding sequence from within SEQ ID NO: 4, or to the complement of the coding sequence of a native allergen, such as those listed in Table 1.

Whenever the first and/or second polypeptide sequence included in the fusion molecules of the invention is an amino acid variant of a native immunoglobulin constant region sequence, it is required to retain the ability to bind to the corresponding native receptor, such as a native IgG inhibitory receptor (e.g. FcγRIIb) and a native high-affinity IgE receptor (e.g. FcϵRI) or native low-affinity IgE receptor (FcϵRII, CD23), respectively. As discussed above, the receptor binding domains within the native IgG and IgE heavy chain constant region sequences have been identified. Based on this knowledge, the amino acid sequence variants may be designed to retain the native amino acid residues essential for receptor binding, or to perform only conservative amino acid alterations (e.g. substitutions) at such residues.

In making amino acid sequence variants that retain the required binding properties of the corresponding native sequences, the hydropathic index of amino acids may be considered. For example, it is known that certain amino acids may be substituted for other amino acids having a similar hydropathic index or score without significant change in biological activity. Thus, isoleucine, which has a hydrophatic index of +4.5, can generally be substituted for valine (+4.2) or leucine (+3.8), without significant impact on the biological activity of the polypeptide in which the substitution is made. Similarly, usually lysine (−3.9) can be substituted for arginine (−4.5), without the expectation of any significant change in the biological properties of the underlying polypeptide.

Other considerations for choosing amino acid substitutions include the similarity of the side-chain substituents, for example, size, electrophilic character, charge in various amino acids. In general, alanine, glycine and serine; arginine and lysine; glutamate and aspartate; serine and threonine; and valine, leucine and isoleucine are interchangeable, without the expectation of any significant change in biological properties. Such substitutions are generally referred to as conservative amino acid substitutions, and, as noted above, are the preferred type of substitutions within the polypeptides of the present invention.

Alternatively or in addition, the amino acid alterations may serve to enhance the receptor binding properties of the fusion molecules of the invention. Variants with improved receptor binding and, as a result, superior biological properties can be readily designed using standard mutagenesis techniques, such as alanine-scanning mutagenesis, PCR mutagenesis or other mutagenesis techniques, coupled with receptor binding assays, such as the assay discussed below or described in the Example.

In a preferred embodiment, the fusion molecules of the present invention comprise a first polypeptide sequence including functionally active hinge, CH2 and CH3 domains of the constant region of an $IgG_1$ heavy chain (γhinge-CHγ2-CHγ3 sequence) linked at its C-terminus to the N-terminus of a second polypeptide including functionally active CH2, CH3 and CH4 domains of the constant region of an IgE heavy chain (CHϵ2-CHϵ3-CHϵ4 sequence). In a particularly preferred embodiment, the first polypeptide sequence is composed of functionally active hinge, CH2 and CH3 regions of a native human $IgG_1$ heavy chain, linked at its C-terminus to the N-terminus of a second polypeptide composed of functionally active CH2, CH3 and CH4 domains of a native human IgE heavy chain constant region.

While it is preferred to fuse the IgG heavy chain constant region sequence (or a homologous sequence) C-terminally to the N-terminus of the IgE heavy chain constant region sequence (or a homologous sequence), fusion molecules in which the IgE heavy chain constant region sequence (or a homologous sequence) is fused C-terminally to the N-terminus of the IgG heavy chain constant region sequence (or a homologous sequence) are also within the scope of the invention. The fusion molecules may also comprise repeats of identical or different IgG and/or IgE heavy chain constant region sequences. For example, two repeats of IgG heavy chain constant region sequences; each including an IgG inhibitory receptor-binding domain, can be followed by IgE heavy chain constant region sequences (GGE structure), or two repeats of identical or different IgG heavy chain constant region sequences may flank an IgE heavy chain constant region sequence (GEG structure), etc. Fusion molecules comprising more than one binding sequence for a target receptor (e.g. an FcγRIIb receptor) are expected to have superior biological, e.g. anti-allergic properties.

The same considerations apply to the structure of fusion molecules where the second polypeptide sequence comprises, is or is derived from an allergen protein. Such molecules may also include repeats of the IgG heavy chain constant region sequences, fused to either or both sides of the allergen sequence.

Similarly, molecules in which the first polypeptide sequence binds to a different inhibitory receptor expressed on mast cells and/or basophils, e.g. an ITIM-containing inhibitory receptor functionally connected to a second polypeptide sequence binding directly or indirectly to an IgE receptor, e.g. FcϵRI, may contain multiple repeats of the inhibitory receptor binding regions and/or the IgE binding regions.

In all embodiments, the two polypeptide sequences are functionally connected, which means that they retain the ability to bind to the respective native receptors, such as a native IgG inhibitory receptor, e.g. a low-affinity FcγRIIb receptor, and to a native high-affinity IgE receptor, e.g. FcϵRI or low-affinity IgE receptor, as desired. As a result, the fusion molecules, comprising the first and second polypeptide sequences functionally connected to each other, are capable of cross-linking the respective native receptors, such as FcγRIIb and FcϵRI or FcγRIIb and FcϵRII. In order to achieve a functional connection between the two binding sequences within the fusion molecules of the invention, it is preferred that they retain the ability to bind to the corresponding receptor with a binding affinity similar to that of a native immunoglobulin ligand of that receptor.

The fusion molecules of the present invention are typically produced and act as homodimers or heterodimers, comprising two of the fusion molecules hereinabove described covalently linked to each other. The covalent attachment is preferably achieved via one or more disulfide bonds. For example, the prototype protein designated GE2 is produced as a homodimer composed of the two γhinge-CHγ2-CHγ3-15aa linker-CHϵ2-CHϵ3-CHϵ4 chains connected to each other by interchain disulfide bonds, to provide an immunoglobulin-like structure. It is also possible to produce heterodimers, in which two different fusion molecules are linked to each other by one or more covalent linkages, e.g. disulfide bond(s). Such bifunctional structures might be advantageous in that they are able to cross-link the same or different IgɛR(s) with different inhibitory receptors.

Receptor binding can be tested using any known assay method, such as competitive binding assays, direct and indirect sandwich assays. Thus, binding of a first polypeptide sequence included in the fusion molecules herein to a low-affinity IgG inhibitory receptor, or the binding of a second polypeptide sequence included herein to a high-affinity or low-affinity IgE receptor can be tested using conventional binding assays, such as competitive binding assays, including RIAs and ELISAs. Ligand/receptor complexes can be identified using traditional separation methods as filtration, centrifugation, flow cytometry, and the results from the binding assays can be analyzed using any conventional graphical representation of the binding data, such as Scatchard analysis. The assays may be performed, for example, using a purified receptor, or intact cells expressing the receptor. One or both of the binding partners may be immobilized and/or labeled. A particular cell-based binding assay is described in the Example below.

The two polypeptide sequences present in the fusion molecules of the invention may be associated with one another by any means that allows them to cross-link the relevant receptors. Thus, association may take place by a direct or indirect covalent linkage, where "indirect" covalent linkage means that the two polypeptide sequences are part of separate molecules that interact with one another, either directly or indirectly. For example, each polypeptide sequence can be directly linked to one member of an interacting pair of molecules, such as, for example, a biotin/avidin pair. Alternatively, the two polypeptide sequences can be linked using a "dimerizer" system based on linkage to an entity that associates with a common ligand, such as dimerizer systems based on cyclosporin, FK506, rapamycin, countermycin, and the like.

In a preferred embodiment, the first and second polypeptide sequences, such as, for example, two immunoglobulin constant region segments, or an immunoglobulin constant region sequence and an allergen sequence, are connected by a polypeptide linker. The polypeptide linker functions as a "spacer" whose function is to separate the functional receptor binding domains, or the Fcγ receptor binding domain and the IgE-binding sequence in the allergen, so that they can independently assume their proper tertiary conformation. The polypeptide linker usually comprises between about 5 and about 25 residues, and preferably contains at least about 10, more preferably at least about 15 amino acids, and is composed of amino acid residues which together provide a hydrophilic, relatively unstructured region. Linking amino acid sequences with little or no secondary structure work well. The specific amino acids in the spacer can vary, however, cysteines should be avoided. Suitable polypeptide linkers are, for example, disclosed in WO 88/09344 (published on Dec. 1, 1988), as are methods for the production of multifunctional proteins comprising such linkers.

In a less preferred embodiment, the IgG and IgE constant region sequences, the IgG constant region sequences and the allergen sequences, or sequences showing high degree of sequence identity with such sequences, may be directly fused to each other, or connected by non-polypeptide linkers. Such linkers may, for example, be residues of covalent bifunctional cross-linking agents capable of linking the two sequences without the impairment of the receptor (antibody) binding function. The bifunctional cross-linking reagents can be divided according to the specificity of their functional groups, e.g. amino, sulthydryl, guanidino, indole, carboxyl specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group (for review, see Ji, T. H. "Bifunctional Reagents" in: Meth. Enzymol. 91:580-609 (1983)).

In a further specific embodiment, the two polypeptide sequences (including variants of the native sequences) are dimerized by amphiphilic helices. It is known that recurring copies of the amino acid leucine (Leu) in gene regulatory proteins can serve as teeth that "zip" two protein molecules together to provide a dimer. For further details about leucine zippers, which can serve as linkers for the purpose of the present invention, see for example: Landschulz, W. H., et al. *Science* 240:1759-1764 (1988); O'Shea, E. K. et al., *Science* 243: 38-542 (1989); McKnight, S. L., *Scientific American* 54-64, April 1991; Schmidt-Dorr. T. et al., *Biochemistry* 30:9657-9664 (1991); Blondel, A. and Bedouelle, H. *Protein Engineering* 4:457-461 (1991), and the references cited in these papers.

In a different approach, the two polypeptide sequences (including variants of the native sequences) are linked via carbohydrate-directed bifunctional cross-linking agents, such as those disclosed in U.S. Pat. No. 5,329,028.

The cross-linking of an inhibitory receptor expressed on mast cells and/or basophils, such as an ITIM-containing receptor, including IgG inhibitory receptors, e.g. FcγRIIb and a high-affinity IgE receptor, e.g. FcεRI or low-affinity IgE receptor, e.g. FcεRII, inhibit FcεR mediated biological responses. Such biological responses preferably are the mediation of an allergic reactions or autoimmune reactions via FcεR, including, without limitation, conditions associated with IgE mediated reactions, such as, for example, asthma, allergic rhinitis, food allergies, chronic urticaria and angioedema, allergic reactions to hymenophthera (e.g. bee and yellow jacket) stings or medications such as penicillinup to and including the severe physiological reaction of anaphylactic shock.

2. Preparation of the Fusion Molecules

When the fusion molecules are polypeptides, in which the first and second polypeptide sequences are directly fused or functionally connected by a polypeptide linker, they can be prepared by well known methods of recombinant DNA technology or traditional chemical synthesis. If the polypeptides are produced by recombinant host cells, cDNA encoding the desired polypeptide of the present invention is inserted into a replicable vector for cloning and expression. As discussed before, the nucleotide and amino acid sequences of native immunoglobulin constant regions, including native IgG and IgE constant region sequences, are well known in the art and are readily available, for example, from Kabat et al., *Sequences of Proteins of Immunological Interest,* 5th Ed. Public Health Service, National Institute of Health, Bethesda, Md. (1991).

Similarly, the sequences of a large number of allergens are well known in the art. According to a nomenclature system established for allergens by the WHO/IUIS Allergen Nomenclature Subcommittee, the designation of any particular allergen is composed of the first three letters of the genus; a space; the first letter of the species name; a space and an arabic number. In the event that two species names have identical designations, they are discriminated from one another by adding one or more letters to each species designation. Using this designation, the allergen Aln G 1 is a major pollen allergen from the genus *Alnus* and the species *glutinosa*, the sequence of which is available from the SWISS-PROT database under the entry name MPAC_ALNGL (Primary Accession number: P38948) (Breitender et al., *J. Allergy Clin. Immunol.* 90:909-917 (1992)). A list of known antigens, including their origin, entry name and Primary Accession Number in the SWISS-PROT database is provided in Table 1. The molecular weight of most food allergens is between 10,000 and 70,000 Da. Some allergens, such as Ara h 1 (63.5 kDa) and Ara h 2 (17 kDa), occur as polymers that are larger, e.g. 200 to 300 kDa.

As noted earlier, it might be advantageous to use in the fusion molecules of the present invention a fragment of a native or variant allergen that contains only a single IgE-binding site. For many of the allergen proteins listed in Table 1, the IgE-binding sites have been determined. For example, the IgE-binding epitopes of Par j 2, a major allergen of *Parietaria judaica* pollen, have been determined by Costa et al., *Allergy* 55:246-50 (2000). The IgE-binding epitopes of major peanut antigens Ara h 1 (Burks et al., *Eur. J. Biochem.* 254: 334-9 (1997)); Ara h 2 (Stanley et al., *Arch Biochem. Biophys.* 342:244-53 (1997)); and Ara h 3 (Rabjohn et al., *J. Clin. Invest.* 103:535-42 (1999)) are also known, just to mention a few.

TABLE 1

| Allergen | SWISS-PROT Entry | SWISS-PROT Accession No. | Protein Name | Source | SEQ ID NO. |
|---|---|---|---|---|---|
| Aln g 1 | MPAG_ALNGL | P38948 | Major Pollen Allergen Aln g 1 | Pollen of *Alnus glutinosa* (Alder) | 8 |
| Alt a 6 | RLA2_ALTAL | P42037 | 60S Acidic Ribosomal Protein P2 | *Alternaria alternata* | 9 |
| Alt a 7 | ALA7_ALTAL | P42058 | Minor Allergen Alt a 7 | *Alternaria alternata* | 10 |
| Alt a 10 | DHAL_ALTAL | P42041 | Aldehyde Dehydrogenase | *Alternaria alternata* | 11 |
| Alt a 12 | RLA1_ALTAL | P49148 | 60S Acidid Ribosomol Protein P1 | *Alternaria alternata* | 12 |
| Amb a 1 | MP11_AMBAR | P27759 | Pollen Allergen Amb a 1.1 [Precursor] | *Ambrosia artemisiifolia* (Short ragweed) | 13 |
| Amb a 1 | MP12_AMBAR | P27760 | Pollen Allergen Amb a 1.2 [Precursor] | *Ambrosia artemisiifolia* (Short ragweed) | 14 |
| Amb a 1 | MP13_AMBAR | P27761 | Pollen Allergen Amb a 1.3 [Precursor] | *Ambrosia artemisiifolia* (Short ragweed) | 15 |
| Amb a 1 | MP14_AMBAR | P28744 | Pollen Allergen Amb a 1.4 [Precursor] | *Ambrosia artemisiifolia* (Short ragweed) | 16 |
| Amb a 2 | MPA2_AMBAR | P27762 | Pollen Allergen Amb a 2 [Precursor] | *Ambrosia artemisiifolia* (Short ragweed) | 17 |
| Amb a 3 | MPA3_AMBEL | P00304 | Pollen Allergen Amb a 3 | *Ambrosia artemisiifolia* var. *elatior* (Short ragweed) | 18 |
| Amb a 5 | MPA5_AMBEL | P02878 | Pollen Allergen Amb a 5 | *Ambrosia artemisiifolia* var. *elatior* (Short ragweed) | 19 |
| Amb p 5 | MPA5_AMBPS | P43174 | Pollen Allergen Amb p 5-a [Precursor] | Ambrosia *psilostachya* (Western ragweed) | 20 |
| Amb p 5 | MP5B_AMBPS | P43175 | Pollen Allergen Amb p 5b [Precursor] | *Ambrosia psilostachya* (Western ragweed) | 21 |
| Amb t 5 | MPT5_AMBTR | P10414 | Pollen Allergen Amb t 5 [Precursor] | *Ambrosia trifida* (Giant ragweed) | 22 |
| Api g 1 | MPAG_APIGR | P49372 | Major Allergen Api g | *Apium grayeolens* (Celery) | 23 |
| Api m 1 | PA2_APIME | P00630 | Phospholipase A2 [Precursor] [Fragment] | *Apis mellifera* (Honeybee) | 24 |
| Api m 2 | HUGA_APIME | Q08169 | Hyaluronoglucosamin-idase [Precursor] | *Apis mellifera* (Honeybee) | 25 |
| Api m 3 | MEL_APIME | P01501 | Melittin [Precursor] | *Apis mellifera* (Honeybee) *Apis cerana* (Indian honeybee) | 26 |
| Ara h 1 | AH11_ARAHY | P43237 | Allergen Ara h 1, Clone P17 | *Arachis hypogaea* (Peanut) | 27 |
| Ara h 1 | AH12_ARAHY | P43238 | Allergen Ara h 1, Clone P41b | *Arachis hypogaea* (Peanut) | 28 |
| Ara t 8 | PRO1_ARATH | Q42449 | Profilin 1 | *Arabidopsis thaliana* (Mouse-ear cress) | 29 |

TABLE 1-continued

| Allergen | SWISS-PROT Entry | SWISS-PROT Accession No. | Protein Name | Source | SEQ ID NO. |
|---|---|---|---|---|---|
| Asp f 1 | RNMG_ASPRE | P04389 | Ribonuclease Mitogillin [Precursor] | *Aspergillus restrictus*; *Aspergillus fumigatus* (*Sartorya fumigata*) | 30 |
| Asp f 2 | MAF2_ASPFU | P79017 | Major Allergen Asp f 2 [Precursor] | *Aspergillus fumigatus* (*Sartorya fumigata*) | 31 |
| Asp f 3 | PM2O_ASPFU | O43099 | Probable Peroxisomal Membrane Protein PMP20 | *Aspergillus fumigatus* (*Sartorya fumigata*) | 32 |
| Asp f 13 | AF13_ASPFU | O60022 | Allergen Asp f 13 [Precursor] | *Aspergillus fumigatus* (*Sartorya fumigata*) | 33 |
| Bet v 1 | BV1A_BETVE | P15494 | Major Pollen Allergen Bet v 1-a | *Betula verrucosa* (White birch) (*Betula pendula*) | 34 |
| Bet v 1 | BV1C_BETVE | P43176 | Major Pollen Allergen Bet v 1-c | *Betula verrucosa* (White birch) (*Betula pendula*) | 35 |
| Bet v 1 | BV1D_BETVE | P43177 | Major Pollen Allergen Bet v 1-d/h | *Betula verrucosa* (White birch) (*Betula pendula*) | 36 |
| Bet v 1 | BV1E_BETVE | P43178 | Major Pollen Allergen Bet v 1-e | *Betula verrucosa* (White birch) (*Betula pendula*) | 37 |
| Bet v 1 | BV1F_BETVE | P43179 | Major Pollen Allergen Bet v 1-f/i | *Betula verrucosa* (White birch) (*Betula pendula*) | 38 |
| Bet v 1 | BV1G_BETVE | P43180 | Major Pollen Allergen Bet v 1-g | *Betula verrucosa* (White birch) (*Betula pendula*) | 39 |
| Bet v 1 | BV1J_BETVE | P43183 | Major Pollen Allergen Bet v 1-j | *Betula verrucosa* (White birch) (*Betula pendula*) | 40 |
| Bet v 1 | BV1K_ETVE | P43184 | Major Pollen Allergen Bet v 1-k | *Betula verrucosa* (White birch) (*Betula pendula*) | 41 |
| Bet v 1 | BV1L_BETVE | P43185 | Major Pollen Allergen Bet v 1-l | *Betula verrucosa* (White birch) (*Betula pendula*) | 42 |
| Bet v 1 | BV1M_BETVE | P43186 | Major Pollen Allergen Bet v 1-m/n | *Betula verrucosa* (White birch) (*Betula pendula*) | 43 |
| Bet v 2 | PROF-BETVE | P25816 | Profilin | (*Betula verrucosa* (White birch) (*Betula pendula*) | 44 |
| Bet v 3 | BTV3_BETVE | P43187 | Allergen Bet v 3 | *Betula verrucosa* (White birch) (*Betula pendula*) | 45 |
| Bla g 2 | ASP2_BLAGE | P54958 | Aspartic Protease Bla g 2 [Precursor] | *Blattella germanica* (German cockroach) | 46 |
| Bla g 4 | BLG4_BLAGE | P54962 | Allergen Bla g 4 [Precursor] [Fragment] | *Blattella germanica* (German cockroach) | 47 |
| Bla g 5 | GTS1_BLAGE | O18598 | Glutathione-S-transferase | *Blattella germanica* (German cockroach) | 48 |
| Blo t 12 | BT12_BLOTA | Q17282 | Allergen Blo t 12 [Precursor] | *Blomia tropicalis* (Mite) | 49 |
| Bos d 2 | ALL2_BOVIN | Q28133 | Allergen Bos d 2 [Precursor] | *Bos taurus* (Bovine) | 50 |
| Bos d 5 | LACB_BOVIN | P02754 | Beta-lactoglobulin [Precursor] | *Bos taurus* (Bovine) | 51 |
| Bra j 1 | ALL1_BRAJU | P80207 | Allergen Bra j 1-e, Small and Large Chains | *Brassica juncea* (Leaf mustard) (Indian mustard) | 52 |
| Can a 1 | ADH1_CANAL | P43067 | Alcohol Dehydrogenase 1 | *Candida albicans* (Yeast) | 53 |
| Can f 1 | ALL1_CANFA | O18873 | Major Allergen Can f 1 [Precursor] | *Canis familiaris* (Dog) | 54 |
| Can f 2 | ALL2_CANFA | O18874 | Minor Allergen Can f 2 [Precursor] | *Canis familiaris* (Dog) | 55 |
| Car b 1 | MPA1_CARBE | P38949 | Major Pollen Allergen Car b 1, Isoforms 1A and 1B | *Carpinus betulus* (Hornbeam) | 56 |

TABLE 1-continued

| Allergen | SWISS-PROT Entry | SWISS-PROT Accession No. | Protein Name | Source | SEQ ID NO. |
|---|---|---|---|---|---|
| Car b 1 | MPA2_CARBE | P38950 | Major Pollen Allergen Car b 1, Isoform 2 | *Carpinus betulus* (Hornbeam) | 57 |
| Cha o 1 | MPA1_CHAOB | Q96385 | Major Pollen Allergen Cha o 1 [Precursor] | *Chamaecyparis obtusa* (Japanese cypress) | 58 |
| Cla h 3 | DHAL_CLAHE | P40108 | Aldehyde Dehydrogenase | *Cladosporium herbarum* | 59 |
| Cla h 3 | RLA3_CLAHE | P42038 | 60S Acidic Ribosomal Protein P2 | *Cladosporium herbarum* | 60 |
| Cla h 4 | HS70_CLAHE | P40918 | Heat Shock 70 KDa Protein | *Cladosporium herbarum* | 61 |
| Cla h 4 | RLA4_CLAHE | P42039 | 60S Acidic Ribosomal Protein P2 | *Cladosporium herbarum* | 62 |
| Cla h 5 | CLH5_CLAHE | P42059 | Minor Allergen Cla h 5 | *Cladosporium herbarum* | 63 |
| Cla h 6 | ENO_CLAHE | P42040 | Enolase | *Cladosporium herbarum* | 64 |
| Cla h 12 | RLA1_CLAHE | P50344 | 60S Acidic Ribosomal Protein P1 | *Cladosporium herbarum* | 65 |
| Cop c 2 | THIO_CAPCM | | | | |
| Cor a 1 | MPAA_CORAV | Q08407 | Major Pollen Allergen Cor a 1, Isoforms 5, 6, 11 and 16 | *Corylus avellana* (European hazel) | 66 |
| Cup a 1 | MPA1_CUPAR | Q9SCG9 | Major Pollen Allergen Cup a 1 | *Cupressus arizonica* | 67 |
| Cry j 1 | SBP_CRYJA | P18632 | Sugi Basic Protein [Precursor] | *Cryptometia japonica* (Japanese cedar) | 68 |
| Cry j 2 | MPA2_CRYJA | P43212 | Possible Polygalacturonase | *Cryptomeria japonica* (Japanese cedar) | 69 |
| Cyn d 12 | PROF_CYNDA | O04725 | Profilin | *Cynodon dactylon* (Bermuda grass) | 70 |
| Dac g 2 | MPG2_DACGL | Q41183 | Pollen Allergen Dac g 2 [Fragment] | *Dactylis glomerata* (Orchard grass) (Cocksfoot grass) | 71 |
| Dau c 1 | DAU1_DAUCA | O04298 | Major Allergen Dau c 1 | *Daucus carota* (Carrot) | 72 |
| Der f 1 | MMAL_DERFA | P16311 | Major Mite Fecal Allergen Der f 1 [Precursor] | *Dermatophagoides farinae* (House-dust mite) | 73 |
| Der f 2 | DEF2_DERFA | Q00855 | Mite Allergen Der f 2 [Precursor] | *Dermatophagoides ferinae* (House-dust mite) | 74 |
| Der f 3 | DEF3_DERFA | P49275 | Mite Allergen Der f 3 [Precursor] | *Dermatophagoides ferinae* (House-dust mite) | 75 |
| Der f 6 | DEF6_DERFA | P49276 | Mite Allergen Der f 6 [Fragment] | *Dermatophagoides ferinae* (House-dust mite) | 76 |
| Der f 7 | DEF7_DERFA | Q26456 | Mite Allergen Der f 7 [Precursor] | *Dermatophagoides ferinae* (House-dust mite) | 77 |
| Der m 1 | MMAL_DERMI | P16312 | Major Mite Fecal Allergen Der m 1 [Fragment] | *Dermatophagoides microceras* (House-dust mite) | 78 |
| Der p 1 | MMAL_DERPT | P08176 | Major Mite Fecal Allergen Der p 1 [Precursor] | *Dermatophagoides pteronyssinus* (House-dust mite) | 79 |
| Der p 2 | DER2_DERPT | P49278 | Mite Allergen Der p 2 [Precursor] | *Dermatophagoides pteronyssinus* (House-dust mite) | 80 |
| Der p 3 | DER3_DERPT | P39675 | Mite Allergen Der p 3 [Precursor] | *Dermatophagoides pteronyssinus* (House-dust mite) | 81 |
| Der p 4 | AMY_DERPT | P49274 | Alpha-Amylase [Fragment] | *Dermatophagoides pteronyssinus* (House-dust mite) | 82 |
| Der p 5 | DER5_DERPT | P14004 | Mite Allergen Der p 5 | *Dermatophagoides pteronyssinus* (House-dust mite) | 83 |
| Der p 6 | DER6_DERPT | P49277 | Mite Allergen Der p 6 [Fragment] | *Dermatophagoides pteronyssinus* (House-dust mite) | 84 |

TABLE 1-continued

| Allergen | SWISS-PROT Entry | SWISS-PROT Accession No. | Protein Name | Source | SEQ ID NO. |
|---|---|---|---|---|---|
| Der p 7 | DER7_DERPT | P49273 | Mite Allergen Der p 7 [Precursor] | *Dermatophagoides pteronyssinus* (House-dust mite) | 85 |
| Dol a 5 | VA5_DOLAR | Q05108 | Venom Allergen 5 | *Dolichovespula arenaria* (Yellow hornet) | 86 |
| Dol m 1 | PA11_DOLMA | Q06478 | Phospholipase A1 1 [Precursor] [Fragment] | *Dolichovespula maculata* (White-face hornet) (Bald-faced hornet) | 87 |
| Dol m 1 | PA12_DOLMA | P53357 | Phospholipase A1 2 | *Dolichovespula maculata* (White-face hornet) (Bald-faced hornet) | 88 |
| Dol m 2 | HUGA_DOLMA | P49371 | Hyaluronoglucosaminidase | *Dolichovespula maculata* (White-face hornet) (Bald-faced hornet) | 89 |
| Dol m 5 | VA52_DOLMA | P10736 | Venom Allergen 5.01 [Precursor] | *Dolichovespula maculata* (White-face hornet) (Bald-faced hornet) | 90 |
| Dol m 5 | VA53_DOLMA | P10737 | Venom Allergen 5.02 [Precursor] [Fragment] | *Dolichovespula maculata* (White-face hornet) (Bald-faced hornet) | 91 |
| Equ c 1 | ALL1_HORSE | Q95182 | Major Allergen Equ c 1 [Precursor] | *Equus caballus* (Horse) | 92 |
| Equ c 2 | AL21_HORSE | P81216 | Dander major Allergen Equ c 2.0101 [Fragment] | *Equus caballus* (Horse) | 93 |
| Equ c 2 | AL22_HORSE | P81217 | Dander Major Allergen Equ c 2.0102 [Fragment] | *Equus caballus* (Horse) | 94 |
| Eur m 1 | EUM1_EURMA | P25780 | Mite Group I Allergen Eur m 1 [Fragment] | *Euroglyphus maynei* (House-dust mite) | 95 |
| Fel d 1 | FELA_FELCA | P30438 | Major Allergen I Polypeptide Chain 1 Major Form [Precursor] | *Felis silvestris catus* (Cat) | 96 |
| Fel d 1 | FELB_FELCA | P30439 | Major Allergen I Polypeptide Chain 1 Minor Form [Precursor] | *Felis silvestris catus* (Cat) | 97 |
| Fel d 1 | FEL2_FELCA | P30440 | Major Allergen I Polypeptide Chain 2 [Precursor] | *Felis silvestris catus* (Cat) | 98 |
| Gad c 1 | PRVB_GADCA | P02622 | Parvalbumin Beta | *Gadus callarias* (Baltic cod) | 99 |
| Gal d 1 | IOVO_CHICK | P01005 | Ovomucoid [Precursor] | *Gallus gallus* (Chicken) | 100 |
| Gal d 2 | OVAL_CHICK | P01012 | Ovalbumin | *Gallus gallus* (Chicken) | 101 |
| Gal d 3 | TRFE_CHICK | P02789 | Ovotransferrin [Precursor] | *Gallus gallus* (Chicken) | 102 |
| Gal d 4 | LYC_CHICK | P00698 | Lysozyme C [Precursor] | *Gallus gallus* (Chicken) | 103 |
| Hel a 2 | PROF_HELAN | O81982 | Profilin | *Helianthus animus* (Common sunflower) | 104 |
| Hev b 1 | REF_HEVBR | P15252 | Rubber Elongation Factor Protein | *Hevea brasiliensis* (Para rubber tree) | 105 |
| Hev b 5 | HEV5_HEVBR | Q39967 | Major Latex Allergen Hev b 5 | *Hevea brasiliensis* (Para rubber tree) | 106 |
| Hol l 1 | MPH1_HOLLA | P43216 | Major Pollen Allergen Hol l 1 [Precursor] | *Holcul lanatus* (Velvet grass) | 107 |
| Hor v 1 | IAA1_HORVU | P16968 | Alpha-amylase Inhibitor Bmai-1 [Precursor] [Fragment] | *Hordeum vulgare* (Barley) | 108 |
| Jun a 1 | MPA1_JUNAS | P81294 | Major Pollen Allergen Jun a 1 [Precursor] | *Juniperus ashei* (Ozark white cedar) | 109 |

TABLE 1-continued

| Allergen | SWISS-PROT Entry | SWISS-PROT Accession No. | Protein Name | Source | SEQ ID NO. |
|---|---|---|---|---|---|
| Jun a 3 | PRR3_JUNAS | P81295 | Pathogenesis-Related Protein [Precursor] | *Juniperus ashei* (Ozark white cedar) | 110 |
| Lep d 1 | LEP1_LEPDS | P80384 | Mite Allergen Lep d 1 [Precursor] | *Lepidoglyphus destructor* (Storage mite) | 111 |
| Lol p 1 | MPLI_LOLPR | P14946 | Pollen Allergen Lol p 1 [Precursor] | *Lolium perenne* (Perennial ryegrass) | 112 |
| Lol p 2 | MPL2_LOLPR | P14947 | Pollen Allergen Lol p 2-a | *Lolium perenne* (Perennial ryegrass) | 113 |
| Lol p 3 | MPL3_LOLPR | P14948 | Pollen Allergen Lol p 3 | *Lolium perenne* (Perennial ryegrass) | 114 |
| Lol p 5 | MP5A_LOLPR | Q40240 | Major Pollen Allergen Lol p 5a [Precursor] | *Lolium perenne* (Perennial ryegrass) | 115 |
| Lol p 5 | MP5B_LOLPR | Q40237 | Major Pollen Allergen Lol p 5b [Precursor] | *Lolium perenne* (Perennial ryegrass) | 116 |
| Mal d 1 | MAL1_MALDO | P43211 | Major Allergen Mal d 1 | *Malus domestica* (Apple) (*Malus sylvestris*) | 117 |
| Mer a 1 | PROF_MERAN | O49894 | Profilin | *Mercurialis annua* (Annual mercury) | 118 |
| Met e 1 | TPM1_METEN | Q25456 | Tropomyosin | *Metapenaeus ensis* (Greasyback shrimp) (Sand shrimp) | 119 |
| Mus m 1 | MUP6_MOUSE | P02762 | Major Urinary Protein 6 [Precursor] | *Mus musculus* (Mouse) | 120 |
| Myr p 1 | MYR1_MYRPI | Q07932 | Major Allergen Myr p 1 [Precursor] | *Myrmecia pilosula* (Bulldog ant) (Australian jumper ant) | 121 |
| Myr p 2 | MYR2_MYRPI | Q26464 | Allergen Myr p 2 [Precursor] | *Myrmecia pilosula* (Bulldog ant) (Australian jumper ant) | 122 |
| Ole e 1 | ALL1_OLEEU | P19963 | Major Pollen Allergen | *Olea europaea* (Common olive) | 123 |
| Ole e 4 | ALL4_OLEEU | P80741 | Major Pollen Allergen Ole e 4 [Fragments] | *Olea europaea* (Common olive) | 124 |
| Ole e 5 | SODC_OLEEU | P80740 | Superoxide Dismutase [CU-ZN] [Fragment] | *Olea europaea* (Common olive) | 125 |
| Ole e 7 | ALL7_OLEEU | P81430 | Pollen Allergen Ole e 7 [Fragment] | *Olea europaea* (Common olive) | 126 |
| Ory s 1 | MPO1_ORYSA | Q40638 | Major Pollen Allergen Ory s 1 [Precursor] | *Oryza sativa* (Rice) | 127 |
| Par j 1 | NL11_PARJU | P43217 | Probable Nonspecific Lipid-Transfer Protein [Fragment] | *Parietaria judaica* | 128 |
| Par j 1 | NL12_PARJU | O04404 | Probable Nonspecific Lipid-Transfer Protein 1 [Precursor] | *Parietaria judaica* | 129 |
| Par j 1 | NL13_PARJU | Q40905 | Probable Nonspecific Lipid-Transfer Protein 1 [Precursor] | *Parietaria judaica* | 130 |
| Par j 2 | NL21_PARJU | P55958 | Probable Nonspecific Lipid-Transfer Protein 2 [Precursor] | *Parietaria judaica* | 131 |
| Par j 2 | NL22_PARJU | O04403 | Probable Nonspecific Lipid-Transfer Protein 2 [Precursor] | *Parietaria judaica* | 132 |
| Pha a 1 | MPA1_PHAAQ | Q41260 | Major Pollen Allergen Pha a 1 [Precursor] | *Phalaris aquatica* (Canary grass) | 133 |
| Pha a 5 | MP51_PHAAQ | P56164 | Major Pollen Allergen Pha a 5.1 [Precursor] | *Phalaris aquatica* (Canary grass) | 134 |
| Pha a 5 | MP52_PHAAQ | P56165 | Major Pollen Allergen Pha a 5.2 [Precursor] | *Phalaris aquatica* (Canary grass) | 135 |
| Pha a 5 | MP53_PHAAQ | P56166 | Major Pollen Allergen Pha a 5.3 [Precursor] | *Phalaris aquatica* (Canary grass) | 136 |
| Pha a 5 | MP54_PHAAQ | P56167 | Major Pollen Allergen Pha a 5.4 [Fragment] | *Phalaris aquatica* (Canary grass) | 137 |

TABLE 1-continued

| Allergen | SWISS-PROT Entry | SWISS-PROT Accession No. | Protein Name | Source | SEQ ID NO. |
|---|---|---|---|---|---|
| Phl p 1 | MPP1_PHLPR | P43213 | Pollen Allergen Phl p 1 [Precursor] | *Phleum pratense* (Common timothy) | 138 |
| Phl p 2 | MPP2_PHLPR | P43214 | Pollen Allergen Phl p 2 Precursor] | *Phleum pratense* (Common timothy) | 139 |
| Phl p 5 | MP5A_PHLPR | Q40962 | Pollen Allergen Phl p 5a [Fragment] | *Phleum pratense* (Common timothy) | 140 |
| Phl p 5 | MP5B_PHLPR | Q40963 | Pollen Allergen Phl p 5b [Precursor] [Fragment] | *Phleum pratense* (Common timothy) | 141 |
| Phl p 6 | MPP6_PHLPR | P43215 | Pollen Allergen Phl p 6 [Precursor] | *Phleum pratense* (Common timothy) | 1412 |
| Phl p 11 | PRO1_PHLPR | P35079 | Profilin 1 | *Phleum pratense* (Common timothy) | 143 |
| Phl p 11 | PRO2_PHLPR | O24650 | Profilin 2/4 | *Phleum pratense* (Common timothy) | 144 |
| Phl p 11 | PRO3_PHLPR | O24282 | Profilin 3 | *Phleum pratense* (Common timothy) | 145 |
| Poa p 9 | MP91_POAPR | P22284 | Pollen Allergen Kbg 31 [Precursor] | *Poa pratensis* (Kentucky bluegrass) | 146 |
| Poa p 9 | MP92_POAPR | P22285 | Pollen Allergen Kbg 41 [Precursor] | *Poa pratensis* (Kentucky bluegrass) | 147 |
| Poa p 9 | MP93_POAPR | P22286 | Pollen Allergen Kbg 60 [Precursor] | *Poa pratensis* (Kentucky bluegrass) | 148 |
| Pol a 5 | VA5_POLAN | Q05109 | Venom Allergen 5 [Precursor] [Fragment] | *Polistes annularis* (Paper wasp) | 149 |
| Pol d 5 | VA5_POLDO | P81656 | Venom Allergen 5 | *Polistes dominulus* (European paper wasp) | 150 |
| Pol e 5 | VA5_POLEX | P35759 | Venom Allergen 5 | *Polistes exclamans* (Paper wasp) | 151 |
| Pol f 5 | VA5_POLFU | P35780 | Venom Allergen 5 | *Polistes fuscatus* (Paper wasp) | 152 |
| Pru a 1 | PRU1_PRUAV | O24248 | Major Allergen Pm a 1 | *Prunus avium* (Cherry) | 153 |
| Rat n 1 | MUP_RAT | P02761 | Major Urinary Protein [Precursor] | *Rattus norvegicus* (Rat) | 154 |
| Sol i 2 | VA2_SOLIN | P35775 | Venom Allergen II [Precursor] | *Solenopsis invicta* (Red imported fire ant) | 155 |
| Sol i 3 | VA3_SOLIN | P35778 | Venom Allergen III | *Solenopsis invicta* (Red imported fire ant) | 156 |
| Sol i 4 | VA4_SOLIN | P35777 | Venom Allergen IV | *Solenopsis invicta* (Red imported fire ant) | 157 |
| Sol r 2 | VA2SOLRI | P35776 | Venom Allergen II | *Solenopsis richteri* (Black imported fire ant) | 158 |
| Sol r 3 | VA3_SOLRI | P35779 | Venom Allergen III | *Solenopsis richteri* (Black imported fire ant) | 159 |
| Ves c 5 | VA51_VESCR | P35781 | Venom Allergen 5.01 | *Vespa crabro* (European hornet) | 160 |
| Ves c 5 | VA52_VESCR | P35782 | Venom Allergen 5.02 | *Vespa crabro* (European hornet) | 161 |
| Ves f 5 | VA5_VESFL | P35783 | Venom Allergen 5 | *Vespula flavopilosa* (Yellow jacket) (Wasp) | 162 |
| Ves g 5 | VA5_VESGE | P35784 | Venom Allergen 5 | *Vespula germanica* (Yellow jacket) (Wasp) | 163 |
| Ves m 1 | PA1_VESMC | P51528 | Phospholipase Al | *Vespula maculifrons* (Eastern yellow jacket) (Wasp) | 164 |
| Ves m 5 | VA5_VESMC | P35760 | Venom Allergen 5 | *Vespula maculifrons* (Eastern yellow jacket) (Wasp) | 165 |
| Ves p 5 | VA5_VESPE | P35785 | Venom Allergen 5 | *Vespula pensylvanica* (Western yellow jacket) (Wasp) | 166 |
| Ves s 5 | VA5_VESSQ | P35786 | Venom Allergen 5 | *Vespula squamosa* (Southern yellow jacket) (Wasp) | 167 |
| Ves v 1 | PA1_VESVU | P49369 | Phospholipase Al [Precursor] | *Vespula vulgaris* (Yellow jacket) (Wasp) | 168 |
| Ves v 2 | HUGA_VESVU | P49370 | Hyaluronoglucosaminidase | *Vespula vulgaris* (Yellow jacket) (Wasp) | 169 |
| Ves v 5 | VA5_VESVU | Q05110 | Venom Allergen 5 [Precursor] | *Vespula vulgaris* (Yellow jacket) (Wasp) | 170 |

TABLE 1-continued

| Allergen | SWISS-PROT Entry | SWISS-PROT Accession No. | Protein Name | Source | SEQ ID NO. |
|---|---|---|---|---|---|
| Ves vi 5 I | VA5_VESV | P35787 | Venom Allergen 5 | *Vespula vidua* (Yellow jacket) (Wasp) | 171 |
| Vesp m 5 | VA5_VESMA | P81657 | Venom Allergen 5 | *Vespa mandarinia* (Hornet) | 172 |
| Zea m 1 | MPZ1_MAIZE | Q07154 | Pollen Allergen Zea m 1 | *Zea mays* (Maize) | 173 |

Suitable vectors are prepared using standard techniques of recombinant DNA technology, and are, for example, described in "Molecular Cloning: A Laboratory Manual", $2^{nd}$ edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology", $4^{th}$ edition (D. M. Weir & C. C. Blackwell, eds., Blackwell Science Inc., 1987); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991). Isolated plasmids and DNA fragments are cleaved, tailored, and ligated together in a specific order to generate the desired vectors. After ligation, the vector containing the gene to be expressed is transformed into a suitable host cell.

Host cells can be any eukaryotic or prokaryotic hosts known for expression of heterologous proteins. Accordingly, the polypeptides of the present invention can be expressed in eukaryotic hosts, such as eukaryotic microbes (yeast) or cells isolated from multicellular organisms (mammalian cell cultures), plants and insect cells. Examples of mammalian cell lines suitable for the expression of heterologous polypeptides include monkey kidney CV1 cell line transformed by SV40 (COS-7, ATCC CRL 1651); human embryonic kidney cell line 293S (Graham et al, *J. Gen. Virol.* 36:59 [1977]); baby hamster kidney cells (BHK, ATCC CCL 10); Chinese hamster ovary (CHO) cells (Urlaub and Chasin, *Proc. Natl. Acad. Sci. USA* 77:4216 [1980]; monkey kidney cells (CV1-76, ATCC CCL 70); African green monkey cells (VERO-76, ATCC CRL-1587); human cervical carcinoma cells (HELA, ATCC CCL 2); canine kidney cells (MDCK, ATCC CCL 34); human lung cells (W138, ATCC CCL 75); and human liver cells (Hep G2, HB 8065). In general myeloma cells, in particular those not producing any endogenous antibody, e.g. the non-immunoglobulin producing myeloma cell line SP2/0, are preferred for the production of the fusion molecules herein.

Eukaryotic expression systems employing insect cell hosts may rely on either plasmid or baculoviral expression systems. The typical insect host cells are derived from the fall army worm (*Spodoptera frugiperda*). For expression of a foreign protein these cells are infected with a recombinant form of the baculovirus *Autographa californica* nuclear polyhedrosis virus which has the gene of interest expressed under the control of the viral polyhedrin promoter. Other insects infected by this virus include a cell line known commercially as "High 5" (Invitrogen) which is derived from the cabbage looper (*Trichoplusia ni*). Another baculovirus sometimes used is the *Bombyx mori* nuclear polyhedorsis virus which infect the silk worm (*Bombyx mori*). Numerous baculovirus expression systems are commercially available, for example, from Invitrogen (Bac-N-Blue™), Clontech (BacPAK™ Baculovirus Expression System), Life Technologies (BAC-TO-BAC™), Novagen (Bac Vector System™), Pharmingen and Quantum Biotechnologies). Another insect cell host is common fruit fly, *Drosophila melanogaster*, for which a transient or stable plasmid based transfection kit is offered commercially by Invitrogen (The DES™ System).

*Saccharomyces cerevisiae* is the most commonly used among lower eukaryotic hosts. However, a number of other genera, species, and strains are also available and useful herein, such as *Pichia pastoris* (EP 183,070; Sreekrishna et al., *J. Basic Microbiol.* 28:165-278 (1988)). Yeast expression systems are commercially available, and can be purchased, for example, from Invitrogen (San Diego, Calif.). Other yeasts suitable for bi-functional protein expression include, without limitation, *Kluyveromyces* hosts (U.S. Pat. No. 4,943,529), e.g. *Kluyveromyces lactis*; *Schizosaccharomyces pombe* (Beach and Nurse, *Nature* 290:140 (1981); *Aspergillus* hosts, e.g. *A. niger* (Kelly and Hynes, *EMBO J.* 4:475-479 (1985)]) and *A. nidulans* (Ballance et al., *Biochem. Biophys. Res. Commun.* 112:284-289 (1983)), and *Hansenula* hosts, e.g. *Hansenula polymorpha*. Yeasts rapidly growth on inexpensive (minimal) media, the recombinant can be easily selected by complementation, expressed proteins can be specifically engineered for cytoplasmic localization or for extracellular export, and are well suited for large-scale fermentation.

Prokaryotes are the preferred hosts for the initial cloning steps, and are particularly useful for rapid production of large amounts of DNA, for production of single-stranded DNA templates used for site-directed mutagenesis, for screening many mutants simultaneously, and for DNA sequencing of the mutants generated. *E. coli* strains suitable for the production of the peptides of the present invention include, for example, BL21 carrying an inducible T7 RNA polymerase gene (Studier et al., *Methods Enzymol.* 185:60-98 (1990)); AD494 (DE3); EB105; and CB (*E. coli* B) and their derivatives; K12 strain 214 (ATCC 31,446); W3110 (ATCC 27,325); X1776 (ATCC 31,537); HB101 (ATCC 33,694); JM101 (ATCC 33,876); NM522 (ATCC 47,000); NM538 (ATCC 35,638); NM539 (ATCC 35,639), etc. Many other species and genera of prokaryotes may be used as well. Indeed, the peptides of the present invention can be readily produced in large amounts by utilizing recombinant protein expression in bacteria, where the peptide is fused to a cleavable ligand used for affinity purification.

Suitable promoters, vectors and other components for expression in various host cells are well known in the art and are disclosed, for example, in the textbooks listed above.

Whether a particular cell or cell line is suitable for the production of the polypeptides herein in a functionally active form, can be determined by empirical analysis. For example, an expression construct comprising the coding sequence of the desired molecule may be used to transfect a candidate cell line. The transfected cells are then growth in culture, the medium collected, and assayed for the presence of secreted polypeptide. The product can then be quantitated by methods known in the art, such as by ELISA with an antibody specifically binding the IgG, IgE, or allergen portion of the molecule.

In certain instances, especially if the two polypeptide sequences making up the bifunctional molecule of the present invention are connected with a non-polypeptide linker, it may be advantageous the individually synthesize the first and second polypeptide sequences, e.g. by any of the recombinant approaches discussed above, followed by functionally linking the two sequences.

Alternatively, the two polypeptide sequences, or the entire molecule, may be prepared by chemical synthesis, such as solid phase peptide synthesis. Such methods are well known to those skilled in the art. In general, these methods employ either solid or solution phase synthesis methods, described in basic textbooks, such as, for example, J. M. Stewart and J. D. Young, Solid Phase Peptide Synthesis, 2nd Ed., Pierce Chemical Co., Rockford, Ill. (1984) and G. Barany and R. B. Merrifield, The Peptide: Analysis Synthesis, Biology, editors E. Gross and J. Meienhofer, Vol. 2, Academic Press, New York, (1980), pp. 3-254, for solid phase peptide synthesis techniques; and M. Bodansky, Principles of Peptide Synthesis, Springer-Verlag, Berlin (1984) and E. Gross and J. Meienhofer, Eds., The Peptides: Analysis, Synthesis, Biology, supra, Vol. 1, for classical solution synthesis.

The fusion molecules of the present invention may include amino acid sequence variants of native immunoglobulin (e.g. IgG and/or IgE) or allergen (e.g., Ara h 2 sequences. Such amino acid sequence variants can be produced by expressing the underlying DNA sequence in a suitable recombinant host cell, or by in vitro synthesis of the desired polypeptide, as discussed above. The nucleic acid sequence encoding a polypeptide variant is preferably prepared by site-directed mutagenesis of the nucleic acid sequence encoding the corresponding native (e.g. human) polypeptide. Particularly preferred is site-directed mutagenesis using polymerase chain reaction (PCR) amplification (see, for example, U.S. Pat. No. 4,683,195 issued 28 Jul. 1987; and *Current Protocols In Molecular Biology*, Chapter 15 (Ausubel et al., ed., 1991). Other site-directed mutagenesis techniques are also well known in the art and are described, for example, in the following publications: *Current Protocols In Molecular Biology*, supra, Chapter 8; *Molecular Cloning: A Laboratory Manual.*, 2$^{nd}$ edition (Sambrook et al., 1989); Zoller et al., *Methods Enzymol.* 100:468-500 (1983); Zoller & Smith, *DNA* 3:479-488 (1984); Zoller et al., *Nucl. Acids Res.,* 10:6487 (1987); Brake et al., *Proc. Natl. Acad. Sci. USA* 81:4642-4646 (1984); Botstein et al., *Science* 229:1193 (1985); Kunkel et al., *Methods Enzymol.* 154:367-82 (1987), Adelman et al., *DNA* 2:183 (1983); and Carter et al., *Nucl. Acids Res.,* 13:4331 (1986). Cassette mutagenesis (Wells et al., *Gene,* 34:315 [1985]), and restriction selection mutagenesis (Wells et al., *Philos. Trans. R. Soc. London SerA,* 317:415 [1986]) may also be used.

Amino acid sequence variants with more than one amino acid substitution may be generated in one of several ways. If the amino acids are located close together in the polypeptide chain, they may be mutated simultaneously, using one oligonucleotide that codes for all of the desired amino acid substitutions. If, however, the amino acids are located some distance from one another (e.g. separated by more than ten amino acids), it is more difficult to generate a single oligonucleotide that encodes all of the desired changes. Instead, one of two alternative methods may be employed. In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. The alternative method involves two or more rounds of mutagenesis to produce the desired mutant.

The polypeptides of the invention can also be prepared by the combinatorial peptide library method disclosed, for example, in International Patent Publication PCT WO 92/09300. This method is particularly suitable for preparing and analyzing a plurality of molecules, that are variants of a given predetermined sequences, and is, therefore, particularly useful in identifying polypeptides with improved biological properties, which can then be produced by any technique known in the art, including recombinant DNA technology and/or chemical synthesis.

3. Therapeutic Uses of the Fusion Molecules of the Invention

The present invention provides a new therapeutic strategy for treating immediate hypersensitivity diseases mediated through the high-affinity IgE receptor. In particular, the invention provides compounds for use in the treatment of both allergic diseases where IgE bridging of FcϵR receptors occurs and autoimmune disorders where autoantibodies bind to the FcϵR.

Nature of the diseases targeted Following the Gell and Coombs Classification, allergic reactions are classified depending on the type of immune response induced and the resulting tissue damage that develops as a result of reactivity to an antigen. A Type I reaction (immediate hypersensitivity) occurs when an antigen (called an allergen in this case) entering the body encounters mast cells or basophils which are sensitized as a result of IgE to that antigen being attached to its high-affinity receptor, FcϵRI. Upon reaching the sensitized mast cell, the allergen cross-links IgE bound to FcϵRI, causing an increase in intracellular calcium ($Ca^{2+}$) that triggers the release of pre-formed mediators, such as histamine and proteases, and newly synthesized, lipid-derived mediators such as leukotrienes and prostaglandins. These autocoids produce the acute clinical symptoms of allergy. The stimulated basophils and mast cells will also produce and release proinflammatory mediators, which participate in the acute and delayed phase of allergic reactions.

As discussed before and shown in Table 1 above, a large variety of allergens has been identified so far, and new allergens are identified, cloned and sequenced practically every day.

Ingestion of an allergen results in gastrointestinal and systemic allergic reactions. The most common food allergens involved are peanuts, shellfish, milk, fish, soy, wheat, egg and tree nuts such as walnuts. In susceptible people, these foods can trigger a variety of allergic symptoms, such as nausea, vomiting, diarrhea, urticaria, angioedema, asthma and full-blown anaphylaxis.

Inhalation of airborne allergens results in allergic rhinitis atid allergic asthma, which can be acute or chronic depending on the nature of the exposure(s). Exposure to airborne allergens in the eye results in allergic conjunctivitis. Common airborne allergens includes pollens, mold spores, dust mites and other insect proteins. Grass and weed and tree pollens are the most common cause of seasonal hay fever and allergic asthma.

Cutaneous exposure to an allergen, e.g. natural rubber latex proteins as found in latex gloves, may result in local allergic reactions manifest as hives (urticaria) at the places of contact with the allergen.

Systemic exposure to an allergen such as occurs with a bee sting, the injection of penicillin, or the use of natural rubber latex (NRL) gloves inside a patient during surgery may result in, cutaneous, gastrointestinal and respiratory reactions up to and including airway obstruction and full blown anaphylaxis. Hymenoptera stings are insects that commonly cause allergic reactions, often leading the anaphylactic shock. Examples include various bees including honeybees, yellow jackets, yellow hornets, wasps and white-faced hornets. Certain ants known as fire ants (*Solenopsis invicta*) are an increasing cause of allergy in the US as they expand their range in this country. Proteins in NRL gloves have become an increasing concern to health care workers and patients and at present, there is no successful form of therapy for this problem except avoidance.

Uses of compounds for targeted diseases The compounds disclosed herein can be used to acute or chronically inhibit IgE mediated reaction to major environmental and occupational allergens, can be used to provide for allergy vaccination (immunotherapy) to induce a state of non-allergic reactivity to specific allergens and can also have a prophylactic effect against allergic disease by preventing allergic sensitization to environmental and occupational allergens when administered to at-risk individuals (e.g., those at genetic risk of asthma and those exposed to occupational allergens in the workplace).

The bifunctional gamma-epsilon compounds described can be used to prevent allergic reactions to any specific allergen or group of allergens. By occupying a critical number of FcεRI receptors, these molecules will inhibit the ability of basophils and mast cells to react to any allergen so as to prevent including, without limitation, asthma, allergic rhinitis, atopic dermatitis, food allergies, urticaria and angioedema, up to and including anaphylactic shock. Thus these compounds could be used acutely to desensitize a patient so that the administration of a therapeutic agent (e.g. penicillin) can be given safely. Similarly, they can be used to desensitize a patient so that standard allergen vaccination may be given with greater safety, e.g. peanut or latex treatment. They can also be used as chronic therapy to prevent clinical reactivity to prevent environmental allergens such as foods or inhalant allergens.

The present invention as gamma allergen bifunctional fusion molecules provides for a novel form of allergy vaccination that will be safer and more effective the treatment of a varieties of IgE mediated allergic reactivity, including, without limitation, asthma, allergic rhinitis, atopic dermatitis, food allergies, urticaria and angioedema, up to and including anaphylactic shock. Having the allergen fused to a molecule that will bind to FcγRIIb on mast cells basophils will prevent the allergen being able to induce local or systemic allergic reactions. Such local or systemic allergic reactions are major problem in allergen vaccination as currently practiced. The gamma-allergen fusion proteins will be able to be given in higher doses over a shorter interval and with greater safety than standard allergen therapy. In addition, use of the gamma-allergen compounds will cause antigen specific desensitization to that specific allergen. Thus the gamma-allergen compounds will give a window of safe exposure to the allergen be it as an acute or recurring treatment as would be needed in using a therapeutic monoclonal antibody to which a patient has developed an allergic (IgE) response or as chronic treatment for prevention of unintentional exposures such as occurs with peanut allergens. This use is expected gain added importance, as the number of recombinant biological products entering the clinical arena will be increasing dramatically in the near future. The gamma-allergen compounds can even be used along with conventional allergen vaccination so as to provide an extra margin of safety while large doses of standard allergen are given.

In addition, the chimeric gamma-epsilon compounds herein hold great promise for the treatment of chronic urticaria and angioedema. Urticaria is a skin symptom that may accompany allergies but often is idiopathic. It is a relatively common disorder caused by localized cutaneous mast cell degranulation, with resultant increased dermal vascular permeability culminating in pruritic wheals. Angioedema is a vascular reaction involving the deep dermis or subcutaneous or submucosal tissues caused by localized mast cell degranulation. This results in tissue swelling that is pruritic or painful. Chronic urticaria and angioedema often occur together although they occur individually as well. These conditions are common and once present for more than six months, they often last a decade or more. Although not fatal, they are very troubling to patients as the frequent recurring attaching disrupt daily activities and thereby result in significant morbidity. Standard therapy is often unsuccessful in these conditions and they are distressing to the point that chemotherapy with cyclosporine and other potent immunosuppressive drugs has recently been advocated Increasing evidence suggests that as many as 60% of patients with these conditions actually have an autoimmune disease, in which they make functional antibodies against the FcεRI receptor. For further details, see Hide et al., *N. Engl. J. Med.* 328:1599-1604 (1993); Fiebiger et al., *J. Clin. Invest.* 96:2606-12 (1995); Fiebiger et al., *J. Clin. Invest.* 101:243-51 (1998); Kaplan, A. P., Urticaria and Angioedema, In: *Inflammation: Basic Principles and Clinical Correlates* (Galliin and Snyderman eds.), 3rd Edition, Lippincott & Wilkins, Philadelphia, 1999, pp. 915-928. The fusion molecules of the present invention are believed to form the basis for a novel and effective treatment of these diseases by safely blocking access to the FcεRI.

For therapeutic uses, including prevention, the compounds of the invention can be formulated as pharmaceutical compositions in admixture with pharmaceutically acceptable carriers or diluents. Methods for making pharmaceutical formulations are well known in the art. Techniques and formulations generally may be found in *Remington's Pharmaceutical Sciences,* 18th Edition, Mack Publishing Co., Easton, Pa. 1990. See, also, Wang and Hanson "*Parenteral Formulations of Proteins and Peptides: Stability and Stabilizers", Journal of Parenteral Science and Technology*, Technical Report No. 10, Supp. 42-2S (1988). A suitable administration format can best be determined by a medical practitioner for each patient individually.

Pharmaceutical compositions of the present invention can comprise a fusion molecule of the present invention along with conventional carriers and optionally other ingredients.

Suitable forms, in part, depend upon the use or the route of entry, for example oral, transdermal, inhalation, or by injection. Such forms should allow the agent or composition to reach a target cell whether the target cell is present in a multicellular host or in culture. For example, pharmacological agents or compositions injected into the blood stream should be soluble. Other factors are known in the art, and include considerations such as toxicity and forms that prevent the agent or composition from exerting its effect.

Carriers or excipients can also be used to facilitate administration of the compound. Examples of carriers and excipients include calcium carbonate, calcium phosphate, various sugars such as lactose, glucose, or sucrose, or types of starch, cellulose derivatives, gelatin, vegetable oils, polyethylene glycols and physiologically compatible solvents. The compositions or pharmaceutical composition can be administered by different routes including, but not limited to, oral, intravenous, intra-arterial, intraperitoneal, subcutaneous, intranasal or intrapulmonary routes.

The desired isotonicity of the compositions can be accomplished using sodium chloride or other pharmaceutically acceptable agents such as dextrose, boric acid, sodium tartrate, propylene glycol, polyols (such as mannitol and sorbitol), or other inorganic or organic solutes.

For systemic administration, injection is preferred, e.g., intramuscular, intravenous, intra-arterial, etc. For injection, the compounds of the invention are formulated in liquid solutions, preferably in physiologically compatible buffers such as Hank's solution or Ringer's solution. Alternatively, the compounds of the invention are formulated in one or more excipients (e.g., propylene glycol) that are generally accepted as safe as defined by USP standards. They can, for example, be suspended in an inert oil, suitably a vegetable oil such as sesame, peanut, olive oil, or other acceptable carrier. Preferably, they are suspended in an aqueous carrier, for example, in an isotonic buffer solution at pH of about 5.6 to 7.4. These compositions can be sterilized by conventional sterilization techniques, or can be sterile filtered. The compositions can contain pharmaceutically acceptable auxiliary substances as required to approximate physiological conditions, such as pH buffering agents. Useful buffers include for example, sodium acetate/acetic acid buffers. A form of repository or "depot" slow release preparation can be used so that therapeutically effective amounts of the preparation are delivered into the bloodstream over many hours or days following transdermal injection or delivery. In addition, the compounds can be formulated in solid form and redissolved or suspended immediately prior to use. Lyophilized forms are also included.

Alternatively, certain molecules identified in accordance with the present invention can be administered orally. For oral administration, the compounds are formulated into conventional oral dosage forms such as capsules, tablets and tonics.

Systemic administration can also be by transmucosal or transdermal. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents can be used to facilitate permeation. Transmucosal administration can be, for example, through nasal sprays or using suppositories.

A preferred route for administration of the compounds of the invention may be inhalation for intranasal and/or intrapulmonary delivery. For administration by inhalation, usually inhalable dry power compositions or aerosol compositions are used, where the size of the particles or droplets is selected to ensure deposition of the active ingredient in the desired part of the respiratory tract, e.g. throat, upper respiratory tract or lungs. Inhalable compositions and devices for their administration are well known in the art. For example, devices for the delivery of aerosol medications for inspiration are known. One such device is a metered dose inhaler that delivers the same dosage of medication to the patient upon each actuation of the device. Metered dose inhalers typically include a canister containing a reservoir of medication and propellant under pressure and a fixed volume metered dose chamber. The canister is inserted into a receptacle in a body or base having a mouthpiece or nosepiece for delivering medication to the patient. The patient uses the device by manually pressing the canister into the body to close a filling valve and capture a metered dose of medication inside the chamber and to open a release valve which releases the captured, fixed volume of medication in the dose chamber to the atmosphere as an aerosol mist. Simultaneously, the patient inhales through the mouthpiece to entrain the mist into the airway. The patient then releases the canister so that the release valve closes and the filling valve opens to refill the dose chamber for the next administration of medication. See, for example, U.S. Pat. No. 4,896,832 and a product available from 3M Healthcare known as Aerosol Sheathed Actuator and Cap.

Another device is the breath actuated metered dose inhaler that operates to provide automatically a metered dose in response to the patient's inspiratory effort. One style of breath actuated device releases a dose when the inspiratory effort moves a mechanical lever to trigger the release valve. Another style releases the dose when the detected flow rises above a preset threshold, as detected by a hot wire anemometer. See, for example, U.S. Pat. Nos. 3,187,748; 3,565,070; 3,814,297; 3,826,413; 4,592,348; 4,648,393; 4,803,978.

Devices also exist to deliver dry powdered drugs to the patient's airways (see, e.g. U.S. Pat. No. 4,527,769) and to deliver an aerosol by heating a solid aerosol precursor material (see, e.g. U.S. Pat. No. 4,922,901). These devices typically operate to deliver the drug during the early stages of the patient's inspiration by relying on the patient's inspiratory flow to draw the drug out of the reservoir into the airway or to actuate a heating element to vaporize the solid aerosol precursor.

Devices for controlling particle size of an aerosol are also known, see, for example, U.S. Pat. Nos. 4,790,305; 4,926,852; 4,677,975; and 3,658,059.

For topical administration, the compounds of the invention are formulated into ointments, salves, gels, or creams, as is generally known in the art.

If desired, solutions of the above compositions can be thickened with a thickening agent such as methyl cellulose. They can be prepared in emulsified form, either water in oil or oil in water. Any of a wide variety of pharmaceutically acceptable emulsifying agents can be employed including, for example, acacia powder, a non-ionic surfactant (such as a Tween), or an ionic surfactant (such as alkali polyether alcohol sulfates or sulfonates, e.g., a Triton).

Compositions useful in the invention are prepared by mixing the ingredients following generally accepted procedures. For example, the selected components can be mixed simply in a blender or other standard device to produce a concentrated mixture which can then be adjusted to the final concentration and viscosity by the addition of water or thickening agent and possibly a buffer to control pH or an additional solute to control tonicity.

The amounts of various compounds for use in the methods of the invention to be administered can be determined by standard procedures. Generally, a therapeutically effective amount is between about 100 mg/kg and $10^{-12}$ mg/kg depending on the age and size of the patient, and the disease or disorder associated with the patient. Generally, it is an amount between about 0.05 and 50 mg/kg, more preferably between about 1.0 and 10 mg/kg for the individual to be treated. The determination of the actual dose is well within the skill of an ordinary physician.

The compounds of the present invention may be administered in combination with one or more further therapeutic agent for the treatment of IgE-mediated allergic diseases or conditions. Such further therapeutic agents include, without limitation, corticosteroids, β-antagonists, theophylline, leukotriene inhibitors, allergen vaccination, soluble recombinant human soluble IL-4 receptors (Immunogen), anti-IL-4 monoclonal antibodies (Protein Design Labs), and anti-IgE antibodies, such as the recombinant human anti-IgE monoclonal antibody rhuMAb-E25 (Genentech, Inc.) which is currently in advanced clinical trials for the treatment of patients with atopic asthma, and other allergic diseases, such as allergic rhinitis and atopic dermatitis (see, e.g. Barnes, *The New England Journal of Medicine* 341:2006-2008 (1999)). Thus the compounds of the present invention can be used to supplement traditional allergy therapy, such as corticosteroid therapy performed with inhaled or oral corticosteroids.

4. Articles of Manufacture

The invention also provides articles of manufacture comprising the single-chain fusion compounds herein. The article of manufacture comprises a container and a label or package insert on or associated with the container. Suitable containers include, for example, bottles, vials, syringes, etc. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The container may also be an inhalation device such as those discussed above. At least one active agent in the composition is a fusion compound of the invention. The label or package insert indicates that the composition is used for treating the condition of choice, such as an allergic condition, e.g. asthma or any of the IgE-mediated allergies discussed above. The article of manufacture may further comprise a further container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Further details of the invention are illustrated by the following non-limiting Example.

Example

Construction and Expression of a Chimeric Human Fcγ-Fcε Fusion Protein

Materials and Methods

Plasmids, vectors and cells—Plasmid pAG 4447 containing genomic DNA encoding human IgE constant region and expression vector pAN 1872 containing human genomic DNA encoding the hinge-CH2-CH3 portion of IgG₁ constant region were obtained from the laboratory of Dr. Morrison. pAN 1872 is derived from the pDisplay vector (Invitrogen). pAG 4447 was developed and used as a cloning intermediate in the construction of a human IgE expression vector disclosed in *J. Biol. Chem.* 271:3428-3436 (1996). To construct the chimeric gene, a pair of primers were designed to amplify the human IgE constant region (CH2-CH3-CH4). 5'-end primer:

5'GCTCGAGGGTGGAGGCGGTTCAGGCGGAGGTGGCTCTGGCGGTGGCG
GATCGTTCACCCCGCCCACCGTGAAG3', (SEQ ID NO: 174)

containing a flexible linker sequence and an XhoI site.

3' end primer:

5'GGCGGCCGCTCATTTACCGGGATTTACAGACAC3',
(SEQ ID NO: 175)

containing an NotI.

After amplification, the PCR products were cloned into pCR2.1 vector (Invitrogen). The sequences of the products were confirmed. Then, the ZhoI-NotI fragment was inserted into the 1782 pAN vector, following the IgG₁ CH3 domain in the same reading frame by a (Gly₄Ser)₃ flexible linker. SP2.0 murine myeloma cell line was selected as host for expression because it does not secrete any antibody.

Expression and Purification—The expression vector containing chimeric Fcγ-Fcε gene was linearized at the PcuI site and transfected into SP2/0 cells by electroporation (Bio-Rad). Stable transfectants were selected for growth in medium containing 1 mg/ml geneticine. Clones producing the fusion protein were identified by ELISA using plates coating anti-human IgE (CIA7.12) or IgG (Sigma) antibody. Supernatants from clones were added to wells, and bound protein was detected using goat anti-human IgE or IgG conjugated to alkaline phosphatase (KPL). The fusion protein was purified from the supernatants and ascites by using rProtein A column (Pharmacia).

Western Blotting—The purified protein was run on 7.5% SDS polyacrylamide gel. After transfer, the nylon membrane was blocked by 4% bovine serum albumin/PBS/Tween overnight at 4° C. For protein detection, the blot was probed with either goat anti-human IgE (ε chain specific) or goat anti-human IgG (γ chain-specific) conjugated to alkaline psophatase (KPL). Color development was performed with an alkaline phosphatase conjugated substrate kit (Bio-Rad).

Binding Test—In order to confirm the binding, FcεRI transfected cells (CHO 3D10) or human HMC-1 cells that express FcγRIIb but not FcεRI were stained with purified fusion protein and then analyzed by flow cytometry. Briefly, cells were collected and washed. The cells were then incubated with 5 μl of 1 mg/ml GE2, PS IgE or human IgG at 4° C. for 60 minutes. After two washes, the cells were stained with FITC conjugated anti-human IgE or IgG at 4° C. for 60 minutes, and visualized by flow cytometry.

Inhibition of Basophil Histamine Release—Acid-stripped Percoll-enriched human blood basophils were primed with 1-10 μg/ml of chimeric human anti-NP IgE at 37° C. in a 5% CO2 incubator and one hour later, challenged with 30 ng of NP-BSA (Kepley, J. Allergy Clin. Immunol. 106:337-348 (2000)). Histamine release was measured in the supernatants 30 minutes later. GE2 or control human myeloma IgE was added at various doses and times to test the effects on histamine release.

Passive Cutaneous Anaphylaxis Model—Transgenic mice expressing the human FcεR1a chain and with the murine FcεR1α chain knocked out (provided by Dr. Jean-Pierre Kinet, Harvard Medical School, Boston, Mass., Dombrowicz, et al, *J. Immunol.* 157:1645-1654. (1996)) were primed cutaneously with either recombinant human anti-dansyl or anti-NP IgE. Individual sites were then injected with saline, GE2 or IgE myeloma protein. Four hours later, mice were given a systemic challenge with dansyl-OVA or NP-BSA plus Evans blue, and the resulting area of reaction was measured.

Results

Western blotting showed that the chimeric protein (designated GE2) was expressed as the predicted dimer of approximately 140 kD. The GE2 protein reacted with both anti-human ε and anti-human γ chain-specific antibodies.

GE2 showed the ability to inhibit IgE-mediated release of histamine from fresh human basophils. The results of the dose-dependent inhibition of basophil histamine release using the fusion protein GE2 (±SEM; n+3 separate donors, each in duplicate) are shown in FIG. 8. The data show that, when added to fresh human basophils along with the sensitizing anti-NP IgE antibody, GE2 inhibited subsequent NP-induced release of histamine in a dose-dependent manner, more effectively than an equivalent amount of native human IgE protein. This was time dependent as expected with the greatest effect being observed when the GE2 was added with the sensitizing anti-NP IgE antibody. No effect was observed if the GE2 was given simultaneously with the antigen challenge.

Figure 9:
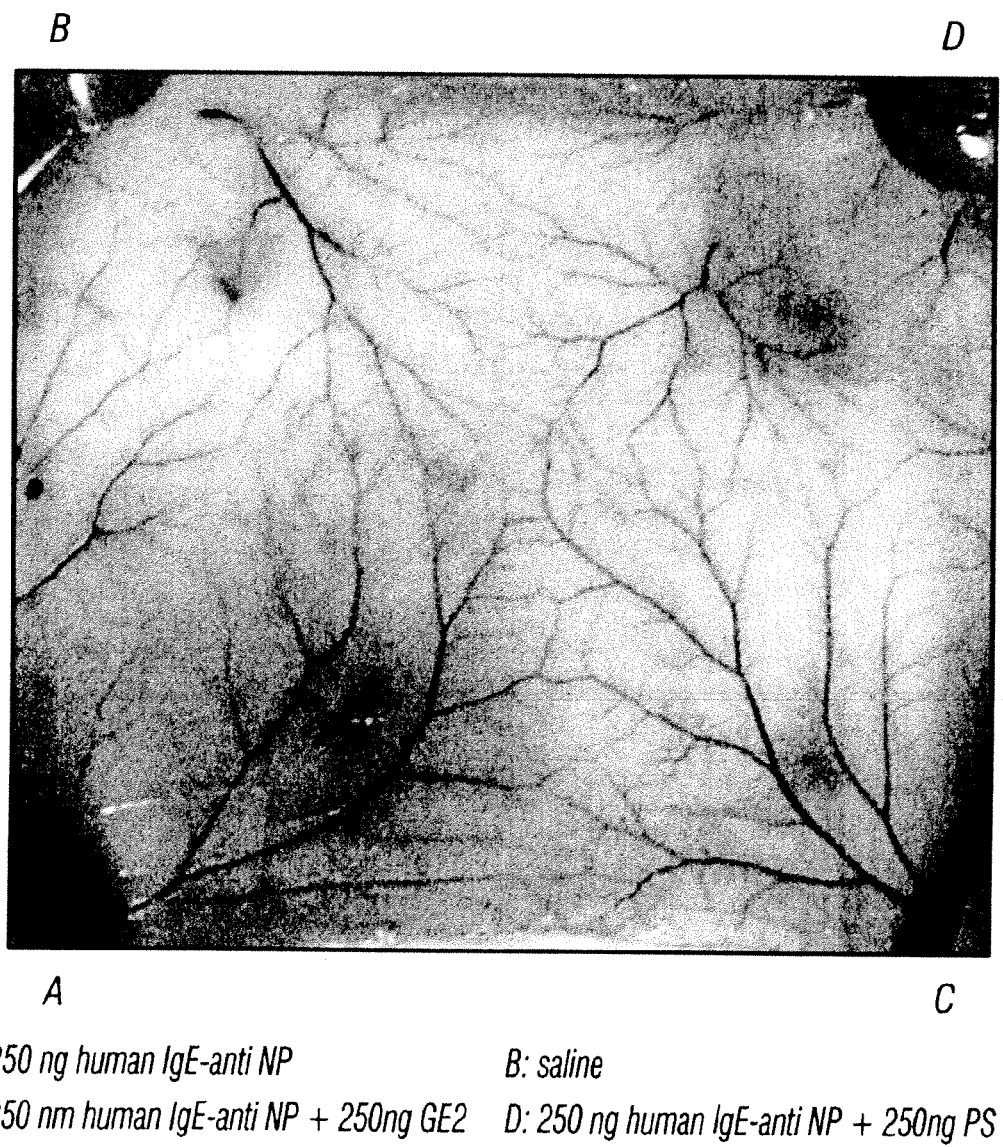
FIG. 9 shows results obtained in the transgenic passive cutaneous anaphylaxis (PCA) model described in the Example. Sites were injected with 250 ng of human anti-IgE NP along with the indicated amounts of PS (non-specific human IgE) or GE2 chimeric fusion protein. Four hours later, the animals were challenged intravenously (IV) with 500 μg of NP-BSA.

To test the in vivo function of GE2, the transgenic passive cutaneous anaphylaxis described above was used. The results are shown in FIG. 9. The size and color of the reaction at the sites of GE2 injection were decreased compared to those injected with comparable amount of human IgE. These results demonstrate that the GE2 protein is able to inhibit mast cell/basophil function greater than an equivalent amount of IgE and implicates binding to both FcεRI and FCγR.

Analysis of binding using flow cytometry showed that the GE2 protein bound in a fashion similar to native IgE to the human FcγRII expressed on HMC-1 cells. The data are shown in FIG. 10. Similar results were obtained for the FcεRI on 3D10 cells, as shown in FIG. 11.

All references cited throughout the specification are hereby expressly incorporated by reference. It is understood that the application of the teachings of the present invention to a specific problem or situation will be within the capabilities of one having ordinary skill in the art in light of the teachings contained herein. Examples of the products of the present invention and representative processes for their production and use should not be construed to limit the invention.

What is claimed is:

1. An isolated fusion molecule comprising a first polypeptide sequence consisting of the amino acid sequence of SEQ ID NO: 3 and being capable of specific binding to a native IgG inhibitory receptor comprising an immune receptor tyrosine-based inhibitory motif (ITIM), expressed on mast cells, basophils or B cells, said first polypeptide sequence being functionally connected with a polypeptide linker of between about 5 to 25 amino acids to a second polypeptide sequence consisting of a native allergen polypeptide sequence selected from SEQ ID NOs: 8 through 173, said second polypeptide sequence being capable of specific binding indirectly to a native IgE receptor (FcεR), wherein said polypeptide linker allows said first polypeptide and said second polypeptide to independently assume a tertiary conformation effective to allow binding with a native receptor, and wherein said isolated fusion molecule is capable of cross-linking said native IgG inhibitory receptor and said native IgE receptor.

2. The fusion molecule of claim 1 wherein said inhibitory receptor is a low-affinity IgG receptor FcγRIIb.

3. The fusion molecule of claim 2 wherein said IgE receptor is a high-affinity FcεRI receptor.

4. The fusion molecule of claim 2 wherein said IgE receptor is a low-affinity IgE receptor FcεRII (CD23).

5. The fusion molecule of claim 3 wherein said FcγRIIb and FcεRI receptors are of human origin.

6. The fusion molecule of claim 4 wherein said FcγRIIb and FcεRII receptors are of human origin.

7. The fusion molecule of claim 1 wherein said allergen sequence is that of a food allergen.

8. The fusion molecule of claim 7 wherein said food allergen is selected from the group consisting of peanut, shellfish, milk, fish, soy, wheat, egg and tree nut allergens.

9. The fusion molecule of claim 1 wherein said allergen sequence is that of a pollen allergen.

10. The fusion molecule of claim 1 wherein said IgE receptor is a high-affinity FcεRI receptor.

11. The fusion molecule of claim 1 wherein said native IgE receptor is a low-affinity FcεRII receptor (CD23).

12. The fusion molecule of claim 1 wherein said IgG inhibitory receptor is a low affinity FcγRIIb receptor.

13. The fusion molecule of claim 12 wherein said IgE receptor is a high-affinity FcεRI receptor.

14. The fusion molecule of claim 13 wherein said FcγRIIb and FcεRI receptors are of human origin.

15. The fusion molecule of claim 1 wherein said polypeptide linker consists of 10 to 25 amino acid residues.

16. The fusion molecule of claim 15 wherein said polypeptide linker consists of 15 to 25 amino acid residues.

17. An isolated fusion molecule consisting of a first polypeptide sequence encoded by nucleic acid of SEQ ID NO: 1, wherein said first polypeptide sequence is capable of specific binding to a native human FcγRIIb receptor, and said first polypeptide sequence being functionally connected with a polypeptide linker of between about 5 to 25 amino acids to a second polypeptide sequence consisting of a native allergen polypeptide sequence selected from SEQ ID NOs: 8 through 173, said second polypeptide sequence being capable of specific binding indirectly to a high-affinity FcεRI receptor, wherein said polypeptide linker allows said first polypeptide and said second polypeptide to independently assume a tertiary conformation effective to allow binding with a native receptor, and wherein said isolated fusion molecule is capable of cross-linking said native IgG inhibitory receptor and said high-affinity FcεRI receptor.

18. A pharmaceutical composition comprising the fusion molecule of claim 1 in admixture with a pharmaceutically acceptable ingredient.

19. A pharmaceutical composition comprising the fusion molecule of claim 3 in admixture with a pharmaceutically acceptable ingredient.

20. An article of manufacture comprising a container, the fusion molecule of claim 1 within the container, and a label or package insert on or associated with the container.

21. The article of manufacture of claim 20 wherein said label or package insert comprises instructions for the treatment of an IgE-mediated biological response.

22. The article of manufacture of claim 21 wherein said biological response is a mediated hypersensitivity reaction.

23. The article of manufacture of claim 22 wherein said label or package insert contains instruction for the treatment of a condition selected from the group consisting of asthma, allergic rhinitis, atopic dermatitis, severe food allergies, chronic urticaria, angioedema, and anaphylactic shock.

24. The isolated fusion molecule of claim 1, wherein said first polypeptide consisting of the γ-hinge-CH2-CH3 domain of a native IgG immunoglobulin heavy chain constant region and consisting of the amino acid sequence of SEQ ID NO: 3.

* * * * *